(12) United States Patent
Chen et al.

(10) Patent No.: US 9,873,701 B2
(45) Date of Patent: Jan. 23, 2018

(54) HETEROCYCLIC COMPOUNDS AND THEIR USES

(71) Applicant: AMGEN INC., Thousand Oaks, CA (US)

(72) Inventors: Yi Chen, San Jose, CA (US); Timothy D. Cushing, Pacifica, CA (US); Jason A. Duquette, Milbrae, CA (US); Felix Gonzalez Lopez De Turiso, San Mateo, CA (US); Xiaolin Hao, Foster City, CA (US); Xiao He, Foster City, CA (US); Brian S. Lucas, Arlington, MA (US); Lawrence R. McGee, Pacifica, CA (US); Andreas Reichelt, Moorpark, CA (US); Robert M. Rzasa, Ventura, CA (US); Jennifer L. Seganish, Plainfield, NJ (US); Youngsook Shin, Emeryville, CA (US); Dawei Zhang, Thousand, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/520,899

(22) Filed: Oct. 22, 2014

(65) Prior Publication Data

US 2015/0045361 A1 Feb. 12, 2015

Related U.S. Application Data

(60) Division of application No. 13/468,234, filed on May 10, 2012, now Pat. No. 8,901,135, which is a continuation of application No. 12/079,406, filed on Mar. 24, 2008, now Pat. No. 8,193,199.

(60) Provisional application No. 60/919,568, filed on Mar. 23, 2007.

(51) Int. Cl.
| | | |
|---|---|---|
| C07D 487/04 | (2006.01) | |
| C07D 473/30 | (2006.01) | |
| C07D 473/34 | (2006.01) | |
| C07D 471/04 | (2006.01) | |

(52) U.S. Cl.
CPC ......... *C07D 487/04* (2013.01); *C07D 471/04* (2013.01); *C07D 473/30* (2013.01); *C07D 473/34* (2013.01)

(58) Field of Classification Search
None
See application file for complete search history.

(56) References Cited

U.S. PATENT DOCUMENTS

| 8,193,199 B2 | 6/2012 | Chen et al. |
| 2005/0153989 A1 | 7/2005 | Grotzfeld et al. |
| 2008/0176892 A1 | 7/2008 | Heinrich et al. |
| 2010/0331306 A1 | 12/2010 | Bui et al. |
| 2011/0105508 A1 | 5/2011 | Allen et al. |
| 2011/0281866 A1 | 11/2011 | Ren et al. |
| 2012/0077815 A1 | 3/2012 | Allen et al. |

FOREIGN PATENT DOCUMENTS

| WO | 2005117909 A2 | 12/2005 |
| WO | 2006114180 A1 | 11/2006 |
| WO | 2008118468 A1 | 10/2008 |
| WO | 2009041521 A1 | 4/2009 |
| WO | 2010036380 A1 | 4/2010 |
| WO | 2010046639 A1 | 4/2010 |
| WO | 2010061180 A1 | 6/2010 |
| WO | 2010092340 A1 | 8/2010 |
| WO | 2010129816 A2 | 11/2010 |
| WO | 2011058113 A1 | 5/2011 |
| WO | 2011075628 A1 | 6/2011 |

OTHER PUBLICATIONS

Tzenaki. Frontiers in Oncology, 2013, 3(40), 1-16.*
"MeSH record", https://www.nlm.nih.gov/cgi/mesh/2016/MB_cgi?mode=&index=8291&field=all&HM=&ll=&PA=&form=&input=, accessed Jun. 13, 2016.*
"Solid Tumors", https://www.cancer.gov/publications/dictionaries/cancer-terms?cdrid=45301, accessed Mar. 31, 2017.*
Rodrigues Alves. Life Sciences, 2011, pp. 532-539.*
Schwab. Seminars in Cancer Biology, 1999, 9, 319-25.*
Schow et al., "Synthesis and activity of 2,6,9-trisubstituted purines" Bioorganic and Medicinal Chemistry Letters.
PCT/US2008/003962 International Search Report dated Aug. 18, 2008.

* cited by examiner (Continued)

Primary Examiner — Noble E Jarrell
(74) Attorney, Agent, or Firm — Joseph F. Reidy

(57) ABSTRACT

Substituted bicyclic heteroaryls and compositions containing them, for the treatment of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions including all forms of hypersensitivity, The present invention also enables methods for treating cancers that are mediated, dependent on or associated with p110δ activity, including but not restricted to leukemias, such as Acute Myeloid leukaemia (AML) Myelo-dysplastic syndrome (MDS) myelo-proliferative diseases (MPD) Chronic Myeloid Leukemia (CML) T-cell Acute Lymphoblastic leukaemia (T-ALL) B-cell Acute Lymphoblastic leukaemia (B-ALL) Non Hodgkins Lymphoma (NHL) B-cell lymphoma and solid tumors, such as breast cancer.

16 Claims, No Drawings

HETEROCYCLIC COMPOUNDS AND THEIR USES

This application is a divisional of U.S. Ser. No. 13/468,234, filed May 10, 2012, which claims the benefit of U.S. Ser. No. 12/079,406, filed Mar. 24, 2008 and U.S. Provisional Application No. 60/919,568, filed Mar. 23, 2007, which are hereby incorporated by reference.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274:8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu. Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Sternmark et al., J Cell Sci, 112:4175-83 (1999); Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of to AGC family. Members of the Tec family containing PH domains with apparent selectivity for PtdIns (3,4,5)$P_3$ include Tec, Btk, Itk and Etk. Binding of PH to $PIP_3$ is critical for tyrsosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C (PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu. Rev. Immunol. 22_563-598 (2004)). In vitro, some isoforms of protein kinase C (PKC) are directly activated by PIP3. (Buggering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan et al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85α, p55α and p50 proteins (Deane and Fruman, Annu. Rev. Immunol. 22: 563-598 (2004)). p85α is ubiquitously expressed while p85β, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3Kgamma was originally cloned in swine, and the human ortholog identified subsequently (Krugmann et al., J Biol Chem, 274:17152-8 (1999)). Interaction between the N-terminal region of p101 with the N-terminal region of p110γ is known to activate PI3Kγ through Gβγ. Recently, a p101-homologue has been identified, p84 or p87$^{PIKAP}$ (PI3Kγ adapter protein of 87 kDa) that binds p110γ (Voigt et al. JBC, 281: 9977-9986 (2006), Suire et al. Curr. Biol. 15: 566-570 (2005)). p87$^{PIKAP}$ is homologous to p101 in areas that bind p110γ and Gβγ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of Saccharomyces cerevisiae (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the $IC_{50}$ values of wortmannin against each of the various Class I PI 3-kinases are in the range of 1-10 nM. Similarly, the $IC_{50}$ values for LY294002 against each of these PI 3-kinases is about 1 μM (Fruman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, inasmuch as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110 alpha and beta (Bi et al. Mamm. Genome, 13:169-172 (2002); Bi et al. J. Biol. Chem. 274:10963-10968 (1999)). More recently, p110α kinase dead knock in mice were generated with a single point mutation in the DFG motif of the ATP binding pocket (p110αD$^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p110αD$^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinaemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CDS+ B1 cells nearly undetectable, and B- and T cell antigen receptor signaling (Clayton et al. J. Exp. Med. 196:753-763 (2002); Okkenhaug et al. Science, 297: 1031-1034 (2002)). The p110δ$^{D910A}$ mice have been studied extensively and have elucidated the diverse role that delta plays in the immune system. T cell dependent and T cell independent immune responses are severely attenuated in p110δ$^{D910A}$ and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A taiwanese boy with a primary B cell immunodeficiency and a gamma-hypoglobulinemia of previously unkown aetiology presented with a single base-pair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations and his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)) Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equi-potently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosis (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ$^{D910A}$) it was shown that in addition to playing a key role in B and T cell activation, delta is also partially involved in neutrophil migration and primed neutrophil respiratory burst and leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ$^{D910A}$ mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ$^{D910A}$ mutant mice using the same model of allergic airway inflammation by a different group (Nashed et al. Eur. J. Immunol. 37:416-424 (2007)).

There exists a need for further characterization of PI3Kδ function in inflammatory and auto-immune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110 alpha (insulin signaling) and beta (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new class of compounds having the general formula

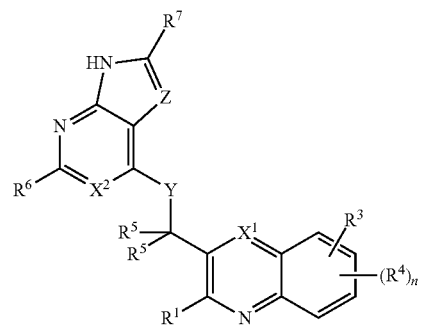

which are useful to inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

DETAILED DESCRIPTION

One aspect of the invention relates to compounds having the structure:

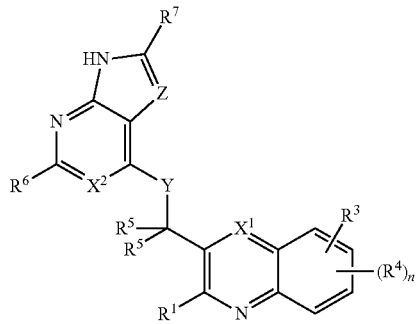

or any pharmaceutically-acceptable salt thereof, wherein:

$X^1$ is $C(R^9)$ or N;

$X^2$ is $C(R^{10})$ or N;

Y is $N(R^{11})$, O or S;

Z is $CR^8$ or N;

n is 0, 1, 2 or 3;

$R^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1$R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}alkyl)C_{1-4}$alkyl and $C_{1-4}$haloalkyl;

$R^2$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; or $R^2$ is selected from $C_{1-6}$alkyl, phenyl, benzyl, heteroaryl, heterocycle, —(C$_{1-3}$alkyl)heteroaryl, —(C$_{1-3}$ alkyl)heterocycle, —O(C$_{1-3}$ alkyl)heteroaryl, —O(C$_{1-3}$ alkyl)heterocycle, —N$R^a$(C$_{1-3}$ alkyl)heteroaryl, —N$R^a$(C$_{1-3}$ alkyl)heterocycle, —(C$_{1-3}$alkyl)phenyl, —O(C$_{1-3}$ alkyl)phenyl and —N$R^a$(C$_{1-3}$ alkyl)phenyl all of which are substituted by 0, 1, 2 or 3 substituents selected from $C_{1-4}$haloalkyl, $OC_{1-4}$alkyl, Br, Cl, F, I and $C_{1-4}$alkyl;

$R^3$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;

$R^4$ is, independently, in each instance, halo, nitro, cyano, $C_{1-4}$alkyl, $OC_{1-4}$alkyl, $OC_{1-4}$haloalkyl, $NHC_{1-4}$alkyl, $N(C_{1-4}alkyl)C_{1-4}$alkyl or $C_{1-4}$haloalkyl;

$R^5$ is, independently, in each instance, H, halo, $C_{1-6}$alkyl, $C_{1-4}$haloalkyl, or $C_{1-6}$ alkyl substituted by 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}alkyl)C_{1-4}$alkyl; or both $R^5$ groups together form a $C_{3-6}$spiroalkyl substituted by 0, 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}alkyl)C_{1-4}$alkyl;

$R^6$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^7$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^8$ is selected from H, $C_{1-6}$haloalkyl, Br, Cl, F, I, O$R^a$, N$R^aR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;

$R^9$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C (=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{10}$ is H, C$_{1-3}$alkyl, C$_{1-3}$haloalkyl, cyano, nitro, CO$_2$R$^a$, C(=O)NR$^a$R$^a$, —C(=NR$^a$)NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, S(=O)R$^b$, S(=O)$_2$R$^b$ or S(=O)$_2$NR$^a$R$^a$;

R$^{11}$ is H or C$_{1-4}$alkyl;

R$^a$ is independently, at each instance, H or R$^b$; and

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl.

Another aspect of the invention relates to compounds having the structure:

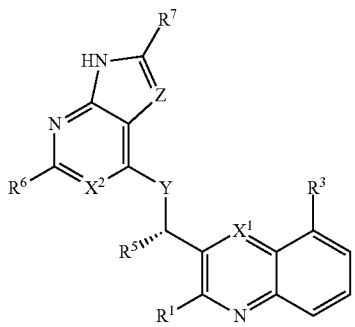

or any pharmaceutically-acceptable salt thereof, wherein:

X$^1$ is C(R$^9$) or N;

X$^2$ is C(R$^{10}$) or N;

Y is N(R$^{11}$), O or S;

Z is CR$^8$ or N;

n is 0, 1, 2 or 3;

R$^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1R$^2$ substituents, and the ring is additionally substituted by 0, 1, 2 or 3 substituents independently selected from halo, nitro, cyano, C$_{1-4}$alkyl, OC$_{1-4}$alkyl, OC$_{1-4}$haloalkyl, NHC$_{1-4}$alkyl, N(C$_{1-4}$alkyl)C$_{1-4}$alkyl and C$_{1-4}$haloalkyl;

R$^2$ is selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^2$ is selected from C$_{1-6}$alkyl, phenyl, benzyl, heteroaryl, heterocycle, —(C$_{1-3}$alkyl)heteroaryl, —(C$_{1-3}$alkyl)heterocycle, —O(C$_{1-3}$alkyl)heteroaryl, —O(C$_{1-3}$alkyl)heterocycle, —NR$^a$(C$_{1-3}$alkyl)heteroaryl, —NR$^a$(C$_{1-3}$alkyl)heterocycle, —(C$_{1-3}$ alkyl)phenyl, —O(C$_{1-3}$alkyl)phenyl and —NR$^a$(C$_{1-3}$alkyl)phenyl all of which are substituted by 0, 1, 2 or 3 substituents selected from C$_{1-4}$haloalkyl, OC$_{1-4}$alkyl, Br, Cl, F, I and C$_{1-4}$alkyl;

R$^3$ is selected from H, halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$, —NR$^a$C$_{2-6}$alkylOR$^a$, C$_{1-6}$alkyl, phenyl, benzyl, heteroaryl and heterocycle, wherein the C$_{1-6}$alkyl, phenyl, benzyl, heteroaryl and heterocycle are additionally substituted by 0, 1, 2 or 3 substituents selected from C$_{1-6}$haloalkyl, OC$_{1-6}$alkyl, Br, Cl, F, I and C$_{1-6}$alkyl;

R$^4$ is, independently, in each instance, halo, nitro, cyano, C$_{1-4}$alkyl, OC$_{1-4}$alkyl, OC$_{1-4}$haloalkyl, NHC$_{1-4}$alkyl, N(C$_{1-4}$alkyl)C$_{1-4}$alkyl or C$_{1-4}$haloalkyl;

R$^5$ is, independently, in each instance, H, halo, C$_{1-6}$alkyl, C$_{1-4}$haloalkyl, or C$_{1-6}$alkyl substituted by 1, 2 or 3 substituents selected from halo, cyano, OH, OC$_{1-4}$alkyl, C$_{1-4}$alkyl, C$_{1-3}$haloalkyl, OC$_{1-4}$alkyl, NH$_2$, NHC$_{1-4}$alkyl, N(C$_{1-4}$alkyl)C$_{1-4}$alkyl; or both R$^5$ groups together form a C$_{3-6}$spiroalkyl substituted by 0, 1, 2 or 3 substituents selected from halo, cyano, OH, OC$_{1-4}$alkyl, C$_{1-4}$alkyl, C$_{1-3}$haloalkyl, OC$_{1-4}$alkyl, NH$_2$, NHC$_{1-4}$alkyl, N(C$_{1-4}$alkyl)C$_{1-4}$alkyl;

R$^6$ is selected from H, halo, C$_{1-6}$alkyl, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$;

R$^7$ is selected from H, halo, C$_{1-6}$alkyl, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$;

R$^8$ is selected from H, C$_{1-6}$haloalkyl, Br, Cl, F, I, OR$^a$, NR$^a$R$^a$, C$_{1-6}$alkyl, phenyl, benzyl, heteroaryl and heterocycle, wherein the C$_{1-6}$alkyl, phenyl, benzyl, heteroaryl and heterocycle are additionally substituted by 0, 1, 2 or 3 substituents selected from C$_{1-6}$haloalkyl, OC$_{1-6}$alkyl, Br, Cl, F, I and C$_{1-6}$alkyl;

R$^9$ is selected from H, halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$, —NR$^a$C$_{2-6}$alkylOR$^a$, C$_{1-6}$alkyl, phenyl, benzyl, heteroaryl and heterocycle, wherein the C$_{1-6}$alkyl, phenyl, benzyl, heteroaryl and heterocycle are additionally substituted by 0, 1, 2 or 3 substituents selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$;

$R^{10}$ is H, $C_{1-3}$alkyl, $C_{1-3}$haloalkyl, cyano, nitro, CO$_2R^a$, C(=O)N$R^aR^a$, —C(=N$R^a$)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, S(=O)$R^b$, S(=O)$_2R^b$ or S(=O)$_2$N$R^aR^a$;

$R^{11}$ is H or $C_{1-4}$alkyl;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NHC$_{1-4}$alkyl, —N($C_{1-4}$ alkyl)$C_{1-4}$alkyl.

Another aspect of the invention relates to compounds having the structure:

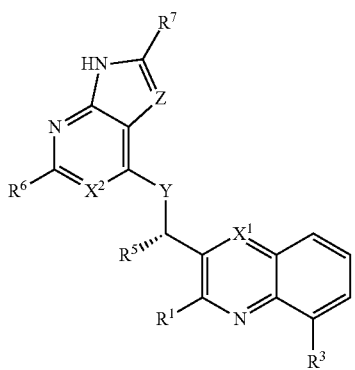

or any pharmaceutically-acceptable salt thereof, wherein:

$X^1$ is C($R^9$) or N;

$X^2$ is C($R^{10}$) or N;

Y is N($R^{11}$), O or S;

Z is CR$^8$ or N;

n is 0, 1, 2 or 3;

$R^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1$R^2$ substituents, and the ring is additionally substituted by 0, 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)$C_{1-4}$alkyl and $C_{1-4}$haloalkyl;

$R^2$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; or $R^2$ is selected from $C_{1-6}$alkyl, phenyl, benzyl, heteroaryl, heterocycle, —($C_{1-3}$alkyl)heteroaryl, —($C_{1-3}$alkyl)heterocycle, —O($C_{1-3}$ alkyl)heteroaryl, —O($C_{1-3}$alkyl)heterocycle, —N$R^a$($C_{1-3}$ alkyl)heteroaryl, —N$R^a$($C_{1-3}$ alkyl)heterocycle, —($C_{1-3}$alkyl)phenyl, —O($C_{1-3}$ alkyl)phenyl and —N$R^a$($C_{1-3}$ alkyl)phenyl all of which are substituted by 0, 1, 2 or 3 substituents selected from $C_{1-4}$haloalkyl, O$C_{1-4}$alkyl, Br, Cl, F, I and $C_{1-4}$alkyl;

$R^3$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, O$C_{1-6}$alkyl, Br, Cl, F, I and $C_{1-6}$alkyl;

$R^4$ is, independently, in each instance, halo, nitro, cyano, $C_{1-4}$alkyl, O$C_{1-4}$alkyl, O$C_{1-4}$haloalkyl, NH$C_{1-4}$alkyl, N($C_{1-4}$alkyl)$C_{1-4}$alkyl or $C_{1-4}$haloalkyl;

$R^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, O$C_{1-4}$alkyl, $C_{1-4}$alkyl, $C_{1-3}$haloalkyl, O$C_{1-4}$alkyl, NH$_2$, NH$C_{1-4}$alkyl, N($C_{1-4}$alkyl)$C_{1-4}$alkyl; or both $R^5$ groups together form a $C_{3-6}$spiroalkyl substituted by 0, 1, 2 or 3 substituents selected from halo, cyano, OH, O$C_{1-4}$alkyl, $C_{1-4}$alkyl, $C_{1-3}$haloalkyl, O$C_{1-4}$ alkyl, NH$_2$, NH$C_{1-4}$alkyl, N($C_{1-4}$alkyl)$C_{1-4}$alkyl;

$R^6$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^7$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^8$ is selected from H, $C_{1-6}$haloalkyl, Br, Cl, F, I, O$R^a$, N$R^aR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, O$C_{1-6}$alkyl, Br, Cl, F, I and $C_{1-6}$alkyl;

$R^9$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$ —N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkylN$R^a R^a$, —N$R^a$C$_{2-6}$alkylO$R^a$, C$_{1-6}$alkyl, phenyl, benzyl, heteroaryl and heterocycle, wherein the C$_{1-6}$alkyl, phenyl, benzyl, heteroaryl and heterocycle are additionally substituted by 0, 1, 2 or 3 substituents selected from halo, C$_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkylN$R^a R^a$, —N$R^a$C$_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, C$_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkylN$R^a R^a$ and —N$R^a$C$_{2-6}$alkylO$R^a$;

$R^{10}$ is H, C$_{1-3}$alkyl, C$_{1-3}$haloalkyl, cyano, nitro, CO$_2 R^a$, C(=O)N$R^a R^a$, —C(=N$R^a$)N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, S(=O)$R^b$, S(=O)$_2 R^b$ or S(=O)$_2$N$R^a R^a$;

$R^{11}$ is H or C$_{1-4}$alkyl;

$R^a$ is independently, at each instance, H or $R^b$; and $R^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl.

Another aspect of the invention relates to compounds having the structure:

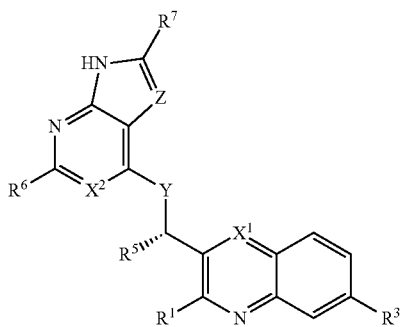

or any pharmaceutically-acceptable salt thereof, wherein:

$X^1$ is C($R^9$) or N;
$X^2$ is C($R^{10}$) or N;
Y is N($R^{11}$), O or S;
Z is C$R^8$ or N;
n is 0, 1, 2 or 3;

$R^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1$R^2$ substituents, and the ring is additionally substituted by 0, 1, 2 or 3 substituents independently selected from halo, nitro, cyano, C$_{1-4}$alkyl, OC$_{1-4}$alkyl, OC$_{1-4}$haloalkyl, NHC$_{1-4}$alkyl, N(C$_{1-4}$alkyl)C$_{1-4}$alkyl and C$_{1-4}$haloalkyl;

$R^2$ is selected from halo, C$_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkylN$R^a R^a$, —N$R^a$C$_{2-6}$alkylO$R^a$; or $R^2$ is selected from C$_{1-6}$alkyl, phenyl, benzyl, heteroaryl, heterocycle, —(C$_{1-3}$alkyl)heteroaryl, —(C$_{1-3}$alkyl)heterocycle, —O(C$_{1-3}$alkyl)heteroaryl, —O(C$_{1-3}$alkyl)heterocycle, —N$R^a$(C$_{1-3}$alkyl)heteroaryl, —N$R^a$(C$_{1-3}$alkyl)heterocycle, —(C$_{1-3}$ alkyl)phenyl, —O(C$_{1-3}$alkyl)phenyl and —N$R^a$(C$_{1-3}$alkyl)phenyl all of which are substituted by 0, 1, 2 or 3 substituents selected from C$_{1-4}$haloalkyl, OC$_{1-4}$alkyl, Br, Cl, F, I and C$_{1-4}$alkyl;

$R^3$ is selected from H, halo, C$_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkylN$R^a R^a$, —N$R^a$C$_{2-6}$alkylO$R^a$, C$_{1-6}$alkyl, phenyl, benzyl, heteroaryl and heterocycle, wherein the C$_{1-6}$alkyl, phenyl, benzyl, heteroaryl and heterocycle are additionally substituted by 0, 1, 2 or 3 substituents selected from C$_{1-6}$haloalkyl, OC$_{1-6}$alkyl, Br, Cl, F, I and C$_{1-6}$alkyl;

$R^4$ is, independently, in each instance, halo, nitro, cyano, C$_{1-4}$alkyl, OC$_{1-4}$alkyl, OC$_{1-4}$haloalkyl, NHC$_{1-4}$alkyl, N(C$_{1-4}$alkyl)C$_{1-4}$alkyl or C$_{1-4}$haloalkyl;

$R^5$ is, independently, in each instance, H, halo, C$_{1-6}$alkyl, C$_{1-4}$haloalkyl, or C$_{1-6}$alkyl substituted by 1, 2 or 3 substituents selected from halo, cyano, OH, OC$_{1-4}$alkyl, C$_{1-4}$alkyl, C$_{1-3}$haloalkyl, OC$_{1-4}$alkyl, NH$_2$, NHC$_{1-4}$alkyl, N(C$_{1-4}$alkyl)C$_{1-4}$alkyl; or both $R^5$ groups together form a C$_{3-6}$spiroalkyl substituted by 0, 1, 2 or 3 substituents selected from halo, cyano, OH, OC$_{1-4}$alkyl, C$_{1-4}$alkyl, C$_{1-3}$haloalkyl, OC$_{1-4}$alkyl, NH$_2$, NHC$_{1-4}$alkyl, N(C$_{1-4}$alkyl)C$_{1-4}$alkyl;

$R^6$ is selected from H, halo, C$_{1-6}$alkyl, C$_{1-4}$haloalkyl, cyano, nitro, —C(=O)$R^a$, —C(=O)O$R^a$, —C(=O)N$R^a R^a$, —C(=N$R^a$)N$R^a R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$;

$R^7$ is selected from H, halo, C$_{1-6}$alkyl, C$_{1-4}$haloalkyl, cyano, nitro, —C(=O)$R^a$, —C(=O)O$R^a$, —C(=O)N$R^a R^a$, —C(=N$R^a$)N$R^a R^a$, —S(=O)$R^a$, —S(=O)$_2 R^a$,

—S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ;

R⁸ is selected from H, $C_{1-6}$haloalkyl, Br, Cl, F, I, ORᵃ, NRᵃRᵃ, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;

R⁹ is selected from H, halo, $C_{1-4}$haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkylNRᵃRᵃ, —OC$_{2-6}$alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkylNRᵃRᵃ, —NRᵃC$_{2-6}$alkylORᵃ, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkylNRᵃRᵃ, —OC$_{2-6}$alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkylNRᵃRᵃ, —NRᵃC$_{2-6}$alkylORᵃ; or R⁹ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkylNRᵃRᵃ, —OC$_{2-6}$alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkylNRᵃRᵃ and —NRᵃC$_{2-6}$alkylORᵃ;

R¹⁰ is H, $C_{1-3}$alkyl, $C_{1-3}$haloalkyl, cyano, nitro, CO₂Rᵃ, C(=O)NRᵃRᵃ, —C(=NRᵃ)NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, S(=O)Rᵇ, S(=O)₂Rᵇ or S(=O)₂NRᵃRᵃ;

R¹¹ is H or $C_{1-4}$alkyl;

Rᵃ is independently, at each instance, H or Rᵇ; and

Rᵇ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH₂, —NHC$_{1-4}$alkyl, —N(C$_{1-4}$alkyl)C$_{1-4}$alkyl.

One aspect of the invention relates to compounds having the structure:

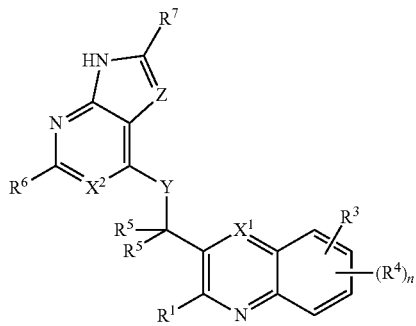

or any pharmaceutically-acceptable salt or hydrate thereof, wherein:

X¹ is C(R⁹) or N;
X² is C(R¹⁰) or N;
Y is N(R¹¹), O or S;
Z is CR⁸ or N;
n is 0, 1, 2 or 3;

R¹ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1R² substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl and $C_{1-4}$haloalkyl;

R² is selected from halo, $C_{1-4}$haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkylNRᵃRᵃ, —OC$_{2-6}$alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkylNRᵃRᵃ and —NRᵃC$_{2-6}$alkylORᵃ; or R² is selected from $C_{1-6}$alkyl, phenyl, benzyl, heteroaryl and heterocycle, all of which are substituted by 0, 1, 2 or 3 substituents selected from $C_{1-4}$haloalkyl, $OC_{1-4}$alkyl, Br, Cl, F, I and $C_{1-4}$alkyl;

R³ is selected from H, halo, $C_{1-4}$haloalkyl, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkylNRᵃRᵃ, —OC$_{2-6}$alkylORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkylNRᵃRᵃ, —NRᵃC$_{2-6}$alkylORᵃ, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;

R⁴ is, independently, in each instance, halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl or $C_{1-4}$haloalkyl;

R⁵ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}$alkyl)$C_{1-4}$alkyl; or both R5 groups together form a $C_{3-6}$spiroalkyl substituted by 0, 1, 2 or 3 substituents selected from halo, cyano, OH, $OC_{1-4}$alkyl, $C_{1-4}$ alkyl, $C_{1-3}$haloalkyl, $OC_{1-4}$ alkyl, $NH_2$, $NHC_{1-4}$alkyl, $N(C_{1-4}$alkyl)$C_{1-4}$alkyl;

$R^6$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^7$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$;

$R^8$ is selected from H, $C_{1-6}$haloalkyl, Br, Cl, F, I, O$R^a$, N$R^aR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;

$R^9$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$;

$R^{10}$ is H, $C_{1-3}$alkyl, $C_{1-3}$haloalkyl, cyano, nitro, $CO_2R^a$, C(=O)N$R^aR^a$, —C(=N$R^a$)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, S(=O)$R^b$, S(=O)$_2R^b$ or S(=O)$_2$N$R^aR^a$;

$R^{11}$ is H or $C_{1-4}$alkyl;

$R^a$ is independently, at each instance, H or $R^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$alkyl, —N(C$_{1-4}$alkyl)C$_{1-4}$alkyl.

In another embodiment, in conjunction with any of the above or below embodiments, $X^1$ is C($R^9$) and $X^2$ is N.

In another embodiment, in conjunction with any of the above or below embodiments, $X^1$ is C($R^9$) and $X^2$ is C($R^{10}$).

In another embodiment, in conjunction with any of the above or below embodiments, $R^1$ is phenyl substituted by 0 or 1$R^2$ substituents, and the phenyl is additionally substituted by 0, 1, 2 or 3 substituents independently selected from halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl and $C_{1-4}$haloalkyl.

In another embodiment, in conjunction with any of the above or below embodiments, $R^1$ is phenyl.

In another embodiment, in conjunction with any of the above or below embodiments, $R^1$ is phenyl substituted by $R^2$, and the phenyl is additionally substituted by 0, 1, 2 or 3 substituents independently selected from halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl and $C_{1-4}$haloalkyl.

In another embodiment, in conjunction with any of the above or below embodiments, $R^1$ is selected from 2-methylphenyl, 2-chlorophenyl, 2-trifluoromethylphenyl, 2-fluorophenyl and 2-methoxyphenyl.

In another embodiment, in conjunction with any of the above or below embodiments, $R^1$ is phenoxy.

In another embodiment, in conjunction with any of the above or below embodiments, $R^1$ is a direct-bonded or oxygen-linked saturated, partially-saturated or unsaturated 5-, 6- or 7-membered monocyclic ring containing 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1$R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl and $C_{1-4}$haloalkyl.

In another embodiment, in conjunction with any of the above or below embodiments, $R^1$ is an unsaturated 5- or 6-membered monocyclic ring containing 1, 2, 3 or 4 atoms selected from N, O and S, but containing no more than one O or S, wherein the ring is substituted by 0 or 1$R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl and $C_{1-4}$haloalkyl.

In another embodiment, in conjunction with any of the above or below embodiments, $R^1$ is an unsaturated 5- or 6-membered monocyclic ring containing 1, 2, 3 or 4 atoms selected from N, O and S, but containing no more than one O or S, wherein the ring is substituted by 0 or 1$R^2$ substituents, and the ring is additionally substituted by 1, 2 or 3 substituents independently selected from halo, nitro, cyano, $C_{1-4}$alkyl, $OC_{1-4}$alkyl, $OC_{1-4}$haloalkyl, NHC$_{1-4}$alkyl, N(C$_{1-4}$alkyl)C$_{1-4}$alkyl and $C_{1-4}$haloalkyl.

In another embodiment, in conjunction with any of the above or below embodiments, $R^1$ is an unsaturated 5- or 6-membered monocyclic ring containing 1, 2, 3 or 4 atoms selected from N, O and S.

In another embodiment, in conjunction with any of the above or below embodiments, $R^1$ is selected from pyridyl and pyrimidinyl.

In another embodiment, in conjunction with any of the above or below embodiments, $R^3$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, OC$_{1-6}$alkyl, Br, Cl, F, I and $C_{1-6}$alkyl.

In another embodiment, in conjunction with any of the above or below embodiments, $R^3$ is H.

In another embodiment, in conjunction with any of the above or below embodiments, $R^3$ is selected from F, Cl, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, OC$_{1-6}$alkyl, Br, Cl, F, I and $C_{1-6}$alkyl.

In another embodiment, in conjunction with any of the above or below embodiments, $R^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, OC$_{1-4}$alkyl, $C_{1-4}$alkyl, $C_{1-3}$haloalkyl, OC$_{1-4}$alkyl, NH$_2$, NHC$_{1-4}$alkyl, N(C$_{1-4}$alkyl)C$_{1-4}$alkyl; or both $R^5$ groups together form a $C_{3-6}$spiroalkyl substituted by 0, 1, 2 or 3 substituents selected from halo, cyano, OH, OC$_{1-4}$ alkyl, $C_{1-4}$alkyl, $C_{1-3}$haloalkyl, OC$_{1-4}$alkyl, NH$_2$, NHC$_{1-4}$ alkyl, N(C$_{1-4}$alkyl)C$_{1-4}$alkyl.

In another embodiment, in conjunction with any of the above or below embodiments, $R^5$ is H.

In another embodiment, in conjunction with any of the above or below embodiments, one $R^5$ is S-methyl, the other is H.

In another embodiment, in conjunction with any of the above or below embodiments, at least one $R^5$ is halo, $C_{1-6}$alkyl, $C_{1-4}$haloalkyl, or $C_{1-6}$alkyl substituted by 1, 2 or 3 substituents selected from halo, cyano, OH, OC$_{1-4}$alkyl, $C_{1-4}$alkyl, $C_{1-3}$haloalkyl, OC$_{1-4}$alkyl, NH$_2$, NHC$_{1-4}$alkyl, N(C$_{1-4}$alkyl)C$_{1-4}$alkyl.

In another embodiment, in conjunction with any of the above or below embodiments, $R^6$ is H.

In another embodiment, in conjunction with any of the above or below embodiments, $R^6$ is F, Cl, cyano or nitro.

In another embodiment, in conjunction with any of the above or below embodiments, $R^7$ is H.

In another embodiment, in conjunction with any of the above or below embodiments, $R^7$ is F, Cl, cyano or nitro.

In another embodiment, in conjunction with any of the above or below embodiments, $R^8$ is selected from H, CF$_3$, $C_{1-3}$alkyl, Br, Cl and F.

In another embodiment, in conjunction with any of the above or below embodiments, $R^8$ is selected from H.

In another embodiment, in conjunction with any of the above or below embodiments, $R^8$ is selected from CF$_3$, $C_{1-3}$alkyl, Br, Cl and F.

In another embodiment, in conjunction with any of the above or below embodiments, $R^9$ is H.

In another embodiment, in conjunction with any of the above or below embodiments, $R^9$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkylN$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$.

In another embodiment, in conjunction with any of the above or below embodiments, $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkyl-N$R^aR^a$, —OC$_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any of the above or below embodiments, $R^{10}$ is H.

In another embodiment, in conjunction with any of the above or below embodiments, $R^{10}$ is cyano, nitro, CO$_2R^a$, C(=O)N$R^aR^a$, —C(=N$R^a$)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, S(=O)$R^b$, S(=O)$_2R^b$ or S(=O)$_2$N$R^aR^a$.

In another embodiment, in conjunction with any of the above or below embodiments, $R^{11}$ is H.

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or auto-immune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and auto-immune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha-\beta}$alkyl" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of $C_{1-6}$alkyl include, but are not limited to the following:

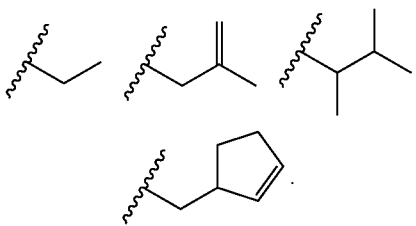

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

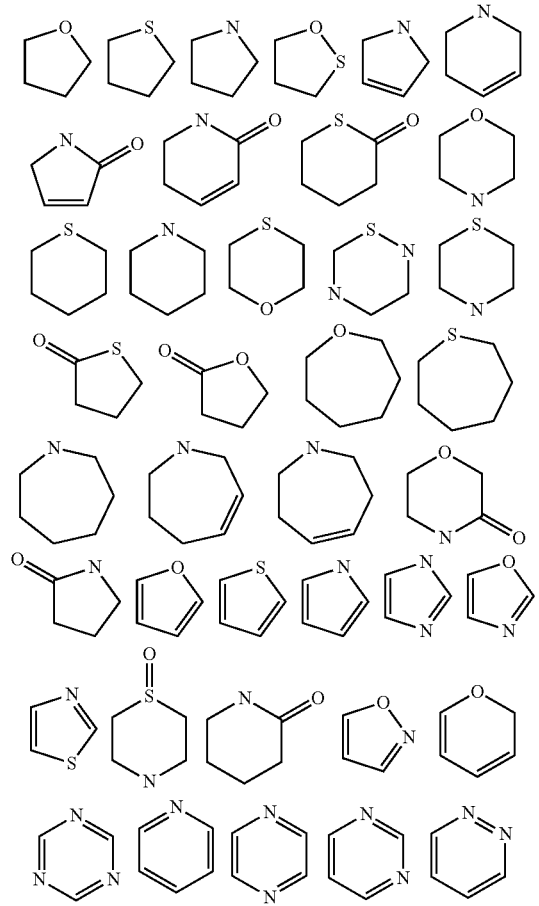

-continued

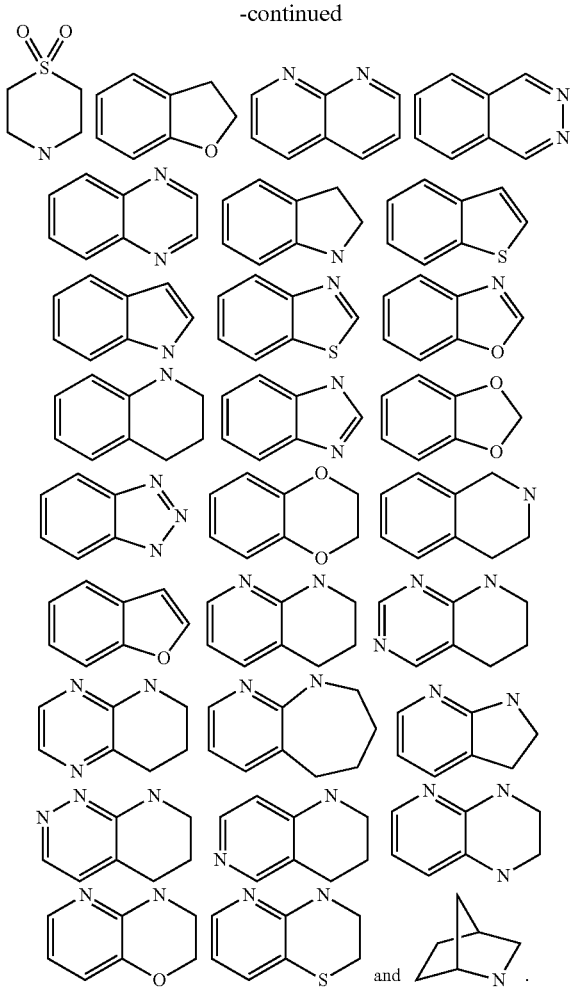

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

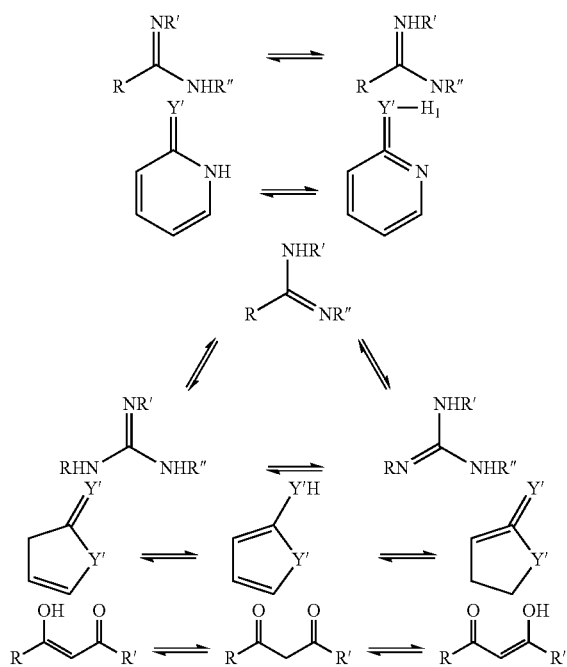

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

The following abbreviations are used:
aq.—aqueous
BINAP—2,2'-bis(diphenylphosphino)-1,1'-binaphthyl
cond—concentrated
DCM DCM
DMF—DMF
$Et_2O$—diethyl ether
EtOAc—ethyl acetate
EtOH—ethyl alcohol
h—hour(s)
min—minutes
MeOH—methyl alcohol
rt room temperature
satd—saturated
THF—tetrahydrofuran

GENERAL

Reagents and solvents used below can be obtained from commercial sources. $^1$H-NMR spectra were recorded on a Bruker 400 MHz and 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Mass spectrometry results are reported as the ratio of mass over charge, followed by the relative abundance of each ion (in parentheses Electrospray ionization (ESI) mass spectrometry analysis was conducted on a Agilent 1100 series LC/MSD electrospray mass spectrometer. All compounds could be analyzed in the positive ESI mode using acetonitrile:water with 0.1% formic acid as the delivery solvent. Reverse phase analytical HPLC was carried out using a Agilent 1200 series on Agilent Eclipse XDB-C18 5 μm column (4.6×150 mm) as the stationary phase and eluting with acetonitrile:$H_2O$ with 0.1% TFA. Reverse phase Semi-Prep HPLC was carried out using a Agilent 1100 Series on a Phenomenex Gemini™ 10 μm C18 column (250×21.20 mm) as the stationary phase and eluting with acetonitrile:$H_2O$ with 0.1% TFA.

Procedure A

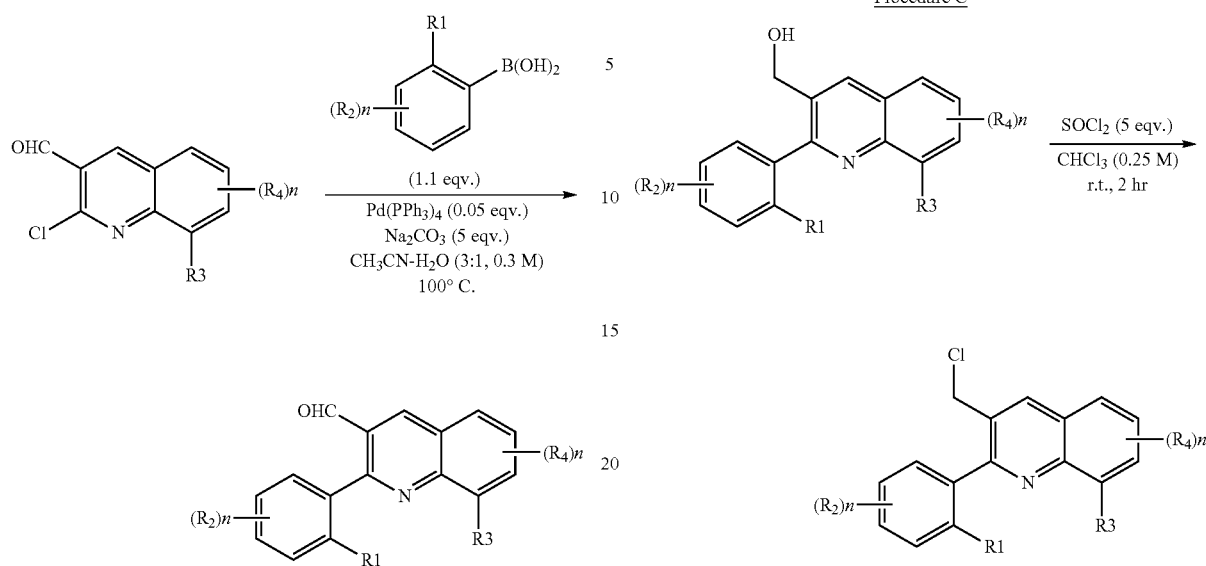

A mixture of 2-chloro-quinoline-3-carbaldehyde (1 eq), arylboronic acid (1.1 eq), tetrakis(triphenylphosphine)palladium (5 mol %), and sodium carbonate (2M aq. Sol., 5.0 eq) in $CH_3CN$-water (3:1, 0.1 M) was heated at 100° C. under $N_2$ for several hours. The mixture was partitioned between EtOAc and $H_2O$, the organic layer was separated, and the aqueous layer was extracted with EtOAc. The combined organic layers were dried over $Na_2SO_4$, filtered, concentrated under reduced pressure, and purified by column chromatography on silica gel using 0% to 25% gradient of EtOAc in hexane to provide 2-arylquinoline-3-carbaldehydes.

Procedure B

Solid sodium borohydride (1.5 eq) was added to a solution of 2-arylquinoline-3-carbaldehyde (1 eq) in THF (0.5M) at 0° C. and the mixture was stirred at 0° C. for 2 h. The reaction was quenched by addition of water. The aqueous layer was extracted with EtOAc (3 times). The combined organic layers were dried over $Na_2SO_4$, filtered, and concentrated under reduced pressure. The residue was purified by column chromatography on silica gel using 50% of EtOAc in hexane to provide (2-arylquinolin-3-yl)methanols.

Procedure C

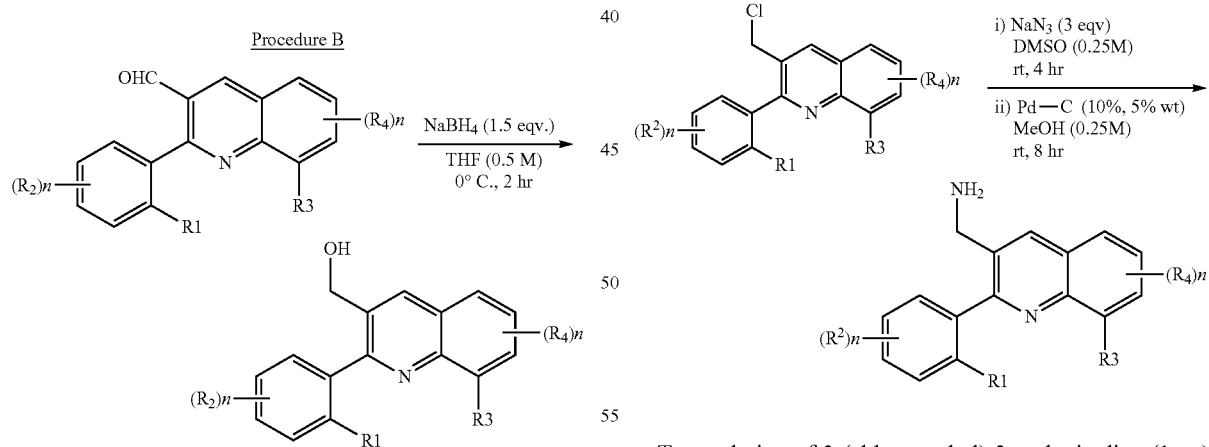

(2-Arylquinolin-3-yl)methanol (1 eq) in $CHCl_3$ (0.25M) was treated with $SOCl_2$ (5 eq) at rt for 2 h. Solvents were removed under reduced pressure and the residue was partitioned between EtOAc and saturated aq. $NaHCO_3$ solution. The organic layer was separated, washed with water and brine, dried over $Na_2SO_4$, filtered, and concentrated under reduced pressure. The crude product was purified by column chromatography on a Redi-Sep™ column using 0 to 100% gradient of EtOAc in hexane to provide 3-(chloromethyl)-2-arylquinolines.

Procedure D

To a solution of 3-(chloromethyl)-2-arylquinoline (1 eq) in DMSO (0.25 M) was added $NaN_3$ (3 eq) at rt and the mixture was stirred for 4 h at rt. The mixture was diluted with water, extracted with EtOAc (2 times) and the combined organic layers were washed with water (2 times), dried over $Na_2SO_4$, filtered, and concentrated under reduced pressure. The residue was dissolved in MeOH and treated with 10% Pd—C (5 wt %) and the mixture was then stirred under $H_2$ balloon over night. The mixture was filtered through a Celite™ pad followed by removal of solvents to give (2-arylquinolin-3-yl)methanamines.

Procedure E

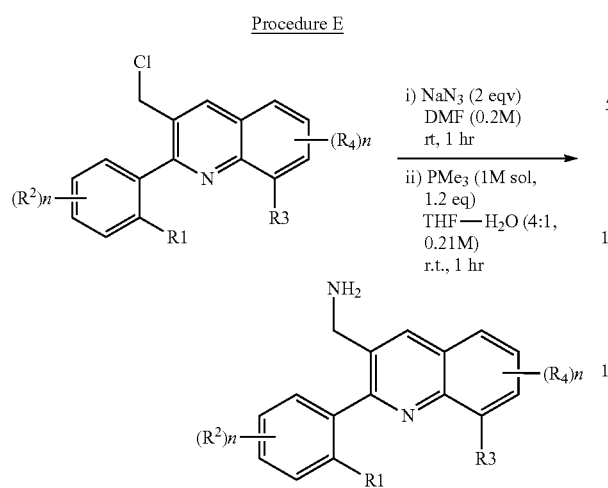

To a stirring solution of 3-(chloromethyl)-2-arylquinoline (1 eq) in 16 mL of DMF was added NaN$_3$ (2 eq) at rt. The mixture was stirred at rt for 1 h. The mixture was partitioned between EtOAc and H$_2$O. The organic layer was dried over MgSO$_4$, filtered, and concentrated under reduced pressure to provide 3-(azidomethyl)-2-arylquinolines. The crude product was carried on without purification for the next step. To a stirring solution of 3-(azidomethyl)-2-arylquinoline in THF—H$_2$O (4:1, 0.21 M) was added dropwise PMe$_3$ (1.0 M solution in THF, 1.2 eq) at rt and the mixture was stirred at rt for 1 h. To the mixture was added EtOAc and the mixture was extracted with 1N HCl (2 times). The combined extracts were neutralized with solid sodium bicarbonate, and extracted with EtOAc (2 times). The combined organic extracts were dried over MgSO$_4$, filtered, and concentrated under reduced pressure to give dark syrup. The crude product was purified by column chromatography on a Redi-Sep™ column using 0 to 100% gradient of CH$_2$Cl$_2$:MeOH:NH$_4$OH (89:9:1) in CH$_2$Cl$_2$ as eluent to provide (2-arylquinolin-3-yl)methanamines

Procedure F

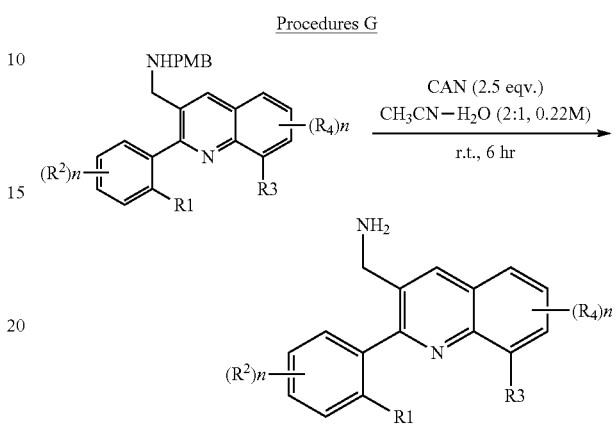

A mixture of 2-arylquinoline-3-carbaldehyde (1 eq), DCE (0.2 M), and PMBNH$_2$ (1.5 eq) was stirred at rt. After 1 h, to the mixture was added NaBH(OAc)$_3$ (3 eq) and the mixture was stirred at 50° C. for 2 h. To the mixture was added saturated aq. NaHCO$_3$ and the mixture was stirred for 15 min. The organic layer was separated and the aqueous layer was extracted with CH$_2$Cl$_2$ (2 times). The combined organic layers were washed with brine, dried over MgSO$_4$, filtered, and concentrated under reduced pressure. The residue was purified by column chromatography on a Redi-Sep™ column using 0 to 100% gradient of EtOAc in hexane to provide N-(4-methoxybenzyl)(2-arylquinolin-3-yl)methanamines

Procedures G

A mixture of N-(4-methoxybenzyl)(2-arylquinolin-3-yl)methanamine (1 eq) and ammonium cerium(iv) nitrate (3.5 eq) in CH$_3$CN—H$_2$O (2:1, 0.22M) was stirred at rt for 24 h. To the mixture wad added 0.5M HCl (12 eq) and the mixture was washed with CH$_2$Cl$_2$ (3 times) to remove 4-methoxybenzaldehyde produced. The organic fraction was then extracted with 0.5M HCl (2 times). The combined acidic aqueous layer was basified to pH 9.0 with 2N HaOH. The resulting precipitate was collected by filtration. The crude product was purified by column chromatography on a Redi-Sep™ column using 0 to 100% gradient of CH$_2$Cl$_2$:MeOH:NH$_4$OH (89:9:1) in CH$_2$Cl$_2$ as eluent to provide (2-arylquinolin-3-yl)methanamines

Procedures H

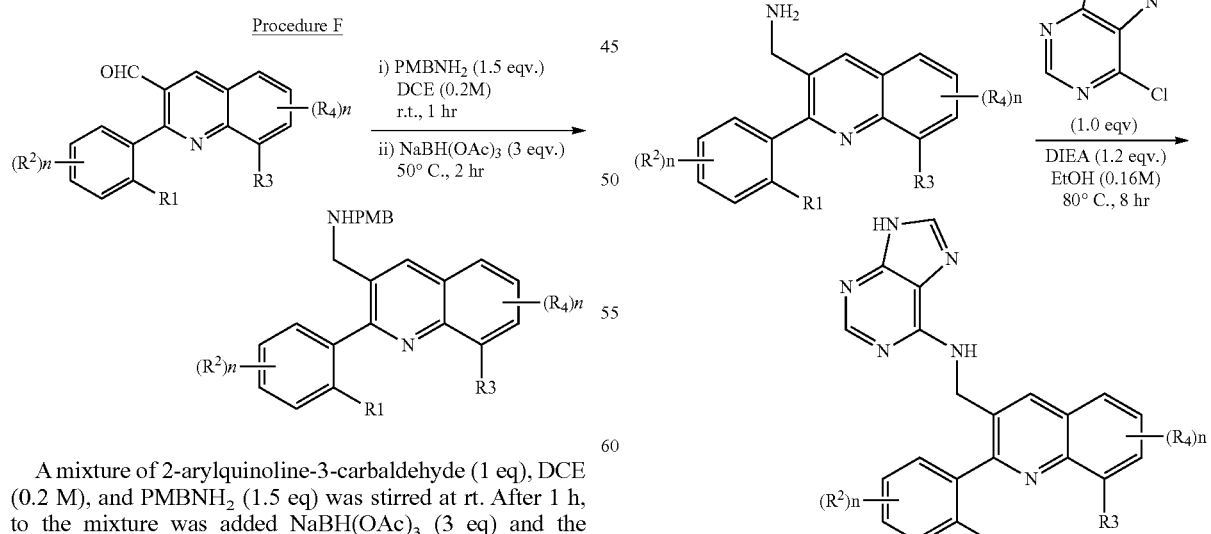

A mixture (2-arylquinolin-3-yl)methanamine (1 eq) in EtOH (0.16 M) was treated with iPr$_2$NEt (1.2 eq) followed with 6-chloropurine (1 eq) at 80° C. for 8 h. The reaction mixture was concentrated and purified by column chromatography on a Redi-Sep™ column using 0 to 100% gradient of CH$_2$Cl$_2$:MeOH:NH$_4$OH (89:9:1) in CH$_2$Cl$_2$ as eluent to provide N-((2-arylquinolin-3-yl)methyl)-9H-purin-6-amines.

Procedure K

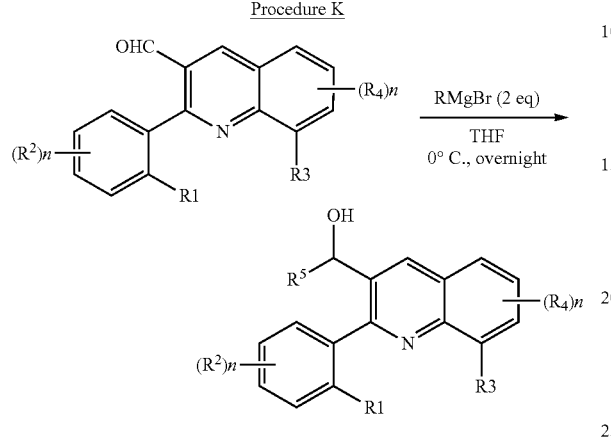

To a mixture of 2-phenylquinoline-3-carbaldehyde (1.0 eq) in THF (0.28M) at 0° C. was added dropwise a solution of a Grignard reagent (3 M, 2 eq) and the reaction was stirred overnight before being quenched with NH$_4$Cl saturated solution. The mixture was extracted with EtOAc (2×10 mL) and the combined organic layers were dried (Na$_2$SO$_4$) and concentrated under reduced pressure. The residue was purified by column chromatography on silica gel (eluent: EtOAc/hexane, 1/1) to provide 1-(2-phenylquinolin-3-yl) alcohols.

Procedure L

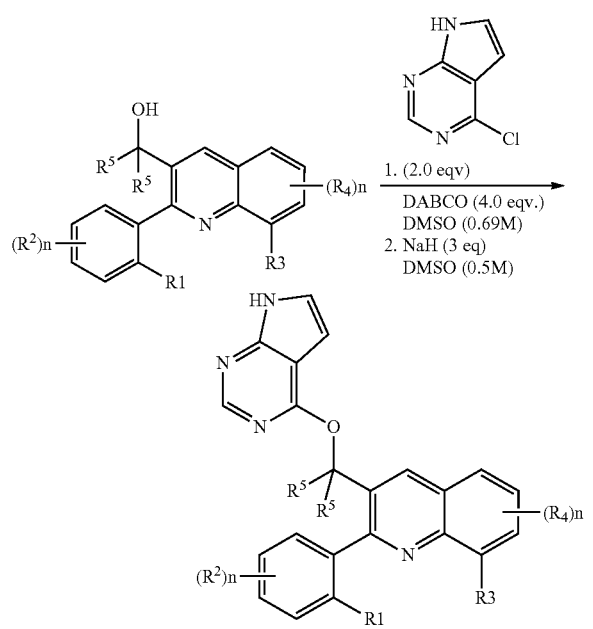

A mixture of 4-chloro-7H-pyrrolo[2,3-d]pyrimidine (2.0 eq) and 1,4-diazabicyclo[2.2.2]octane (4.0 eq) in anhydrous DMSO (0.69M) was stirred at rt for 5 h and then added via cannula to a mixture of 1-(2-phenylquinolin-3-yl) alcohol (1 eq) and sodium hydride, 60% dispersion in mineral oil (3 eq) in DMSO (0.5M) that had been stirred for 30 min at rt and 30 min at 50° C. prior to the addition. The mixture was stirred at rt for 6 h before addition of water, and the mixture was extracted with EtOAc (4×). The combined organic layers were washed with water, brine, dried (MgSO$_4$) and concentrated under reduced pressure. The residue was purified by column chromatography on silica gel (eluent: CH$_2$Cl$_2$/MeOH, 50/1) to provide the desired product.

Example 1: Preparation of N-((8-Methyl-2-o-tolylquinolin-3-yl)methyl)-9H-purin-6-amine 8-Methyl-2-o-tolylquinoline-3-carbaldehyde

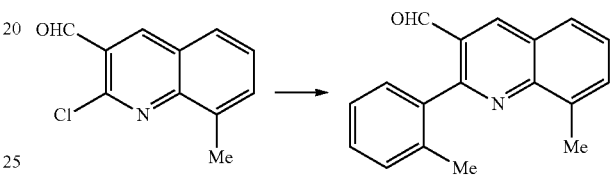

Prepared according to Procedure A using 2-chloro-8-methylquinoline-3-carbaldehyde (2.1 g, 10 mmol), o-tolyl-boronic acid (1.5 g, 1.1 eq), tetrakis(triphenyl-phosphine)palladium (575 mg, 0.05 eq), and sodium carbonate (5.5 g, 5 eq) in MeCN (75 mL) and water (25 mL). After purification, 8-methyl-2-o-tolylquinoline-3-carbaldehyde was obtained as white solid. $^1$H-NMR (CDCl$_3$) 9.96 (s, 1H), 8.83 (s, 1H), 7.88 (d, J=7.8 Hz, 1H), 7.74 (d, J=6.3 Hz, 1H), 7.55 (t, J=7.8 Hz, 1H), 7.36-7.46 (m, 4H), 2.84 (s, 3H), δ 2.30 (s, 3H). Mass Spectrum (ESI) m/e=262 (M+1).

(8-Methyl-2-o-tolylquinolin-3-yl)methanol

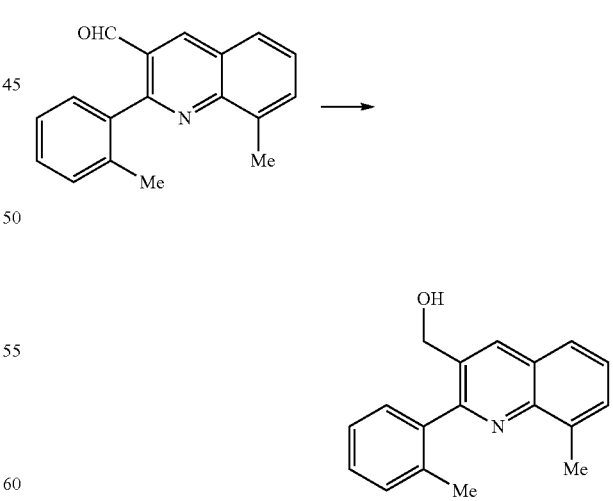

Prepared according to Procedure B using 8-methyl-2-o-tolylquinoline-3-carbaldehyde (1.28 g, 4.9 mmol) and solid NaBH$_4$ (278 mg, 1.5 eq) in THF (10 mL). After purification, (8-methyl-2-o-tolylquinolin-3-yl) methanol was obtained as white solid.

3-(Chloromethyl)-8-methyl-2-o-tolylquinoline

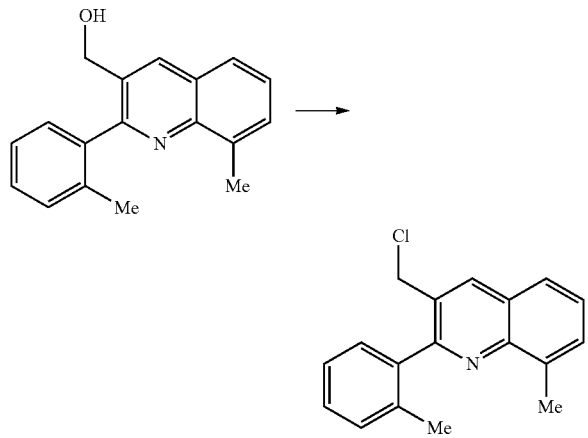

Prepared according to Procedure C using (8-methyl-2-o-tolylquinolin-3-yl)-methanol (670 mg, 2.5 mmol) and SOCl$_2$ (0.91 mL, 5 eq) in CHCl$_3$ (10 mL). After isolation, the resultant oil was carried on crude without purification for the next step.

(8-Methyl-2-o-tolylquinolin-3-yl)methanamine

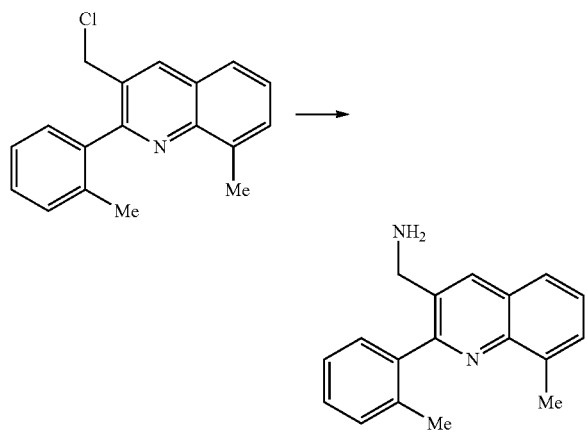

Prepared according to Procedure D using 3-(chloromethyl)-8-methyl-2-o-tolylquinoline (667 mg, 2.4 mmol) in DMSO (10 mL) was added NaN$_3$ (500 mg, 3 eq). After purification, (8-methyl-2-o-tolylquinolin-3-yl)methanamine was obtained as pale yellow oil.

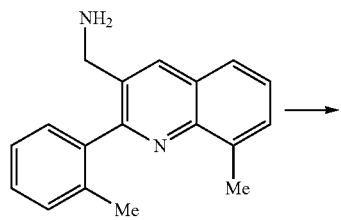

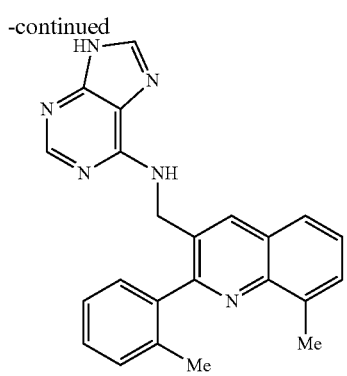

Prepared according to procedure H. A mixture of (8-methyl-2-o-tolylquinolin-3-yl)methanamine (80 mg, 0.31 mmol) in EtOH (2 mL) was treated with iPr$_2$NEt (65 µL, 1.2 eq) followed with 6-chloropurine (46.4 mg, 0.3 mmol) at 80° C. for 8 h. The reaction mixture was concentrated and purified by column chromatography on silica gel (eluent: DCM/MeOH, 25/1) to provide a white solid [PI3Kδ IC$_{50}$=84 nM]. $^1$H-NMR (DMSO-d$^6$) δ 8.24 (s, 1H), 8.19 (s, br, 1H), 8.15 (s, 1H), 7.81 (d, J=8.0 Hz, 1H), 7.63 (d, J=7.1 Hz, 1H), 7.50 (t, J=7.4 Hz, 1H), 7.39-7.42 (m, 4H), 4.62 (s, br, 2H), 2.66 (s, 3H), 2.16 (s, 3H). Mass Spectrum (ESI) m/e=381 (M+1).

Example 2: Preparation of N-((8-Chloro-2-(2-chlorophenyl)quinolin-3-yl)-methyl)-9H-purin-6-amine

2,8-Dichloroquinoline-3-carbaldehyde

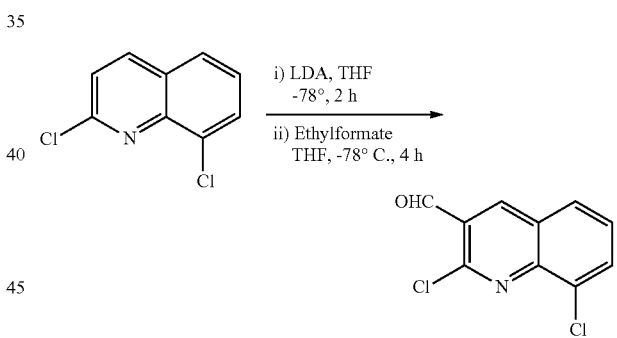

A solution of LDA (14.8 mL 1.5M in cyclohexene, 22.2 mmol, 1.1 eq) in THF (30 mL) was stirred at −78° C. as a solution of 2,8-dichloroquinoline (4.0 g, 20.2 mmol) in THF (15 mL) was added dropwise. The mixture stirred for two hours, at which time a solution of ethylformate (6.5 mL, 80.8 mmol, 4 eq) in THF (10 mL) was added slowly, and the mixture continued to stir at −78° C. for four hours. Wet THF (1 mL H$_2$O in 5 mL THF) was added to quench the reaction and it was warmed to room temperature. After partitioning between Et$_2$O and water, the aqueous layer was further extracted with Et$_2$O, and the combined organic layers were dried over MgSO$_4$, filtered and condensed under reduced pressure. The residue was chromatographed on a silica column using a 0-50% gradient of EtOAc in hexane. 2,3-Dichloroquinoline-3-carbaldehyde was obtained as a yellow solid. 1H NMR (400 MHz, DMSO-d$_6$) δ ppm 10.25 (1H, s), 8.93 (1H, s), 8.14 (1H, d, J=8.6 Hz), 8.03 (1H, d, J=9.0 Hz), 7.55-7.64 (1H, t, J=8.0 Hz) Mass Spectrum (ESI) m/e=226.0 and 227.9 (M+1)

8-Chloro-2-(2-chlorophenyl)quinoline-3-carbaldehyde

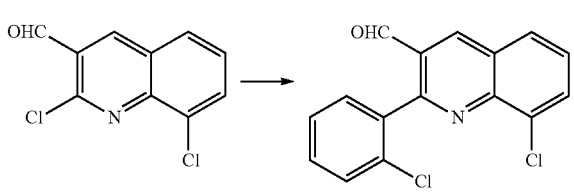 [SMILES: O=Cc1cc2cccc(Cl)c2nc1Cl ; O=Cc1cc2cccc(Cl)c2nc1-c1ccccc1Cl]

Prepared according to Procedure A using 2,8-dichloroquinoline 3-carbaldehyde (1.70 g, 7.5 mmol), 2-chlorophenyl boronic acid (1.29 g, 8.25 mmol, 1.1 eq), tetrakis(triphenylphosphine)palladium (0.430 g, 0.375 mmol, 0.05 eq), and sodium carbonate (3.97 g, 37.5 mmol, 5 eq) in acetonitrile (57 mL) and water (19 mL). After purification, 8-chloro-2-(2-chlorophenyl)quinoline-3-carbaldehyde was obtained as a yellow solid. 1H NMR (400 MHz, DMSO-$d_6$) δ ppm 10.25 (1H, s), 8.93 (1H, s), 8.14 (1H, d, J=8.6 Hz), 8.03 (1H, d, J=9.0 Hz), 7.55-7.64 (1H, t, J=8.0 Hz) Mass Spectrum (ESI) m/e=302.0 and 304.0 (M+1)

(8-Chloro-2-(2-chlorophenyl)quinolin-3-yl)methanol

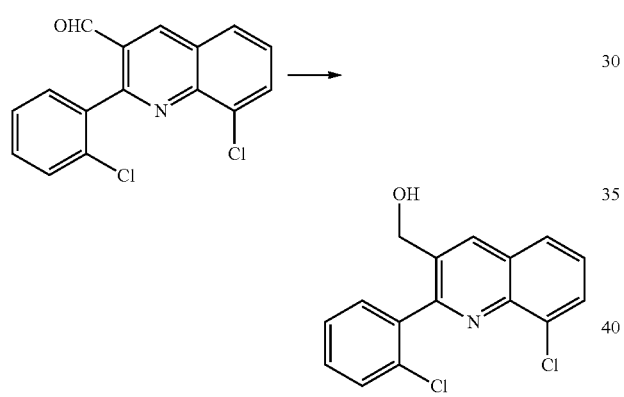

Prepared according to Procedure B using 2-(2-chlorophenyl)-8-chloroquinoline-3-carbaldehyde (1.18 g, 3.9 mmol), and sodium borohydride (0.222 g, 5.86 mmol, 1.5 eq) in THF (20 mL). (2-(2-chlorophenyl)-8-chloroquinolin-3-yl)methanol was obtained as a yellow solid. 1H NMR (400 MHz, DMSO-$d_6$) δ ppm 8.56 (1H, s), 8.10 (1H, dd, J=8.2, 1.2 Hz), 7.94 (1H, dd, J=7.6, 1.4 Hz), 7.63 (2H, t, J=7.8 Hz), 7.44-7.59 (3H, m), 5.54 (1H, t, J=5.3 Hz) Mass Spectrum (ESI) m/e=304.0 and 306.1 (M+1)

8-Chloro-3-(chloromethyl)-2-(2-chlorophenyl)quinoline

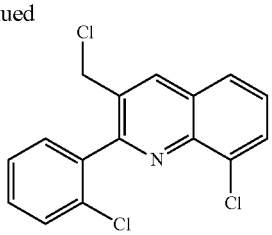

Prepared according to Procedure C using (2-(2-chlorophenyl)-8-chloroquinolin-3-yl)methanol (0.675 g, 2.22 mmol) and SOCl$_2$ (0.81 mL). 8-Chloro-3-(chloromethyl)-2-(2-chlorophenyl)quinoline was obtained as a yellow foam. 1H NMR (400 MHz, DMSO-$d_6$) δ ppm 8.53 (1H, s), 7.88 (1H, dd, J=8.2, 1.2 Hz), 7.81 (1H, dd, J=7.4, 1.2 Hz), 7.48 (1H, d, J=7.4 Hz), 7.42-7.46 (1H, m), 7.27-7.41 (3H, m), 4.63 (1H, d, J=9.8 Hz), 4.33-4.45 (1H, m) Mass Spectrum (ESI) m/e=322.0 and 324.0 (M+1)

(8-Chloro-2-(2-chlorophenyl)quinolin-3-yl)methanamine

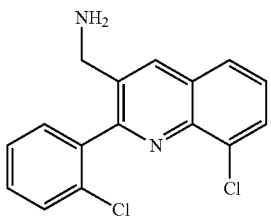

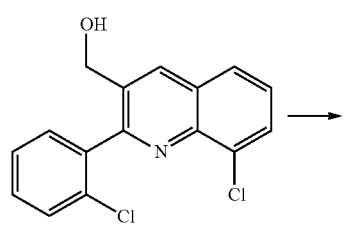

Prepared according to Procedure E using 8-chloro-3-(chloromethyl)-2-(2-chloro-phenyl)quinoline (0.685 g, 2.12 mmol) and sodium azide (1.10 g, 17 mmol, 8 eq) in DMF (10 mL). The resulting intermediate was submitted to trimethyl phosphine (1.0M) in THF (2.5 mL, 2.5 mmol, 1.2 eq) in THF (8 mL) and water (2 mL). (8-Chloro-2-(2-chlorophenyl)quinolin-3-yl)methanamine was obtained as a light yellow solid. 1H NMR (400 MHz, DMSO-$d_6$) δ ppm 8.62 (1H, s), 8.05 (1H, dd, J=8.6, 1.2 Hz), 8.00 (1H, dd, J=7.4, 1.2 Hz), 7.63-7.73 (2H, m), 7.47-7.62 (3H, m), 3.90 (1H, s), 3.75 (1H, s) Mass Spectrum (ESI) m/e=303.1 and 305.0 (M+1)

N-((8-Chloro-2-(2-chlorophenyl)quinolin-3-yl)methyl)-9H-purin-6-amine

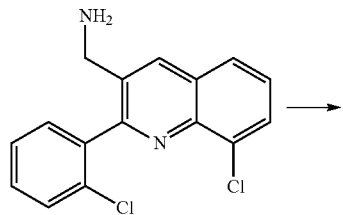

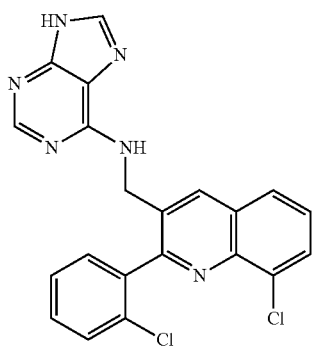

Prepared according to Procedure H using (8-chloro-2-(2-chlorophenyl)quinolin-3-yl)methanamine (0.100 g, 0.33 mmol), 6-chloropurine (0.051 g, 0.33 mmol, 1 eq) and DIEA (0.07 mL, 0.4 mmol, 1.2 eq) in ethanol (3 mL). N-((8-chloro-2-(2-chlorophenyl)quinolin-3-yl)methyl)-9H-purin-6-amine [PI3Kδ IC$_{50}$=68 nM] was obtained after purification as a white solid. 1H NMR (400 MHz, DMSO-d$_6$) δ ppm 8.37 (1H, s), 8.11 (1H, s), 8.08 (1H, s), 8.00 (1H, dd, J=8.2, 1.2 Hz), 7.93 (1H, dd, J=7.4, 1.2 Hz), 7.42-7.67 (5H, m) Mass Spectrum (ESI) m/e=421.0 and 423.1 (M+1)

Example 3: Preparation of 2-Chloro-N-((8-chloro-2-(2-chlorophenyl)-quinolin-3-yl)methyl)-9H-purin-6-amine

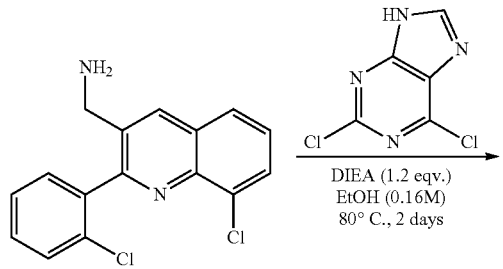

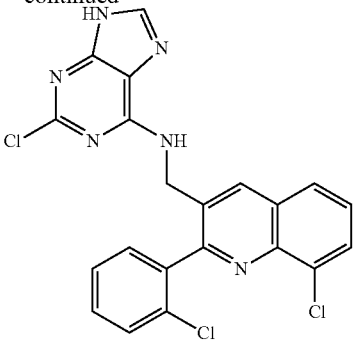

Prepared according to Procedure H using (8-chloro-2-(2-chlorophenyl)quinolin-3-yl)methanamine (0.100 g, 0.33 mmol), 2,6-dichloropurine (0.062 g, 0.33 mmol, 1 eq) and DIEA (0.07 mL, 0.4 mmol, 1.2 eq) in ethanol (5 mL). 2-Chloro-N-((8-chloro-2-(2-chlorophenyl)quinolin-3-yl)methyl)-9H-purin-6-amine [PI3Kδ IC$_{50}$=615 nM] was obtained after purification as a white solid. 1H NMR (500 MHz, DMSO-d$_6$) δ ppm 8.44 (1H, s), 8.15 (1H, s), 8.04 (1H, dd, J=8.5, 1.2 Hz), 7.96 (1H, d, J=6.7 Hz), 7.60 (1H, d, J=7.3 Hz), 7.61 (1H, t, J=7.9 Hz), 7.54 (1H, d, J=6.7 Hz), 7.50 (1H, t, J=6.7 Hz), 7.44 (1H, t, J=7.3 Hz), 4.62 (2H, d, J=26.9 Hz) Mass Spectrum (ESI) m/e=455.0 and 457.0 (M+1)

Example 4: Preparation of N-((8-chloro-2-(2-chlorophenyl)quinolin-3-yl)-methyl)-2-methoxy-7H-pyrrolo[2,3-d]pyrimidin-4-amine

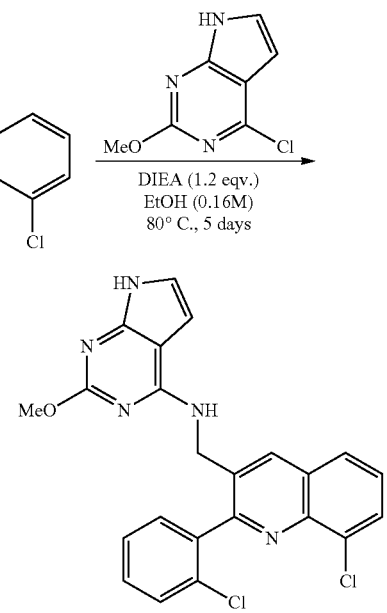

Prepared according to Procedure H using (8-chloro-2-(2-chlorophenyl)quinolin-3-yl)methanamine (0.100 g, 0.33 mmol), 4-chloro-2-methoxy-pyrrolo[2,3-d]pyrimidine (0.061 g, 0.33 mmol, 1 eq) and DIEA (0.07 mL, 0.4 mmol, 1.2 eq) in ethanol (3 mL). N-((8-Chloro-2-(2-chlorophenyl)quinolin-3-yl)methyl)-2-methoxy-7H-pyrrolo[2,3-d]pyrimidin-4-amine [PI3Kδ IC$_{50}$=5420 nM] was obtained after purification as a tan solid. 1H NMR (400 MHz, DMSO-d$_6$)

δ ppm 11.28 (1H, s), 8.37 (1H, s), 8.03 (1H, dd, J=8.4, 1.0 Hz), 7.94-7.99 (1H, m), 7.94 (1H, dd, J=7.6, 1.4 Hz), 7.40-7.65 (5H, m), 6.88 (1H, dd, J=3.3, 2.2 Hz), 6.47 (1H, s), 4.59 (2H, s), 3.67 (3H, s) Mass Spectrum (ESI) m/e=450.1 and 452.0 (M+1)

Example 5: Preparation of 3-(1-(9H-Purin-6-yloxy) ethyl)-8-methyl-2-o-tolylquinoline 1-(8-Methyl-2-o-tolylquinolin-3-yl)ethanol

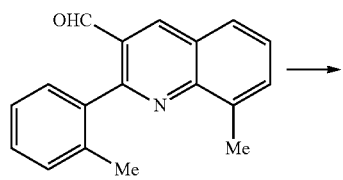

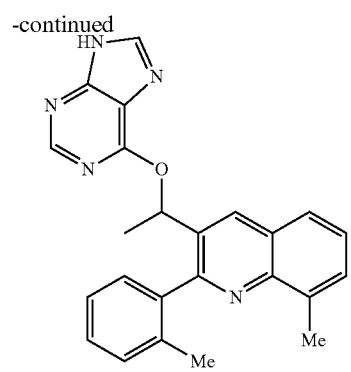

Prepared according to procedure K using 1-(8-methyl-2-o-tolylquinolin-3-yl)-ethanol, 3-(1-(9H-purin-6-yloxy) ethyl)-8-methyl-2-o-tolylquinoline [PI3Kδ IC$_{50}$=12 nM] was prepared. $^1$H-NMR (DMSO-d$^6$) δ 13.3 (s, 1H), 8.60 (s, br, 1H), 8.36 (s, br, 1H), 7.88 (d, J=7.9 Hz, 1H), 7.62 (d, J=6.6 Hz, 1H), 7.50 (t, J=7.2 Hz, 1H), 7.02-7.21 (m, 4H), 6.28-6.41 (m, 1H), 2.65 (s, 3H), 2.10 (s, 3H), 1.74 (s, br, 3H, major), 1.62 (s, br, 3H, minor). Mass Spectrum (ESI) m/e=396 (M+1).

Example 6: Preparation of N-(1-(2-(2-chlorophenyl)-8-methylquinolin-3-yl)-ethyl)-9H-purin-6-amine

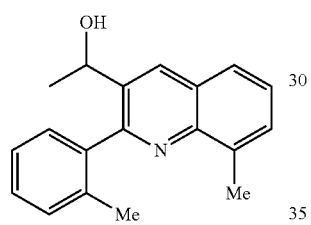

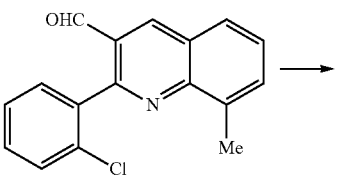

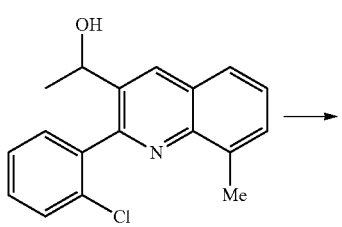

Prepared according to Procedure K. To a mixture of 8-methyl-2-o-tolylquinoline-3-carbaldehyde (434 mg, 1.7 mmol) in THF (6 mL) at 0° C. was added dropwise a solution of MeMgCl (3M, 2 eq, 1.1 mL) and the reaction was stirred over night before quenched with NH$_4$Cl saturated solution. The mixture was extracted with EtOAc (2×10 mL) and the combined organic layers were dried (Na$_2$SO$_4$) and concentrated under reduced pressure. The residue was purified by column chromatography on silica gel (eluent: EtOAc/hexane, 1/1) to provide 1-(8-methyl-2-o-tolylquinolin-3-yl) ethanol as a white solid. $^1$H-NMR (CDCl$_3$) δ 8.34 (s, 1H), 7.66 (d, J=8.2 Hz, 1H), 7.48 (d, J=6.7 Hz, 1H), 7.39 (t, J=7.8 Hz, 1H), 7.19-7.27 (m, 4H), 2.69 (s, 3H), 2.08 (s, 3H), 1.30 (m, 3H). Mass Spectrum (ESI) m/e=278 (M+1).

3-(1-(9H-Purin-6-yloxy)ethyl)-8-methyl-2-o-tolylquinoline

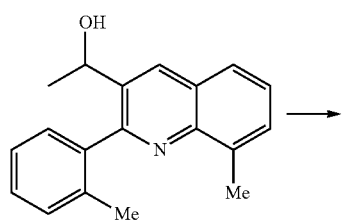

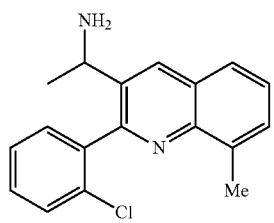

Prepared by procedure K, C and E: 1-(2-(2-Chlorophenyl)-8-methylquinolin-3-yl)ethanamine $^1$H-NMR (CDCl$_3$) δ 8.47 (s, major, 1H), 8.38 (s, minor, 1H), 7.40-7.74 (m, 7H), 4.19-4.21 (m, 1H), 2.78 (s, 3H), 1.49 (d, J=6.3 Hz, minor, 3H), 1.22 (d, J=6.7 Hz, major, 3H). Mass Spectrum (ESI) m/e=297 (M+1).

N-(1-(2-(2-Chlorophenyl)-8-methylquinolin-3-yl)ethyl)-9H-purin-6-amine

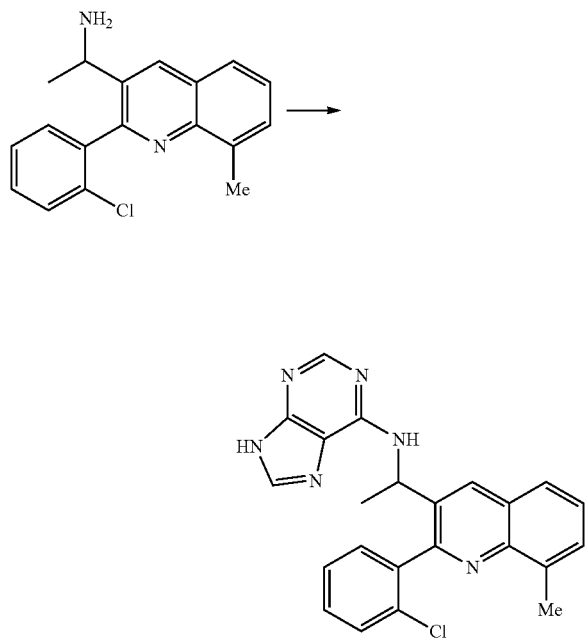

Prepared according to procedure H [PI3Kδ IC$_{50}$=31 nM]. $^1$H-NMR (DMSO-d$^6$) δ 10.21-10.32 (m, 1H), 8.40-8.78 (m, 2H), 7.88 (d, J=7.4 Hz, 1H), 7.65 (d, J=6.6 Hz, 1H), 7.19-7.56 (m, 6H), 5.46-5.58 (m, 1H), 2.63 (s, 3H), 1.66 (d, J=6.6 Hz, 3H). Mass Spectrum (ESI) m/e=415 (M+1).

Example 7: Preparation of 3-((9H-Purin-6-yloxy)methyl)-2-(2-methoxyphenyl)-8-methylquinoline 2-(2-Methoxyphenyl)-8-methylquinoline-3-carbaldehyde

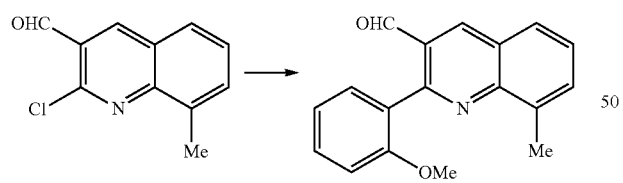

Prepared according to Procedure A using 2-chloro-8-methylquinoline 3-carbaldehyde (0.206 g, 1 mmol), 2-methoxyphenyl boronic acid (0.167 g, 1.1 mmol, 1.1 eq), tetrakis(triphenylphosphine)palladium (0.058 g, 0.05 mmol, 0.05 eq), and sodium carbonate (0.530 g, 5 mmol, 5 eq) in acetonitrile (7.5 mL) and water (2.5 mL). After purification, 2-(2-methoxyphenyl)-8-methylquinoline-3-carbaldehyde (0.250 g, 90%) was obtained as a white solid. 1H NMR (500 MHz, DMSO-d$_6$) δ ppm 9.86 (1H, s), 8.88 (1H, s), 8.13 (1H, d, J=8.1 Hz), 7.85 (1H, d, J=7.1 Hz), 7.56-7.74 (3H, m), 7.22-7.30 (2H, m), 3.78 (3H, s), 2.80 (3H, s) Mass Spectrum (ESI) m/e=278.0 (M+1)

(2-(2-Methoxyphenyl)-8-methylquinolin-3-yl)methanol

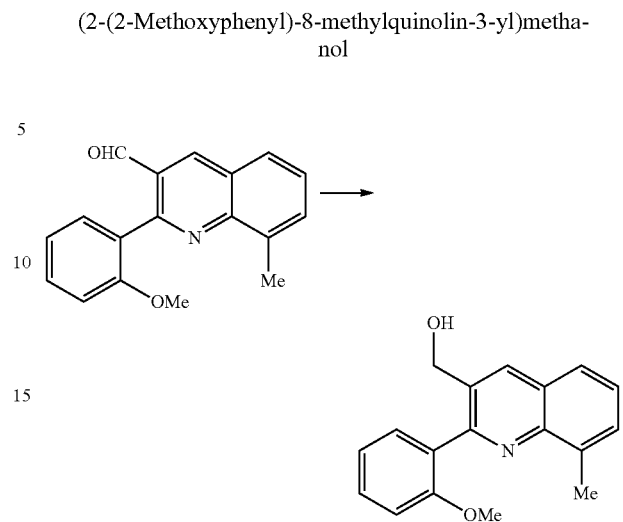

Prepared according to Procedure B using 2-(2-methoxyphenyl)-8-methylquinoline-3-carbaldehyde (0.250 g, 0.9 mmol), and sodium borohydride (0.0378 g, 1.35 mmol, 1.5 eq), in THF (5 mL). (2-(2-Methoxyphenyl)-8-methylquinolin-3-yl)-methanol was obtained as a white solid. 1H NMR (400 MHz, DMSO-d$_6$) δ ppm 8.41 (1H, s), 7.92 (1H, d, J=7.8 Hz), 7.64 (1H, d, J=7.0 Hz), 7.50-7.59 (2H, m), 7.33 (1H, dd, J=7.4, 1.6 Hz), 7.22 (1H, d, J=7.8 Hz), 7.16 (1H, t, J=7.2 Hz), 5.37 (1H, t, J=5.5 Hz), 3.79 (3H, s), 2.72 (3H, s) Mass Spectrum (ESI) m/e=280.1 (M+1)

3-((9H-Purin-6-yloxy)methyl)-2-(2-methoxyphenyl)-8-methylquinoline

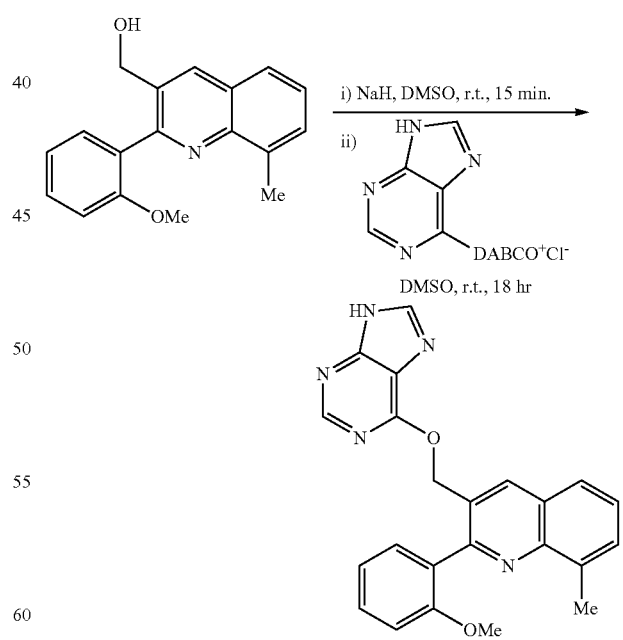

Prepared according to modified Procedure L. 6-Chloropurine (0.077 g, 0.5 mmol, 2 eq) and DABCO (0.112 g, 1 mmol, 4 eq) were stirred in DMSO (0.7 mL) at room temperature for 5 h. In a separate flask, sodium hydride (0.040 g, 1 mmol, 4 eq) was added portion-wise to a stirring solution of (2-(2-methoxyphenyl)-8-methylquinolin-3-yl)methanol (0.070 g, 0.25 mmol) in DMSO (0.5 mL), and after 30 minutes, the purine-DABCO salt was added to this mixture. The reaction stirred at room temperature 18 h. 3-((9H-purin-6-yloxy)methyl)-2-(2-methoxyphenyl)-8-methylquinoline [PI3Kδ IC$_{50}$=38 nM] was isolated as a white solid after purification on a silica column. 1H NMR (400 MHz, DMSO-d$_6$) δ ppm 13.41 (1H, s), 8.51 (1H, s), 8.39 (1H, s), 7.87 (1H, d, J=7.8 Hz), 7.65 (1H, d, J=7.0 Hz), 7.49-7.56 (1H, m), 7.34-7.46 (2H, m), 7.12 (1H, d, J=8.2 Hz), 7.03 (1H, t, J=7.2 Hz), 5.58 (2H, s), 3.72 (3H, s), 2.69 (3H, s) Mass Spectrum (ESI) m/e=398.2 (M+1)

Example 8: Preparation of 3-((9H-Purin-6-yloxy)methyl)-2-(biphenyl)-8-methylquinoline 2-(Biphenyl)-8-methylquinoline-3-carbaldehyde

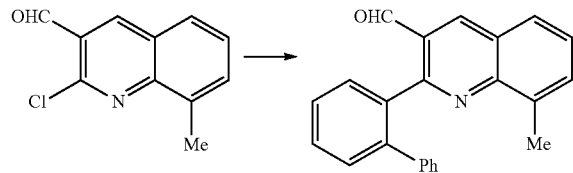 [SMILES: Cc1cccc2cc(C=O)c(Cl)nc12 ; Cc1cccc2cc(C=O)c(-c3ccccc3-c3ccccc3)nc12]

Prepared according to Procedure A using 2-chloro-8-methylquinoline 3-carbaldehyde (0.206 g, 1 mmol), 2-phenylbenzene boronic acid (0.218 g, 1.1 mmol, 1.1 eq), tetrakis(triphenylphosphine)palladium (0.058 g, 0.05 mmol, 0.05 eq), and sodium carbonate (0.530 g, 5 mmol, 5 eq) in acetonitrile (7.5 mL) and water (2.5 mL). After purification, 2-(2-biphenyl)-8-methylquinoline-3-carbaldehyde (0.312 g, 97%) was obtained as a white solid. 1H NMR (500 MHz, DMSO-d$_6$) δ ppm 9.71 (1H, s), 8.66 (1H, s), 8.01 (1H, d, J=8.1 Hz), 7.79 (1H, d, J=6.8 Hz), 7.65-7.72 (2H, m), 7.53-7.65 (3H, m), 7.11-7.19 (3H, m), 7.00-7.09 (2H, m), 2.66 (3H, s) Mass Spectrum (ESI) m/e=324.1 (M+1)

(2-(Biphenyl)-8-methylquinolin-3-yl)methanol

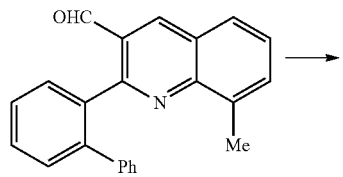

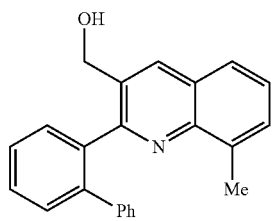

Prepared according to Procedure B using 2-(biphenyl)-8-methylquinoline-3-carbaldehyde (0.312 g, 0.96 mmo), and sodium borohydride (0.055 g, 1.44 mmol, 1.5 eq) in THF (5 mL). (2-(Biphenyl)-8-methylquinolin-3-yl)methanol was obtained as a white solid. 1H NMR (400 MHz, DMSO-d$_6$) δ ppm 8.19 (1H, s), 7.77 (1H, d, J=7.8 Hz), 7.55-7.62 (1H, m), 7.48-7.55 (3H, m), 7.44 (2H, d, J=8.2 Hz), 7.11 (5H, s), 5.24 (1H, t, J=5.3 Hz), 2.57 (3H, s) Mass Spectrum (ESI) m/e=326.2 (M+1)

3-((9H-Purin-6-yloxy)methyl)-2-(biphenyl)-8-methylquinoline

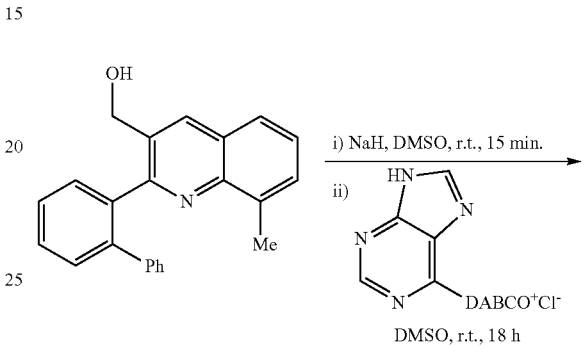

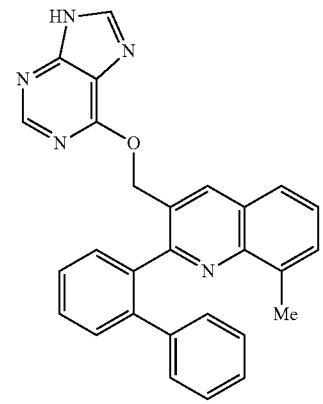

Prepared according to modified Procedure L: 6-Chloropurine (0.077 g, 0.5 mmol, 2 eq) and DABCO (0.112 g, 1 mmol, 4 eq) were stirred in DMSO (0.7 mL) at room temperature for 5 h. In a separate flask, sodium hydride (0.040 g, 1 mmol, 4 eq) was added portion-wise to a stirring solution of (2-(biphenyl)-8-methylquinolin-3-yl)methanol (0.081 g, 0.25 mmol) in DMSO (0.5 mL), and after 30 minutes, the purine-DABCO salt was added to this mixture. The reaction stirred at room temperature 18 h. 3-((9H-Purin-6-yloxy)methyl)-2-(biphenyl)-8-methylquinoline [PI3Kδ IC$_{50}$=22 nM] was isolated as a white solid after purification on a silica column. 1H NMR (400 MHz, DMSO-d$_6$) δ ppm 13.39 (1H, s), 8.37 (2H, d, J=9.8 Hz), 7.77 (1H, d, J=7.8 Hz), 7.54-7.63 (2H, m), 7.37-7.54 (4H, m), 7.14-7.21 (2H, m), 7.07-7.14 (3H, m), 5.51 (1H, d, J=12.5 Hz), 5.29 (1H, d, J=9.4 Hz), 2.54 (3H, s) Mass Spectrum (ESI) m/e=444.2 (M+1)

Example 9: Preparation of 3-(1-(7H-Pyrrolo[2,3-d]pyrimidin-4-yloxy)but-3-enyl)-2-(2-chlorophenyl)-8-methylquinoline 1-(2-(2-Chlorophenyl)-8-methylquinolin-3-yl)but-3-en-1-ol

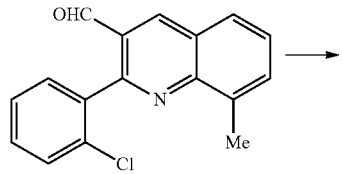

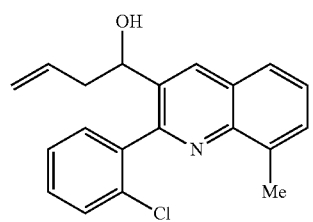

Prepared according to procedure K: To a solution of 2-(2-chlorophenyl)-8-methylquinoline-3-carbaldehyde (1.4 g, 5 mmol) in THF (20 mL) at 0° C. under N₂ was added dropwise a solution of allylmagenisiumbromide (1M, 1.1 eq, 5.5 mL) in THF and the mixture was stirred at 0° C. for 2 h. The mixture was partitioned between EtOAc (50 mL) and H₂O (30 mL), the layers were separated, and the aqueous layer was extracted with EtOAc (2×30 mL). The combined organic layers were dried (Na₂SO₄), concentrated and purified by flash chromatography (0% to 25% EtOAc/hexane) to provide 1-(2-(2-chlorophenyl)-8-methylquinolin-3-yl)but-3-en-1-ol as a colorless oil. ¹H-NMR (CDCl₃) δ 8.45 (s, major, 1H), 8.40 (s, minor, 1H), 7.77 (d, J=7.9 Hz, 1H), 7.43-7.60 (m, 6H), 5.56-5.73 (m, 1H), 4.96-5.17 (m, 2H), 4.80-4.84 (m, 1H), 2.80 (s, 3H), 2.34-2.59 (m, 2H). Mass Spectrum (ESI) m/e=324 (M+1).

3-(1-(7H-Pyrrolo[2,3-d]pyrimidin-4-yloxy)but-3-enyl)-2-(2-chlorophenyl)-8-methylquinoline

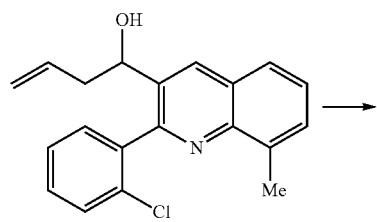

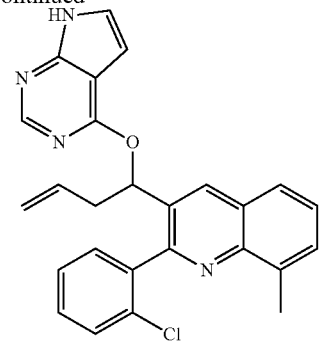

Prepared according to procedure L. A mixture of 4-chloro-7H-pyrrolo[2,3-d]pyrimidine (474 mg, 3.1 mmol) and 1,4-diazabicyclo[2.2.2]octane (694 mg, 6.2 mmol) in anhydrous DMSO (4.5 mL) was stirred at rt for 5 h and then added via cannula to a mixture of 1-(2-(2-chlorophenyl)-8-methylquinolin-3-yl)but-3-en-1-ol (500 mg, 1.5 mmol) and sodium hydride, 60% dispersion in mineral oil (180 mg, 4.5 mmol) in DMSO (3 mL) that had been stirred for 30 min at rt and 30 min at 50° C. prior to the addition. The mixture was stirred at rt for 6 h before addition of water (10 mL), and the mixture was extracted with EtOAc (4×20 mL). The combined organic layers were washed with water, brine, dried (MgSO₄) and concentrated under reduced pressure. The residue was purified by column chromatography on silica gel (eluent: DCM/MeOH, 50/1) to provide 3-(1-(7H-pyrrolo[2,3-d]pyrimidin-4-yloxy)but-3-enyl)-2-(2-chlorophenyl)-8-methylquinoline [PI3Kδ IC₅₀=28 nM] as a white solid. ¹H-NMR (CDCl₃) δ 10.20 (s, br, 1H), 8.22 (d, J=7.5 Hz, 1H), 7.15-7.64 (m, 8H), 6.59-6.62 (m, 1H), 6.34-6.37 (m, 1H), 5.64-5.79 (m, 1H), 4.93-5.01 (m, 2H), 2.74 (t, J=8.7 Hz, 2H), 2.70 (s, 3H). Mass Spectrum (ESI) m/e=441 (M+1).

Example 10: 3-((9H-Purin-6-yloxy)methyl)-2-(2-chlorophenyl)-8-methylquinoline

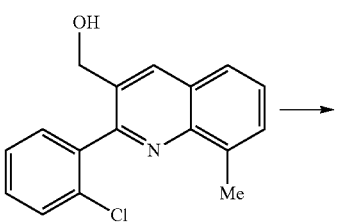

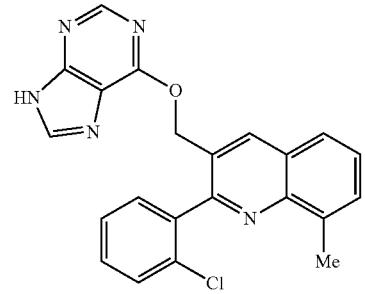

Prepared according to procedure L A mixture of 6-chloropurine (75 mg, 0.49 mmol) and 1,4-diazabicyclo[2.2.2]octane (109 mg, 0.97 mmol) in DMSO (0.5 mL) was stirred at rt for 5 h and was then added via cannula to a mixture of (2-(2-chlorophenyl)-8-methylquinolin-3-yl)methanol (69 mg, 0.24 mmol) and sodium hydride, 60% dispersion in mineral oil (39 mg, 0.97 mmol) in DMSO (0.5 mL) that had been stirred at rt for 15 min prior to the addition. The mixture was stirred at rt for 3.5 h, cooled to 0° C., and H$_2$O (5 mL) was added carefully. The mixture was extracted with EtOAc (3×10 mL), and the combined organic layers were dried (MgSO$_4$) and concentrated under reduced pressure. The resulting yellow oil was dissolved in CH$_2$Cl$_2$, evaporated onto silica gel (deactivated with 2M NH$_3$ in MeOH), and purified by flash chromatography (Biotage® Si 25+M) eluting with 2M NH$_3$ in MeOH/CH$_2$Cl$_2$ (5%) to provide a white solid [PI3Kδ IC$_{50}$=25 nM]. MS (ESI+) m/z=402.0 (M+1).

Example 11: 3-((9H-Purin-6-yloxy)methyl)-8-methyl-2-o-tolylquinoline

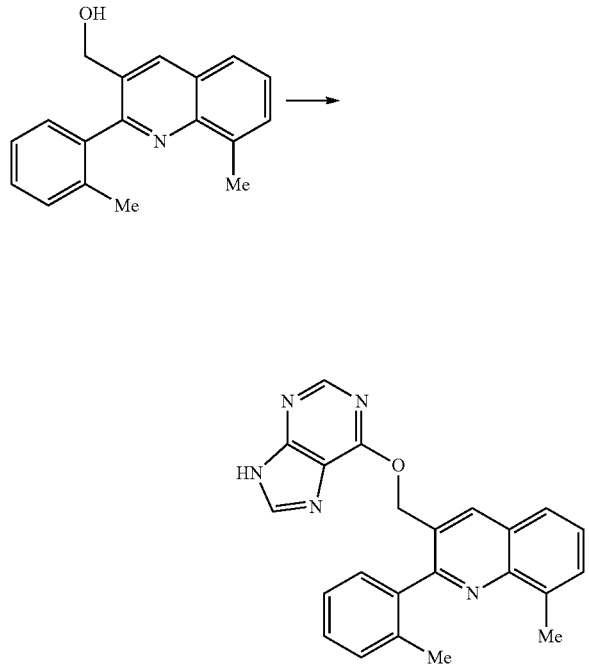

Prepared according to procedure L A mixture of 6-chloropurine (110 mg, 0.71 mmol) and 1,4-diazabicyclo[2.2.2]octane (160 mg, 1.43 mmol) in DMSO (0.7 mL) was stirred at rt for 4 h and was then added via cannula to a mixture of (8-methyl-2-o-tolylquinolin-3-yl)methanol (94 mg, 0.36 mmol) and sodium hydride, 60% dispersion in mineral oil (57 mg, 1.43 mmol) in DMSO (1 mL) that had been stirred at rt for 15 min prior to the addition. The mixture was stirred at rt for 3.5 h, neutralized by the addition of glacial acetic acid, diluted with brine (15 mL), and extracted with EtOAc (3×15 mL). The combined organic layers were dried (MgSO$_4$) and concentrated under reduced pressure. The resulting yellow oil was dissolved in CH$_2$Cl$_2$, evaporated onto silica gel (deactivated with 2M NH$_3$ in MeOH), and purified by flash chromatography (Biotage® Si 25+M) eluting with 2 M NH$_3$ in MeOH/CH$_2$Cl$_2$ (5%) to provide a white solid [PI3Kδ IC$_{50}$=27 nM]. MS (APCI+) m/z=282.3 (M+1).

Example 12: 3-((9H-Purin-6-ylthio)methyl)-8-methyl-2-o-tolylquinoline

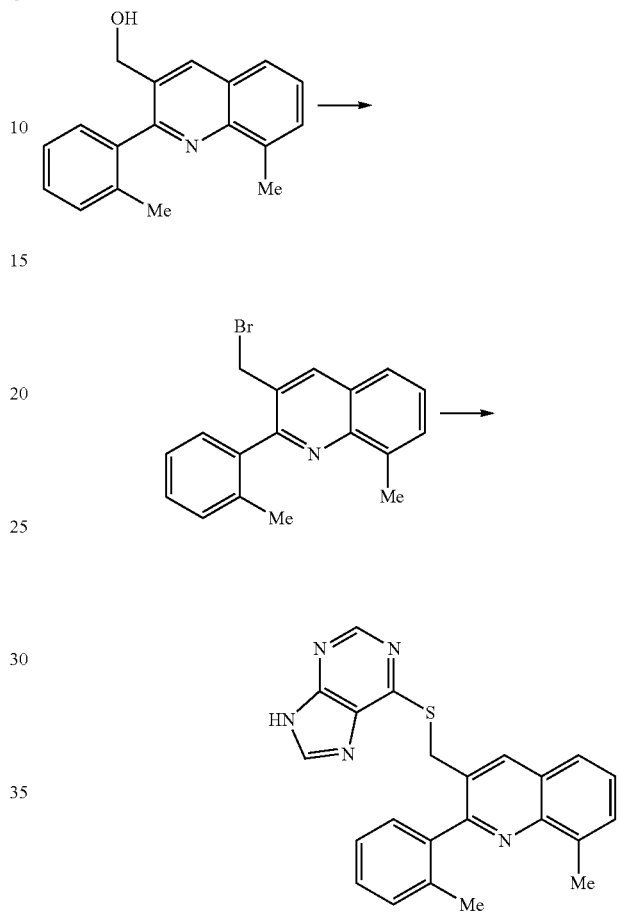

Solid carbontetrabromide (429 mg, 1.29 mmol) was added to a mixture of (8-methyl-2-o-tolylquinolin-3-yl)methanol (227 mg, 0.86 mmol) and triphenyl-phosphine (339 mg, 1.29 mmol) in CH$_2$Cl$_2$ (5 mL) at 0° C., and the mixture was stirred at 0° C. for 0.5 h. The crude mixture was concentrated under reduced pressure, evaporated onto silica gel, and purified by flash chromatography (Biotage® Si 25+M) eluting with EtOAc/hexane (0% to 10%) to provide an off-white solid; used without further purification, MS (ESI+) m/z=326.0 (M). A 2.0M aqueous solution of sodium hydroxide (0.86 mL, 1.72 mmol) was added to a mixture of 3-(bromomethyl)-8-methyl-2-o-tolylquinoline (140 mg, 0.43 mmol) and 6-mercaptopurine monohydrate (146 mg, 0.86 mmol) in THF (1.6 mL), and the biphasic mixture was heated under reflux for 5 h. The reaction mixture was cooled to 0° C., neutralized by the addition of 1N aqueous HCl, diluted with brine (10 mL), and extracted with THF (3×15 mL). The combined organic layers were dried (MgSO$_4$) and concentrated under reduced pressure. The resulting yellow solid was dissolved in THF/DMSO, evaporated onto silica gel, and purified by flash chromatography (Biotage® Si 25+M) eluting with acetone/hexane (20% to 50%). The resulting off-white solid was recrystallized from THF/MeOH to provide a white solid [PI3Kδ IC$_{50}$=889 nM]. MS (ESI+) m/z=398.1 (M+1).

Example 13: N6-((8-Methyl-2-o-tolylquinolin-3-yl)methyl)-9H-purine-2,6-diamine

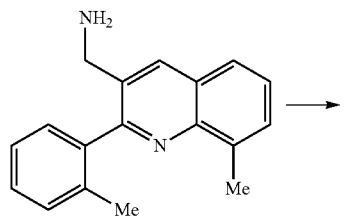

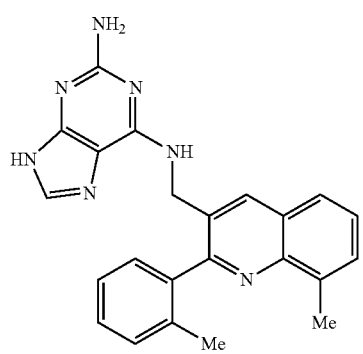

A mixture of (8-methyl-2-o-tolylquinolin-3-yl)methanamine (40 mg, 0.15 mmol), 2-amino-6-chloropurine (52 mg, 0.30 mmol), and triethylamine (42 μL, 0.30 mmol) in i-PrOH (0.8 mL) was heated in a microwave reactor at 150° C. four times for 20 min. The mixture was partitioned between saturated aqueous NaHCO$_3$ (15 mL) and EtOAc (15 mL), the layers were separated, and the aqueous layer was extracted with EtOAc (2×15 mL). The combined organic layers were dried (MgSO$_4$) and concentrated under reduced pressure. The resulting yellow oil was dissolved in CH$_2$Cl$_2$, evaporated onto silica gel, and purified by flash chromatography (Biotage® Si 25+M) eluting with MeOH/CH$_2$Cl$_2$ (5% to 10%) to provide a white solid. The compound was further purified by reversed-phase HPLC (Gilson) eluting with H$_2$O/MeCN/TFA to provide a white solid [PI3Kδ IC$_{50}$=82 nM]. MS (ESI+) m/z=396.2 (M+1).

Example 14: Preparation of 3-(1-(7H-Pyrrolo[2,3-d]pyrimidin-4-yloxy)but-3-enyl)-2-(2-chlorophenyl)-8-methylquinoline

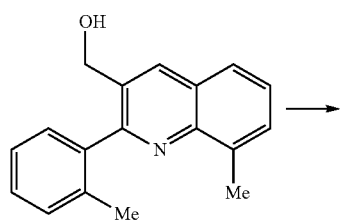

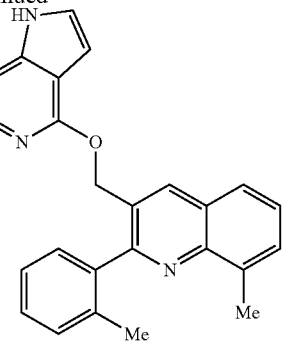

Prepared according to procedure L [PI3Kδ IC$_{50}$=56 nM]. $^1$H-NMR (DMSO-d$^6$) δ 12.0 (s, 1H), 8.60 (s, 1H), 8.26 (s, 1H), 7.90 (d, J=7.9 Hz, 1H), 7.66 (d, J=7.0 Hz, 1H), 7.54 (t, J=7.4 Hz, 1H), 7.22-7.37 (m, 5H), 6.50 (d, J=2.1 Hz, 1H), 5.45 (s, 2H), 2.68 (s, 3H), 2.11 (s, 3H). Mass Spectrum (ESI) m/e=381 (M+1).

Example 15: Preparation of 3-47H-Pyrrolo[2,3-d]pyrimidin-4-yloxy)methyl)-8-methyl-2-phenylquinoline (8-Methyl-2-phenylquinolin-3-yl)methanol

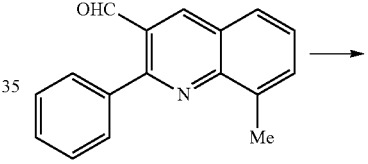

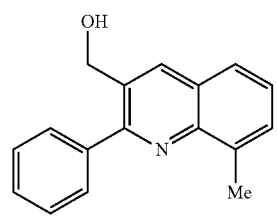

Prepared according to procedures A and B. $^1$H-NMR (DMSO-d6) δ 8.45 (s, 1H), 7.86-7.88 (d, 1H), 7.71-7.72 (m, 2H), 7.61-7.62 (d, 1H), 7.49-7.53 (m, 4H), 5.47-5.48 (t, 1H), 4.64-4.65 (d, J=5 Hz, 2H), 2.72 (s, 3H). Mass Spectrum (ESI) m/e=250 (M+1).

3-((7H-Pyrrolo[2,3-d]pyrimidin-4-yloxy)methyl)-8-methyl-2-phenylquinoline

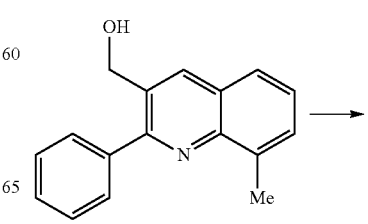

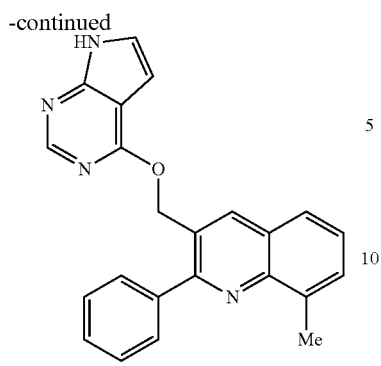

Prepared according to procedure L [PI3Kδ IC$_{50}$=68 nM]. $^1$H-NMR (DMSO-d$^6$)-δ 8.65 (s, 1H), 8.32 (s, 1H), 7.89-7.01 (d, 1H), 7.74-7.75 (m, 2H), 7.67-7.68 (d, 1H), 7.47-7.55 (m, 5H), 7.37-7.38 (d, J=5 Hz, 1H), 6.53-6.54 (d, J=5 Hz, 1H), 5.70 (s, 2H), 2.74 (s, 3H). Mass Spectrum (ESI) m/e=367 (M+1).

Example 16: Preparation of N-((8-Methyl-2-(2-(trifluoromethyl)phenyl)-quinolin-3-yl)methyl)-9H-purin-6-amine 8-Methyl-2-(2-(trifluoromethyl)phenyl)quinoline-3-carbaldehyde

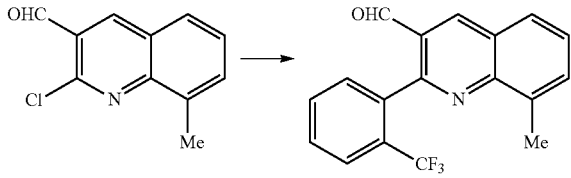

Prepared according to Procedure A using 2-chloro-8-methylquinoline-3-carbaldehyde (2.0 g, 9.73 mmol), 2-(trifluoromethyl)phenylboronic acid (2.032 g, 10.7 mmol, 1.1 eq), tetrakis(triphenylphosphine)palladium (562 mg, 5% mmol), and sodium carbonate (5.15 g, 48.6 mol, 5 eq) in MeCN (75 mL) and water (25 mL). After purification, 8-methyl-2-(2-(trifluoromethyl)phenyl)quinoline-3-carbaldehyde was obtained as a white solid. $^1$H NMR (DMSO-d$_6$) δ ppm 9.93 (1H, s), 9.04 (1H, s), 8.13 (1H, d, J=8.1 Hz), 7.93 (1H, d, J=7.3 Hz), 7.85 (1H, d, J=7.1 Hz), 7.72-7.82 (2H, m), 7.64-7.71 (1H, m), 7.59 (1H, d, J=7.3 Hz), 2.67 (3H, s). Mass Spectrum (ESI) m/e=316.1 (M+1).

N-(4-Methoxybenzyl)(8-methyl-2-(2-(trifluoromethyl)phenyl)quinolin-3-yl)-methanamine

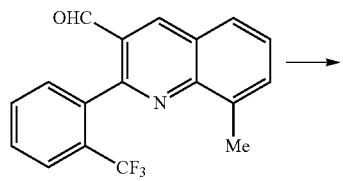

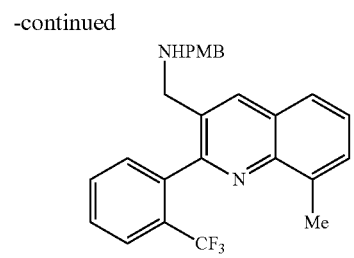

Prepared according to Procedure F using 8-methyl-2-(2-(trifluoromethyl)phenyl)-quinoline-3-carbaldehyde (1 g, 3.17 mmol), DCE (16 mL), PMBNH$_2$ (0.62 mL, 4.75 mmol, 1.5 eq), and NaBH(OAc)$_3$ (2.0166 g, 9.52 mmol, 3 eq). After purification, N-(4-methoxybenzyl)(8-methyl-2-(2-(trifluoromethyl)phenyl)-quinolin-3-yl)methanamine was obtained as light yellow syrup. $^1$H NMR (DMSO-d$_6$) δ ppm 8.48 (1H, s), 7.87 (2H, t, J=7.2 Hz), 7.64-7.77 (2H, m), 7.48-7.62 (3H, m), 7.14 (2H, d, J=8.6 Hz), 6.81 (2H, d, J=8.6 Hz), 3.71 (3H, s), 3.44-3.62 (4H, m), 2.61 (3H, s), 2.54 (1H, s). Mass Spectrum (ESI) m/e=437.2 (M+1).

(8-Methyl-2-(2-(trifluoromethyl)phenyl)quinolin-3-yl)methanamine

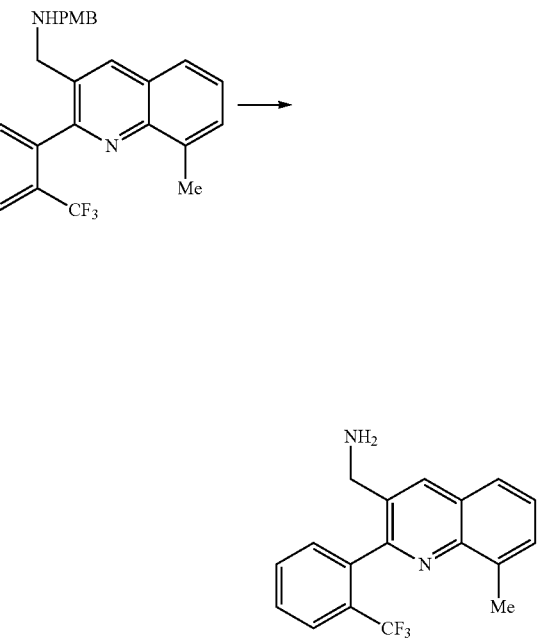

Prepared according to Procedure G using N-(4-methoxybenzyl)(8-methyl-2-(2-(trifluoromethyl)phenyl)quinolin-3-yl)methanamine (1.1427 g, 2.62 mmol, 1 eq) and ammonium cerium(iv) nitrate (3.59 g, 6.55 mmol, 2.5 eq) in CH$_3$CN—H$_2$O (2:1, 12 mL). After purification, (8-methyl-2-(2-(trifluoromethyl)phenyl)quinolin-3-yl)methanamine was obtained as brown syrup. $^1$H NMR (DMSO-d$_6$) δ ppm 8.47 (1H, s), 7.91 (1H, d, J=7.4 Hz), 7.84 (1H, d, J=7.4 Hz), 7.67-7.81 (2H, m), 7.47-7.62 (3H, m), 3.46-3.70 (2H, m), 2.61 (3H, s), 1.86 (2H, br. s.). Mass Spectrum (ESI) m/e=317.0 (M+1).

N-((8-Methyl-2-(2-(trifluoromethyl)phenyl)quinolin-3-yl)methyl)-9H-purin-6-amine

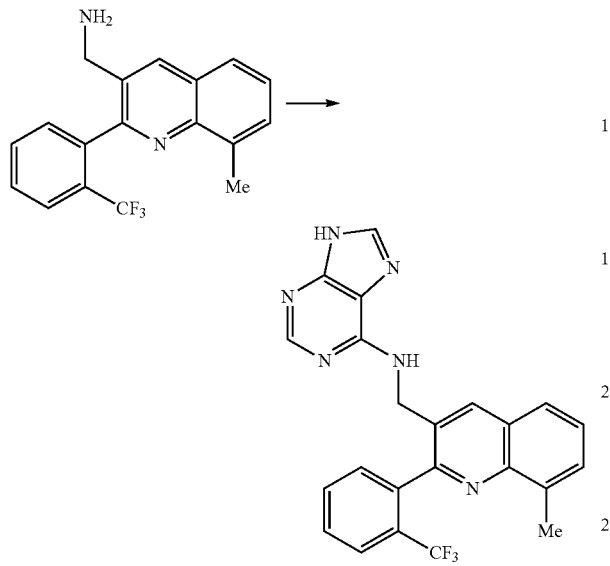

Prepared according to Procedure H using (8-methyl-2-(2-(trifluoromethyl)-phenyl)quinolin-3-yl)methanamine (0.1 g, 0.316 mmol, 1 eq) in EtOH (2 mL) was treated with ⁱPr₂NEt (0.07 mL, 0.4 mmol, 1.2 eq) followed by 6-chloropurine (0.049 g, 0.317 mmol, 1 eq). After purification, N-((8-methyl-2-(2-(trifluoro-methyl)phenyl)quinolin-3-yl)methyl)-9H-purin-6-amine as yellow syrup. The yellow syrup was triturated with CH₂Cl₂ and filtered to provide N-((8-methyl-2-(2-(trifluoromethyl)phenyl)quinolin-3-yl)methyl)-9H-purin-6-amine [PI3Kδ IC₅₀=91 nM] as yellow syrup. ¹H NMR (DMSO-d₆) δ ppm 12.93 (1H, s), 7.98-8.31 (4H, m), 7.90 (1H, d, J=7.8 Hz), 7.74-7.82 (2H, m), 7.69 (2H, t, J=6.5 Hz), 7.59 (1H, d, J=7.0 Hz), 7.42-7.52 (1H, m), 4.42-4.77 (2H, m), 2.62 (3H, s). Mass Spectrum (ESI) m/e=435.1 (M+1).

Example 17: Preparation of N-((2-(2-Fluoro-6-methoxyphenyl)-8-methylquinolin-3-yl)methyl)-9H-purin-6-amine 2-(2-Fluoro-6-methoxyphenyl)-8-methylquinoline-3-carbaldehyde

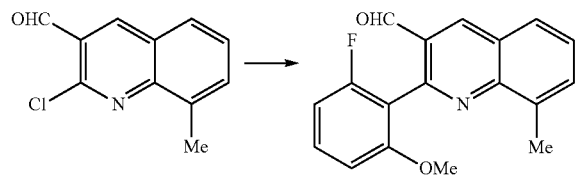 [SMILES: Cc1cccc2cc(C=O)c(Cl)nc12 ; COc1cccc(F)c1-c1nc2c(C)cccc2cc1C=O]

Prepared according to Procedure A using 2-chloro-8-methylquinoline-3-carbaldehyde (1.07 g, 5.21 mmol), 2-fluoro-6-methoxyphenylboronic acid (0.9738 g, 5.73 mmol, 1.1 eq), tetrakis(triphenylphosphine)palladium (0.3011 g, 5% mmol), and sodium carbonate (2.76 g, 26.1 mmol, 5 eq) in MeCN (37.5 mL) and water (12.5 mL). After purification, 2-(2-fluoro-6-methoxyphenyl)-8-methylquinoline-3-carbaldehyde was obtained as white solid. ¹H NMR (DMSO-d₆) δ ppm 9.88 (1H, s), 8.95 (1H, s), 8.10 (1H, d, J=8.1 Hz), 7.82 (1H, d, J=7.1 Hz), 7.62-7.69 (1H, m), 7.49-7.59 (1H, m), 6.96-7.10 (2H, m), 3.71 (3H, s), 2.70 (3H, s). Mass Spectrum (ESI) m/e=296.0 (M+1).

N-(4-Methoxybenzyl)(2-(2-fluoro-6-methoxyphenyl)-8-methylquinolin-3-yl)-methanamine

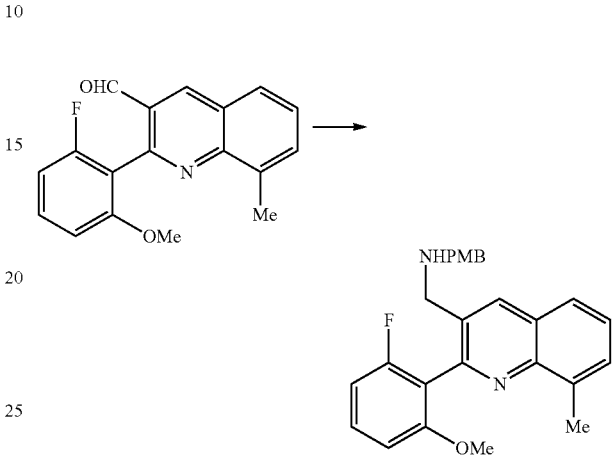

Prepared according to Procedure F using 2-(2-fluoro-6-methoxyphenyl)-8-methylquinoline-3-carbaldehyde (1.086 g, 3.68 mmol), DCE (18 mL), PMBNH₂ (0.95 mL, 7.36 mmol, 2.0 eq), and NaBH(OAc)₃ (2.3387 g, 11.03 mmol, 3 eq) After purification, N-(4-methoxybenzyl)(2-(2-fluoro-6-methoxyphenyl)-8-methylquinolin-3-yl)methanamine was obtained as yellow syrup. ¹H NMR (DMSO-d₆) δ ppm 8.42 (1H, s), 7.84 (1H, d, J=7.4 Hz), 7.55-7.62 (1H, m), 7.43-7.54 (2H, m), 7.13 (2H, d, J=8.6 Hz), 6.90-7.01 (2H, m), 6.77-6.85 (2H, m), 3.71 (3H, s), 3.65 (3H, s), 3.47-3.62 (4H, m), 2.64 (3H, s), 2.43 (1H, s). Mass Spectrum (ESI) m/e=417.3 (M+1).

(2-(2-Fluoro-6-methoxyphenyl)-8-methylquinolin-3-yl)methanamine

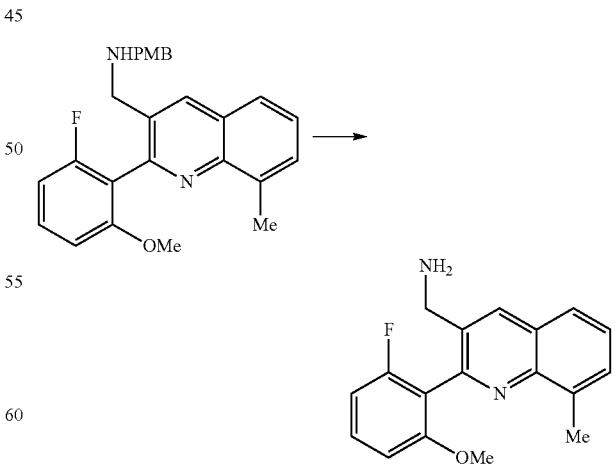

Prepared according to Procedure G using N-(4-methoxybenzyl)(2-(2-fluoro-6-methoxyphenyl)-8-methylquinolin-3-yl)methanamine (1.1795 g, 2.8320 mmol, 1 eq) and ammonium cerium(iv) nitrate (5.434 g, 9.912 mmol, 3.5 eq) in CH₃CN—H₂O (2:1, 13 mL). After purification, (2-(2-fluoro-6-methoxyphenyl)-8-methylquinolin-3-yl)methanamine was obtained as yellow sticky solid. ¹H NMR (DMSO-d₆) δ ppm 8.41 (1H, s), 7.82 (1H, d, J=7.4 Hz), 7.55-7.60 (1H, m), 7.45-7.54 (2H, m), 7.03 (1H, d, J=8.2 Hz), 6.92-7.00 (1H, m), 3.71 (3H, s), 3.59 (2H, q, J=16.6 Hz), 2.64 (3H, s), 1.88 (2H, br. s.). Mass Spectrum (ESI) m/e=297.1 (M+1).

N-((2-(2-Fluoro-6-methoxyphenyl)-8-methylquinolin-3-yl)methyl)-9H-purin-6-amine

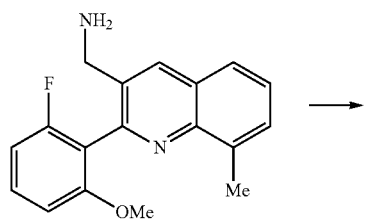

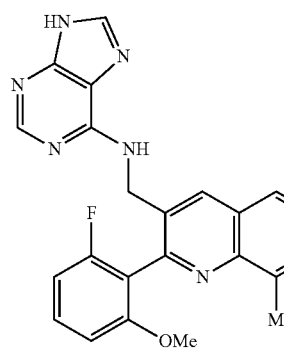

Prepared according to Procedure H using (2-(2-fluoro-6-methoxyphenyl)-8-methylquinolin-3-yl)methanamine (0.1000 g, 0.337 mmol, 1 eq) in EtOH (2 mL) was treated with ⁱPr₂NEt (0.0764 mL, 0.439 mmol, 1.3 eq) followed by 6-chloropurine (0.0522 g, 0.337 mmol, 1 eq). After purification, N-((8-methyl-2-(2-(trifluoromethyl)phenyl)quinolin-3-yl)methyl)-9H-purin-6-amine was obtained as as yellow syrup. The yellow syrup was triturated with CH₂Cl₂ and filtered to provide N-((2-(2-fluoro-6-methoxyphenyl)-8-methylquinolin-3-yl)methyl)-9H-purin-6-amine as yellow syrup. The yellow syrup was triturated with CH₂Cl₂ and the resulting solid was filtered to provide N-((2-(2-fluoro-6-methoxyphenyl)-8-methylquinolin-3-yl)methyl)-9H-purin-6-amine [PI3Kδ IC₅₀=651 nM] as white solid. ¹H NMR (DMSO-d₆) δ ppm 12.87 (1H, s), 8.19 (1H, s), 8.11 (1H, s), 8.07 (1H, s), 8.00 (1H, s), 7.77 (1H, d, J=7.8 Hz), 7.58 (1H, d, J=7.0 Hz), 7.40-7.51 (2H, m), 6.87-7.02 (2H, m), 4.64 (2H, br. s.), 3.74 (3H, s), 2.64 (3H, s). Mass Spectrum (ESI) m/e=415.1 (M+1).

Examples 18 and 19: N-((3-(2-Chlorophenyl)-8-methylquinoxalin-2-yl)-methyl)-9H-purin-6-amine and N-((3-(2-Chlorophenyl)-5-methylquinoxalin-2-yl)methyl)-9H-purin-6-amine 1-(2-Chlorophenyl)propane-1,2-dione

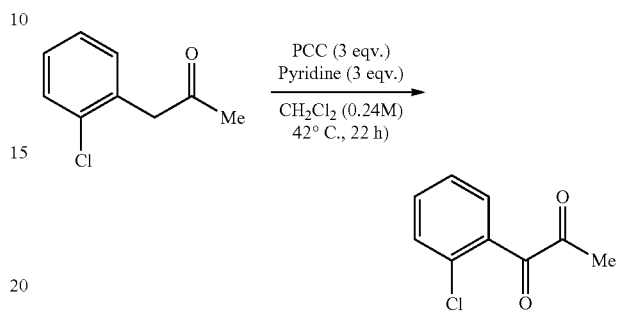

To a solution of 2-chlorophenylacetone (7.14 g, 42 mmol) in CH₂Cl₂ (184 mL), PCC (27 g, 127 mmol, 3 eq) and pyridine (10 mL, 127 mmol, 3 eq) in three portions were added over five hours at reflux under vigorous stirring. After the addition was complete, the mixture was further refluxed under vigorous stirring for 21.5 h. The mixture was filtered through a pad of silica gel, washed the pad with CH₂Cl₂, and concentrated under reduced pressure to provide a dark red syrup. The residue was purified by column chromatography on a 120 g of Redi-Sep™ column using 0-15% gradient of EtOAc in hexane over 40 min as eluent to provide 1-(2-chlorophenyl)propane-1,2-dione as yellow liquid. ¹H NMR (choroform-d) δ ppm 7.66 (1H, dd, J=7.6, 1.8 Hz), 7.48-7.54 (1H, m), 7.37-7.46 (2H, m), 2.58 (3H, s). Mass Spectrum (ESI) m/e=182.9 (M+1).

3-Bromo-1-(2-chlorophenyl)propane-1,2-dione

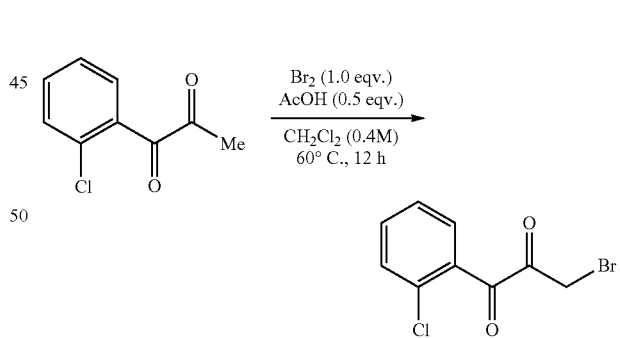

A mixture of 1-(2-chlorophenyl)propane-1,2-dione (1.2592 g, 6.9 mmol), glacial acetic acid (0.20 mL, 3.4 mmol, 0.5 eq), and bromine (0.35 mL, 6.8 mmol, 1 eq) in CHCl₃ (17 mL) was heated at 60° C. for 12 h. The mixture was concentrated under reduced pressure to provide 3-bromo-1-(2-chlorophenyl)propane-1,2-dione as yellow liquid. The yellow liquid was carried on crude without purification for the next step. ¹H NMR (CDCl₃) δ ppm 7.71 (1H, dd, J=7.8, 1.6 Hz), 7.53-7.59 (1H, m), 7.40-7.49 (2H, m), 4.52 (2H, s). Mass Spectrum (ESI) m/e=261.0 [M+1 (⁷⁹Br)] and 262.9 [M+1 (⁸¹Br)].

3-(Bromomethyl)-2-(2-chlorophenyl)-5-methylquinoxaline and 2-(Bromomethyl)-3-(2-chlorophenyl)-5-methylquinoxaline

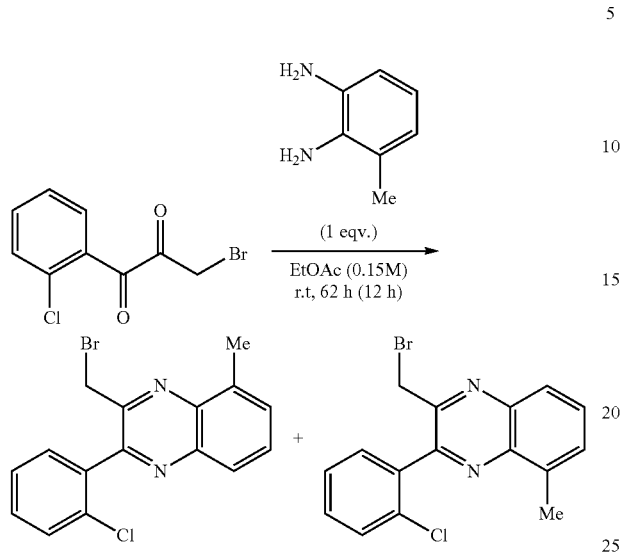

To a solution of 3-bromo-1-(2-chlorophenyl)propane-1,2-dione (1.8030 g, 6.895 mmol) in EtOAc (46 mL) was added 2,3-diaminotoluene (0.8423 g, 6.895 mmol, 1.0 eq) as solid and the mixture was at rt for 62 h. The mixture was concentrated under reduced pressure to provide a mixture of 3-(bromomethyl)-2-(2-chloro-phenyl)-5-methylquinoxaline and 2-(bromomethyl)-3-(2-chlorophenyl)-5-methylquinoxaline as red syrup (2.3845 g, 99.48%). The red syrup was carried on crude without purification for the next step. Mass Spectrum (ESI) m/e=347.0 [M+1 ($^{79}$Br)] and 349.0 [M+1 ($^{81}$Br)].

(3-(2-Chlorophenyl)-8-methylquinoxalin-2-yl)methanamine and (3-(2-Chlorophenyl)-5-methylquinoxalin-2-yl)methanamine

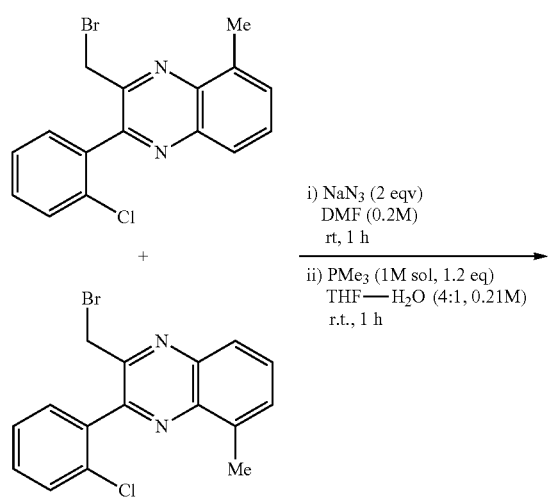

i) NaN$_3$ (2 eqv)
DMF (0.2M)
rt, 1 h ii) PMe$_3$ (1M sol, 1.2 eq)
THF—H$_2$O (4:1, 0.21M)
r.t., 1 h

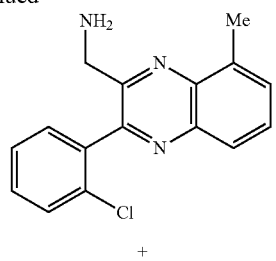

+

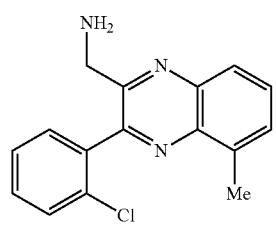

To a stirring solution of 3-(bromomethyl)-2-(2-chlorophenyl)-5-methylquinoxaline and 2-(bromomethyl)-3-(2-chlorophenyl)-5-methylquinoxaline (1.1204 g, 3.223 mmol) in DMF (16 mL) was added sodium azide (0.4190 g, 6.446 mmol, 2 eq) and the mixture was stirred at rt for 1 h. The mixture was partitioned between EtOAc (100 mL) and H$_2$O (100 mL). The organic layer was dried over MgSO$_4$, filtered, and concentrated under reduced pressure to provide a mixture of 3-(azidomethyl)-2-(2-chlorophenyl)-5-methylquinoxaline and 2-(azidomethyl)-3-(2-chlorophenyl)-5-methylquinoxaline. The crude mixture was carried on crude without purification for the next step. Mass Spectrum (ESI) m/e=310.0 (M+1).

To a stirring solution of 3-(azidomethyl)-2-(2-chlorophenyl)-5-methylquinoxaline and 2-(azidomethyl)-3-(2-chlorophenyl)-5-methylquinoxaline (0.9983 g, 3.22 mmol) in THF—H$_2$O (4:1, 15 mL) was added dropwise trimethylphosphine, 1.0M solution in THF (3.8700 mL, 3.87 mmol, 1.2 eq) and the mixture was stirred at rt for 1 h. To the mixture was added EtOAc (100 mL) was added and the mixture was extracted with 1N HCl (2×50 mL). The combined extracts were neutralized with solid sodium bicarbonate, and extracted with EtOAc (2×50 mL). The combined organic extracts were dried over MgSO$_4$, filtered, and concentrated under reduced pressure to provide dark syrup. The crude product was purified by column chromatography on a 40 g of Redi-Sep™ column using 0 to 100% gradient of CH$_2$Cl$_2$:MeOH:NH$_4$OH (89:9:1) in CH$_2$Cl$_2$ over 14 min as eluent to provide a mixture of (3-(2-chlorophenyl)-8-methylquinoxalin-2-yl)methanamine and (3-(2-chlorophenyl)-5-methylquinoxalin-2-yl)methanamine Mass Spectrum (ESI) m/e=284.0 (M+1).

N-((3-(2-Chlorophenyl)-8-methylquinoxalin-2-yl)
methyl)-9H-purin-6-amine and N-((3-(2-Chlorophe-
nyl)-5-methylquinoxalin-2-yl)methyl)-9H-purin-6-
amine

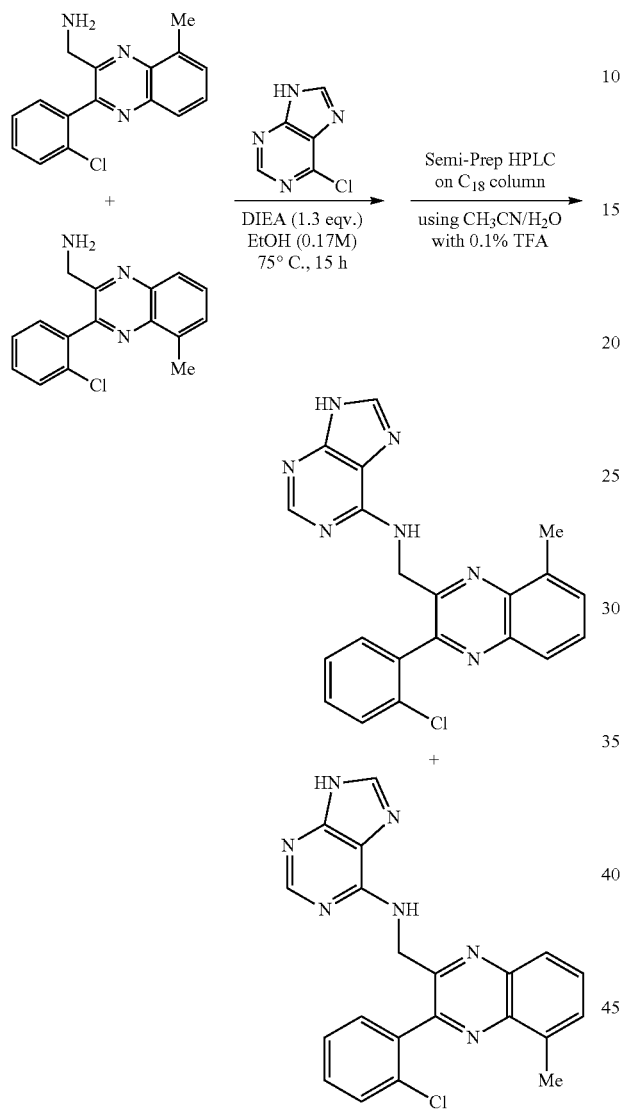

A mixture of the 6-chloropurine (0.126 g, 0.813 mmol, 1 eq), (3-(2-chlorophenyl)-5-methylquinoxalin-2-yl)methanamine (0.2308 g, 0.813 mmol, 1 eq), and N,N-diisopropylethylamine (0.184 mL, 1.06 mmol, 1.3 eq) in EtOH (5 mL) was stirred at 75° C. for 15 h. The mixture was concentrated under reduced pressure to provide green syrup. The green syrup was purified by column chromatography on a 40 g of Redi-Sep™ column using 0 to 100% gradient of $CH_2Cl_2$: MeOH:$NH_4OH$ (89:9:1) in $CH_2Cl_2$ over 14 min as eluent to provide a mixture of N-((3-(2-chlorophenyl)-8-methylquinoxalin-2-yl)methyl)-9H-purin-6-amine and N-((3-(2-chlorophenyl)-5-methylquinoxalin-2-yl)methyl)-9H-purin-6-amine as orange solid. The orange solid was suspended in $CH_2Cl_2$ and filtered to provide a mixture of N-((3-(2-chlorophenyl)-8-methylquinoxalin-2-yl)methyl)-9H-purin-6-amine and N-((3-(2-chlorophenyl)-5-methylquinoxalin-2-yl)methyl)-9H-purin-6-amine as off-white solid. The white solid was dissolved in DMSO (3 mL) and purified by semi-prep-HPLC on C18 column using 20-70% gradient of $CH_3CN$ (0.1% of TFA) in water (0.1% of TFA) over 40 min as eluent to provide N-((3-(2-chlorophenyl)-8-methylquinoxalin-2-yl)methyl)-9H-purin-6-amine [PI3Kδ $IC_{50}$=325 nM] as off-white solid as a TFA salt and N-((3-(2-chlorophenyl)-5-methylquinoxalin-2-yl)methyl)-9H-purin-6-amine [PI3Kδ $IC_{50}$=66 nM] as off-white solid as a TFA salt. Example 18: $^1$H NMR (DMSO-$d_6$) δ ppm 8.50 (1H, s), 8.27 (2H, s), 7.95 (1H, d, J=7.9 Hz), 7.75-7.80 (1H, m), 7.72-7.75 (1H, m), 7.61-7.66 (2H, m), 7.53-7.58 (1H, m), 7.47-7.53 (1H, m), 4.89 (2H, s), 3.17 (1H, s), 2.61 (3H, s); Mass Spectrum (ESI) m/e=402.1 (M+1); HPLC: a peak at 6.439 min. Example 19: $^1$H NMR (DMSO-$d_6$) δ ppm 8.42 (1H, br. s.), 8.18-8.31 (2H, m), 7.94 (1H, d, J=7.9 Hz), 7.76-7.82 (1H, m), 7.71-7.75 (1H, m), 7.67 (1H, dd, J=7.3, 1.8 Hz), 7.63 (1H, d, J=7.9 Hz), 7.52-7.57 (1H, m), 7.48-7.52 (1H, m), 4.87 (2H, br. s.), 2.70 (3H, s); Mass Spectrum (ESI) m/e=402.1 (M+1); HPLC: a peak at 6.758 min.

Example 20: 4-((8-Methyl-2-o-tolylquinolin-3-yl)methoxy)-5H-pyrrolo[2,3-d]pyrimidin-6 (7H)-one

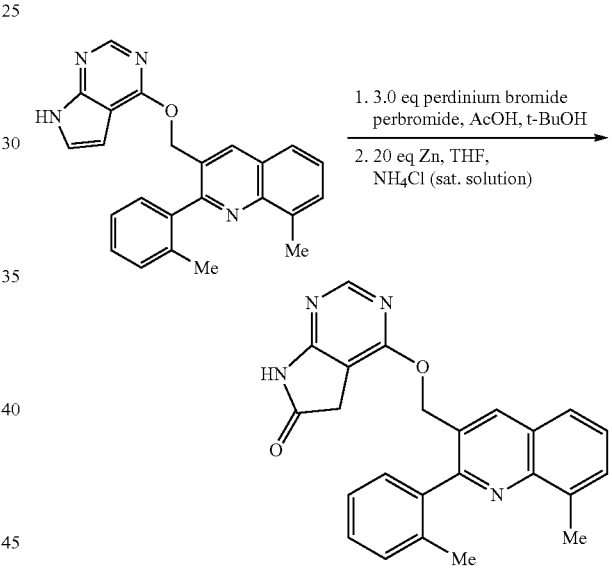

To a solution of 3-((7H-pyrrolo[2,3-d]pyrimidin-4-yloxy)methyl)-8-methyl-2-o-tolylquinoline (120 mg, 0.316 mmol) in AcOH (4 mL) and t-BuOH (2.43 mL) under $N_2$ was added pyridinium bromide perbromide (303 mg, 0.947 mmol) in one portion. After stirring at room temperature for 5 h the solvents was removed, and the remaining solids suspended in $H_2O$ and extracted with ethyl acetate, after drying with brine and $MgSO_4$ the crude dry solid was dissolved in THF (8 mL) followed by 5 mL of a saturated $NH_4Cl$ solution, this was followed in turn by Zn powder (528 mg, 26 mmol) and stirred at room temperature for 24 h. The mixture was then extracted with ethyl acetate and chromatographed {gradient elution DCM/89:9:1 (DCM/MeOH/$NH_4OH$)}. The solid was recrystallized from DCM to provide the pure product [PI3Kδ $IC_{50}$=349 nM]. $^1$H NMR (400 MHz, DMSO-$d_6$) δ ppm 11.29 (1H, s), 8.52 (1H, s), 8.30 (1H, s), 7.89 (1H, d, J=7.8 Hz), 7.65 (1H, d, J=7.0 Hz), 7.51-7.57 (1H, m), 7.30-7.35 (3H, m), 7.22-7.29 (1H, m), 3.47 (2H, s), 2.67 (3H, s), 2.09 (3H, s) Mass Spectrum (ESI) m/e=397.1 [M+1].

Example 21

2,5-Dichloroquinoline-3-carbaldehyde (1)

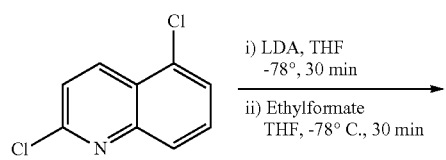

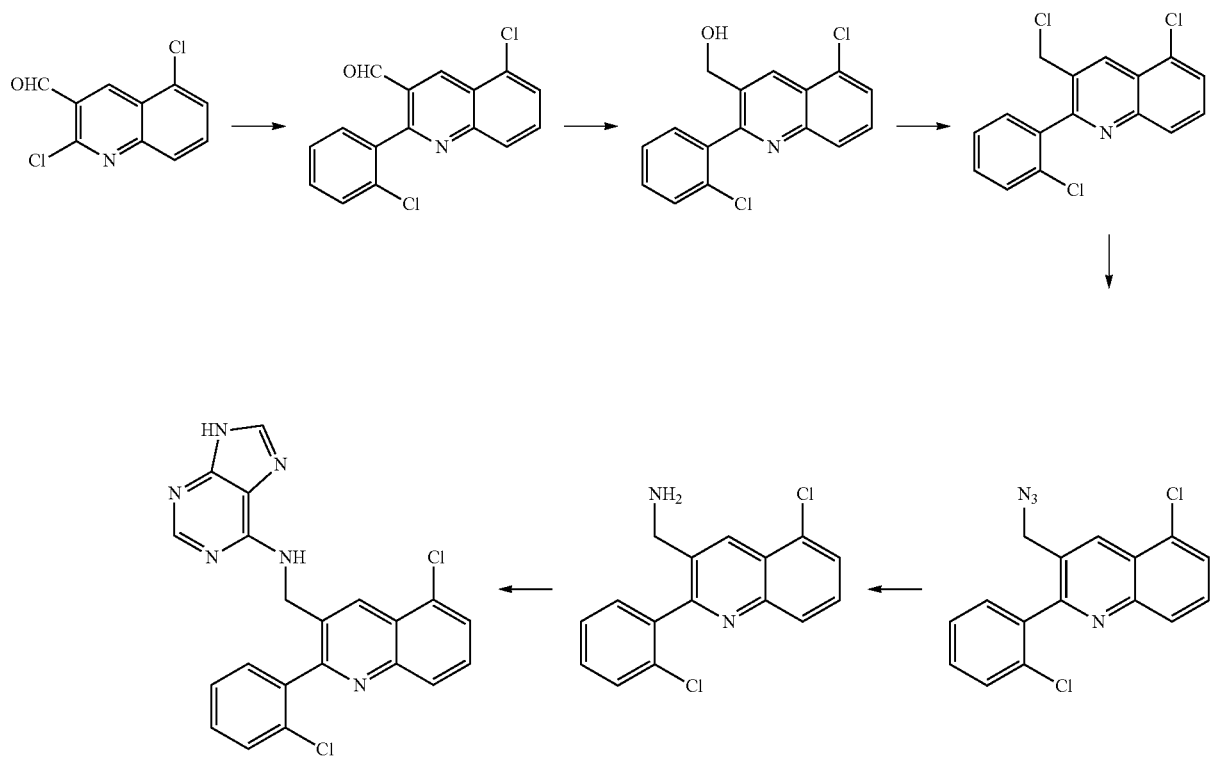

To a cold solution of diisopropylamine (6.6 mL, 1.1 eq) in THF (100 mL) was added dropwise a solution of Bu$^n$Li (1.1 eq, 2.5 M, 18.7 mL) in hexane at −20° C. The resulted LDA solution was kept in 0° C. for 30 min and cooled to −78° C. before addition of a solution of 1 (8.4 g, 42.4 mmol) in THF (44 mL) dropwise. The temperature was controlled below −72° C. by adjusting of adding rate (15 min) The reaction was a clear solution at beginning but turned into a suspension after 25 min. After another 5 min, DMF (5.0 mL) was added dropwise. After 30 min, the reaction was quenched with NH$_4$Cl and partitioned between EtOAc (150 mL) and water (100 mL). The combined organics were washed with water, brine, dried over Na$_2$SO$_4$ Removal of solvent gave a white solid which was washed with hexane (3×50 mL). A white solid was obtained (7.47 g). The combined hexane washings were concentrated and purified by column chromatography on silica gel (DCM/Hexane, 3/2) to give additional 500 mg. Overall, 7.97 g, 83%. 1H NMR (400 MHz, CDCl$_3$) δ ppm 10.60 (1H, s), 9.17 (1H, s), 8.02 (1H, d, J=8.0 Hz), 7.82 (1H, t, J=8.0 Hz), 7.73 (1H, d, J=8.0 Hz) Mass Spectrum (ESI) m/e=226.0 and 228 (M+1).

N-((5-Chloro-2-(2-chlorophenyl)quinolin-3-yl)methyl)-9H-purin-6-amine (2)

Compound 2 was prepared from 1 according to Procedures A, B, C, D, E, and H. $^1$H-NMR (400 Hz, DMSO-d$^6$) δ 9.68 (s, br, 1H), 8.74 (s, 1H), 8.53 (s, br, 1H), 8.42 (s, 1H), 8.05 (d, J=8.0 Hz, 1H), 7.87 (d, J=8.0 Hz, 1H), 7.81 (t, J=8.0 Hz, 1H), 7.51-7.28 (m, 5H), 4.91 (s, 2H). Mass Spectrum (ESI) m/e=422 (M+1).

3-(Azidomethyl)-8-chloro-2-(piperidin-1-yl)quinoline

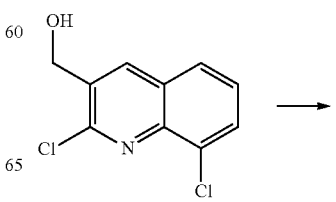

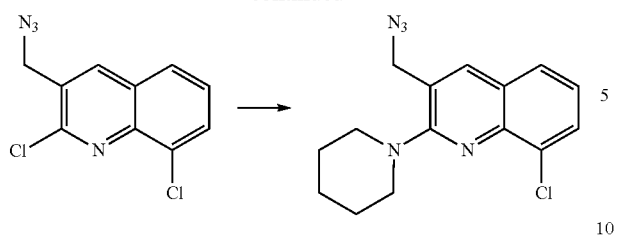

A solution of (2,8-dichloroquinolin-3-yl)methanol (228 mg, 1 mmol) in CHCl₃ (4 mL) was treated with SOCl₂ (0.36 mL, 5 eq) dropwise, and the reaction was stirred at rt for 2 h before removal of solvents and the residue was partitioned between EtOAc and NaHCO₃. The organic was separated and dried over Na₂SO₄. Solvents were removed under reduced pressure and the residue was dried under vacuum. The residue was dissolved in DMSO (2 mL) and treated with NaN₃ (72 mg, 1.1 eq) at rt. LCMS showed completion after 4 h. The reaction mixture was partitioned between EtOAc (2 mL) and water (1 mL), and the water layer was extracted with EtOAc (5 mL) once and combined organics were washed with water, brine, dried over Na₂SO₄ and concentrated to give a pale yellow solid as 3-(azidomethyl)-2,8-dichloroquinoline (215 mg, 85%, 2 steps). This solid (50 mg, 0.2 mmol) in DCM (2 mL) was treated with piperidine (143 μL, 7.3 eq) in EtOH (2 ML) at reflux over night. The reaction was worked up and the residue was purified by column chromatography on silica gel (eluent: EtOAc/hexane, 1/5) to give a yellow solid (30 mg, 50%). 1H NMR (400 MHz, CDCl₃) δ ppm 8.01 (1H, s), 7.62 (1H, t, J=8.0 Hz), 7.53 (1H, d, J=8.0 Hz), 7.49 (1H, d, J=8.0 Hz), 4.02 (2H, s), 3.26-3.23 (m, 4H), 1.74-1.58 (m, 6H). Mass Spectrum (ESI) m/e=302 (M+1).

N-((8-Chloro-2-(piperidin-1-yl)quinolin-3-yl)methyl)-9H-purin-6-amine

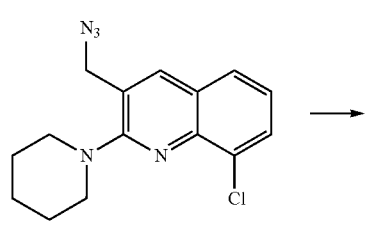

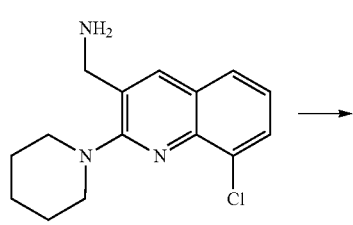

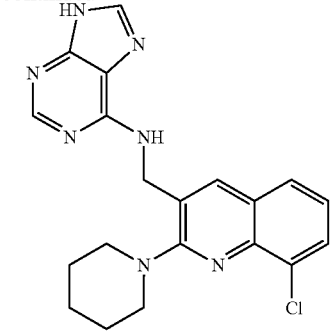

3-(Azidomethyl)-8-chloro-2-(piperidin-1-yl)quinoline (30 mg, 0.1 mmol) was dissolved in MeOH (1 mL) and treated with 10% Pd—C (5 wt %) and the mixture was then stirred under H₂ balloon over night. The mixture was filtered through a Celite™ pad followed by removal of solvents to give (8-chloro-2-(piperidin-1-yl)-quinolin-3-yl)methanamine as a colorless oil. N-((8-chloro-2-(piperidin-1-yl)-quinolin-3-yl)methyl)-9H-purin-6-amine was prepared according to Procedure H. 1H NMR (400 MHz, CDCl₃) δ ppm 8.29 (s, 1H), 7.79 (m, 3H), 7.45 (m, 2H), 5.43 (2H, s), 3.90 (m, 4H), 2.23 (m, 4H), 1.84 (m, 2H). Mass Spectrum (ESI) m/e=394 (M+1).

N-((8-Bromo-2-(3-fluorophenyl)quinolin-3-yl)methyl)-9H-purin-6-amine

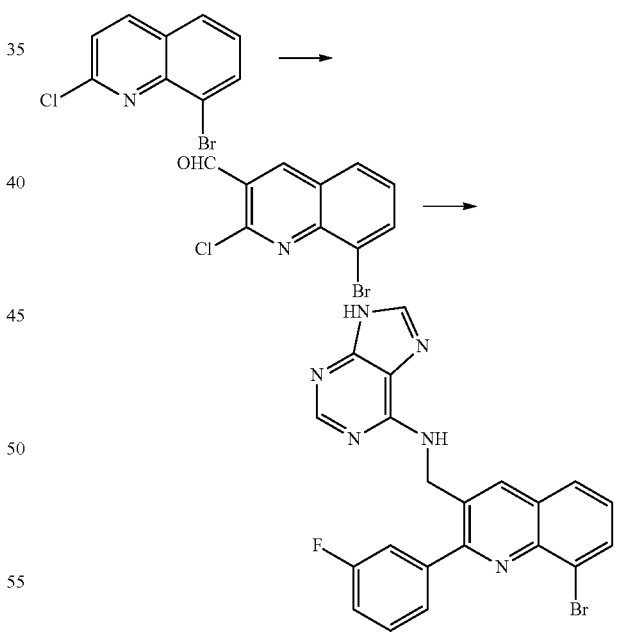

8-Bromo-2-chloroquinoline-3-carbaldehyde was prepared in the similar manner as 1 from 8-bromo-2-chloroquinoline. N-((8-bromo-2-(3-fluorophenyl)quinolin-3-yl)methyl)-9H-purin-6-amine was prepared according to Procedures A, B, C, D, E, and H. ¹H-NMR (400 Hz, DMSO-d⁶) δ 8.43 (s, 1H), 8.27 (s, br, 2H), 8.13 (d, J=8.0 Hz, 1H), 8.02 (d, J=8.0 Hz, 1H), 7.59-7.56 (m, 3H), 7.51 (t, J=8.0 Hz, 1H), 7.37-7.32 (m, 1H), 4.95 (s, 2H). Mass Spectrum (ESI) m/e=449, 451 (M+1).

Example 22

2-((8-Bromo-2-(3-fluorophenyl)quinolin-3-yl)methyl)isoindoline-1,3-dione

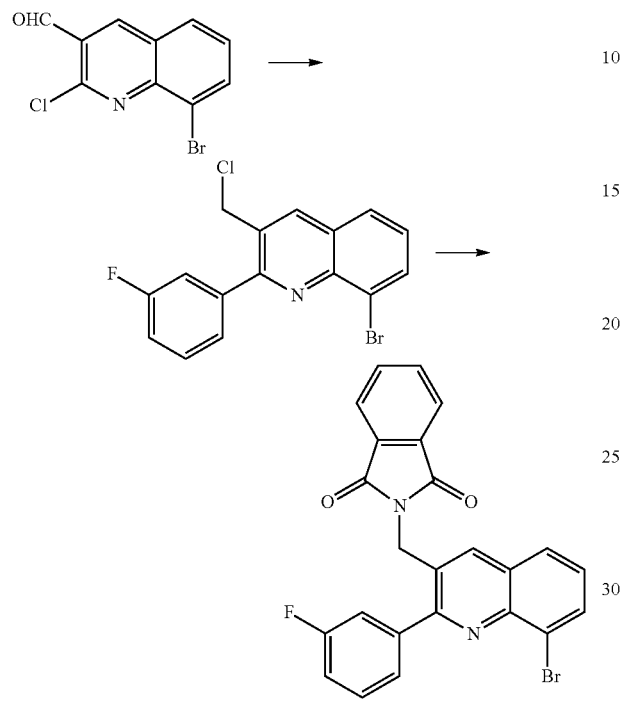

8-Bromo-3-(chloromethyl)-2-(3-fluorophenyl)quinoline was prepared according to Procedures A, B, and C. A solution of 8-bromo-3-(chloromethyl)-2-(3-fluoro-phenyl)-quinoline (1.15 g, 3.3 mmol) in DMF (10 mL) was treated with phthalimide potassium salt (1.52 g, 2.5 eq) at rt. After over night, the reaction was diluted with water. Filtration gave a solid which was washed with water and hot MeOH and dried to give a white solid. $^1$H-NMR (400 Hz, DMSO-$d^6$) δ 8.43 (s, 1H), 8.15-7.84 (m, 7H), 7.62-7.49 (m, 3H), 7.39-7.35 (m, 1H), 4.98 (s, 2H). Mass Spectrum (ESI) m/e=461, 463 (M+1).

N-((2-(3-Fluorophenyl)-8-morpholinoquinolin-3-yl)methyl)-9H-purin-6-amine

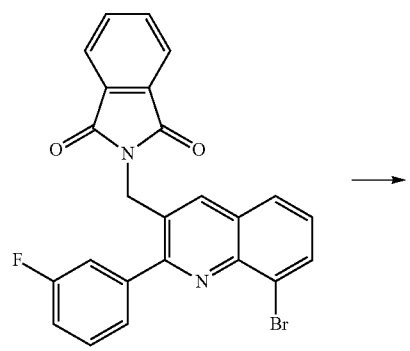

A mixture of 2-((8-bromo-2-(3-fluorophenyl)quinolin-3-yl)methyl)isoindoline-1,3-dione (100 mg, 0.22 mmol), racemic BINAP (16.2 mg, 0.12 eq), Pd$_2$(dba)$_3$ (10 mg, 0.05 eq), NaOBu$^t$ (29.2 mg, 1.4 eq) and morpholine (38 mg, 2 eq) in dioxane (2 mL) was heated to 120° C. under N$_2$ for 8 h. LCMS showed a mixture of starting material and product. To the reaction was added the reactants again. The reaction was further heated for 2 h before partitioned between water and EtOAc.

The water layer was extracted once with EtOAc and acidified to pH 2 by 3 N HCl and extracted with DCM (5 mL×3). Removal of solvent gave a foam, which was treated with NH$_2$NH$_2$ (0.5 mL) in EtOH (2 mL) at reflux. Solvents were removed and the residue was worked up and purified by CombiFlash® (DCM/MeOH/Et$_3$N, 20/1/0.1). A white solid was obtained as (2-(3-fluorophenyl)-8-morpholinoquinolin-3-yl)methanamine N-((2-(3-fluorophenyl)-8-morpholinoquinolin-3-yl)methyl)-9H-purin-6-amine was prepared according to Procedures H. $^1$H-NMR (400 Hz, CD$_3$OD) δ 8.77 (s, 1H), 8.54 (s, 1H), 8.50 (s, 1H), 8.25 (d, J=8.0 Hz, 2H), 7.85 (t, J=8.0 Hz, 1H), 7.61-7.54 (m, 3H), 7.24 (t, J=8.0 Hz, 1H), 5.24 (s, 2H), 4.20 (s, 4H), 4.02 (s, 4H). Mass Spectrum (ESI) m/e=456 (M+1).

Example 23 tert-Butyl(2-(3-fluorophenyl)-8-(methylsulfonyl)quinolin-3-yl)methylcarbamate

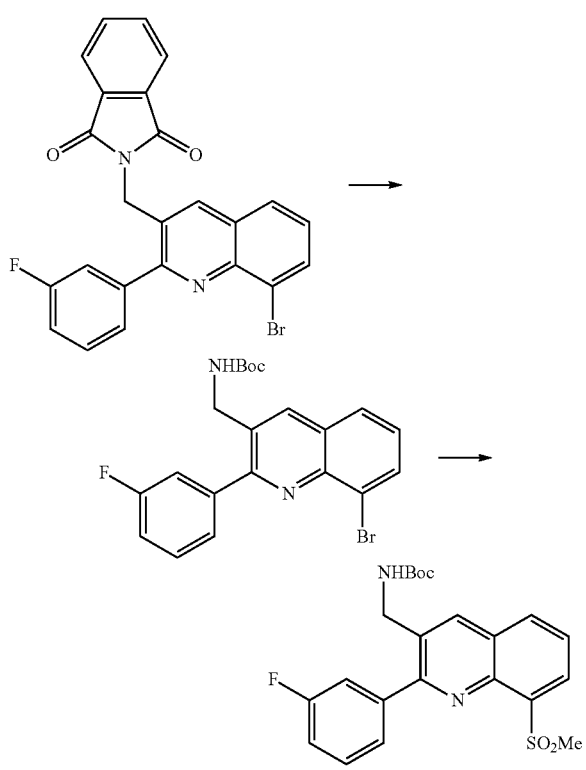

N-((2-(3-Fluorophenyl)-8-(methylsulfonyl)quinolin-3-yl)methyl)-9H-purin-6-amine

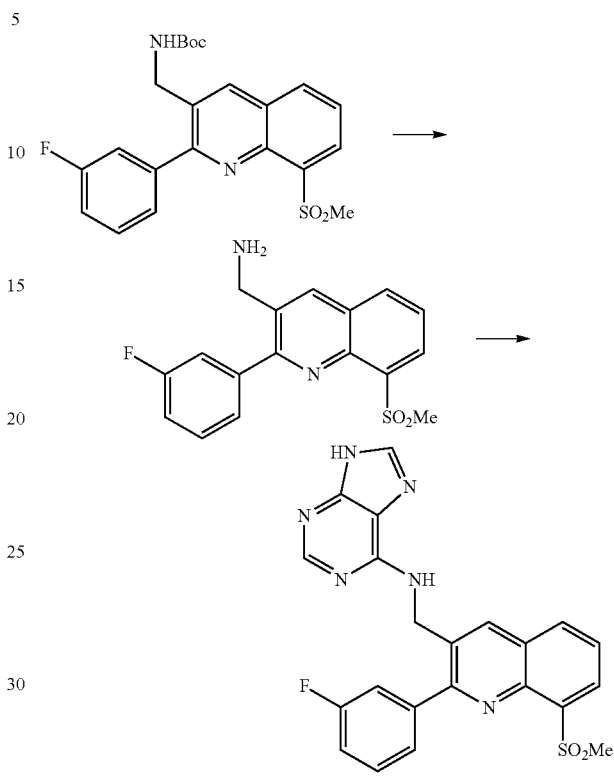

2-((8-Bromo-2-(3-fluorophenyl)quinolin-3-yl)methyl)isoindoline-1,3-dione (1.1 g, 2.4 mmol) in EtOH (10 mL) was treated with $NH_2NH_2$ (0.75 mL, 10 eq) at reflux for 30 min. After cool to rt, the by product was filtered and washed with MeOH. The filtrate was concentrated and purified by CombiFlash® (DCM/MeOH, 20/1) to give an off white solid as amine (720 mg, 91%). A mixture of amine (500 mg, 1.5 mmol), $Boc_2O$ (362 mg, 1.1 eq) and $Et_3N$ (0.25 mL, 1.2 eq) in THF (10 mL) was heated to 80° C. for 2 h before cool to rt and separated by CombiFlash® (EtOAc/Hexane, 1/4). A white solid was obtained as tert-butyl(8-bromo-2-(3-fluorophenyl)quinolin-3-yl)methylcarbamate (640 mg, 98%). A mixture tert-butyl(8-bromo-2-(3-fluorophenyl)quinolin-3-yl)methylcarbamate (184 mg, 0.43 mmol), MeSNa (29 mg, 1 eq) and $Pd(PPh_3)_4$ (25 mg, 5% mmol) in BuOH (3 mL) was purged with $N_2$ for 5 min before heating to 110° C.

After over night, the reaction mixture was purified by CombiFlash® to give an impure sulfide (65 mg) was treated with oxone (200 mg, 2 eq) in THF (1 mL) and water (1 mL) at rt for 8 h. Work up, the residue was purified by column (EtOAc/Hexane, 1/9 to 9/1) to give tert-butyl(2-(3-fluorophenyl)-8-(methylsulfonyl)quinolin-3-yl)methylcarbamate as a white solid. $^1$H NMR (400 MHz, $CDCl_3$) δ ppm 8.54 (d, J=4.0 Hz, 1H), 8.26 (d, J=4.0 Hz, 1H), 8.05 (d, J=8.0 Hz, 1H), 7.62 (t, J=8.0 Hz, 1H), 7.43-7.36 (m, 2H), 7.30 (d, J=8.0 Hz, 1H), 7.13 (t, J=8.0 Hz, 1H), 4.53-4.47 (m, 2H), 4.01 (t, J=8.0 Hz, 1H), 3.49 (s, 3H). Mass Spectrum (ESI) m/e=431 (M+1).

tert-Butyl(2-(3-fluorophenyl)-8-(methylsulfonyl)quinolin-3-yl)methylcarbamate (18 mg, 0.042 mmol) was treated with 50% TFA in DCM (1 mL) for 30 min at rt and the reaction mixture was concentrated to driness. The resulted solid was treated with 6-chloropurine (7.1 mg, 1.1 eq) and hunig's base (0.04 mL, 4 eq) in Bu$^n$OH (1 mL) at 90° C. HPLC on reverse phase gave a white solid. $^1$H-NMR (400 Hz, $CD_3OD$) δ 8.47 (s, 1H), 8.38 (dd, J=8.0, 4.0 Hz, 1H), 8.24 (s, 1H), 8.18 (dd, J=8.0, 4.0 Hz, 1H), 7.68 (t, J=8.0 Hz, 1H), 7.50-7.39 (m, 3H), 7.11 (t, J=8.0 Hz, 1H), 5.24 (s, 2H), 3.45 (s, 3H). Mass Spectrum (ESI) m/e=449 (M+1).

Example 24

(8-Chloro-2-(pyridin-2-yl)quinolin-3-yl)methanamine

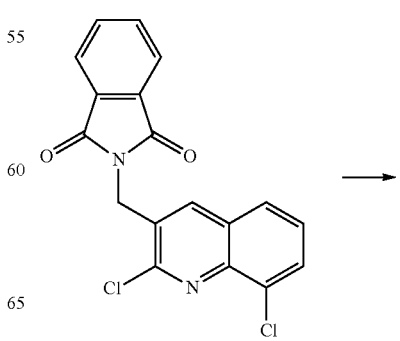

2-((8-Chloro-2-(pyridin-2-yl)quinolin-3-yl)methyl)isoindoline-1,3-dione

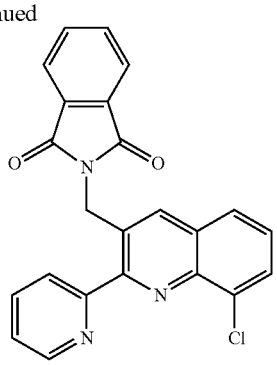

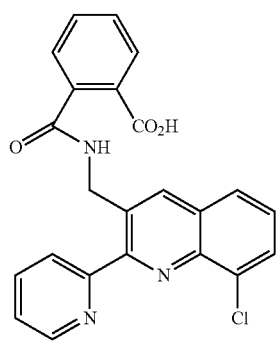

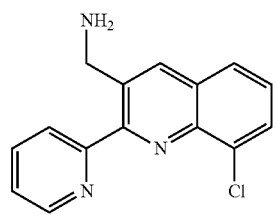

2-((2,8-Dichloroquinolin-3-yl)methyl)isoindoline-1,3-dione was prepared in the similar manner as 2-((8-bromo-2-(3-fluorophenyl)quinolin-3-yl)methyl)-isoindoline-1,3-dione from 2,8-dichloroquinoline-3-carbaldehyde. A mixture of 2-((2,8-dichloroquinolin-3-yl)methyl)isoindoline-1,3-dione (71 mg, 0.2 mmol), 2-pyridylzinc bromide (0.5 M, 0.8 mL, 2.0 eq) and tetrakis(triphenylphosphine) palladium (11 mg, 5%) in dioxane (3 mL) was purged with $N_2$ and heated to 65° C. After 12 h, the reaction was cooled to rt and quenched with $NH_4Cl$ solution. After work up, The residue containing a mixture of 2-((8-chloro-2-(pyridin-2-yl)-quinolin-3-yl)methyl)isoindoline-1,3-dione and 2-(((8-chloro-2-(pyridin-2-yl)-quinolin-3-yl)methyl)carbamoyl)benzoic acid was treated with $NH_2NH_2$ (31 μL) in EtOH (1 mL) at reflux. After usual work up, the residue was purified on column chromatography on silica gel (DCM/MeOH/Et₃N, 20/1/0.1) to give a pale yellow solid as (8-chloro-2-(pyridin-2-yl)quinolin-3-yl)methanamine. ¹H NMR (400 MHz, CDCl₃) δ ppm 8.60 (d, J=8.0 Hz, 1H), 8.31 (d, J=8.0 Hz, 1H), 8.17 (s, 1H), 7.84 (t, J=8.0 Hz, 1H), 7.74 (d, J=8.0 Hz, 1H), 7.66 (d, J=8.0 Hz, 1H), 7.38 (t, J=8.0 Hz, 1H), 7.30 (t, J=8.0 Hz, 1H), 4.13 (s, 3H). Mass Spectrum (ESI) m/e=270 (M+1).

(8-Chloro-2-(pyridin-2-yl)quinolin-3-yl)methanamine (20 mg, 0.074 mmol) was treated with 6-chloropurine (13 mg, 1.1 eq) and hunig's base (0.053 mL, 4 eq) in Bu"OH (1 mL) at 120° C. (modification of procedure H) HPLC on reverse phase gave a white solid. ¹H-NMR (400 Hz, CD₃OD) δ 8.72 (d, J=8.0 Hz, 1H), 8.54-8.28 (m, 4H), 8.04 (t, J=8.0 Hz, 1H), 7.82 (t, J=8.0 Hz, 1H), 7.53-7.44 (m, 2H), 5.27 (s, br, 2H). Mass Spectrum (ESI) m/e=388 (M+1).

Example 25

1-(2,8-Dichloroquinolin-3-yl)ethanol

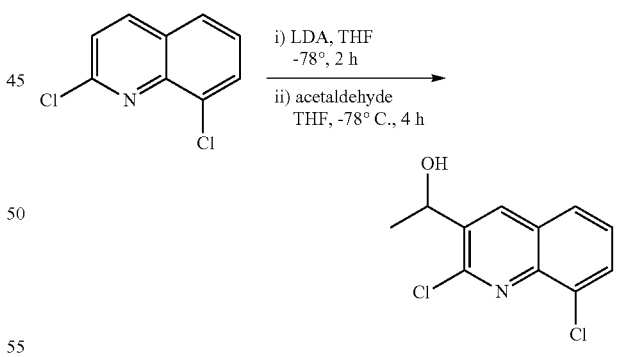

To a cold solution of diisopropylamine (6.6 mL, 1.1 eq) in THF (100 mL) was added dropwise a solution of Bu"Li (1.1 eq, 2.5 M, 18.7 mL) in hexane at −20° C. The resulted LDA solution was kept in 0° C. for 30 min and cooled to −78° C. before addition of a solution of 2,8-dichloroquinoline (8.4 g, 42.4 mmol) in THF (44 mL) dropwise. The temperature was controlled below −72° C. by adjusting of adding rate (15 min) After 45 min, MeCHO (3.6 mL, 1.5 eq) was added dropwise. After 30 min, the reaction was quenched with $NH_4Cl$ and partitioned between EtOAc (150 mL) and water (100 mL). The combined organics were washed with water, brine, dried over Na$_2$SO$_4$ Removal of solvent gave colorless oil which was purified by column chromatography on silica gel (DCM/Hexane, 3/2) to give an oil. Hexane was added (80 mL) and the mixture was left over night. Filtration gave a white solid. $^1$H NMR (400 MHz, CDCl$_3$) δ ppm 8.43 (s, 1H), 7.84 (d, J=8.0 Hz, 1H), 7.79 (d, J=8.0 Hz, 1H), 7.50 (t, J=8.0 Hz, 1H), 5.40 (q, J=8.0 Hz, 1H), 1.63 (d, J=8.0 Hz, 3H). Mass Spectrum (ESI) m/e=242 (M+1).

(R)-1-(2,8-Dichloroquinolin-3-yl)ethanol

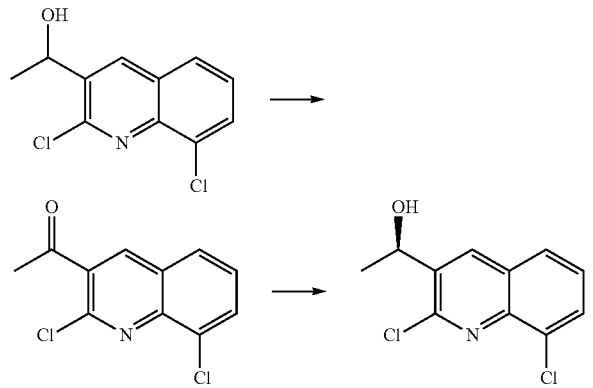

A mixture of 1-(2,8-dichloroquinolin-3-yl)ethanol (5.0 g, 21 mmol) and MnO$_2$ (18 g, 10 eq) in toluene (200 mL) were heated to reflux for 2 h. Filtration followed with removal of solvent gave a white solid as 1-(2,8-dichloroquinolin-3-yl)-ethanone (4.5 g, 91%). A solution of this solid (5.0 g, 21 mmol) in THF (50 mL) was added to a solution of (+)-DIP-Cl (14.7 g, 2.2 eq) in THF (150 mL) at −78° C. dropwise. The reaction was slowly warmed up to rt over night. The reaction was then quenched with acetone (23 mL) and stirred at 0° C. for 1 h before addition of EtOAc. The reaction was warmed up to rt and washed with 10% Na$_2$CO$_3$ and water. Chiral HPLC on IA column (isopropanol in hexane, 10%) showed a ratio of 19:1 for two enantiomers. The combined crude products were concentrated under high vacuum and purified by column chromatography on silica gel (EtOAc/hexane, 1/3) to give a white solid which is recrystalized from a mixture of EtOAc (30 mL) and Hexane (210 mL). A white needle was obtained. $^1$H NMR (400 MHz, CDCl$_3$) δ ppm 8.43 (s, 1H), 7.84 (d, J=8.0 Hz, 1H), 7.79 (d, J=8.0 Hz, 1H), 7.50 (t, J=8.0 Hz, 1H), 5.40 (q, J=8.0 Hz, 1H), 1.63 (d, J=8.0 Hz, 3H). Mass Spectrum (ESI) m/e=242 (M+1).

(S)-2-(1-(2,8-Dichloroquinolin-3-yl)ethyl)isoindoline-1,3-dione

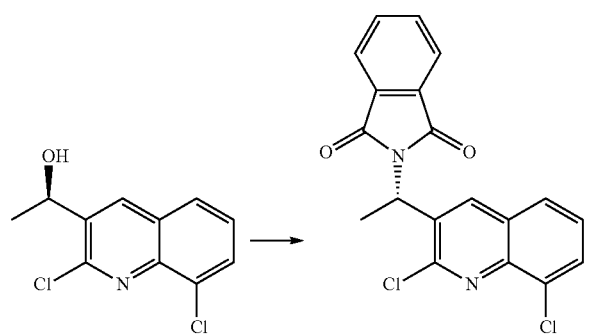 [SMILES: C[C@@H](O)c1cc2cccc(Cl)c2nc1Cl ; C[C@@H](c1cc2cccc(Cl)c2nc1Cl)N1C(=O)c2ccccc2C1=O]

To a solution of (R)-1-(2,8-dichloroquinolin-3-yl)ethanol (22.00 g, 91 mmol) in THF (500 mL) were added PPh$_3$ (28.60 g, 1.2 eq), phthalimide (16.04 g, 1.2 eq), and DIAD (21.47 mL, 1.2 eq) dropwise. The reaction mixture was stirred at rt for 6 h and TLC (EtOAc/Hexane, 1/4) showed small amount of 1. To the reaction mixture were added PPh$_3$ (2.86 g, 0.12 eq), phthalimide (1.60 g, 0.12 eq), and DIAD (2.15 mL, 0.12 eq) and the mixture was stirred over night. The reaction mixture was concentrated and purified by column chromatography on silica gel (EtOAc/hexane, 1/4) to give a semi solid ~50 g To the semi solid was added hexane and EtoAc (10/1, 200 mL), the resulted solid was washed with hexane. The filtrate was concentrated and purified by column chromatography on silica gel (DCM/hexane, 2/1) to give a white foam. $^1$H NMR (400 MHz, CDCl$_3$) δ ppm 8.49 (s, 1H), 7.77-7.73 (m, 4H), 7.66-7.63 (m, 2H), 7.43 (t, J=8.0 Hz, 1H), 5.89 (q, J=8.0 Hz, 1H), 1.91 (d, J=8.0 Hz, 3H). Mass Spectrum (ESI) m/e=372 (M+1).

2-((S)-1-(8-Chloro-2-(pyridin-2-yl)quinolin-3-yl)ethyl)isoindoline-1,3-dione

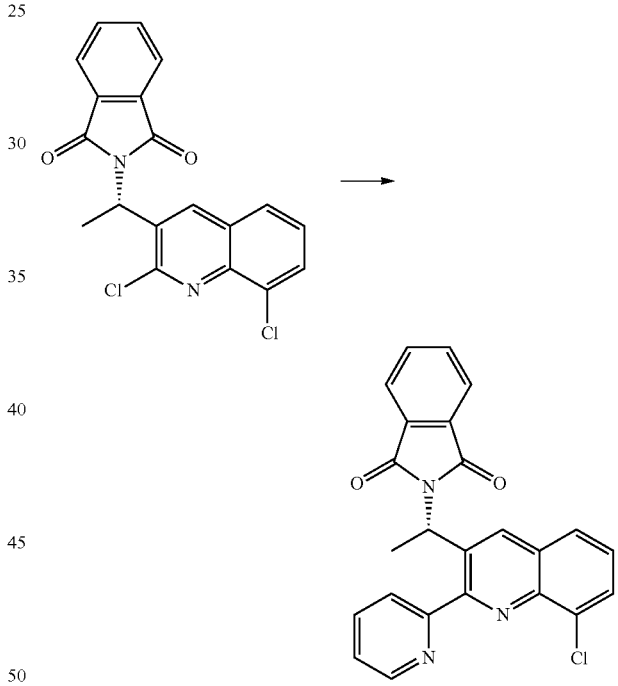

A mixture of (S)-2-(1-(2,8-dichloroquinolin-3-yl)ethyl) isoindoline-1,3-dione (22.7 g, 61 mmol), Pd(PPh$_3$)$_4$ (3.53 g, 0.05 eq) and 2-(tributylstannyl)pyridine (33.8 g, 80%, 1.2 eq) in dioxane (840 mL) was heated to 100° C. under N$_2$. After over night, LCSM showed around 50% starting material left. The reaction mixture was heated to 110° C. for additional 2 days. LCMS showed less than 10% starting material left. The reaction was heated to 120° C. for 5 h before cool to rt. Removal of solvent followed with column chromatography on silica gel (EtOAc/hexane, 0/1 to 1/3) gave an off white foam 14.2 g and the impure portions were combined and purified in the similar manner to give a white foam. $^1$H NMR (400 MHz, CDCl$_3$) δ ppm 8.69 (s, 1H), 8.66 (d, J=4.0 Hz, 1H), 7.94 (d, J=4.0 Hz, 1H), 7.85 (t, J=8.0 Hz, 1H), 7.75 (t, J=8.0 Hz, 1H), 7.70-7.65 (m, 4H), 7.50 (t, J=8.0

Hz, 1H), 7.33-7.29 (m, 1H), 6.58 (q, J=8.0 Hz, 1H), 2.02 (d, J=8.0 Hz, 3H). Mass Spectrum (ESI) m/e=414 (M+1).

N—((S)-1-(8-Chloro-2-(pyridin-2-yl)quinolin-3-yl)ethyl)-9H-purin-6-amine

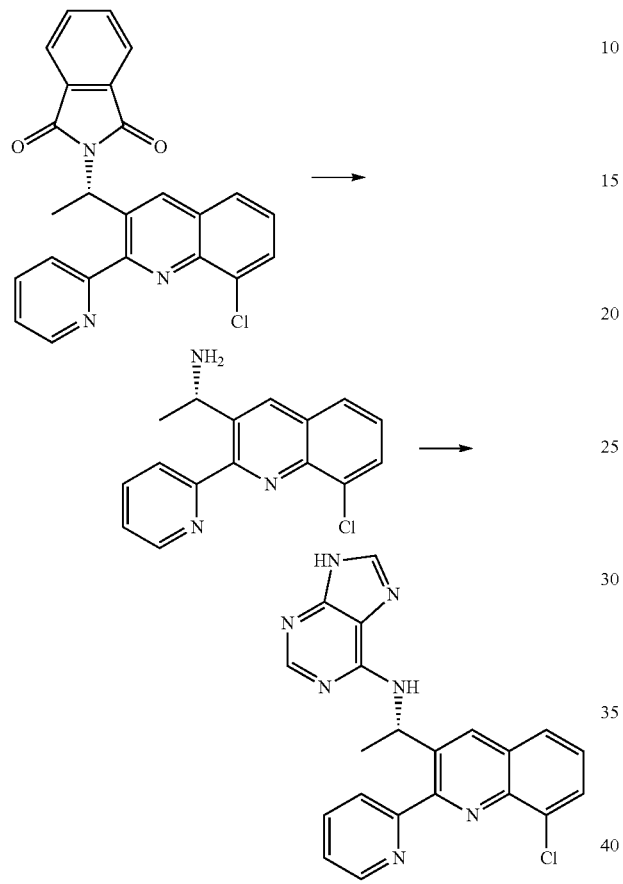

A solution of 2-((S)-1-(8-chloro-2-(pyridin-2-yl)quinolin-3-yl)ethyl)isoindoline-1,3-dione (16.8 g, 41 mmol) in EtOH (350 mL) was treated with NH$_2$NH$_2$ (29 mL) dropwise at rt (formation of a white solid upon addition) before heating at 90° C. for 30 min (the reaction became homogenous for 5 min and a new white solid formed) and cool to rt. The reaction mixture was filtered. The filter cake was washed with EtOAc. The combined organics were concentrated and partitioned between EtOAc (200 mL) and water (100 mL). The water layer was extracted with EtOAc (100 mL×2). The organics were washed with water, brine, dried over Na$_2$SO$_4$ and concentrated to give a yellow oil (16 g). The crude material was heated to 90° C./2 mmHg to remove a colorless liquid by product to give a heavy tan oil. A mixture of this oil (11 g, 38.8 mmol), 6-chloro-9H-purine (6.6 g, 1.1 eq) and hunig's base (8.2 mL, 1.2 eq) in n-BuOH (200 mL) was heated to 130° C. After over night, the concentrated reaction mixture was partitioned between EtOAc (500 mL) and water (300 mL). Water layer was extracted with EtOAc (200 mL×2). The combined organics were washed with water, brine, dried, concentrated and purified by column (DCM/MeOH, 15/1) to give a yellow foam (15.7 g, 96%) with 96% purity. The foam was further purified by careful column chromatography on silica gel (DCM/MeOH, 1/0 to 20/1) and the front fractions were checked by reverse HPLC (15 min, MeCN/water). The later fractions were combined and concentrated to give a white foam, which was treated with hot hexane to give a fine powder. $^1$H-NMR (400 Hz, DMSO-d$^6$) δ 12.66 (s, br, 1H), 8.54 (s, 1H), 8.50 (s, 1H), 8.12 (s, 1H), 7.92-7.84 (m, 2H), 7.77-7.74 (m, 3H), 7.39 (t, J=8.0 Hz, 1H), 7.34 (t, J=8.0 Hz, 1H), 5.91 (s, 1H), 1.48 (d, J=4.0 Hz, 3H). Mass Spectrum (ESI) m/e=402 (M+1).

Example 26

3-((S)-1-(9H-Purin-6-ylamino)ethyl)-2-(pyridin-2-yl)quinoline-8-carbonitrile

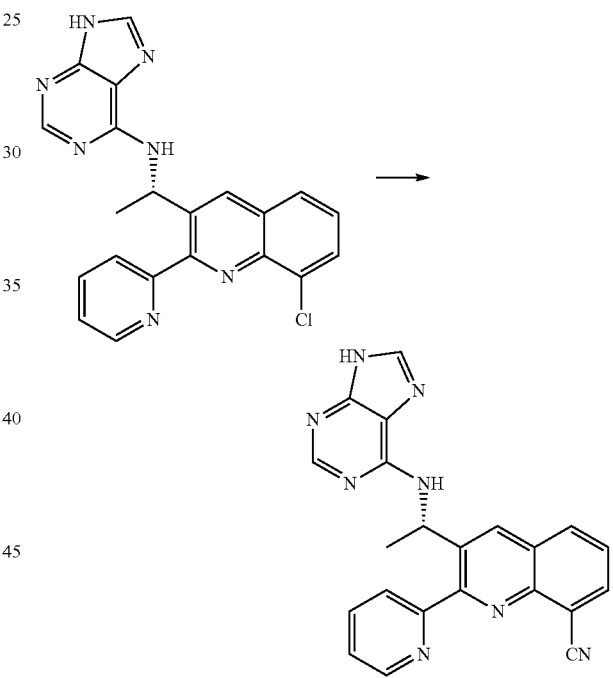

A mixture of N—((S)-1-(8-chloro-2-(pyridin-2-yl)quinolin-3-yl)ethyl)-9H-purin-6-amine (80 mg, 0.2 mmol), Pd(PPh$_3$)$_4$ (23 mg, 0.1 eq) and Zn(CN)$_2$ (117 mg, 5.0 eq) in DMF (5 mL) was purged with N$_2$ for 5 min before heating to 130° C. After 3 h, LCMS showed formation of trace amount of 2. The reaction was then heated to 165° C. over night. After cool to rt, the reaction was filtered through Celite™ and purified by reverse HPLC (MeCN/H$_2$O, 0.1% TFA) to give a white solid. $^1$H-NMR (400 Hz, DMSO-d$^6$) δ 8.83 (s, 1H), 8.72 (s, 1H), 8.52 (s, 1H), 8.42-8.37 (m, 3H), 8.14 (d, J=8.0 Hz, 1H), 8.08 (t, J=8.0 Hz, 1H), 7.79 (t, J=8.0 Hz, 1H), 7.55 (t, J=8.0 Hz, 1H), 6.24 (s, 1H), 1.72 (d, J=8.0 Hz, 3H). Mass Spectrum (ESI) m/e=393 (M+1).

Example 27

N—((S)-1-(2-(Pyridin-2-yl)quinolin-3-yl)ethyl)-9H-purin-6-amine

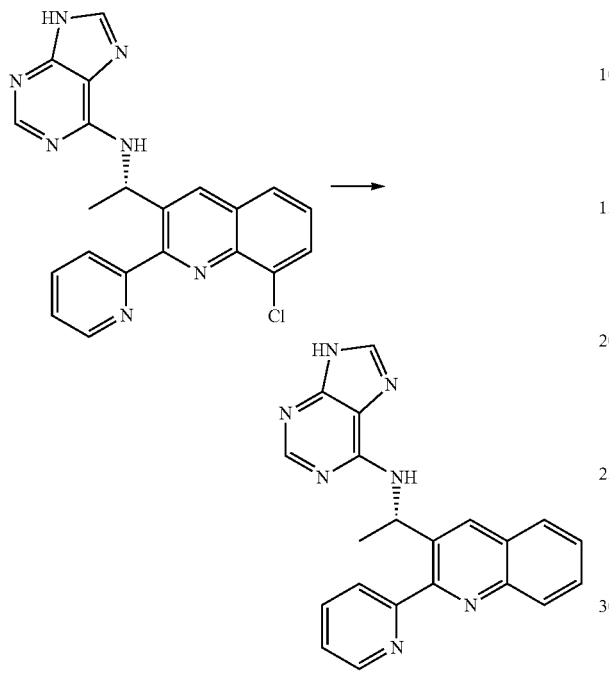

A mixture of 1 (53 mg, 0.13 mmol) in EtOH (1 mL) was treated with Pd/C (10%, 10 mg) and NH$_2$NH$_2$ (21 μl, 5.0 eq) for 2 h at refluxing. After cool to rt, the reaction mixture was partitioned between water and EtOAc. The organic layer was separated, washed with water, brine, dried and concentrated to give a white solid. $^1$H-NMR (400 Hz, CD$_3$OD) δ 9.25 (s, 1H), 9.06 (d, J=4.0 Hz, 1H), 8.55-8.47 (m, 4H), 8.27 (d, J=8.0 Hz, 2H), 8.07-8.02 (m, 2H), 7.88 (t, J=8.0 Hz, 1), 5.56-5.55 (m, 1H), 1.93 (d, J=8.0 Hz, 3H). MS (ESI) m/e=368 (M+1).

Example 28

1-(2-Chloro-7-fluoroquinolin-3-yl)ethanol

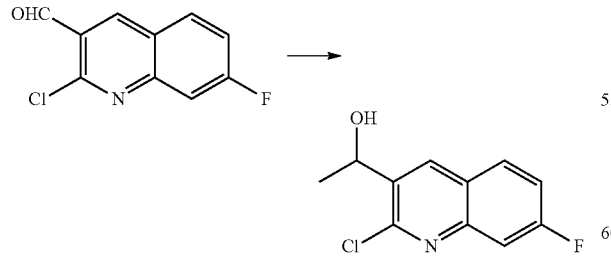

To a suspension of 2-chloro-7-fluoroquinoline-3-carbaldehyde (44.7 g, 213 mmol) in THF (600 mL) was treated with MeMgBr (78 mL, 1.1 eq) dropwise at −20° C. After overnight, the reaction was quenched with NH$_4$Cl solution and extracted with Ether (300 mL and 100 mL). The organics were washed with water, brine, dried over Na$_2$SO$_4$, concentrated and recrystalized from EtOAc (100 mL) and hexane (1 L). A pale yellow solid was obtained (41 g, 85%). $^1$H NMR (400 MHz, CDCl$_3$) δ ppm 8.41 (s, 1H), 7.87 (dd, J=8.0, 4.0 Hz, 1H), 7.67 (dd, J=8.0, 2.0 Hz, 1H), 7.38 (td, J=8.0, 2.0 Hz, 1H), 5.38 (q, J=4.0 Hz, 1H), 1.63 (d, J=4.0 Hz, 3H). Mass Spectrum (ESI) m/e=226 (M+1).

(S)-2-(1-(2-Chloro-7-fluoroquinolin-3-yl)ethyl)isoindoline-1,3-dione

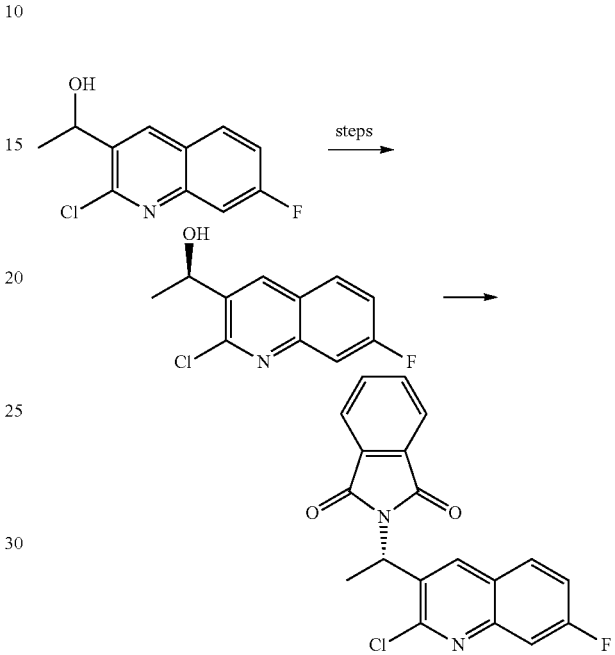

(S)-2-(1-(2-Chloro-7-fluoroquinolin-3-yl)ethyl)isoindoline-1,3-dione was prepared according to corresponding 8-Cl analog. $^1$H NMR (400 MHz, CDCl$_3$) δ ppm 8.48 (s, 1H), 7.85 (dd, J=8.0, 4.0 Hz, 1H), 7.75-7.73 (m, 2H), 7.65-7.63 (m, 2H), 7.55 (dd, J=8.0 Hz, 1H), 7.30 (td, J=8.0, 4.0 Hz, 1H), 5.88 (q, J=8.0 Hz, 1H), 1.90 (d, J=8.0 Hz, 3H). Mass Spectrum (ESI) m/e=355 (M+1).

N—((S)-1-(7-Fluoro-2-(2-(methylsulfonyl)phenyl)quinolin-3-yl)ethyl)-9H-purin-6-amine

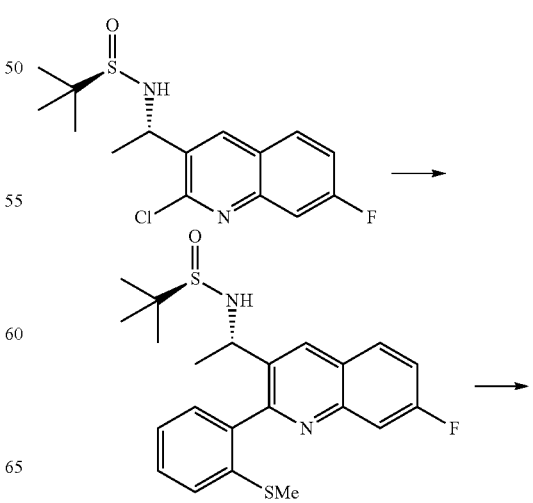

77
-continued

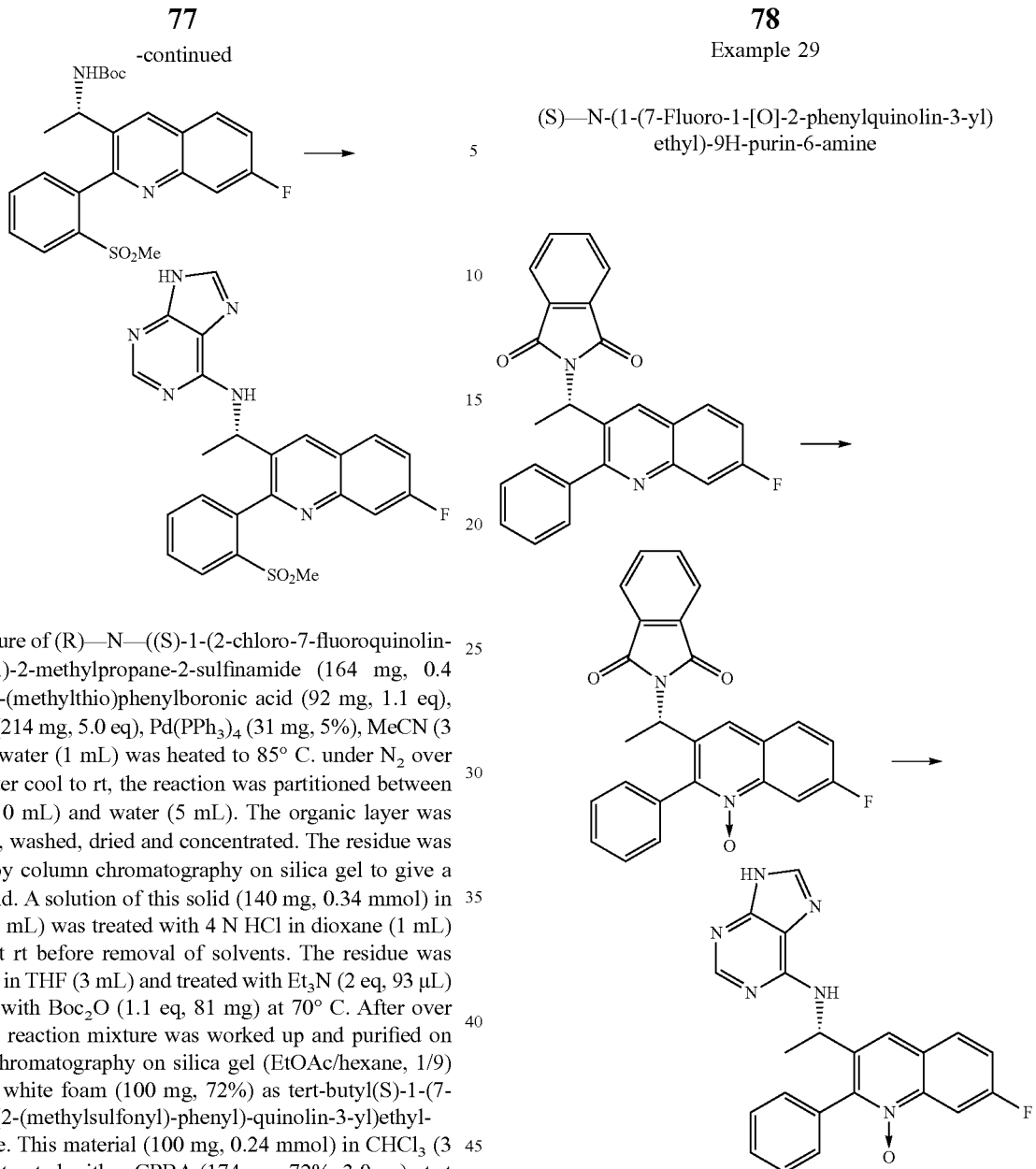

A mixture of (R)—N—((S)-1-(2-chloro-7-fluoroquinolin-3-yl)ethyl)-2-methylpropane-2-sulfinamide (164 mg, 0.4 mmol), 2-(methylthio)phenylboronic acid (92 mg, 1.1 eq), Na$_2$CO$_3$ (214 mg, 5.0 eq), Pd(PPh$_3$)$_4$ (31 mg, 5%), MeCN (3 mL) and water (1 mL) was heated to 85° C. under N$_2$ over night. After cool to rt, the reaction was partitioned between EtOAc (10 mL) and water (5 mL). The organic layer was separated, washed, dried and concentrated. The residue was purified by column chromatography on silica gel to give a white solid. A solution of this solid (140 mg, 0.34 mmol) in MeOH (2 mL) was treated with 4 N HCl in dioxane (1 mL) for 2 h at rt before removal of solvents. The residue was dissolved in THF (3 mL) and treated with Et$_3$N (2 eq, 93 µL) followed with Boc$_2$O (1.1 eq, 81 mg) at 70° C. After over night, the reaction mixture was worked up and purified on column chromatography on silica gel (EtOAc/hexane, 1/9) to give a white foam (100 mg, 72%) as tert-butyl(S)-1-(7-fluoro-2-(2-(methylsulfonyl)-phenyl)-quinolin-3-yl)ethyl-carbamate. This material (100 mg, 0.24 mmol) in CHCl$_3$ (3 mL) was treated with mCPBA (174 mg, 72%, 3.0 eq) at rt for 2 h. LCMS showed the desired MW+16. Work up. The residue was purified by column chromatography on silica gel (EtOAc/hexane, 1/1) to give two fractions, 1st (50 mg) and 2nd (20 mg) with the same M+1=461 on LCMS. The compounds were dissolved in MeOH (2 mL) and water (1 mL) and treated with TiCl$_3$ in water (30%, 10 drops) at rt for 2 h. The reaction mixture was partitioned between EtOAc and water. The organic layer was separated and washed with water, brine, dried and concentrated to give a white solid (83 mg), which was treated with TFA (1 mL) in DCM (1 mL) at rt for 2 h. The residue after removal of solvents was treated with 6-chloro-9H-purine (32 mg, 1.1 eq) and hunig's base (104 µl, 1.2 eq) in BuOH (2 mL) at 130° C. over night. After cool to rt, the reaction mixture was purified by reverse HPLC (MeCN/water/0.1 TFA, 10% to 60%) to give a white solid. $^1$H-NMR (400 Hz, CD$_3$OD) δ 9.35 (s, 1H), 8.53-8.47 (m, 2H), 8.25 (s, 1H), 7.98-7.76 (m, 6H), 5.85 (s, br, 0.4H), 5.58-5.56 (m, 0.6H), 3.19 (s, 3H), 1.88-1.81 (m, 3H). Mass Spectrum (ESI) m/e=463 (M+1).

78

Example 29

(S)—N-(1-(7-Fluoro-1-[O]-2-phenylquinolin-3-yl)ethyl)-9H-purin-6-amine

A mixture of (S)-2-(1-(7-fluoro-2-phenylquinolin-3-yl)ethyl)isoindoline-1,3-dione (33 mg, 83 µmol) and mCPBA (19 mg, 1.3 eq) in CHCl$_3$ (1 mL) was stirred at rt for 2 h. The reaction was partitioned between CHCl$_3$ and NaHCO$_3$. The organic was isolated and purified by column chromatography on silica gel (EtOAc/hexane, 3/1) to give a white solid, which was treated with hydrazine (0.1 mL) in EtOH (1 mL) at 35° C. for 2 h. Usual work up gave a colorless oil (25 mg). This oil was treated with 6-chloro-9H-purine (15 mg, 1.1 eq) and hunig's base (49 µl, 1.2 eq) in BuOH (1 mL) at 130° C. over night. After cool to rt, the reaction mixture was purified by reverse HPLC (MeCN/water/0.1 TFA, 10% to 60%) to give a white solid. $^1$H-NMR (400 Hz, CD$_3$OD) δ 8.67 (s, 1H), 8.48 (s, 2H), 8.30-8.28 (m, 2H), 7.75-7.41 (m, 7H), 5.42 (q, J=4.0 Hz, 1H), 1.71 (d, J=4.0 Hz, 3H). Mass Spectrum (ESI) m/e=401 (M+1).

Example 30

Preparation of N-((8-chloro-2-phenoxyquinolin-3-yl)methyl)-9H-purin-6-amine

8-chloro-2-phenoxyquinoline-3-carbaldehyde

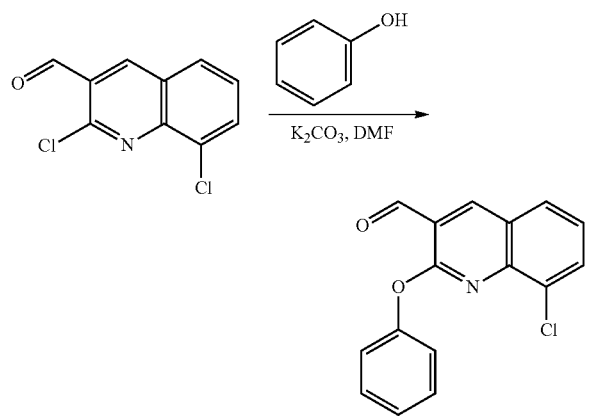

To a solution of 2,8-dichloroquinoline-3-carbaldehyde (1 eq) in DMF (0.25 M) was added phenol (1.5 eq) and K$_2$CO$_3$ (2.0 eq) at rt and the mixture was stirred for 3 h at rt. The mixture was diluted with water, extracted with EtOAc (2 times) and the combined organic layers were washed with water (2 times), dried over Na$_2$SO$_4$, filtered, and concentrated under reduced pressure. The crude product was purified by column chromatography on a Redi-Sep™ column using 0 to 40% gradient of EtOAc in hexane to provide 8-chloro-2-phenoxyquinoline-3-carbaldehyde.

(8-Chloro-2-phenoxyquinolin-3-yl)methanol

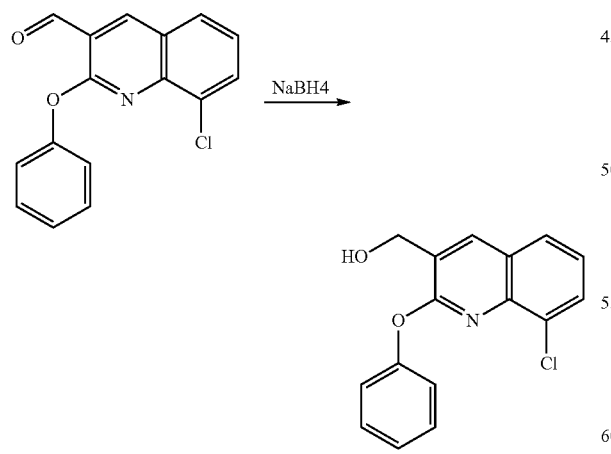

Prepared according to Procedure B using 8-chloro-2-phenoxyquinoline-3-carbaldehyde (1.0 eq) and solid sodium borohydride (1.5 eq) in THF (0.5 M) at 0° C. (8-chloro-2-phenoxyquinolin-3-yl)methanol was obtained after purification as a yellow solid.

8-Chloro-3-(chloromethyl)-2-phenoxyquinoline

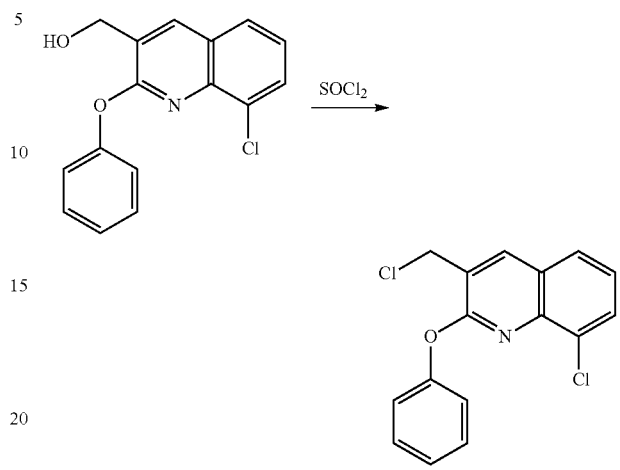

Prepared according to Procedure C using (8-chloro-2-phenoxyquinolin-3-yl)-methanol (1.0 eq) and SOCl$_2$ (5 eq) in CHCl$_3$ (0.25M) at rt. 8-chloro-3-(chloromethyl)-2-phenoxyquinoline was obtained after purification as a yellow oil.

(8-Chloro-2-phenoxyquinolin-3-yl)methanamine

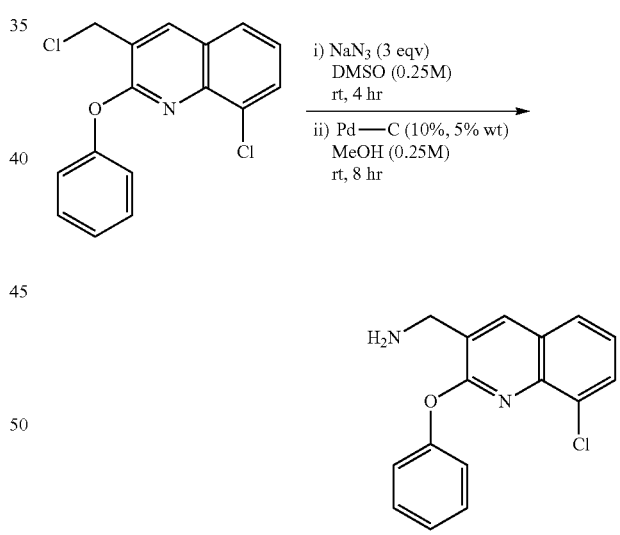

To a solution of 8-chloro-3-(chloromethyl)-2-phenoxyquinoline (1 eq) in DMSO (0.25 M) was added NaN$_3$ (3 eq) at rt and the mixture was stirred for 4 h at rt. The mixture was diluted with water, extracted with EtOAc (2 times) and the combined organic layers were washed with water (2 times), dried over Na$_2$SO$_4$, filtered, and concentrated under reduced pressure. The residue was dissolved in MeOH and treated with 10% Pd—C (5 wt %) and the mixture was then stirred under H$_2$ balloon over night. The mixture was filtered through a Celite™ pad followed by removal of solvents to give (8-chloro-2-phenoxyquinolin-3-yl)methanamine.

81

N-((8-Chloro-2-phenoxyquinolin-3-yl)methyl)-9H-purin-6-amine

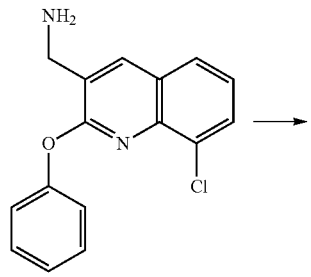

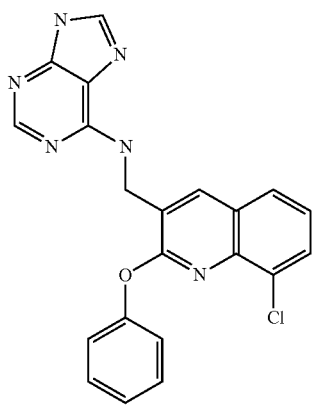

Prepared according to Procedure H using (8-chloro-2-phenoxyquinolin-3-yl)-methanamine (0.110 g, 0.360 mmol), 6-chloropurine (0.072 g, 0.46 mmol, 1.2 eq) and DIEA (0.72 mmol, 2.0 eq) in n-butanol (3 mL). N-((8-chloro-2-phenoxyquinolin-3-yl)methyl)-9H-purin-6-amine [PI3Kδ IC$_{50}$=125 nM] was obtained after purification as a white solid. $^1$H-NMR (MeOD) δ ppm 8.18-8.24 (s, 1H), 8.14-8.20 (s, 1H), 7.85-7.91 (d, J=7.58, 1H), 7.72-7.79 (d, J=7.34, 1H), 7.47-7.55 (m, 3H), 7.42-7.47 (m, 3H), 7.35-7.42 (m, 1H), 4.01-4.14 (m, 2H), Mass Spectrum (ESI) m/e=403 (M+1)

Example 31

N-((8-Chloro-2-(3-fluorophenyl)quinolin-3-yl)methyl)-9H-purin-6-amine

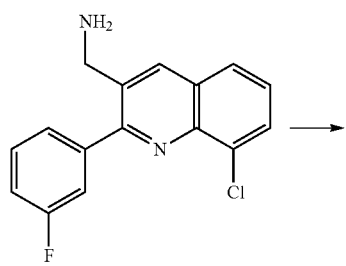

82

-continued

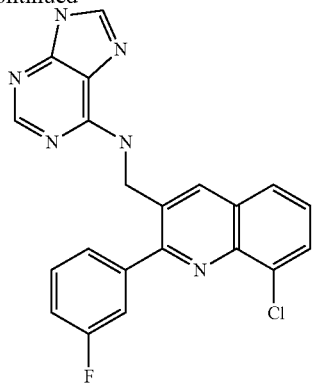

Prepared according to Procedure H using (8-chloro-2-(3-fluorophenyl)quinolin-3-yl)methanamine (0.030 g, 0.11 mmol), 6-chloropurine (0.019 g, 0.13 mmol, 1.2 eq) and DIEA in n-butanol (3 mL). N-((8-chloro-2-(3-fluorophenyl)quinolin-3-yl)methyl)-9H-purin-6-amine [PI3Kδ IC$_{50}$=74 nM] was obtained after purification as a white solid. $^1$H-NMR (MeOD) δ ppm 8.41 (s, 1H), 8.13 (s, 1H), 7.88-8.02 (m, 4H), 7.59 (dd, J=4.40, 2.20 Hz, 4H), 4.80-4.98 (m, 2H), Mass Spectrum (ESI) m/e=405 (M+1).

Example 32

N-((8-Chloro-2-phenylquinolin-3-yl)methyl)-7H-pyrrolo[2,3-d]pyrimidin-4-amine

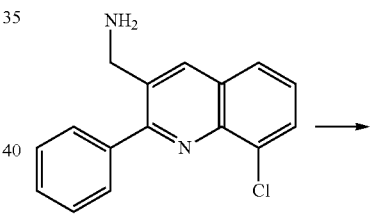

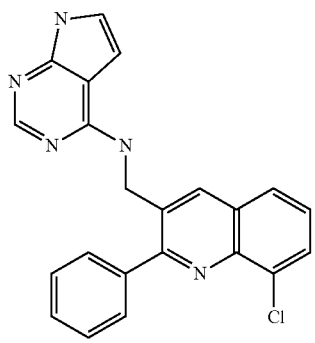

Prepared according to Procedure H using (8-chloro-2-phenylquinolin-3-yl)methanamine (0.050 g, 0.186 mmol), 4-chloro-7H-pyrrolo[2,3-d]pyrimidine (0.034 g, 0.22 mmol, 1.2 eq) and DIEA (0.38 mmol, 2.0 eq) in n-butanol (3 mL). N-((8-chloro-2-phenylquinolin-3-yl)methyl)-7H-pyrrolo[2,3-d]pyrimidin-4-amine [PI3Kδ IC$_{50}$=270 nM] was obtained after purification as a white solid. $^1$H-NMR (MeOD) δ ppm 8.65-8.76 (m, 1H), 8.53 (s, 1H), 8.11-8.20 (m, 4H), 8.07 (d, J=1.96 Hz, 1H), 7.91-8.00 (m, 2H), 7.86 (s, 1H), 7.51-7.58 (m, 2H), 4.73-4.85 (m, 2H), Mass Spectrum (ESI) m/e=386 (M+1).

Example 33

N-((8-Chloro-2-(3,5-difluorophenyl)quinolin-3-yl)methyl)-9H-purin-6-amine

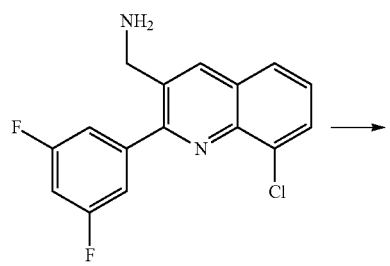

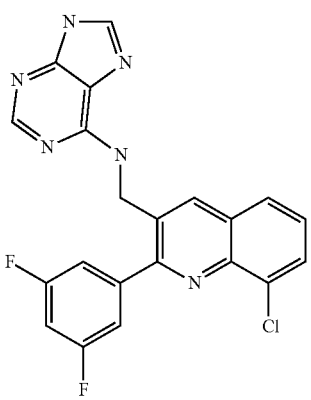

Prepared according to Procedure H using (8-chloro-2-(3,5-difluorophenyl)-quinolin-3-yl)methanamine (0.105 g, 0.345 mmol), 6-chloropurine (0.064 g, 0.41 mmol, 1.2 eq) and DIEA (0.70 mmol, 2.0 eq) in n-butanol (3 mL). N-((8-chloro-2-(3,5-difluorophenyl)quinolin-3-yl)methyl)-9H-purin-6-amine [PI3Kδ IC$_{50}$=76 nM] was obtained after purification as a white solid. $^1$H-NMR (MeOD) δ ppm 8.48 (s, 1H), 8.35 (s, 1H), 8.24 (s, 1H), 7.86-7.94 (m, 2H), 7.52-7.61 (m, 1H), 7.27-7.35 (m, 2H), 6.96-7.06 (m, 1H), 4.73 (d, J=5.71, 2H), Mass Spectrum (ESI) m/e=423 (M+1).

Example 34

N-((8-Chloro-2-(2-chloro-5-fluorophenyl)quinolin-3-yl)methyl)-9H-purin-6-amine

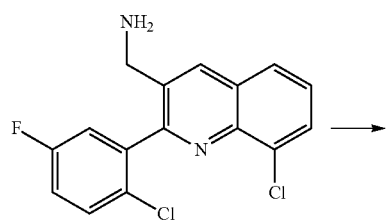

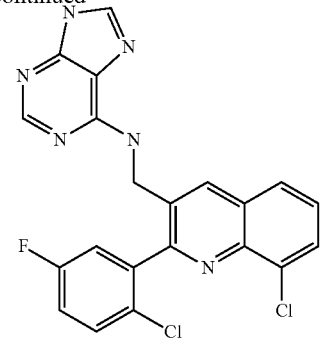

Prepared according to Procedure H using (8-chloro-2-(2-chloro-5-fluorophenyl)-quinolin-3-yl)methanamine (0.050 g, 0.156 mmol), 6-chloropurine (0.027 g, 0.17 mmol, 1.2 eq) and DIEA (0.70 mmol, 2.0 eq) in n-butanol (3 mL). N-((8-chloro-2-(2-chloro-5-fluorophenyl)quinolin-3-yl)methyl)-9H-purin-6-amine [PI3Kδ IC$_{50}$=71 nM] was obtained after purification as a white solid. $^1$H-NMR (MeOD) δ ppm 8.30 (s, 1H), 8.20 (s, 1H), 7.80 (dd, J=7.58, 0.49 Hz, 2H), 7.69-7.75 (m, 1H), 7.42-7.47 (m, 1H), 7.31-7.37 (m, 1H), 7.11-7.16 (m, 1H), 6.99-7.06 (m, 1H), 4.90-497. (m, 2H), Mass Spectrum (ESI) m/e=440 (M+1)

Example 35

N-((8-chloro-2-(2-(methylsulfonyl)phenyl)quinolin-3-yl)methyl)-9H-purin-6-amine

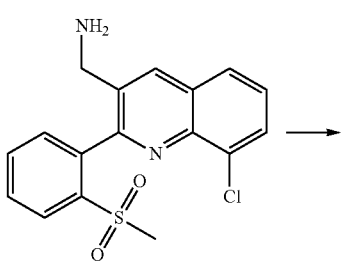

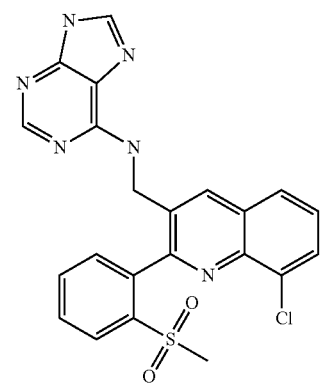

Prepared according to Procedure H using (8-chloro-2-(2-(methylsulfonyl)phenyl) quinolin-3-yl)methanamine (0.060 g, 0.173 mmol), 6-chloropurine (0.032 g, 0.21 mmol, 1.2 eq) and DIEA (0.34 mmol, 2.0 eq) in n-butanol (3 mL). N-((8-chloro-2-(2-(methylsulfonyl)phenyl)quinolin-3-yl)methyl)-9H-purin-6-amine [PI3Kδ IC$_{50}$=222 nM] was obtained after purification as a white solid. $^1$H-NMR (MeOD) δ ppm 8.29 (s, 1H), 8.13 (s, 1H), 8.01-8.09 (m, 2H), 7.78-7.81 (m, 1H), 7.66-7.76 (m, 1H), 7.57-7.65 (m, 1H), 7.46 (d, J=7.83 Hz, 2H), 4.87-4.98 (m, 2H), 3.28 (s, 3H), Mass Spectrum (ESI) m/e=465 (M+1).

Example 36

N-((2-(2-Chlorophenyl)-7-fluoroquinolin-3-yl)methyl)-9H-purin-6-amine

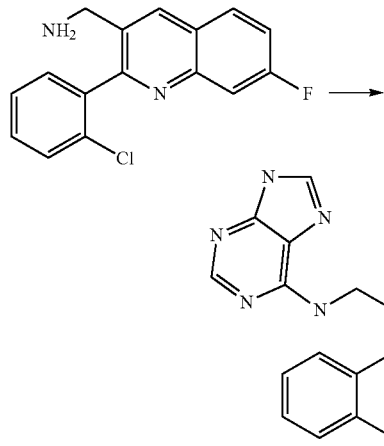

Prepared according to Procedure H using (2-(2-chlorophenyl)-7-fluoroquinolin-3-yl)methanamine (0.080 g, 0.279 mmol), 6-chloropurine (0.065 g, 0.42 mmol, 1.5 eq) and DIEA (0.56 mmol, 2.0 eq) in n-butanol (3 mL). N-((2-(2-chlorophenyl)-7-fluoroquinolin-3-yl)methyl)-9H-purin-6-amine [PI3Kδ IC$_{50}$=225 nM] was obtained after purification as a white solid. $^1$H-NMR (MeOD) δ ppm 8.49 (s, 1H), 8.14 (s, 1H), 8.03-8.10 (m, 2H), 7.66-7.73 (m, 2H), 7.47-7.56 (m, 2H), 7.43-7.44 (m, 1H), 7.33-7.40 (m, 1H), 4.10-4.18 (m, 2H), Mass Spectrum (ESI) m/e=405 (M+1).

Example 37

N-((2-(2-Chlorophenyl)-6-fluoroquinolin-3-yl)methyl)-9H-purin-6-amine

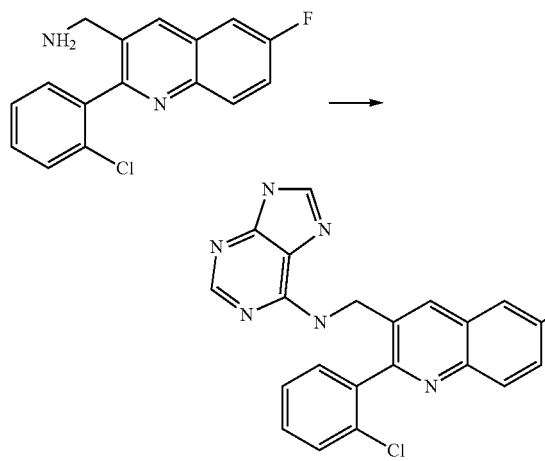

Prepared according to Procedure H using (2-(2-chlorophenyl)-6-fluoroquinolin-3-yl)methanamine (0.080 g, 0.279 mmol), 6-chloropurine (0.065 g, 0.42 mmol, 1.5 eq) and DIEA (0.56 mmol, 2.0 eq) in n-butanol (3 mL). N-((2-(2-chlorophenyl)-6-fluoroquinolin-3-yl)methyl)-9H-purin-6-amine [PI3Kδ IC$_{50}$=1683 nM] was obtained after purification as a white solid. $^1$H-NMR (MeOD) δ ppm 8.44 (s, 1H), 8.14 (s, 1H), 8.07-8.11 (m, 2H), 7.66-7.71 (m, 1H), 7.59-7.66 (m, 1H), 7.49-7.55 (m, 2H), 7.40-7.46 (m, 1H), 7.34-7.40 (m, 1H), 4.05-4.17 (m, 2H), Mass Spectrum (ESI) m/e=405 (M+1).

Example 38

N-((2-(2-Chlorophenyl)-6,7-difluoroquinolin-3-yl)methyl)-9H-purin-6-amine

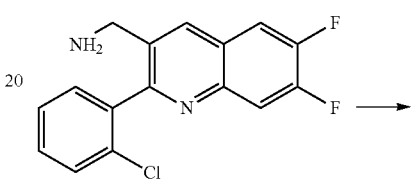

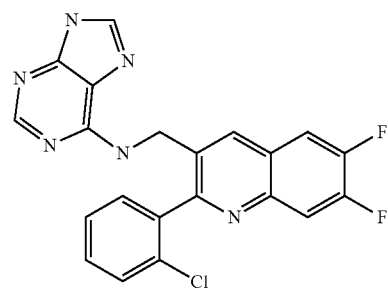

Prepared according to Procedure H using (2-(2-chlorophenyl)-6,7-difluoroquinolin-3-yl)methanamine (0.080 g, 0.279 mmol), 6-chloropurine (0.065 g, 0.42 mmol, 1.5 eq) and DIEA (0.56 mmol, 2.0 eq) in n-butanol (3 mL). N-((2-(2-chlorophenyl)-6,7-difluoroquinolin-3-yl)methyl)-9H-purin-6-amine [PI3Kδ IC$_{50}$=551 nM] was obtained after purification as a white solid. $^1$H-NMR (MeOD) δ ppm 8.46 (s, 1H), 8.13 (s, 1H), 8.09 (s, 1H), 7.83-7.94 (m, 3H), 7.49-7.55 (m, 2H), 7.41-7.48 (m, 1H), 7.35-7.41 (m, 1H), 4.89-4.85 (m, 2H), Mass Spectrum (ESI) m/e=423 (M+1).

Example 39

N-((2-(2-(Benzyloxy)-5-fluorophenyl)-8-chloroquinolin-3-yl)methyl)-9H-purin-6-amine

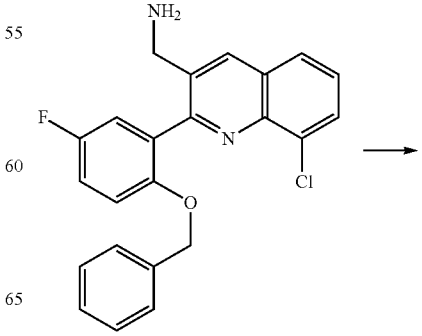

-continued

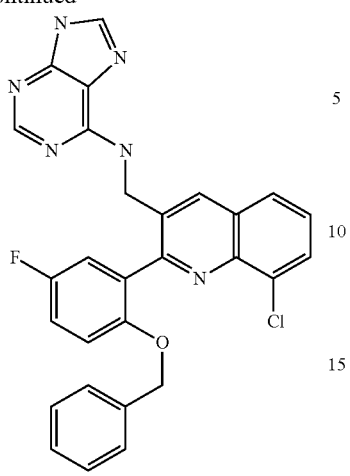

Prepared according to Procedure H using (2-(2-(benzyloxy)-5-fluorophenyl)-8-chloroquinolin-3-yl)methanamine (0.021 g, 0.053 mmol), 6-chloropurine (0.012 g, 0.06 mmol, 1.5 eq) and DIEA (0.1 mmol, 2.0 eq) in n-butanol (3 mL). N-((2-(2-(benzyloxy)-5-fluorophenyl)-8-chloroquinolin-3-yl)methyl)-9H-purin-6-amine [PI3Kδ IC$_{50}$=31 nM] was obtained after purification as a white solid. $^1$H-NMR (MeOD) δ ppm 8.38 (s, 1H), 8.12 (s, 1H), 8.07 (s, 1H), 7.90 (s, 1H), 7.88 (s, 1H), 7.52-7.59 (t, 1H), 7.21-7.25 (m, 2H), 7.19 (m, 4H), 7.06-7.12 (m, 2H), 5.05-5.10 (m, 2H), 4.90-4.96 (s, 2H), Mass Spectrum (ESI) m/e=511 (M+1).

Example 40

N—((S)-1-(8-Chloro-2-(3-fluorophenyl)quinolin-3-yl)ethyl)-9H-purin-6-amine and N—((R)-1-(8-Chloro-2-(3-fluorophenyl)quinolin-3-yl)ethyl)-9H-purin-6-amine

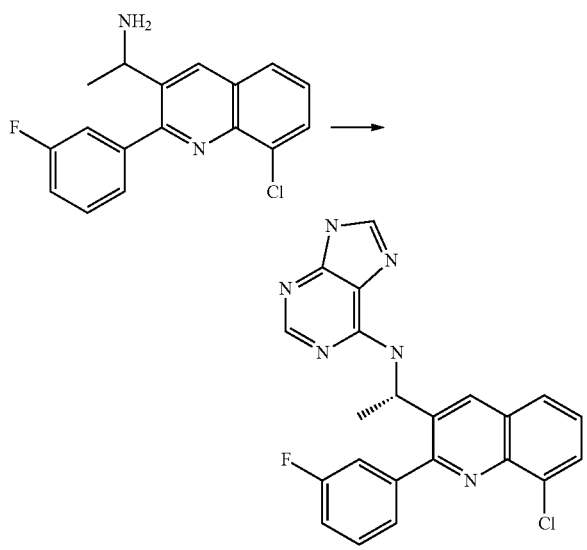

-continued

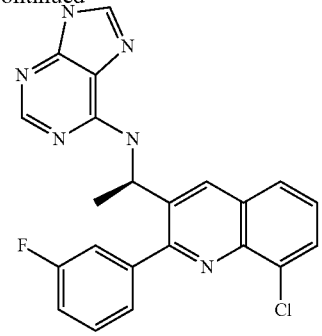

A mixture of (2-(2-(benzyloxy)-5-fluorophenyl)-8-chloroquinolin-3-yl)-methanamine (0.120 g, 0.40 mmol) in n-butanol (5 mL) was treated with DIEA (0.80 mmol, 2.0 eq) followed with 6-chloropurine (0.075 g, 0.48 mmol, 1.2 eq) at 100° C. for 8 h. The reaction mixture was concentrated and purified by column chromatography on a Redi-Sep™ column using 0 to 100% gradient of CH$_2$Cl$_2$:MeOH: NH$_4$OH (89:9:1) in CH$_2$Cl$_2$ as eluent to provide the mixture of N—((S)-1-(8-chloro-2-(3-fluorophenyl)quinolin-3-yl) ethyl)-9H-purin-6-amine and N—((R)-1-(8-chloro-2-(3-fluorophenyl)quinolin-3-yl)ethyl)-9H-purin-6-amine. Further separation by chiral HPLC with IA column at IPA/ Hexane (10%) provides N—((S)-1-(8-chloro-2-(3-fluorophenyl)quinolin-3-yl)ethyl)-9H-purin-6-amine [PI3Kδ IC$_{50}$=6 nM] as a white solid. $^1$H-NMR (MeOD) δ ppm 8.43 (s, 1H), 8.05 (s, 1H), 7.98 (s, 1H), 7.73-7.80 (m, 2H), 7.48-7.53 (m, 1H), 7.44-7.49 (m, 1H), 7.35-7.44 (m, 2H), 7.04-7.11 (m, 1H), 1.44-1.47 (d, 3H), Mass Spectrum (ESI) m/e=419 (M+1), and N—((R)-1-(8-chloro-2-(3-fluorophenyl)-quinolin-3-yl)ethyl)-9H-purin-6-amine [PI3Kδ IC$_{50}$=424 nM] as a white solid. $^1$H-NMR (MeOD) δ ppm, 8.56 (s, 1H), 8.17 (s, 1H), 8.10 (s, 1H), 7.84-7.93 (m, 2H), 7.45-7.66 (m, 4H), 7.14-7.23 (m, 1H), 3.89-3.98 (m, 1H), 1.57-1.60 (d, 3H) Mass Spectrum (ESI) m/e=419 (M+1).

Example 41

N—((S)-1-(8-Chloro-2-(2-chloro-5-fluorophenyl) quinolin-3-yl)ethyl)-9H-purin-6-amine

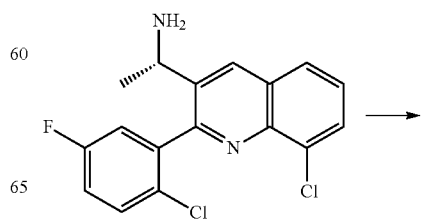

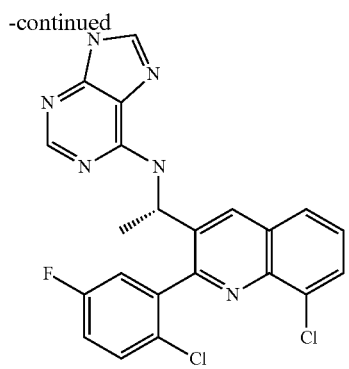

Prepared according to Procedure H using (1S)-1-(8-chloro-2-(2-chloro-5-fluoro-phenyl)quinolin-3-yl)ethanamine (0.072 g, 0.215 mmol), 6-chloropurine (0.040 g, 0.26 mmol, 1.2 eq) and DIEA (0.42 mmol, 2.0 eq) in n-butanol (3 mL). N—((S)-1-(8-chloro-2-(2-chloro-5-fluorophenyl)quinolin-3-yl)ethyl)-9H-purin-6-amine [PI3Kδ IC$_{50}$=8 nM] was obtained after purification as a white solid. $^1$H-NMR (MeOD) δ ppm 8.68 (s, 1H), 8.60 (s, 1H), 8.02-8.10 (m, 2H), 7.92-7.99 (m, 1H), 7.85-7.93 (m, 1H), 7.54-7.63 (m, 1H), 7.50 (dd, J=8.80, 4.89 Hz, 1H), 7.07 (td, J=8.61, 3.13 Hz, 1H), 5.48-5.65 (m, 1H), 1.71 (d, J=7.04 Hz, 3H), Mass Spectrum (ESI) m/e=454 (M+1).

Example 42

N—((S)-1-(8-Chloro-2-(3-fluorophenyl)quinolin-3-yl)propyl)-9H-purin-6-amine

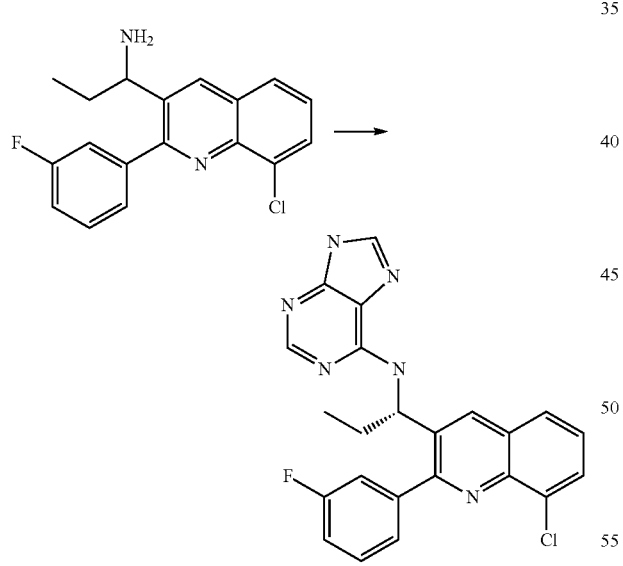

A mixture of 1-(8-chloro-2-(3-fluorophenyl)quinolin-3-yl)propan-1-amine (0.060 g, 0.19 mmol) in n-butanol (5 mL) was treated with DIEA (0.38 mmol, 2.0 eq) followed with 6-chloropurine (0.029 g, 0.19 mmol, 1.0 eq) at 100° C. for 8 h. The reaction mixture was concentrated and purified by column chromatography on a Redi-Sep™ column using 0 to 100% gradient of CH$_2$Cl$_2$:MeOH:NH$_4$OH (89:9:1) in CH$_2$Cl$_2$ as eluent to provide the mixture of N—((S)-1-(8-chloro-2-(3-fluoro-phenyl)quinolin-3-yl)propyl)-9H-purin-6-amine and N—((R)-1-(8-chloro-2-(3-fluorophenyl)quinolin-3-yl)propyl)-9H-purin-6-amine. Further separation by chiral HPLC with IA column at IPA/Hexane (10%) provides N—((S)-1-(8-chloro-2-(3-fluorophenyl)quinolin-3-yl)propyl)-9H-purin-6-amine [PI3Kδ IC$_{50}$=13 nM] as a white solid. $^1$H-NMR (MeOD) δ ppm 8.39 (s, 1H), 8.08 (s, 1H), 8.01 (s, 1H), 7.72-7.78 (m, 2H), 7.51-7.60 (m, 2H), 7.38-7.47 (m, 2H), 7.10-7.16 (m, 1H), 3.82 (m, 1H), 1.74-1.84 (m, 2H), 1.03-1.11 (t, 3H), Mass Spectrum (ESI) m/e=433 (M+1)

Example 43

N—((S)-1-(5-Chloro-3-(3-fluorophenyl)quinolin-2-yl)ethyl)-9H-purin-6-amine

Prepared according to Procedure H using (1S)-1-(5-chloro-3-(3-fluorophenyl)-quinolin-2-yl)ethanamine (0.050 g, 0.166 mmol), 6-chloropurine (0.031 g, 0.20 mmol, 1.2 eq) and DIEA (0.33 mmol, 2.0 eq) in n-butanol (3 mL). N—((S)-1-(5-chloro-3-(3-fluorophenyl)quinolin-2-yl)ethyl)-9H-purin-6-amine [PI3Kδ IC$_{50}$=5 nM] was obtained after purification as a white solid. $^1$H-NMR (MeOD) δ ppm 9.22 (s, 1H), 8.63 (s, 1H), 8.44-8.47 (m, 3H), 8.42 (s, 1H), 8.34 (s, 1H), 7.87-7.94 (m, 2H), 7.56 (t, 1H), 1.79 (d, 3H), Mass Spectrum (ESI) m/e=419 (M+1).

Example 44

N—((S)-1-(8-Chloro-2-(thiazol-4-yl)quinolin-3-yl)ethyl)-9H-purin-6-amine

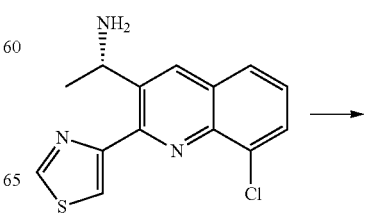

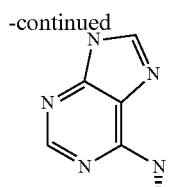

Prepared according to Procedure H using (1S)-1-(8-chloro-2-(thiazol-4-yl)-quinolin-3-yl)ethanamine (0.045 g, 0.155 mmol), 6-chloropurine (0.029 g, 0.19 mmol, 1.2 eq) and DIEA (0.33 mmol, 2.0 eq) in n-butanol (3 mL). N—((S)-1-(8-chloro-2-(thiazol-4-yl)quinolin-3-yl)ethyl)-9H-purin-6-amine [PI3Kδ IC$_{50}$=16 nM] was obtained after purification as a white solid. $^{1}$H-NMR (MeOD) δ ppm 9.22 (s, 1H), 8.63 (s, 1H), 8.44-8.46 (m, 1H), 8.42 (s, 1H), 8.34 (s, 1H), 7.88-7.93 (m, 2H), 7.56 (t, 1H), 1.77 (d, 3H), Mass Spectrum (ESI) m/e=408 (M+1).

Example 45

N—((S)-1-(7-Fluoro-2-(pyridin-3-yl)quinolin-3-yl)ethyl)-9H-purin-6-amine

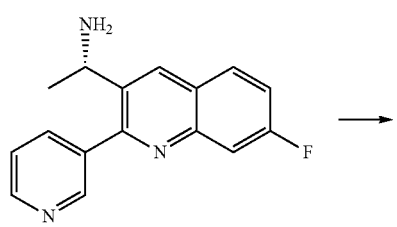

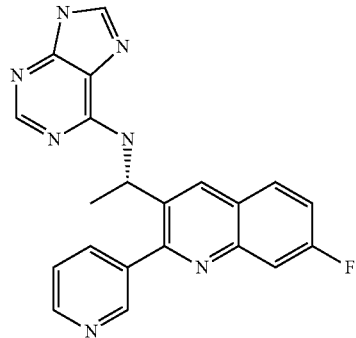

Prepared according to Procedure H using (1S)-1-(7-fluoro-2-(pyridin-3-yl)-quinolin-3-yl)ethanamine (0.067 g, 0.236 mmol), 6-chloropurine (0.044 g, 0.283 mmol, 1.2 eq) and DIEA (0.48 mmol, 2.0 eq) in n-butanol (3 mL). N—((S)-1-(7-fluoro-2-(pyridin-3-yl)quinolin-3-yl)ethyl)-9H-purin-6-amine [PI3Kδ IC$_{50}$=23 nM] was obtained after purification as a white solid. $^{1}$H-NMR (MeOD) δ ppm 8.99 (s, 1H), 8.57-8.65 (m, 2H), 8.33 (d, J=7.83 Hz, 1H), 8.16 (s, 1H), 8.08 (s, 1H), 7.85-7.96 (m, 2H), 1.62 (d, 3H), Mass Spectrum (ESI) m/e=402 (M+1).

Example 46

N—((S)-1-(7-Fluoro-2-(thiophen-2-yl)quinolin-3-yl)ethyl)-9H-purin-6-amine

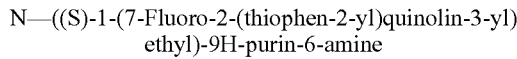

Prepared according to Procedure H using (1S)-1-(7-fluoro-2-(thiophen-2-yl)-quinolin-3-yl)ethanamine (0.078 g, 0.286 mmol), 6-chloropurine (0.053 g, 0.344 mmol, 1.2 eq) and DIEA (0.58 mmol, 2.0 eq) in n-butanol (3 mL). N—((S)-1-(7-fluoro-2-(thiophen-2-yl)quinolin-3-yl)ethyl)-9H-purin-6-amine [PI3Kδ IC$_{50}$=8 nM] was obtained after purification as a white solid. $^{1}$H-NMR (MeOD) δ ppm 8.62 (s, 1H), 8.43 (s, 1H), 8.37 (s, 1H), 8.00-8.07 (m, 1H), 7.62-7.73 (m, 3H), 7.43-7.51 (m, 1H), 7.18 (m 1H), 1.78 (d, J=7.04 Hz, 3H), 1H), Mass Spectrum (ESI) m/e=391 (M+1).

Example 47

1-(2,5-Dichloroquinolin-3-yl)ethanol

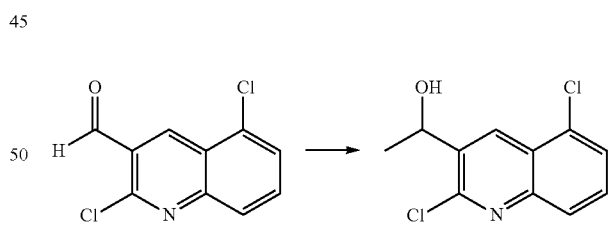

Dissolved 2,5-dichloroquinoline-3-carbaldehyde (2.46 g, 11 mmol) in THF (70 mL) and submerged in an ice-bath. Added methylmagnesium bromide (5.4 mL, 16 mmol) and removed the ice-bath. After 10 min. the reaction mixture was poured into 1.0 N HCl and extracted with EtOAc. The organic layer was dried with sodium sulfate, filtered, and concentrated. The residue was chromatographed on 80 g silica gel column with 0-40% EtOAc:Hex. The desired fractions were combined and concentrated to yield an off white, crystalline solid. 1H NMR (400 MHz, DCM-d$_{2}$) δ ppm 1.60 (d, J=6.26 Hz, 3H) 2.35 (br. s., 1H) 5.36 (q, J=6.39 Hz, 1H) 7.61-7.67 (m, 2H) 7.87-7.94 (m, 1H) 8.75 (s, 1H). LC-MS (+esi, M+H$^{+}$=242.1).

2-(1-(2,5-Dichloroquinolin-3-yl)ethyl)isoindoline-1,3-dione

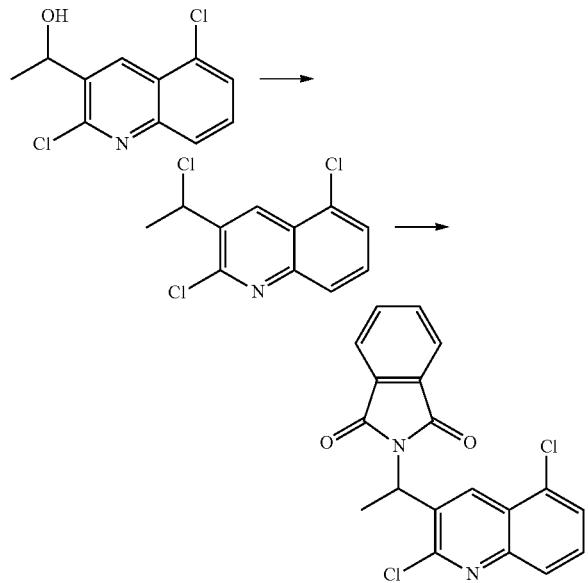

Added DCM (2 mL) to 1-(2,5-dichloroquinolin-3-yl)ethanol (200 mg, 826 µmol). Added thionyl chloride (301 µl, 4131 µmol). Obtained a clear colorless solution within minutes. Concentrated reaction mixture to dryness on the rotavap to obtain an oil, which was used without further purification. LC-MS (+esi, M+H$^+$=260.0). Dissolved 2,5-dichloro-3-(1-chloroethyl)quinoline (215 mg, 825 µmol) in DMF (2 mL) and added phthalimide (127 mg, 866 µmol) and K$_2$CO$_3$ (228 mg, 1650 µmol). Submerged in oil bath and began heating to 55° C. After 10 min the temperature of the oil bath was raised to 80° C. After 30 more minutes the reaction mixture was partitioned between EtOAc:H$_2$O. The organic layer was washed with water (3×), dried with sodium sulfate, filtered, and concentrated. The crude was solid was chromatographed on 12 g silica gel column with 0-20% EtOAc:Hex. The desired fractions were combined and concentrated to yield a white crystalline solid. 1H NMR (400 MHz, DICHLOROMETHANE-d$_2$) δ ppm 1.99 (d, J=7.04 Hz, 3H) 5.93 (q, J=7.17 Hz, 1H) 7.64-7.70 (m, 2H) 7.71-7.76 (m, 2H) 7.77-7.83 (m, 2H) 7.88-7.93 (m, 1H) 8.95 (s, 1H). LC-MS (+esi, M+H$^+$=371.0)

2-(1-(5-Chloro-2-(pyridin-2-yl)quinolin-3-yl)ethyl)isoindoline-1,3-dione

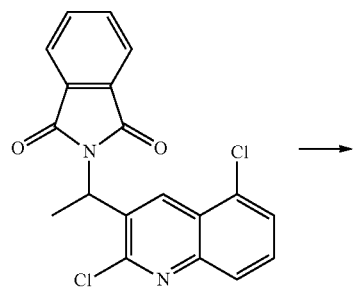

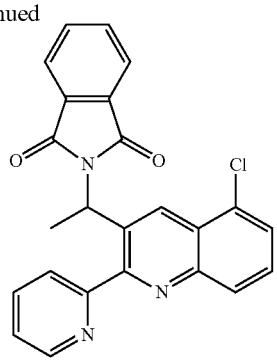

Transferred 2-(1-(2,5-dichloroquinolin-3-yl)ethyl)isoindoline-1,3-dione (197 mg, 531 µmol) from 100 mL flask to 10 mL flask by dissolving/slurrying in toluene and concentrating. Added Pd(Ph$_3$P)$_4$ (61 mg, 53 µmol) and 2-tri-n-butylstannylpyridine (955 µl, 2653 µmol). Bubbled argon through mixture for 30 sec. Equipped with condensor and nitrogen inlet. Heated at 110° C. for ~16 h. The reaction mixture was concentrated and chromatographed on 12 g silica gel column with 0-60% EtOAc. The desired fractions were combined and concentrated to yield an oil. NMR indicates residual EtOAc. LC. 1H NMR (400 MHz, DICHLOROMETHANE-d$_2$) δ ppm 1.98 (d, J=7.04 Hz, 3H) 6.38 (q, J=7.04 Hz, 1H) 7.24-7.37 (m, 1H) 7.62-7.76 (m, 8H) 8.01 (dd, J=8.61, 1.96 Hz, 1H) 8.56-8.66 (m, 1H) 9.02 (s, 1H). -MS (+esi, M+H+=414.1)

1-(5-Chloro-2-(pyridin-2-yl)quinolin-3-yl)ethanamine

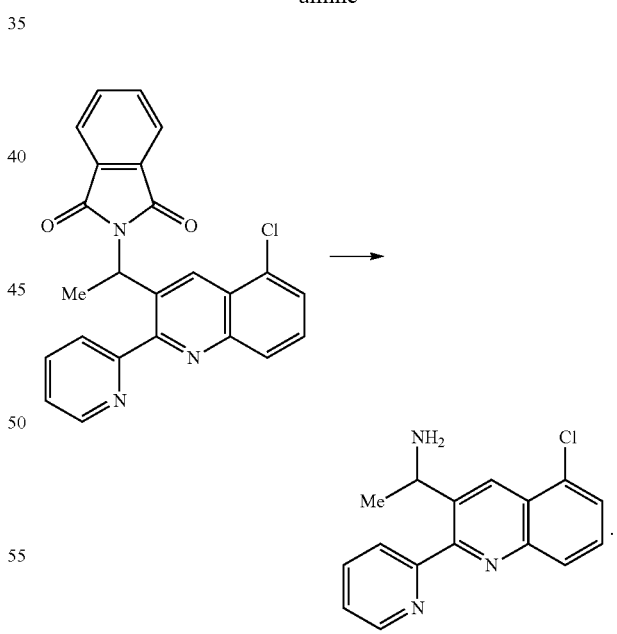

2-(1-(5-Chloro-2-(pyridin-2-yl)quinolin-3-yl)ethyl)isoindoline-1,3-dione (220 mg, 532 µmol) was added to EtOH. To the resulting slurry was added hydrazine hydrate (133 µl, 2658 µmol) and the mixture was heated in an oil bath at 80° C. for 3 h. The reaction mixture was cooled to room temperature, filtered, and rinsed with EtOH (~10 mL). The filtrate was acidified with 1.0 N HCl (~5 mL) and concentrated on the rotavap to remove ethanol. A minor amount of solid precipitated and was removed by filtration. The filtrate was neutralized with solid sodium carbonate and extracted (2×) with DCM:IPA (4:1). The organic extracts were dried with sodium sulfate, filtered and concentrated to obtain 103 mg (68%) of a solid/film. LC-MS (+esi, M+H$^+$=284.0). 1H NMR (400 MHz, DICHLOROMETHANE-d$_2$) δ ppm 1.42 (d, J=6.65 Hz, 3H) 4.71 (q, J=6.65 Hz, 1H) 7.38-7.42 (m, 1H) 7.60-7.68 (m, 2H) 7.88-7.97 (m, 2H) 8.02 (dq, J=7.78, 0.80 Hz, 1H) 8.68-8.71 (m, 1H) 8.82 (t, J=0.78 Hz, 1H). LC-MS (+esi, M+H$^+$=284.0).

N-(1-(5-Chloro-2-(pyridin-2-yl)quinolin-3-yl)ethyl)-9H-purin-6-amine

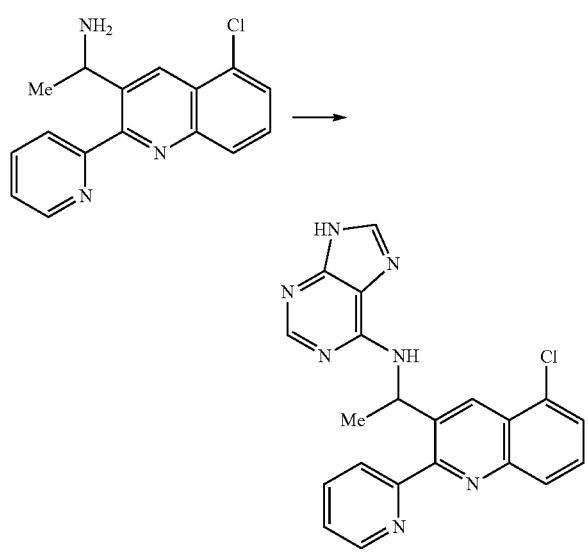

Added 1-(5-chloro-2-(pyridin-2-yl)quinolin-3-yl)ethanamine (103 mg, 363 μmol), 6-bromopurine (72 mg, 363 μmol), n-butanol (2 mL) and DIPEA (190 μl, 1089 μmol) to a 10 mL flask. Submerged in an oil bath and heated at 110° C. for 40 h. The reaction mixture was concentrated on the rotavap to ~0.5 mL of solvent, diluted with DCM, and chromatographed with 0-15% MeOH:DCM on 12 g silica gel column. The desired fractions were combined and concentrated to an oil which was dissolved in ACN:H$_2$O and lyophilized to obtained 100 mg (69%) of a light tan solid. LC-MS (+esi, M+H$^+$=402.1).

N-(1-(8-chloro-2-(3,5-dimethyl-1H-pyrazol-1-yl)quinolin-3-yl)ethyl)-9H-purin-6-amine

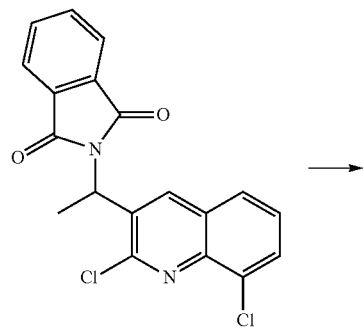

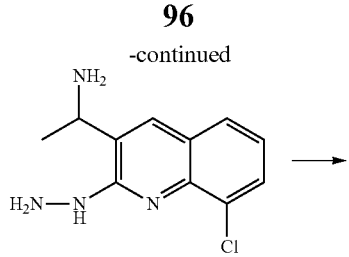

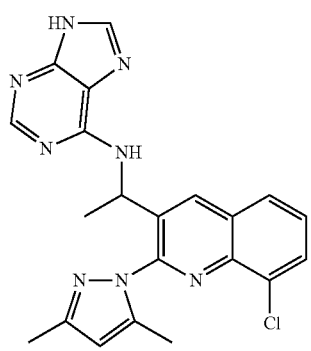

Hydrazine hydrate (1.37 g, 27.4 mmol, 10 eq) was added to a slurry of 2-(1-(2,8-dichloroquinolin-3-yl)ethyl)isoindoline-1,3-dione (1.02 g, 2.74 mmol) in ethanol (30 mL) at 70 C to form a clear solution. In a short time, a precipitate begins to form. Additional ethanol (20 mL) was added to facilitate stirring. The temperature was increased to reflux and continued overnight. Solids were removed by filtration. The filtrate was concentrated to minimize ethanol and redissolved in DCM. The organic layer was washed with water, then dried over MgSO4, and concentrated to afford the arylhydrazine as a yellow solid. mp 133 C, $^1$H NMR (500 MHz, DMSO-d6) δ ppm 9.2 (1H, br s), 7.854 (1H, s), 7.635 (1H, dd, J=8, 1.5 Hz), 7.620 (1H, dd, J=8, 1.5 Hz), 7.139 (1H, t, J=8 Hz), 4.635 (2H, br s), 4.164 (1H, q, J=6.5 Hz), 2.167 (2H, br s), 1.359 (3H, d, J=6.5 Hz) LCMS-ESI (POS), M/Z, M+1. Found 237.1

The intermediate arylhydrazine (0.067 g, 0.66 mmol) was treated with 2,4-pentanedione (0.046 ml, 2 eq) in ethanol at 75 C bath temperature overnight. Residual solvent was removed under vacuum to give an orange oil (~0.1 g). 6-bromopurine (66 mg, 1.5 eq) was added along with ethanol (3 mL) and triethylamine (3 eq). The suspension was heated at 80 c overnight. The reaction was incomplete so the solvent was replaced with n-pentanol and triethylamine (3 eq) and heated at 130 C for 4 h. The solvent was removed under vacuum and the residue purified by flash chromatography on silica gel with DCM and increasing amounts of methanol to 5%. Fractions containing desired product were combined to afford N-(1-(8-chloro-2-(3,5-dimethyl-1H-pyrazol-1-yl)quinolin-3-yl)ethyl)-9H-purin-6-amine $^1$H NMR @ 125 C (500 MHz, DMSO-d6), δ ppm 12.5 (1H, br s), 8.721 (1H, s), 8.046 (1H, s), 7.975 (1H, br s), 7.935 (1H, d, J=7.5 Hz), 7.892 (1H, d, J=7.5 Hz), 7.62 (1H, br s), 7.561 (1H, t, J=7.5 Hz), 6.124 (1H, s), 5.860 (1H, br m), 2.453 (3H, s), 2.264 (3H, s), 1.619 (3H, d, J=7 Hz) LCMS-ESI (POS), M/Z, M+1. Found 419.1

Example 48

N-(2-Fluorophenyl)cinnamamide

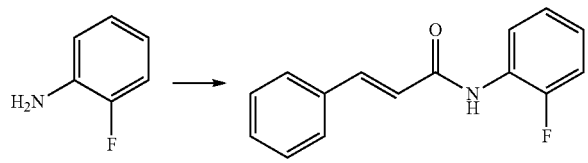 [SMILES: Nc1ccccc1F ; O=C(/C=C/c1ccccc1)Nc1ccccc1F]

To a solution of 2-fluoroaniline (25.0 g, 225 mmol) and potassium carbonate (47 g, 337 mmol) in water (112 mL) and acetone (45 mL) at 0° C. was added cinnamoyl chloride (37 g, 225 mmol, 1 eq) in acetone (45 mL) over 2 h. The reaction was stirred for 1 h @ 0° C., then quenched into 200 mL of ice-water. The white crystalline solid was filtered and washed with water. The solid was air dried for 2 h, then washed with 400 mL of hexanes. The solid was dried under vacuum overnight to afford product. $^1$H NMR (400 MHz, CDCl$_3$) δ ppm 8.49 (br t, J=7.8 Hz, 1H), 7.80 (d, J=15.3 Hz, 1H), 7.57 (m, 3H), 7.41 (m, 3H), 7.17 (m, 3H), 6.61 (d, J=15.6 Hz, 1H). Mass Spectrum (ESI) m/e=242.1 (M+1).

2-Chloro-8-fluoroquinoline

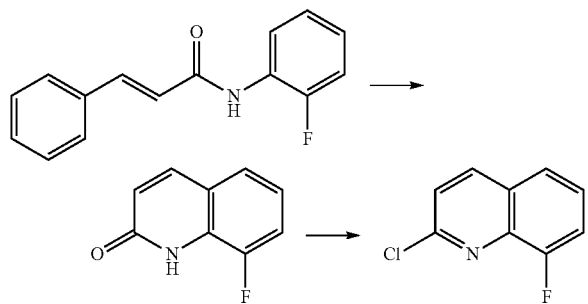

N-(2-Fluorophenyl)cinnamamide (10.5 g, 44 mmol) was dissolved in chlorobenzene (60 mL) and aluminum trichloride (29 g, 218 mmol, 5 eq) was added. The reaction was heated to 125 C for 3 h and then cooled to rt over 45 minutes. The reaction was poured onto 300 g of ice with stirring, producing a tan solid. The solid was filtered and washed with 100 mL of water and 3×100 mL of hexanes and dried under high vacuum. The solid was extracted with 1 L of DCM and filtered to remove insoluble byproducts. The solvent was removed in vacuo to afford 8-fluoroquinolin-2 (1H)-one. $^1$H NMR (400 MHz, CDCl$_3$) δ ppm 10.95 (br s, 1H), 7.77 (dd, J=9.8, 1.6 Hz), 7.35 (d, J=7.8 Hz, 1H), 7.27 (ddd, J=10.2, 7.8, 1.2 Hz, 1H), 7.14 (td, J=8.0, 5.1 Hz, 1H), 6.76 (d, J=9.4 Hz, 1H).

8-Fluoroquinolin-2 (1H)-one (26 g, 159 mmol) was slurried phosphoryl trichloride (163 mL, 1753 mmol, 11 eq) and heated to 125 for 2 h. The reaction was cooled to rt and poured onto 1.2 L of ice water with vigorous stirring. When mixture had cooled to rt, the orange solid was filtered and washed with water and dried under vacuum overnight to afford 27 g of crude material. The crude material was recrystallized from hexanes by dissolving in ~700 mL of hexanes at reflux and decanting away from residual tar. The hexane solution was cooled to 0° C. and the precipitate 2-chloro-8-fluoroquinoline was filtered. The mother liquor was concentrated in vacuo and recrystallized from hexanes to obtain a second crop of 2-chloro-8-fluoroquinoline. $^1$H NMR (400 MHz, CDCl$_3$) δ ppm 8.14 (dd, J=8.6, 1.2 Hz, 1H), 7.62 (br d, 1H), 7.52 (td, J=7.8, 4.7 Hz, 1H), 7.45 (m, 2H).

1-(2-Chloro-8-fluoroquinolin-3-yl)ethanol

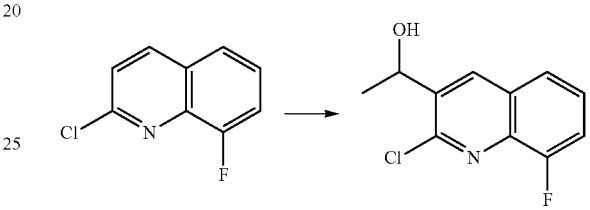

2-Chloro-8-fluoroquinoline (182 mg, 1.0 mmol) was dissolved in THF (2 mL) and cooled to −78° C. To this solution was added Lithium diisopropylamide (1M solution in THF, 1.1 mL, 1.1 mmol, 1.1 eq). The reaction was allowed to stir at −78° C. for 20 min, after which time acetaldehyde (113 μl, 2.0 mmol, 2 eq.) was added via syringe. After 30 minutes, the reaction was quenched with water and diluted with ethyl acetate. The layers were separated and washed with brine. The crude reaction mixture was purified by column chromatography (8:2 hexanes:ethyl acetate) to afford 1-(2-chloro-8-fluoroquinolin-3-yl)ethanol. $^1$H NMR (400 MHz, CDCl$_3$) δ ppm 8.43 (br s, 1H), 7.64 (td, J=7.8, 5.1 Hz, 1H), 7.41 (ddd, J=10.2, 7.4, 1.2 Hz, 1H), 5.39 (qdd, J=6.3, 3.9, 0.8 Hz, 1H), 2.22 (d, J=3.9 Hz, 1H), 1.62 (d, J=6.3 Hz, 3H).

1-(2-Chloro-8-fluoroquinolin-3-yl)ethanone

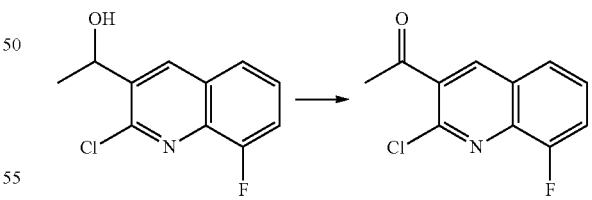

To a round-bottomed flask containing toluene (183 mL) was added 1-(2-chloro-8-fluoroquinolin-3-yl)ethanol (6.2 g, 27.5 mmol) and manganese dioxide (19.1 g, 219.8 mmol, 8 eq). The reaction was heated to reflux for 2 h, cooled to rt, filtered concentrated. The product was diluted with hexanes and filtered to give as a white solid 1-(2-chloro-8-fluoroquinolin-3-yl)ethanone. $^1$H NMR (400 MHz, CDCl$_3$) δ ppm 8.40 (d, J=1.6 Hz, 1H), 7.71 (br d, J=8.2 Hz, 1H), 7.56 (td, J=7.8, 5.1 Hz, 1H), 7.54 (ddd, J=9.8, 7.8, 1.6 Hz, 1H). Mass Spectrum (ESI) m/e=223.9 (M+1).

(R)-1-(2-Chloro-8-fluoroquinolin-3-yl)ethanol

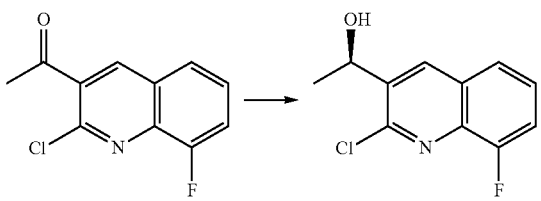

In a round bottomed flask was dissolved (+)-dip-chloride (tm) (4418 mg, 13773 µmol) in anhydrous THF (50 mL) and the solution was cooled to −55° C. (using a dry ice/MeCN bath). To this solution was added 1-(2-chloro-8-fluoroquinolin-3-yl)ethanone (1.4 g, 6.3 mmol) as a solution in THF (10 mL). The reaction was allowed to warm to +10° C. over 5 h. The reaction was quenched with 10 mL acetone and 20 mL of 10% $Na_2CO_3$ and allowed to stir for 1 h at rt. Ethyl acetate (200 mL) was added and the layers were separated. The organic phase was washed with three times with a 50% saturated sodium bicarbonate solution and once with brine. The organic layer was dried over $MgSO_4$, filtered, and concentrated to provide 5 g of crude material. The crude material was purified using 7:3 hexanes:ethyl acetate on 120 g silica gel column to afford (R)-1-(2-chloro-8-fluoroquinolin-3-yl)ethanol. Chiral HPLC (10% IPA in hexanes, chiralcel AD) shows product to be 96.0% ee. $^1$H NMR (400 MHz, $CDCl_3$) δ ppm 8.43 (br s), 7.64 (br d, J=8.2 Hz, 1H), 7.50 (td, J=7.8, 4.7 Hz, 1H), 7.41 (ddd, J=10.2, 7.8, 1.2 Hz, 1H), 5.40 (qd, J=5.9, 0.8 Hz, 1H), 2.22 (br s, 1H), 1.62 (d, J=6.3 Hz, 3H). Mass Spectrum (ESI) m/e=226.0 (M+1).

(S)-3-(1-Azidoethyl)-2-chloro-8-fluoroquinoline

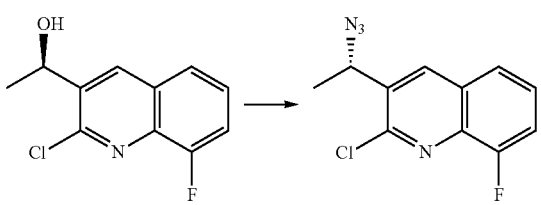 [SMILES: C[C@@H](O)c1cc2cccc(F)c2nc1Cl ; C[C@H](N=[N+]=[N-])c1cc2cccc(F)c2nc1Cl]

Triphenylphosphine (1.81 g, 6.9 mmol, 1.2 eq) was dissolved in anhydrous THF (30 mL) and cooled to 0° C. To this solution was added diisopropylazodicarboxylate (1.36 mL, 6.9 mmol, 1.2 eq). The reaction was stirred for 30 minutes at 0° C. and (R)-1-(2-chloro-8-fluoroquinolin-3-yl) ethanol (1.3 g, 5.7 mmol) in 30 mL of THF was added, followed by diphenylphosphoryl azide (1.37 mL, 6.3 mmol, 1.1 eq). The reaction was allowed to warm to rt and stir at rt overnight. The reaction was deposited on silica gel and concentrated. Purification by column chromatography (3% etoac in hexanes) afforded (S)-3-(1-azidoethyl)-2-chloro-8-fluoroquinoline. $^1$H NMR (400 MHz, $CDCl_3$) δ ppm 8.30 (d, J=1.2 Hz, 1H), 7.67 (br d, J=8.22 Hz, 1H), 7.54 (td, J=7.8, 4.7 Hz, 1H), 7.45 (ddd, J=10.2, 7.8, 1.2 Hz) 5.22 (q, J=6.7 Hz, 1H), 1.68 (d, J=6.7 Hz, 3H). Mass Spectrum (ESI) m/e=250.9 (M+1).

General Procedures for 8-Fluoroquinoline Analogues
Procedure BSL-1

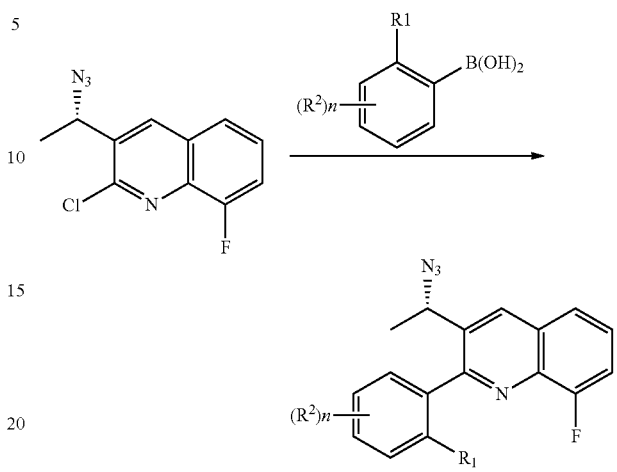

To a round bottomed flask was added (S)-3-(1-azidoethyl)-2-chloro-8-fluoroquinoline (1 eq), tetrakistriphenylphosphine palladium (0) (0.04 eq), sodium carbonate (5 eq), and an aryl boronic acid (1.5 eq). The flask was purged with nitrogen and a 3:1 mixture of $MeCN:H_2O$ was added to give a concentration of 0.1M with respect to the starting azide. The reaction was heated to 80° C. until judged to be complete. The solvent was removed and the residue was redissolved in of ethyl acetate and water. The layers were separated and the organic layer was washed with brine, dried over $MgSO_4$, filtered, and concentrated. The crude reaction was purified column chromatography (ethyl acetate in hexanes, gradient) to afford (S)-3-(1-azidoethyl)-8-fluoro-2-arylquinoline.
Procedure BSL-2

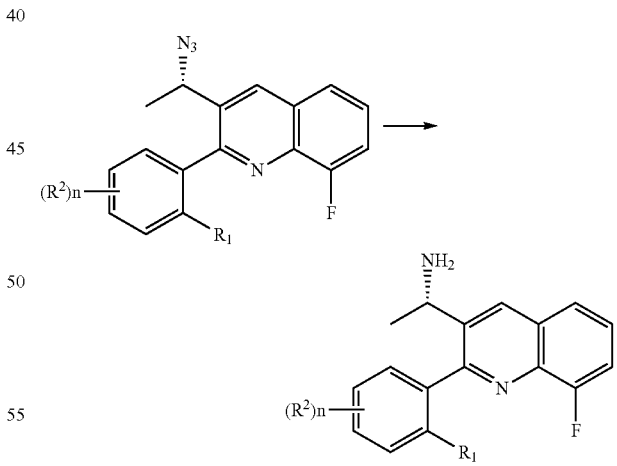

(S)-3-(1-azidoethyl)-8-fluoro-2-arylquinoline was dissolved in THF (to yield a 0.1 M solution) and triphenylphosphine (1.1 eq) and water (20 eq) were added. The reaction was heated to 60° C. overnight. After cooling to rt, the solvent was removed in vacuo and the residue was redissolved in ethyl ether. The ether layer was extracted three times with 1 N HCl. The aqueous layer was brought to a pH of 10-12 by addition of 15% NaOH and the basic aqueous layer was extracted twice with ethyl ether. The ether layers were washed with brine, dried over MgSO₄, filtered, and concentrated to afford (S)-1-(8-fluoro-2-aryllquinolin-3-yl)-ethanamine
Procedure BSL-3

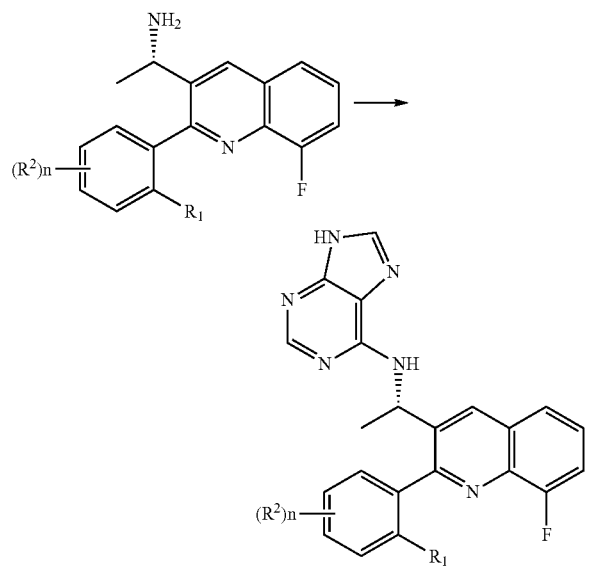

To a round bottomed flask was added (S)-1-(8-fluoro-2-aryllquinolin-3-yl)-ethanamine (1 eq), 6-bromopurine (1.2 eq), and diisopropylethylamine (3 eq). Enough n-butanol was added to make a 0.1 M solution with respect to the (S)-1-(8-fluoro-2-aryllquinolin-3-yl)ethanamine. The mixture was heated to 100-115° C. for 24 h, cooled to rt, and the solvent was removed in vacuo. Purification by reverse phase HPLC afforded (S)—N-(1-(8-fluoro-2-arylquinolin-3-yl)ethyl)-9H-purin-6-amine. The products were dissolved in DCM/NaHCO₃ and the organic layer was separated, dried over MgSO₄, filtered, and concentrated to provide (S)—N-(1-(8-fluoro-2-phenylquinolin-3-yl)ethyl)-9H-purin-6-amine as freebases.

Example 49

3-((S)-1-Azidoethyl)-8-fluoro-2-(3-fluorophenyl)quinoline

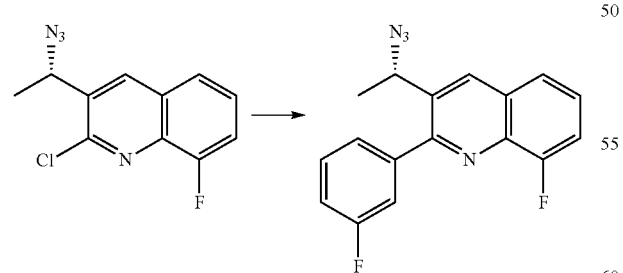

3-((S)-1-Azidoethyl)-8-fluoro-2-(3-fluorophenyl)quinoline was made according to Procedure BSL-1 using (S)-3-(1-azidoethyl)-2-chloro-8-fluoroquinoline (50 mg, 0.199 mmol), tetrakis triphenylphosphine palladium (0) (9 mg, 0.008 µmol, 0.04 eq), sodium carbonate (106 mg, 0.997 mmol, 5 eq), and 3-fluorophenylboronic acid (42 mg, 0.299 mmol, 1.5 eq). 3-((S)-1-azidoethyl)-8-fluoro-2-(3-fluorophenyl)quinoline was obtained after purification. ¹H NMR (400 MHz, CDCl₃) δ ppm 8.39 (d, J=1.6 Hz, 1H), 7.71 (br d, J=8.2 Hz, 1H), 7.54 (td, J=7.8, 4.7 Hz, 1H), 7.52-7.42 (series of m, 2H), 7.35 (dt, J=7.8, 1.2 Hz), 7.31 (ddd, J=9.0, 2.4, 1.6 Hz, 1H), 7.20 (tdd, J=8.6, 2.7, 1.2 Hz, 1H), 4.94 (q, J=6.7 Hz, 1H), 1.56 (d, J=6.7 Hz, 3H). Mass Spectrum (ESI) m/e=310.9 (M+1).

(1S)-1-(8-Fluoro-2-(3-fluorophenyl)quinolin-3-yl)ethanamine

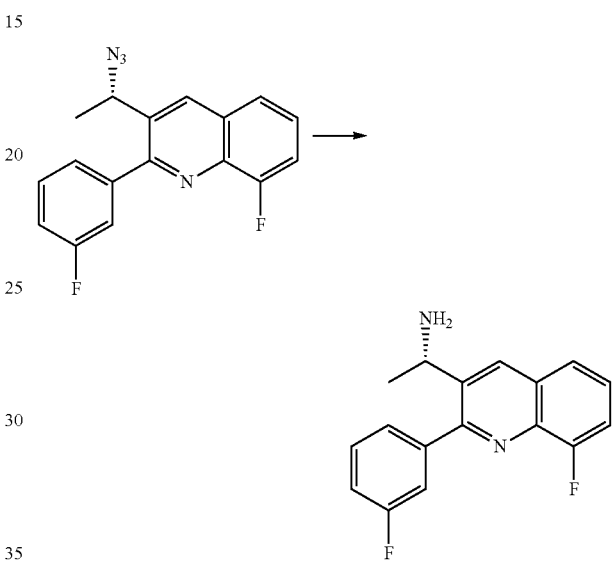

(1S)-1-(8-Fluoro-2-(3-fluorophenyl)quinolin-3-yl)ethanamine was made according to procedure BSL-2 using 3-((S)-1-azidoethyl)-8-fluoro-2-(3-fluoro-phenyl)quinoline (54 mg, 0.174 mmol, triphenylphosphine (50 mg, 0.191 mmol), and water (63 µl, 3.480 mmol). Obtained (1S)-1-(8-fluoro-2-(3-fluorophenyl)-quinolin-3-yl)ethanamine. ¹H NMR (400 MHz, CDCl₃) δ ppm 8.51 (d, J=1.6 Hz, 1H), 7.65 (br d, J=8.21 Hz, 1H), 7.52-7.42 (series of m, 2H), 7.39 (ddd, J=10.5, 7.4, 1.2 Hz, 1H), 7.34 (dt, J=7.5, 1.2 Hz, 1H), 7.30 (ddd, J=9.4, 2.7, 1.6 Hz, 1H), 7.16 (tdd, J=8.6, 2.4, 0.8 Hz, 1H), 4.48 (q, J=6.2 Hz, 1H), 1.37 (d, J=6.7 Hz, 3H). Mass Spectrum (ESI) m/e=285.0 (M+1).

N—((S)-1-(8-Fluoro-2-(3-fluorophenyl)quinolin-3-yl)ethyl)-9H-purin-6-amine

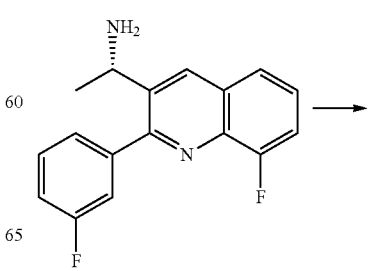

-continued

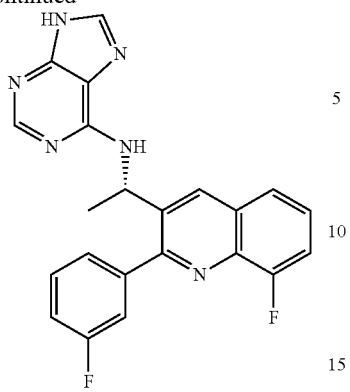

N—((S)-1-(8-Fluoro-2-(3-fluorophenyl)quinolin-3-yl)ethyl)-9H-purin-6-amine was made according to procedure BSL-3 using N-ethyl-N-isopropylpropan-2-amine (27 μl, 155 μmol), 6-bromo-7H-purine (18 mg, 93 μmol), and (1S)-1-(8-fluoro-2-(3-fluorophenyl)quinolin-3-yl)ethanamine (22 mg, 77 μmol). Isolated N—((S)-1-(8-fluoro-2-(3-fluorophenyl)quinolin-3-yl)ethyl)-7H-purin-6-amine  $^1$H NMR (400 MHz, CDCl$_3$) δ ppm 8.33 (s, 2H), 7.97 (s, 1H), 7.65-7.61 (m, 2H), 7.52 (d, J=8.2 Hz, 1H), 7.47-7.39 (series of m, 2H), 7.35 (ddd, J=10.6, 7.8, 1.6 Hz, 1H), 6.76 (br s, 1H), 5.80 (br s, 1H), 1.51 (d, J=7.0 Hz, 3H). Mass Spectrum (ESI) m/e=403.0 (M+1).

The following compounds were made according to the sequence (BSL-1→BSL-2→BSL-3) described above. Data for these compounds is listed below:

Example 50

(S)—N-(1-(8-Fluoro-2-phenylquinolin-3-yl)ethyl)-9H-purin-6-amine

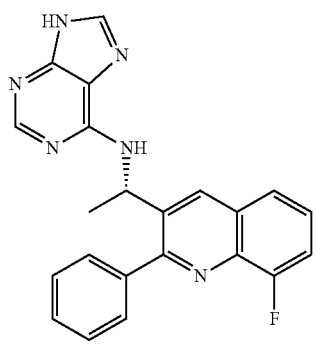 [SMILES: C[C@H](Nc1ncnc2[nH]cnc12)c1cc2cccc(F)c2nc1-c1ccccc1]

Data for (S)—N-(1-(8-fluoro-2-phenylquinolin-3-yl)ethyl)-9H-purin-6-amine: $^1$H NMR (400 MHz, CDCl$_3$) δ ppm 8.32 (s, 2H), 7.95 (s, 1H), 7.84 (d, J=7.0 Hz, 2H), 7.51 (d, J=6.6 Hz, 1H), 6.41 (br s, 1H), 5.83 (br s, 1H), 1.50 (d, J=6.7 Hz, 3H). Mass Spectrum (ESI) m/e=385.0 (M+1).

Example 51

N—((S)-1-(2-(2-Chlorophenyl)-8-fluoroquinolin-3-yl)ethyl)-9H-purin-6-amine

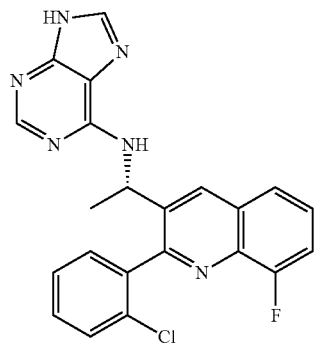 [SMILES: C[C@H](Nc1ncnc2[nH]cnc12)c1cc2cccc(F)c2nc1-c1ccccc1Cl]

Data for N—((S)-1-(2-(2-chlorophenyl)-8-fluoroquinolin-3-yl)ethyl)-9H-purin-6-amine: $^1$H NMR (400 MHz, CDCl$_3$) δ ppm (rotomers present at room temperature) 8.42-8.35 (s, 1H), 8.23 (s, 1H), 7.92 (s, 1H), 7.71-7.23 (series of m, 5H), 6.27 (br s, 1H), 5.60 (br m, 1H), 1.66 (m, 3H). Mass Spectrum (ESI) m/e=418.9 (M+1).

Example 52

(S)—N-(1-(2-(3,5-Difluorophenyl)-8-fluoroquinolin-3-yl)ethyl)-9H-purin-6-amine

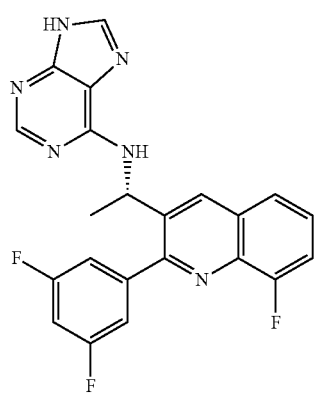 [SMILES: C[C@H](Nc1ncnc2[nH]cnc12)c1cc2cccc(F)c2nc1-c1cc(F)cc(F)c1]

Data for (S)—N-(1-(2-(3,5-difluorophenyl)-8-fluoroquinolin-3-yl)ethyl)-9H-purin-6-amine: $^1$H NMR (400 MHz, CDCl$_3$) δ ppm 8.35 (s, 2H), 8.00 (s, 1H), 7.56 (d, J=8.6 Hz, 1H), 7.46 (m, 3H), 7.38 (ddd, J=10.6, 7.8, 1.6 Hz, 1H), 6.90 (tt, J=9.0, 2.4 Hz, 1H), 6.50 (br s, 1H), 5.80 (br s, 1H), 1.53 (d, J=6.4 Hz, 3H). Mass Spectrum (ESI) m/e=420.9 (M+1).

Example 53

N—((S)-1-(8-Fluoro-2-(pyridin-3-yl)quinolin-3-yl)ethyl)-9H-purin-6-amine

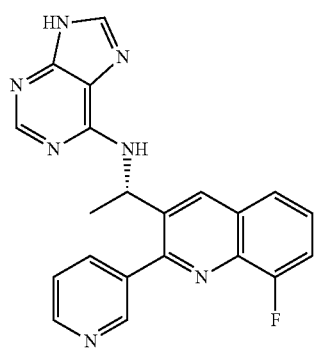 [SMILES: C[C@H](Nc1ncnc2[nH]cnc12)c1cc2cccc(F)c2nc1-c1cccnc1]

Data for N—((S)-1-(8-fluoro-2-(pyridin-3-yl)quinolin-3-yl)ethyl)-9H-purin-6-amine: $^1$H NMR (400 MHz, CDCl$_3$) δ ppm 9.15 (s, 1H), 8.71 (dd, J=4.7, 1.6 Hz, 1H), 8.36 (s, 1H), 8.28 (s, 1H), 8.22 (d, J=7.8 Hz, 1H), 7.97 (s, 1H), 7.54 (d J=7.4 Hz, 1H), 7.46-7.41 (m, 2H), 7.36 (ddd J=10.2, 7.4, 1.2 Hz, 1H), 6.67 (br s, 1H), 5.74 (br s, 1H), 1.53 (d, J=6.7 Hz, 3H). Mass Spectrum (ESI) m/e=385.9 (M+1).

Example 54

N—((S)-1-(2-(2-Chloro-5-fluorophenyl)-8-fluoroquinolin-3-yl)ethyl)-9H-purin-6-amine

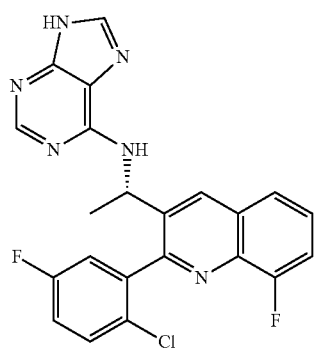 [SMILES: C[C@H](Nc1ncnc2[nH]cnc12)c1cc2cccc(F)c2nc1-c1cc(F)ccc1Cl]

Data for N—((S)-1-(2-(2-chloro-5-fluorophenyl)-8-fluoroquinolin-3-yl)ethyl)-9H-purin-6-amine: $^1$H NMR (400 MHz, CDCl$_3$) δ ppm (rotomers present at room temperature) 8.43-8.37 (s, 1H), 8.25 (s, 1H), 7.95 (s, 1H), 7.69-7.39 (m, 3H), 7.16-7.01 (m, 2H), 6.39 (br s, 1H), 5.60 (br m, 1H), 1.68 (d, J=5.9 Hz, 3H). Mass Spectrum (ESI) m/e=436.9 (M+1).

Example 55

N—((S)-1-(2-(2,5-Difluorophenyl)-8-fluoroquinolin-3-yl)ethyl)-9H-purin-6-amine

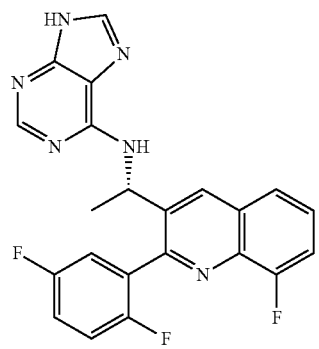 [SMILES: C[C@H](Nc1ncnc2[nH]cnc12)c1cc2cccc(F)c2nc1-c1cc(F)ccc1F]

Data for N—((S)-1-(2-(2,5-difluorophenyl)-8-fluoroquinolin-3-yl)ethyl)-9H-purin-6-amine: $^1$H NMR (400 MHz, CDCl$_3$) δ ppm 8.37 (s, 1H), 8.24 (s, 1H), 7.94 (s, 1H), 7.60 (d, J=8.2 Hz, 1H), 7.49 (td, J=7.8, 4.7 Hz, 1H), 7.40 (ddd, J=10.6, 7.8, 1.6 Hz, 1H), 7.08 (m, 2H), 6.40 (br s, 1H), 5.55 (br s, 1H), 1.67 (d, J=7.0 Hz, 3H). Mass Spectrum (ESI) m/e=420.9 (M+1).

Example 56

N—((S)-1-(2-(3-chloro-5-fluorophenyl)-8-fluoroquinolin-3-yl)ethyl)-9H-purin-6-amine

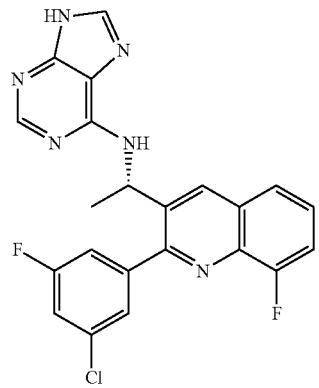 [SMILES: C[C@H](Nc1ncnc2[nH]cnc12)c1cc2cccc(F)c2nc1-c1cc(F)cc(Cl)c1]

Data for N—((S)-1-(2-(3-chloro-5-fluorophenyl)-8-fluoroquinolin-3-yl)ethyl)-9H-purin-6-amine: $^1$H NMR (400 MHz, CD$_3$OD) δ ppm 8.60 (s, 1H), 8.15 (s, 1H), 8.08 (s, 1H), 7.78 (d, J=8.2 Hz, 1H), 7.59 (m, 2H), 7.21 (dt, J=8.6, 2.0 Hz, 1H), 5.70 (br s, 1H), 1.62 (d, J=3H). Mass Spectrum (ESI) m/e=436.9 (M+1).

Example 57

N—((S)-1-(2-(5-Chloro-2-fluorophenyl)-8-fluoro-quinolin-3-yl)ethyl)-9H-purin-6-amine

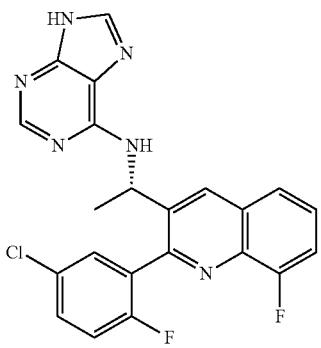 [SMILES: C[C@H](Nc1ncnc2[nH]cnc12)c1cc2cccc(F)c2nc1-c1cc(Cl)ccc1F]

Data for N—((S)-1-(2-(5-chloro-2-fluorophenyl)-8-fluoroquinolin-3-yl)ethyl)-9H-purin-6-amine: $^1$H NMR (400 MHz, CDCl$_3$) δ ppm 8.36 (s, 1H), 8.24 (s, 1H), 7.97 (s, 1H), 7.73 (br s, 1H), 7.60 (d, J=7.8 Hz, 1H), 7.48 (td, J=7.8, 4.7 Hz, 1H), 7.38 (ddd, J=10.6, 7.8, 1.2 Hz, 1H), 7.31 (m, 1H), 7.08 (br s, 1H), 6.61 (br s, 1H), 5.55 (br s, 1H) 1.69 (d, J=7.0 Hz, 3H). Mass Spectrum (ESI) m/e=436.9 (M+1).

Example 58

(S)—N-(1-(8-Fluoro-2-(4-(trifluoromethyl)phenyl)quinolin-3-yl)ethyl)-9H-purin-6-amine

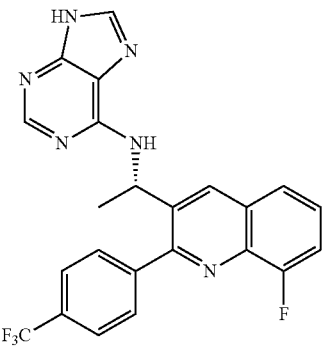 [SMILES: C[C@H](Nc1ncnc2[nH]cnc12)c1cc2cccc(F)c2nc1-c1ccc(C(F)(F)F)cc1]

Data for (S)—N-(1-(8-fluoro-2-(4-(trifluoromethyl)phenyl)quinolin-3-yl)ethyl)-9H-purin-6-amine: $^1$H NMR (400 MHz, CDCl$_3$) δ ppm 8.37 (S, 1H), 8.30 (s, 1H), 7.97 (m, 3H), 7.73 (d, J=7.8 Hz, 2H), 7.60 (d, J=7.8 Hz, 1H), 7.48 (td, J=7.8, 5.1 Hz, 1H), 7.39 (ddd, J=10.6, 7.8, 1.6 Hz, 1H), 6.49 (br s, 1H), 5.77 (br s, 1H), 1.56 (d, J=7.0 Hz, 3H). Mass Spectrum (ESI) m/e=453.0 (M+1).

Example 59

(E)-N-Benzylidene-2-fluorobenzenamine

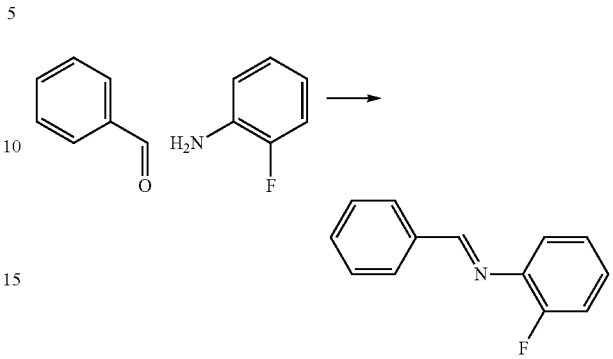

Dissolved 2-fluoroaniline (2.0 mL, 20.8 mmol, 1.05 eq) in 40 mL of anhydrous ether. Added Magnesium Sulfate (7146 mg, 59.3 mmol, 4 eq), 7 g of powdered mol sieves, and benzaldehyde (2.0 mL μl, 19.8 mmol). To this mixture was added pTsOH (18.8 mg, 98.9 μmol, 0.005 eq) and heated to reflux overnight. The reaction was cooled, filtered and concentrated to yield (E)-N-benzylidene-2-fluorobenzenamine. $^1$H NMR (400 MHz, CDCl$_3$) δ ppm 8.55 (s, 1H), 7.95 (m, 2H), 7.52 (m, 5H), 7.18 (m, 4H).

N-((8-Fluoro-2-phenylquinolin-3-yl)methyl)acetamide

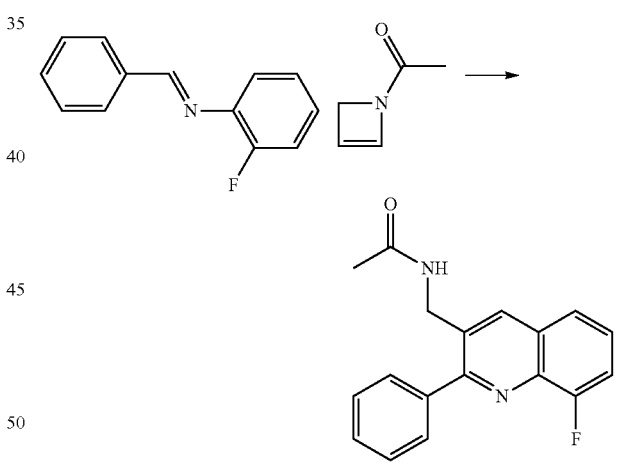

Dissolved 1-(azet-1 (2H)-yl)ethanone (22 mg, 227 μmol, 1 eq), (E)-N-benzylidene-2-fluorobenzenamine (45 mg, 227 μmol, 1 eq), 2-fluorobenzenamine (22 μl, 227 μmol, 1 eq), and yttrium trifluoromethanesulfonate (6 mg, 11 μmol, 0.05 eq) in 9 mL of acetonitrile. The reaction was stirred at rt overnight. The reaction was heated to 90° C. for 5 h. The reaction was cooled to rt and the solvent was removed under vacuum. The residue was dissolved in 20 mL of DCM and washed with 1×5 mL of NaHCO$_3$. The organic layer was dried over MgSO$_4$, filtered and concentrated. Purification by column chromatography (7:3 hexanes:ethyl acetate) afforded N-((8-fluoro-2-phenylquinolin-3-yl)methyl)acetamide. $^1$H NMR (400 MHz, CDCl$_3$) δ ppm 8.20 (s, 1H), 7.60 (d, J=7.83, 1H), 7.50 (m, 2H), 7.45 (m, 4H), 7.37 (ddd, J=10.6, 7.8, 1.6 Hz, 1H), 5.92 (br t, J=5.9 Hz, 1H), 4.55 (d, J=6.3 Hz, 2H), 1.96 (s, 3H). Mass Spectrum (ESI) m/e=295.0 (M+1).

(8-Fluoro-2-phenylquinolin-3-yl)methanamine

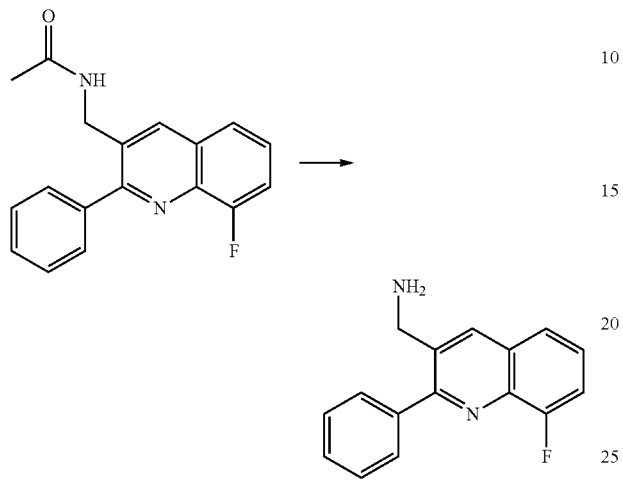

To N-((8-fluoro-2-phenylquinolin-3-yl)methyl)acetamide (28 mg, 95 μmol) was added hydrochloric acid (2M solution in water, 2 mL, 4000 μmol). The reaction was heated to 80 C for 24 h. The reaction was cooled to rt and quenched with 15% NaOH. The product was extracted into ether (2×10 mL) and the combined organics were washed with brine, dried over MgSO₄, filtered, and concentrated to afford (8-fluoro-2-phenylquinolin-3-yl)methanamine. ¹H NMR (400 MHz, CDCl₃) δ ppm 8.34 (s, 1H), 7.65 (d, J=8.2 Hz, 1H), 7.61 (m, 2H), 7.48 (m, 4H), 7.39 (ddd, J=10.6, 7.8, 1.6 Hz, 1H), 4.05 (s, 2H), 2.03 (br s, 2H). Mass Spectrum (ESI) m/e=253.0 (M+1).

N-((8-Fluoro-2-phenylquinolin-3-yl)methyl)-9H-purin-6-amine

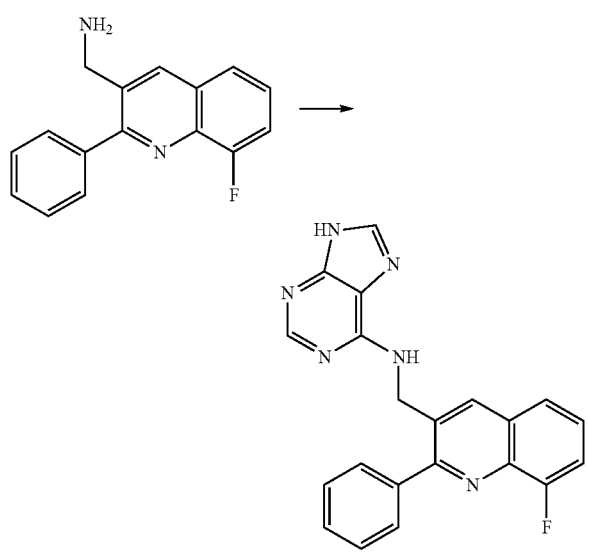

To a reaction flask was added 6-bromopurine (19 mg, 95 μmol, 1.2 eq), diisopropylethylamine (42 μl, 238 μmol, 3 eq), (8-fluoro-2-phenylquinolin-3-yl)-methanamine (20 mg, 79 μmol, 1 eq), and n-butanol (0.75 mL). The reaction was heated to 110° C. for 8 h. The reaction was cooled to rt and the solvent was removed in vacuo. The compound was purified by reverse phase HPLC. The fractions were concentrated and freebased with sat. NaHCO₃. The organic layer was extracted into DCM, dried over MgSO₄, filtered, and concentrated to afford a white solid, N-((8-fluoro-2-phenylquinolin-3-yl)methyl)-7H-purin-6-amine ¹H NMR (400 MHz, CDCl₃) δ ppm 8.35 (s, 1H), 8.31 (s, 1H), 7.90 (s, 1H), 7.68 (m, 2H), 7.45 (m, 6H), 6.78 (br s, 1H), 5.07 (br s, 2H). Mass Spectrum (ESI) m/e=370.9 (M+1).

Example 60

(S)-2-(1-(8-Chloro-2-vinylquinolin-3-yl)ethyl)isoindoline-1,3-dione

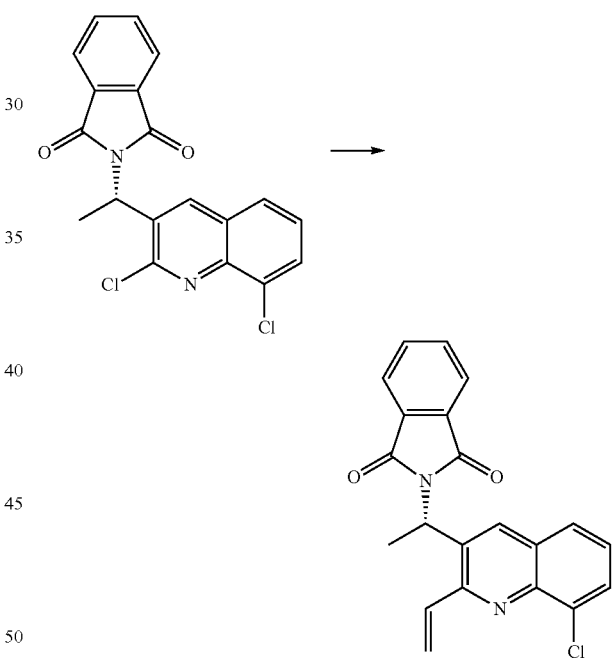

To a stirred solution of (S)-2-(1-(2,8-dichloroquinolin-3-yl)ethyl)isoindoline-1,3-dione (1 g, 2.7 mmol) in dioxane (25 mL) under a nitrogen atmosphere was added vinyl tributyltin (1.28 mL, 4.04 mmol) and tetrakis(triphenylphosphine)palladium (156 mg, 0.13 mmol). The reaction was heated at 100° C. for 3 hours and then the solvent was evaporated in vacuo. The resulting black residue was purified by column chromatography (40 g SiO₂, Hexanes:Ethyl acetate, 1:0 to 3:1) to give (S)-2-(1-(8-chloro-2-vinylquinolin-3-yl)ethyl)isoindoline-1,3-dione as a white solid. 1H-NMR (400 MHz, CDCl₃) δ ppm 8.53 (1H, s), 7.76-7.81 (4H, m), 7.68-7.72 (2H, m), 7.41 (1H, dd, J=7.8, 7.8 Hz), 7.26-7.33 (1H, m), 6.71 (1H, dd, J=16.4, 2.3 Hz), 6.00 (1H, q, J=7.3 Hz), 5.64 (1H, dd, J=10.6, 2.3 Hz), 2.00 (3H, d, J=7.0 Hz). Mass Spectrum (ESI) m/e=362.8 (M+1).

2-((S)-1-(8-Chloro-2-(1,2-dihydroxyethyl)quinolin-3-yl)ethyl)isoindoline-1,3-dione

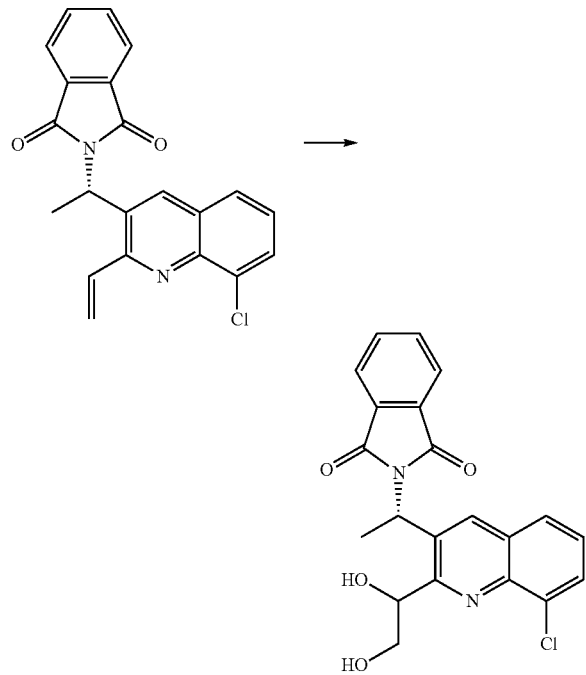

To a stirred solution of (S)-2-(1-(8-chloro-2-vinylquinolin-3-yl)ethyl)isoindoline-1,3-dione (200 mg, 0.55 mmol) in THF (5 mL) and water (1.0 mL) was added potassium osmate(VI) dihydrate (10.2 mg, 27.6 µmol). The reaction was stirred for 5 minutes and then NMO (64.6 mg, 0.55 mmol) was added. The reaction was stirred for 3 hours and then it was diluted with ethyl acetate (80 mL) and 1.0 M aqueous citric acid (40 mL). The separated aqueous layer was extracted with ethyl acetate (140 mL) and the combined organic layers were washed with brine (40 mL), dried (MgSO$_4$), filtered and evaporated in vacuo to give 2-((S)-1-(8-chloro-2-(1,2-dihydroxyethyl)quinolin-3-yl)ethyl)isoindoline-1,3-dione. The product was used without further purification in the next step. 1H NMR (400 MHz, CDCl$_3$) δ ppm 8.77 (1H, d, J=11.7 Hz), 7.61-7.88 (6H, m), 7.49 (1H, q, J=8.1 Hz), 5.95-6.17 (1H, m), 5.22-5.32 (1H, m), 4.02-4.26 (2H, m), 1.94-1.97 (3H, m). Mass Spectrum (ESI) m/e=396.9 (M+1).

(S)-8-Chloro-3-(1-(1,3-dioxoisoindolin-2-yl)ethyl)quinoline-2-carbaldehyde

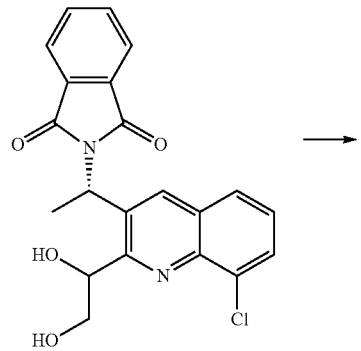

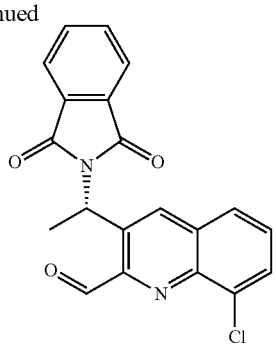

To a stirred solution of 2-((S)-1-(8-chloro-2-(1,2-dihydroxyethyl)quinolin-3-yl)-ethyl)isoindoline-1,3-dione (170 mg, 0.43 mmol) in THF (4.0 mL) and water (1.0 mL) was added sodium periodate (91.6 mg, 0.43 mmol). The reaction was stirred at room temperature for 3 hours and then it was diluted with water (50 mL). The separated aqueous layer was extracted with DCM (2×50 mL) and the combined organic layers were washed with brine (50 mL), dried (MgSO$_4$), filtered and evaporated in vacuo to give (S)-8-chloro-3-(1-(1,3-dioxoisoindolin-2-yl)ethyl)-quinoline-2-carbaldehyde. 1H NMR (400 MHz, CDCl$_3$) δ ppm 10.36 (1H, s), 8.59 (1H, s), 7.89-7.91 (1H, m), 7.82-7.86 (3H, m), 7.71-7.73 (2H, m), 7.57-7.61 (1H, m), 6.67 (1H, q, J=7.0 Hz), 2.00 (3H, d, J=7.0 Hz).

(S)-8-Chloro-3-(1-(1,3-dioxoisoindolin-2-yl)ethyl) quinoline-2-carboxylic acid

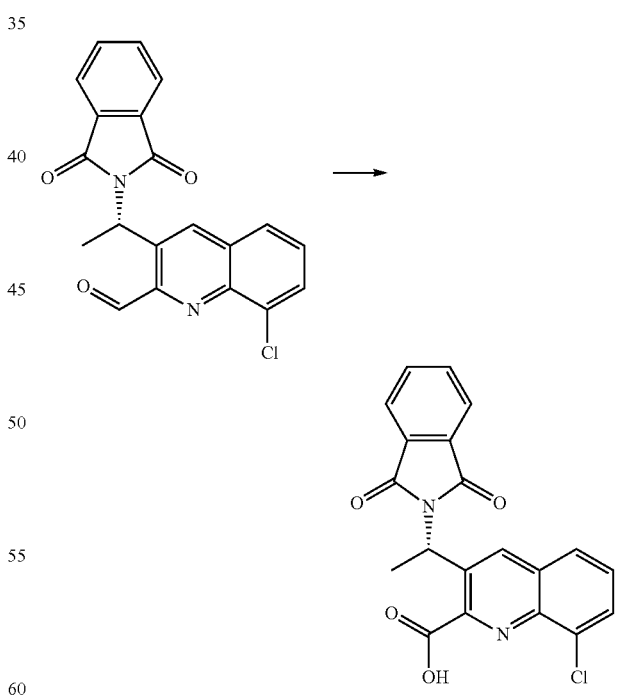

To a stirred solution of (S)-8-chloro-3-(1-(1,3-dioxoisoindolin-2-yl)ethyl)-quinoline-2-carbaldehyde (110 mg, 0.30 mmol) and potassium phosphate monobasic (41.0 mg, 0.30 mmol) in 2-methyl-2-butene (2 mL), tBuOH (2 mL), DCM (1.0 mL) and water (2.0 mL) was added sodium chlorite (27.3 mg, 0.30 mmol) in water (2.0 mL). The reaction was stirred at room temperature. for 2 hours and then it was treated with additional potassium phosphate monobasic (41.0 mg, 0.30 mmol) and sodium chlorite (27.3 mg, 0.30 mmol) in water (2.0 mL). The reaction was stirred for 2 hours and then it was diluted with with 1.0 M citric acid (40 mL) and ethyl acetate (60 mL). The separated aqueous layer was extracted with ethyl acetate (2×60 mL) and the combined organic layers were washed with brine (40 mL), dried (MgSO₄), filtered and evaporated in vacuo to give (S)-8-chloro-3-(1-(1,3-dioxoisoindolin-2-yl)ethyl)quinoline-2-carboxylic acid. 1H NMR (400 MHz, CDCl₃) δ ppm 8.62 (1H, s), 7.72-7.84 (6H, m), 7.65 (1H, dd, J=5.3, 2.9 Hz), 6.80 (1H, q, J=7.0 Hz), 1.96 (3H, d, J=7.0 Hz). Mass Spectrum (ESI) m/e=381.0 (M+1).

(S)—N'-Acetyl-8-chloro-3-(1-(1,3-dioxoisoindolin-2-yl)ethyl)quinoline-2-carbohydrazide

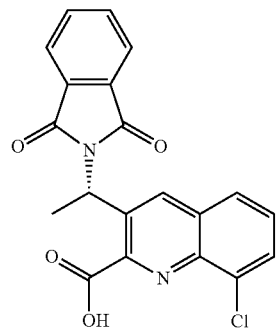

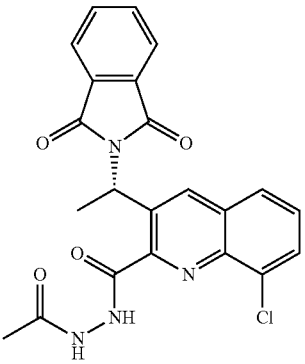

To a stirred solution of (S)-8-chloro-3-(1-(1,3-dioxoisoindolin-2-yl)ethyl)-quinoline-2-carboxylic acid (100 mg, 0.26 mmol) in DMF (3.0 mL) was added sodium bicarbonate (66 mg, 0.79 mmol), hoat (54 mg, 0/39 mmol), acetic hydrazide (23 mg, 0.31 mmol) and edc (76 mg, 0.39 mmol). The reaction was stirred at r.t. for 2 hours and then it was diluted with ethyl acetate (60 mL) and water (20 mL). The separated aqueous layer was extracted with ethyl acetate (30 mL) and the combined organic layers were washed with LiCl (1.0 M aqueous solution, 30 mL), brine (30 mL) and then dried (MgSO₄), filtered and evaporated in vacuo to give (S)—N'-acetyl-8-chloro-3-(1-(1,3-dioxoisoindolin-2-yl)ethyl)-quinoline-2-carbohydrazide. 1H NMR (400 MHz, CDCl₃) δ ppm 10.45 (1H, s), 8.88 (1H, s), 8.64 (1H, s), 7.70-7.84 (4H, m), 7.64-7.66 (2H, m), 7.52 (1H, dd, J=5.3, 2.9 Hz), 6.87 (1H, q, J=7.0 Hz), 2.13 (3H, s), 1.98 (3H, d, J=7.0 Hz). Mass Spectrum (ESI) m/e=437.0 (M+1).

2-((S)-1-(8-Chloro-2-(5-methyl-1,3,4-thiadiazol-2-yl)quinolin-3-yl)ethyl)-isoindoline-1,3-dione

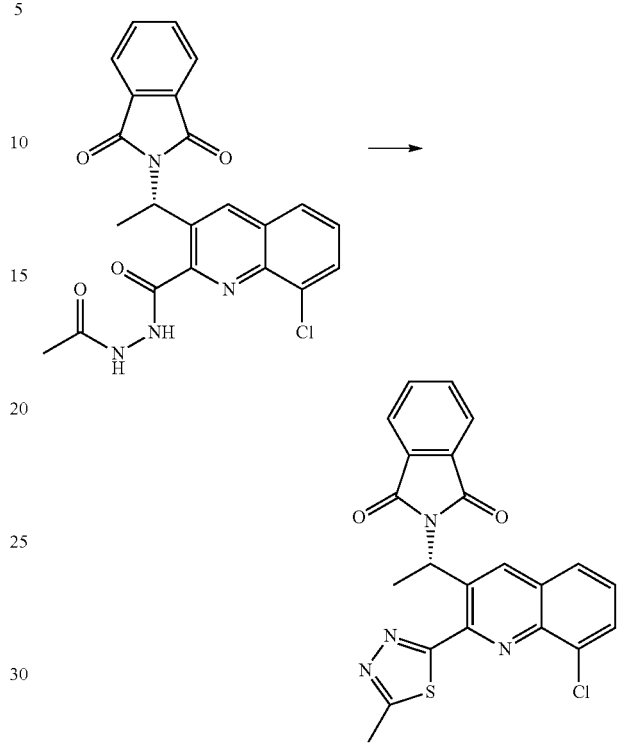

To a stirred solution of (S)—N'-acetyl-8-chloro-3-(1-(1,3-dioxoisoindolin-2-yl)-ethyl)quinoline-2-carbohydrazide (85 mg, 0.19 mmol) in THF (1.5 mL) and toluene (3.0 mL) was added Lawesson's reagent (118 mg, 0.29 mmol). The reaction was heated in the microwave at 120° C. for 20 minutes and then cooled to room temperature and purified by column chromatography (SiO₂, 12 g, hexanes:ethyl acetate, 1:0 to 1:1) to give 2-((S)-1-(8-chloro-2-(5-methyl-1,3,4-thiadiazol-2-yl)quinolin-3-yl)ethyl)isoindoline-1,3-dione. 1H NMR (400 MHz, CDCl₃) δ ppm 8.63 (1H, s), 7.77-7.84 (4H, m), 7.70 (2H, dd, J=5.3, 2.9 Hz), 7.46-7.51 (1H, m), 7.06 (1H, q, J=7.0 Hz), 2.85 (3H, s), 2.11 (3H, d, J=7.0 Hz).

(1S)-1-(8-Chloro-2-(5-methyl-1,3,4-thiadiazol-2-yl)quinolin-3-yl)ethanamine

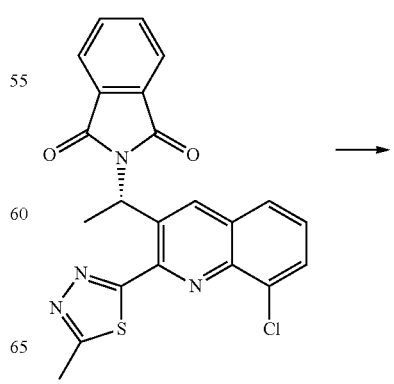

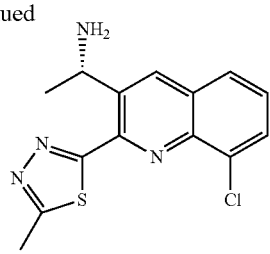

To a stirred solution of 2-((S)-1-(8-chloro-2-(5-methyl-1,3,4-thiadiazol-2-yl)-quinolin-3-yl)ethyl)isoindoline-1,3-dione (30 mg, 69 µmol) in THF (1.0 mL) and ethanol (3.0 mL) was added hydrazine monohydrate (69 µl, 1380 µmol). The reaction was heated to 90° C. for 40 minutes and then cooled to room temperature and evaporated in vacuo. The resulting residue was diluted with ethyl acetate (60 mL) and water (40 mL) and the aqueous layer was extracted with ethyl acetate (30 mL). The combined organic layers were washed with brine and then dried (MgSO$_4$), filtered and evaporated in vacuo to give (1S)-1-(8-chloro-2-(5-methyl-1,3,4-thiadiazol-2-yl)quinolin-3-yl)ethanamine 1H NMR (500 MHz, choroform-d) δ ppm 8.62 (1H, s), 7.79-7.84 (2H, m), 7.49-7.52 (1H, m), 5.61 (1H, d, J=6.4 Hz), 2.86 (3H, s), 1.57 (3H, d, J=6.6 Hz). Mass Spectrum (ESI) m/e=305.0 (M+1).

N—((S)-1-(8-Chloro-2-(5-methyl-1,3,4-thiadiazol-2-yl)quinolin-3-yl)ethyl)-9H-purin-6-amine

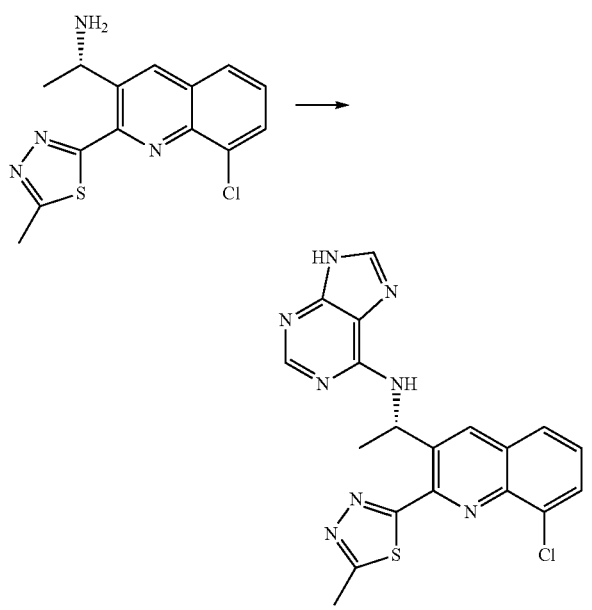

To a stirred solution of (1S)-1-(8-chloro-2-(5-methyl-1,3,4-thiadiazol-2-yl)-quinolin-3-yl)ethanamine (9 mg, 30 µmol) in 1-butanol (1.5 mL) was added huenig's base (6 µl, 35 µmol) and 6-chloropurine (5 mg, 30 µmol). The reaction was heated to 130° C. for 16 hours and then cooled to room temperature. The crude reaction mixture was purified by reverse phase HPLC (gradient: 20% water in acetonitrile to 85% water in acetonitrile) to give N—((S)-1-(8-chloro-2-(5-methyl-1,3,4-thiadiazol-2-yl)quinolin-3-yl)ethyl)-9H-purin-6-amine 1H NMR (400 MHz, MeOH-d$_4$) δ ppm 8.62 (1H, s), 8.05 (1H, s), 7.83-7.89 (2H, m), 7.53-7.57 (1H, m), 2.89 (3H, s), 1.83 (3H, d, J=6.6 Hz). Mass Spectrum (ESI) m/e=423.1 (M+1).

Example 61

8-Chloro-2-(5-fluoro-2methoxyphenylquinoline-3-carbaldehyde

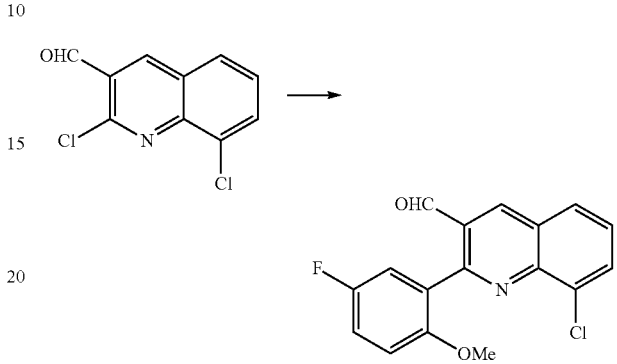

To a stirred degassed solution of 2,8-dichloroquinoline-3-carbaldehyde (305.8 mg, 1.353 mmol) in 12 mL of 3:1 MeCN/H$_2$O was added 5-fluoro-2-methoxyphenylboronic acid (252.9 mg, 1.488 mmol) and sodium carbonate (716.8 mg) and then Pd tetrakis (78.16 mg). The mixture was heated at 100° C. for 4 hour, poured into water and extracted with EtOAc. Chromatography: gradient Hex/EtOAc, 1H NMR (400 MHz, choroform-d) δ ppm 9.90 (1H, s), 8.78 (1H, s), 7.91-8.00 (2H, m), 7.52-7.61 (2H, m), 7.22 (1H, td, J=8.4, 3.1 Hz), 6.96 (1H, dd, J=9.0, 4.3 Hz), 3.74 (3H, s) Mass Spectrum (ESI) m/e=343.1 (M+1).

3-(Azidomethyl)-8-chloro-2-(5-fluoro-2-methoxyphenyl)quinoline

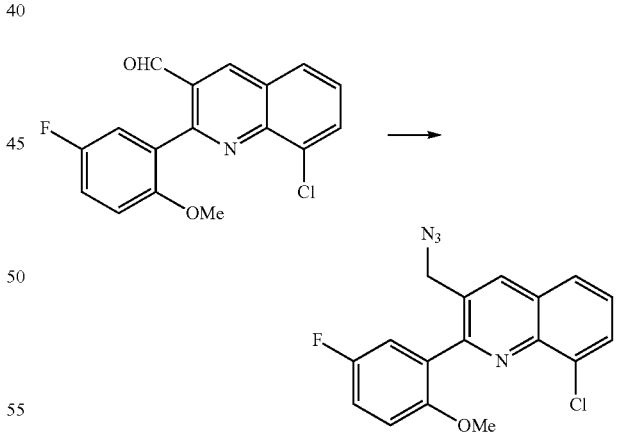

To a stirred solution of 8-chloro-2-(5-fluoro-2-methoxyphenyl)quinoline-3-carbaldehyde (385.4 mg, 1.221 mmol) in THF (6.0 mL) was added sodium borohydride (1.831 mmol) at rt. The solution was stirred 1 hour then diluted with water, and extracted with EtOAc to provide a crude solid after solvent removal, which was used without further purification. To the crude alcohol in CHCl$_3$ (6 mL) was added thionyl chloride (0.445 mL, 6.103 mmol) at r.t. and stirred overnight. After 14 h the solvents were removed (TLC indicates complete.) The solid was dissolved in DMF (6 mL) then sodium azide (2.441 mmol) was added at once, and stirred 1 hour, poured into water and extracted EtOAc to give a crude material: 373.3 mg Chromatography, gradient 89/9/1.

1H NMR (400 MHz, choroform-d) δ ppm 8.28 (1H, s), 7.86 (1H, dd, J=7.4, 1.4 Hz), 7.83 (1H, dd, J=8.2, 1.4 Hz), 7.51 (1H, dd, J=8.1, 7.5 Hz), 7.22 (1H, dd, J=8.2, 3.1 Hz), 7.13-7.19 (1H, m), 6.95 (1H, dd, J=9.0, 4.3 Hz), 4.48 (2H, s), 3.76 (3H, s) Mass Spectrum (ESI) m/e=343.1 (M+1).

(8-Chloro-2-(5-fluoro-2-methoxyphenyl)quinoline-3-yl)methanamine

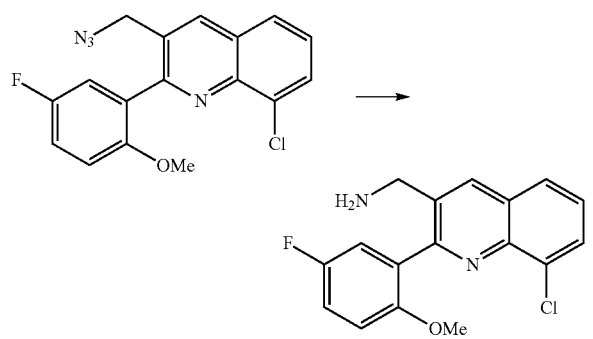

To a stirred solution of 3-(azidomethyl)-8-chloro-2-(5-fluoro-2-methoxyphenyl)-quinoline (210.7 mg, 615 μmol) in THF 5 mL and MeOH 12 mL was added palladium, 10 wt. % on activated carbon (0.329 mmol) and placed under a medium balloon containing H₂. The reaction was complete after 2 h, it was filtered (Celite™) and solvents removed. Chromatography: Gradient 89:9:1. 1H NMR (400 MHz, choroform-d) δ ppm 8.30 (1H, s), 7.80 (2H, ddd, J=7.9, 6.5, 1.3 Hz), 7.49-7.50 (1H, m), 7.47 (1H, dd), 7.09-7.18 (2H, m), 6.93 (1H, dd, J=8.9, 4.2 Hz), 3.89 (2H, br. s), 3.74 (3H, s) Mass Spectrum (ESI) m/e=317.0 (M+1).

N-((8-Chloro-2-(5-fluoro-2-methoxyphenyl)quinoline-3yl)methyl)-9H-purin-6-amine

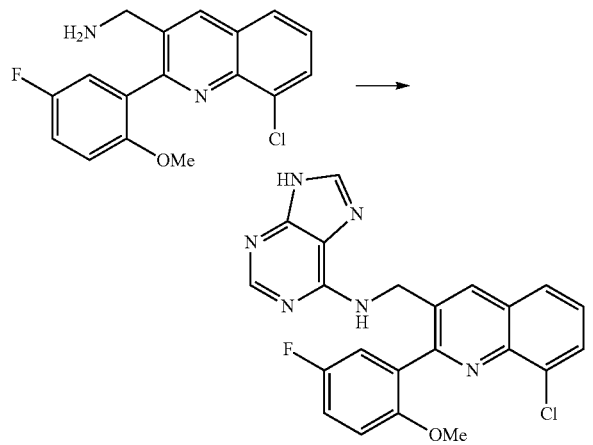

To a stirred mixture of (8-chloro-2-(5-fluoro-2-methoxyphenyl)quinolin-3 yl)-methanamine (190.4 mg, 0.601 mmol) and 6-bromopurine (126 mg, 0.631 mmol) in 1-butanol (3.300 mL, 36.1 mmol) was added N,N-ethyldiisopropylamine (0.209 mL, 1.20 mmol). The mixture was heated to 100° C. overnight. The solvents were removed and the residue subjected to chromatography: gradient/isocratic 1H NMR (500 MHz, DMSO-d₆) δ ppm 12.93 (1H, br. s.), 8.28 (1H, br. s.), 8.09 (2H, s), 7.96 (1H, d, J=8.1 Hz), 7.91 (1H, d, J=7.3 Hz), 7.55 (1H, t, J=7.8 Hz), 7.26-7.33 (1H, m), 7.21 (1H, dd, J=8.6, 3.2 Hz), 7.15 (1H, br. s.), 3.77 (3H, s), 3.32 (2H, s) Mass Spectrum (ESI) m/e=335.1 (M+1).

Example 62

N⁶-((8-Chloro-2-(2-chlorophenyl)quinolin-3-yl)methyl)-9H-purine-2,6-diamine

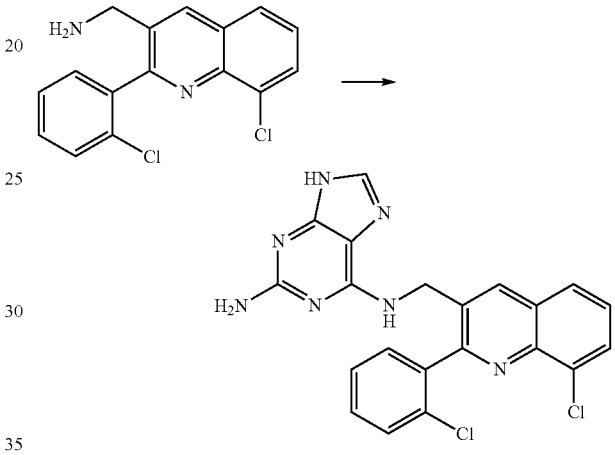

A mixture of (8-chloro-2-(2-chlorophenyl)quinolin-3-yl) methanamine (144.8 mg, 0.478 mmol), 2-amino-6-chloropurine (89.1 mg, 0.525 mmol) and N,N-diisopropylethylamine, redestilled, 99.5% (0.166 mL, 0.955 mmol) in 1-butanol, anhydrous, 99.8% (5.24 mL) was heated to reflux and stirred overnight. The reaction was cooled solvents removed and subjected to chromatography, 89:9:1 (DCM/MeOH, NH4OH) gradient, 1H NMR (400 MHz, DMSO-d₆) δ ppm 12.08 (1H, br. s.), 8.36 (1H, s), 8.01 (1H, d, J=8.2 Hz), 7.92 (1H, d, J=6.3 Hz), 7.47-7.71 (8H, m), 5.56 (2H, br. s.), 4.59 (2H, br. s.) Mass Spectrum (ESI) m/e=436.1 (M+1).

Example 63

N-((8-Chloro-2-(3-isopropylphenyl)quinolin-3-yl)methyl)-9H-purine-6-diamine

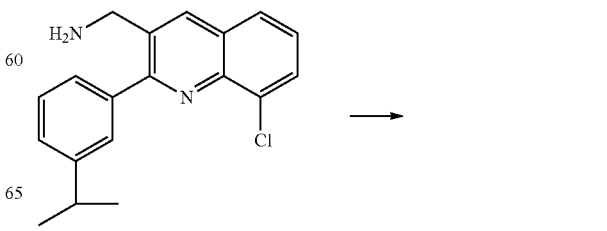

-continued

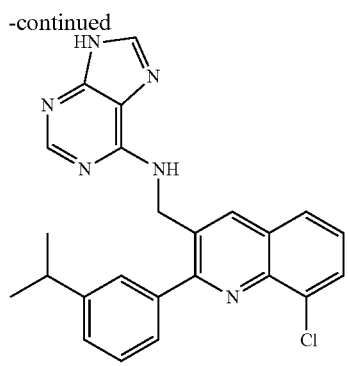

To a stirred solution of (8-chloro-2-(3-isopropylphenyl) quinolin-3-yl)-methanamine (181.7 mg, 585 μmol) in 1-butanol (3210 μl, 35075 μmol) was added N,N-diisopropylethylamine (204 μl, 1169 μmol) and N,N-diisopropylethylamine (204 μl, 1169 μmol) and slowly heated to 100° C., heated 24 h removed from heat and the solvents removed. chromatographed gradient 89:9:1 (DCM/MeOH, NH4OH): 0-20% grad (15 min) isocratic 20%, (10 min) 20-50 grad, (10 min) then isocratic 50% 10 min to give pure desired product, 1H NMR (400 MHz, DMSO-d$_6$) δ ppm 12.97 (1H, br. s.), 8.34 (1H, s), 8.12 (2H, s), 7.94 (1H, dd, J=8.3, 1.1 Hz), 7.91 (1H, dd, J=7.5, 1.3 Hz), 7.62 (1H, s), 7.46-7.55 (3H, m), 7.39 (1H, d, J=7.2 Hz), 4.84 (1H, br. s.), 2.95-3.03 (1H, m), 1.25 (6H, d, J=7.0 Hz) Mass Spectrum (ESI) m/e=429.2 (M+1).

Example 64

2-((S)-1-(8-Chloro-2-(6-methylpyridin-2-yl)quinolin-3-yl)ethyl)isoindoline-1,3-dione

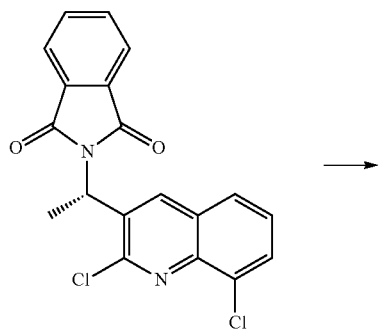

A stirred mixture of (S)-2-(1-(2,8-dichloroquinolin-3-yl) ethyl)isoindoline-1,3-dione (254.3 mg, 0.685 mmol) and tetrakis(triphenylphosphine)palladium (79.16 mg, 68.50 μmol), 2-methyl-6-(tributylstannyl)pyridine (523.6 mg, 1.37 mmol) in dioxane (degassed) was heated at 100° C. for 28 h, complete by LC-MS solvent removed and chromatographed: 89:9:1 (DCM/MeOH, NH4OH) gradient. 1H NMR (400 MHz, DMSO-d$_6$) δ ppm 8.78 (1H, s), 8.15 (1H, dd, J=8.3, 1.3 Hz), 7.98 (1H, dd, J=7.5, 1.3 Hz), 7.73-7.78 (2H, m), 7.58-7.69 (4H, m), 7.36 (1H, d, J=7.6 Hz), 7.16 (1H, d, J=7.6 Hz), 6.11-6.19 (1H, m), 2.33 (3H, s), 1.82 (3H, d, J=7.0 Hz)

Mass Spectrum (ESI) m/e=427.9 (M+1).

(1S)-1-(8-Chloro-2-(6-methylpyridin-2-yl)quinolin-3-yl)ethyl)ethanamine

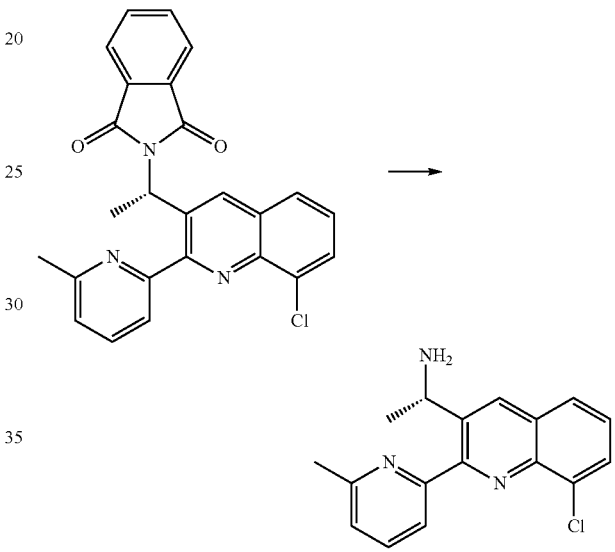

To a flask was charged 2-((S)-1-(8-chloro-2-(6-methylpyridin-2-yl)quinolin-3-yl)-ethyl)isoindoline-1,3-dione (260.0 mg, 0.608 mmol) in ethanol 95% (12.2 mL) and hydrazine hydrate (0.189 mL, 6.076 mmol) was added, followed by refluxing. After 2 h added an additional 10 eq hydrazine, reflux continued for 3 h. All solvents were removed and the residue chromatographed, 89:9:1 (DCM/MeOH, NH4OH). 1H NMR (400 MHz, choroform-d) δ ppm 8.37 (1H, s), 7.90 (1H, d, J=7.4 Hz), 7.68-7.75 (3H, m), 7.38 (1H, dd, J=8.2, 7.4 Hz), 7.17 (1H, d, J=7.4 Hz), 4.69 (1H, q, J=6.7 Hz), 2.58 (3H, s), 1.43 (3H, d, J=6.8 Hz) Mass Spectrum (ESI) m/e=298.0 (M+1).

N—((S)-1-(8-Chloro-2-(6-methylpyridin-2-yl)quinolin-3-yl)ethyl)-9H-purin-6-amine

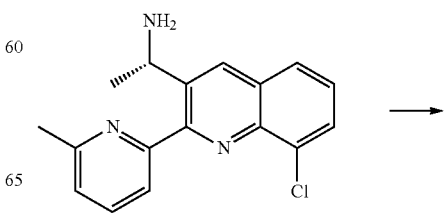

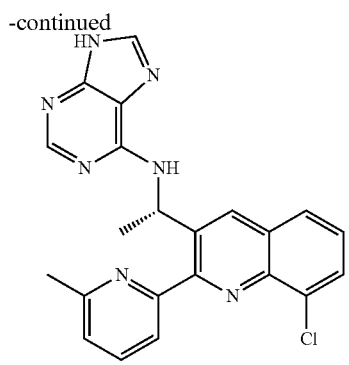

To a stirred solution of (1S)-1-(8-chloro-2-(6-methylpyridin-2-yl)quinolin-3-yl)-ethanamine (146 mg, 0.49 mmol) in 1-butanol (5.4 mL, 59 mmol) was added 6-bromopurine (0.107 g, 0.54 mmol) and N,N-diisopropylethylamine (0.17 mL, 0.98 mmol) with heating (110° C.) overnight. solvents were removed and the residue subjected to chromatography, gradient, 89:9:1 (DCM:MeOH:NH$_4$OH). 1H NMR (400 MHz, DMSO-d$_6$) δ ppm 12.84 (1H, br. s.), 8.67 (1H, s), 8.38 (1H, br. s.), 8.03-8.10 (1H, m), 7.84-7.98 (5H, m), 7.56 (1H, t, J=7.8 Hz), 7.36 (1H, d, J=5.5 Hz), 6.03 (1H, br. s.), 2.58 (3H, br. s.), 1.66 (3H, d, J=6.3 Hz) Mass Spectrum (ESI) m/e=415.9 (M+1).

Example 65

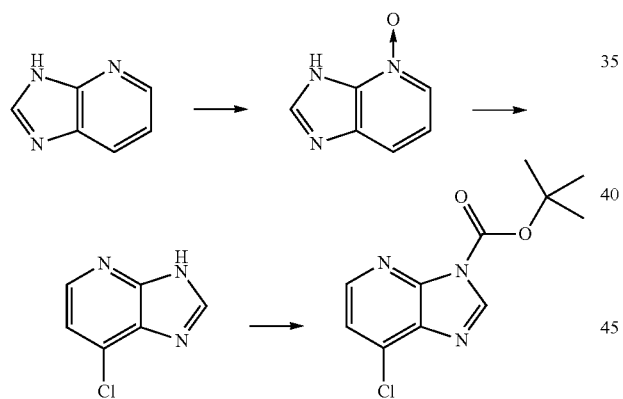

Mcpba (8.7 g, 50 mmol) was added at room temperature to 3H-imidazo[4,5-b]pyridine (5.0 g, 42 mmol) in acetic acid (84 mL, 1469 mmol). The mixture was stirred for 3 hours. The resulting precipitate was filtered and rinsed with Et$_2$O, it gave 4-azabenzimidazole-N-oxide. To 4-azabenzimidazole-N-oxide (2.00 g, 14.8 mmol) phosphorous oxychloride (25.00 mL, 266 mmol) was added at room temperature. The solution was heated to 90° C. for 18 h. The solution was cooled and the rest POCl3 was distilled off in vacuo. The residue was dissolved in CH$_3$CN and quenched with slow addition of ice-water. The mixture was basified to PH 9 with 50% NaOH solution. At room temperature the resulting precipitates were filtered. The collected solid was dissolved in MeOH and insoluble residue was removed by filtration. The filtrates were concentrated and the residue was purified by flash chromatography over silica gel, using 3:7 EtOAc-hexane, gave 7-chloro-3H-imidazo[4,5-b]pyridine (1.20 g, 52.8%). To the mixture of di-tert-butylpyrocarbonate (1193 mg, 5465 μmol), 7-chloro-3H-imidazo[4,5-b]pyridine (0.763 g, 4968 μmol) in acetonitrile (15 mL), 4-(dimethylamino)pyridine (61 mg, 497 μmol) was added. The mixture was stirred at room temperature overnight. Evaporation of the solvent, flash chromatography of the residue over silica gel, using 0% to 25% EtOAc/hexane, gave tert-butyl 7-chloro-3H-imidazo[4,5-b]pyridine-3-carboxylate, Mass Spectrum (ESI) m/e=253.0 (M+1).

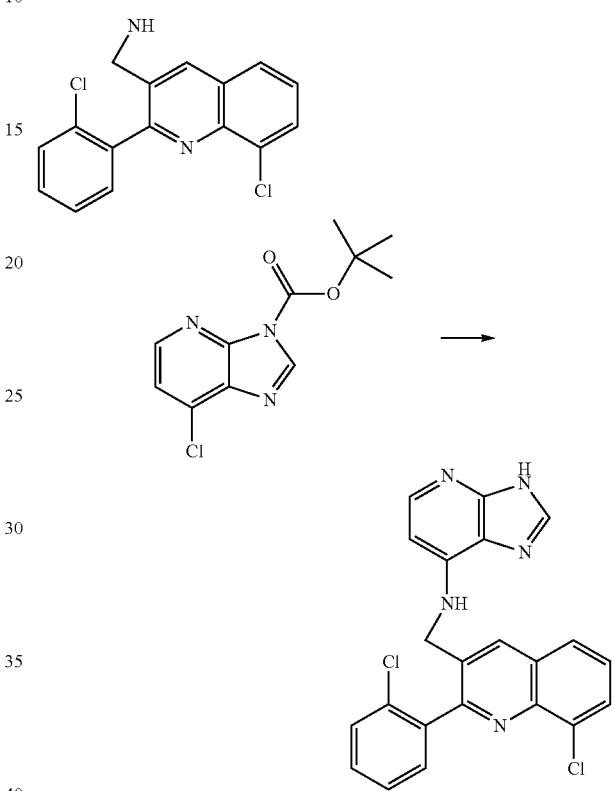

A sealed flask was charged with (8-chloro-2-(2-chlorophenyl)quinolin-3-yl)-methanamine, made in procedure E in A-1216 US PSP, tert-butyl 7-chloro-3H-imidazo[4,5-b]pyridine-3-carboxylate (109 mg, 429 μmol), diisopropylethylamine (0.075 mL, 429 μmol) and 1-butanol (2.0 mL, 21856 μmol). The mixture was subjected to microwave at 180° C. for 120 min. After cooled to room temperature, the mixture was concentrated, and the residue was diluted with MeOH. The solution was purified by HPLC, 25%-45% of B in 35 min. The collected fractions were dissolved in CH$_2$Cl$_2$ and neutralized by washing with aq. NaHCO$_3$, the CH$_2$Cl$_2$ layer was dried, concentrated and gave N #8-chloro-2-(2-chlorophenyl)-quinolin-3-yl)methyl)-3H-imidazo[4,5-b]pyridin-7-amine (20.2 mg, 15%), $^1$H NMR (DMSO-d$_6$) δ ppm 12.72 (1H, s), 8.43 (1H, s), 8.15 (1H, s), 8.09 (1H, d, J=8.0 Hz), 8.05 (1H, d, J=8.0 Hz), 7.73-7.80 (2H, m), 7.63-7.70 (4H, m), 7.45 (1H, s), 6.13 (1H, d, J=8.0 Hz), 4.60 (2H, br). Mass Spectrum (ESI) m/e=420.0 (M+1).

Example 66

Using the above or other analogous synthetic techniques and substituting with appropriate reagents the following compound was prepared:

123

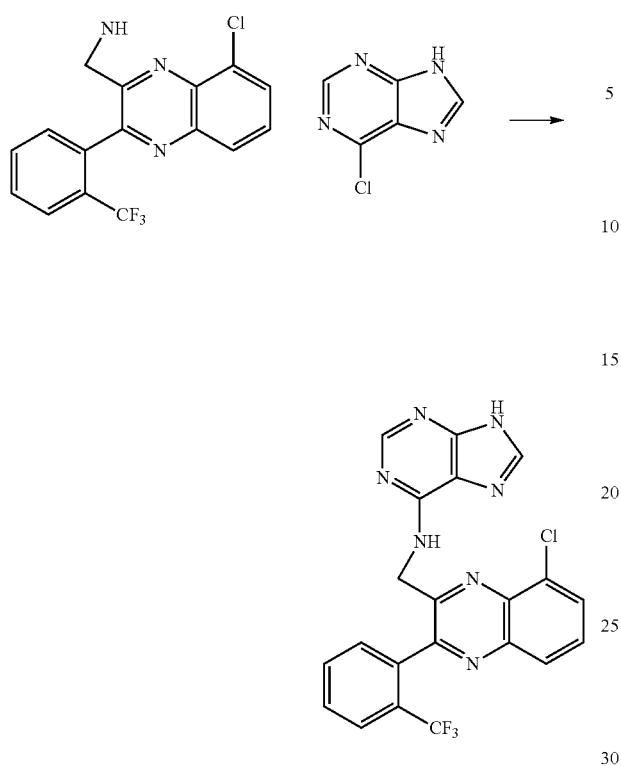

124

Example 68

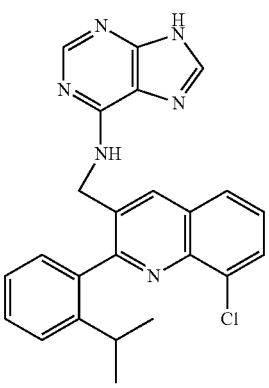 [SMILES: CC(C)c1ccccc1-c1nc2c(Cl)cccc2cc1CNc1ncnc2[nH]cnc12]

N-((8-Chloro-2-(2-isopropylphenyl)quinolin-3-yl)methyl)-9H-purin-6-amine, $^1$H NMR (DMSO-$d_6$) δ ppm 8.30 (1H, s), 8.14 (1H, br), 8.09 (1H, s), 7.97 (1H, d, J=8.0 Hz), 7.90 (1H, d, J=8.0 Hz), 7.45-7.57 (3H, m), 7.31-7.36 (2H, m), 2.62-2.69 (1H, m), 1.15-1.22 (6H, m). Mass Spectrum (ESI) m/e=429.2 (M+1).

Example 69

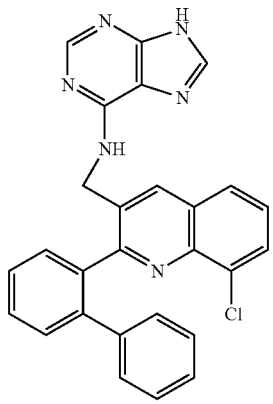 [SMILES: Clc1cccc2cc(CNc3ncnc4[nH]cnc34)c(-c3ccccc3-c3ccccc3)nc12]

N-((8-chloro-3-(2-(trifluoromethyl)phenyl)quinoxalin-2-yl)methyl)-9H-purin-6-amine, $^1$H NMR (MeOD) δ ppm 8.11 (1H, s), 8.08 (1H, br), 8.03 (1H, d, J=8.5 Hz), 7.97 (1H, d, J=8.5 Hz), 7.89 (1H, d, J=8.5 Hz), 7.80 (1H, t, J=8.5 Hz), 7.68-7.75 (4H, m), Mass Spectrum (ESI), m/e=456.1 (M+1).

Using the same or analogous synthetic techniques and substituting with appropriate reagents as in procedure H, the following compounds were prepared:

Example 67

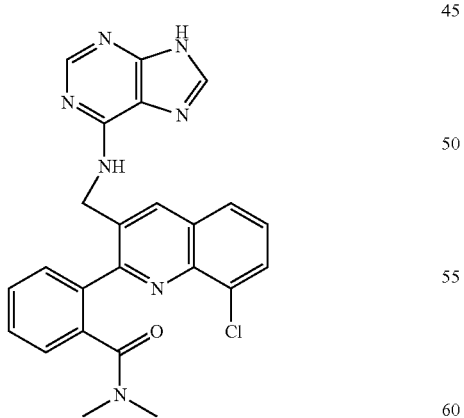

2-(3-((9H-Purin-6-ylamino)methyl)-8-chloroquinolin-2-yl)-N,N-dimethylbenzamide, $^1$H NMR (DMSO-$d_6$) δ ppm 8.39 (1H, s), 8.23 (1H, s), 8.19 (1H, s), 8.01 (1H, d, J=8.0 Hz), 7.96 (1H, d, J=8.0 Hz), 7.82 (1H, br), 7.52-7.64 (4H, m). Mass Spectrum (ESI) m/e=458.2 (M+1).

N-((8-Chloro-2-(2-phenylphenyl)quinolin-3-yl)methyl)-9H-purin-6-amine, $^1$H NMR (DMSO-$d_6$) δ ppm 8.13 (1H, s), 8.09 (1H, br), 8.03 (1H, s), 7.86 (2H, t, J=8.0 Hz), 7.45-7.57 (4H, m), 7.20-7.25 (2H, m), 7.13-7.18 (2H, m). Mass Spectrum (ESI) m/e=463.1 (M+1).

Example 70

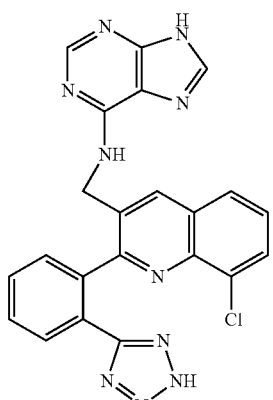

N-((2-(2-(2H-Tetrazol-5-yl)phenyl)-8-chloroquinolin-3-yl)methyl)-9H-purin-6-amine, $^1$H NMR (DMSO-d$_6$) δ ppm 8.24 (1H, s), 8.11 (2H, br), 7.07 (2H, t, J=8.0 Hz), 7.95 (1H, t, J=8.0 Hz), 7.86 (1H, t, J=8.0 Hz), 7.50-7.63 (4H, m), Mass Spectrum (ESI) m/e=455.2 (M+1).

Example 71

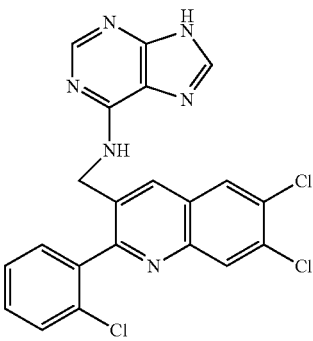 [SMILES: Clc1cc2cc(CNc3ncnc4[nH]cnc34)c(-c3ccccc3Cl)nc2cc1Cl]

N-((6,7-Dichloro-2-(2-chlorophenyl)quinolin-3-yl)methyl)-9H-purin-6-amine, $^1$H NMR (DMSO-d$_6$) δ ppm 8.29 (1H, s), 8.14 (1H, s), 8.01 (2H, br), 7.97 (1H, s), 7.55 (1H, t, J=8.0 Hz), 7.41-7.50 (4H, m), Mass Spectrum (ESI) m/e=457.0 (M+1).

Example 72

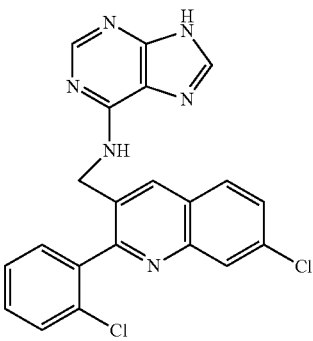 [SMILES: Clc1ccc2cc(CNc3ncnc4[nH]cnc34)c(-c3ccccc3Cl)nc2c1]

N-((7-Chloro-2-(2-chlorophenyl)quinolin-3-yl)methyl)-9H-purin-6-amine, $^1$H NMR (DMSO-d$_6$) δ ppm 8.35 (1H, s), 8.13 (1H, br), 8.09 (3H, br), 8.07 (1H, s), 7.59-7.66 (2H, m), 7.43-7.55 (3H, m), Mass Spectrum (ESI) m/e=421.1 (M+1).

Example 73

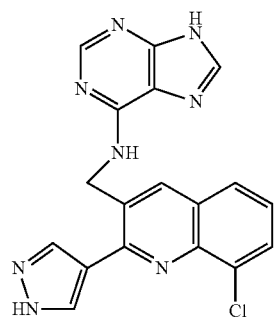 [SMILES: Clc1cccc2cc(CNc3ncnc4[nH]cnc34)c(-c3cn[nH]c3)nc12]

N-((8-Chloro-2-(1H-pyrazol-4-yl)quinolin-3-yl)methyl)-9H-purin-6-amine, $^1$H NMR (DMSO-d$_6$) δ ppm 13.30 (0.5H, s), 13.02 (0.5H, s), 8.47 (0.5H, s), 8.10-8.28 (3.5H, m), 7.82-7.92 (2H, m), 7.44 (1H, t, J=8.0 Hz), 5.07 (1H, s). Mass Spectrum (ESI) m/e=377.0 (M+1).

Example 74

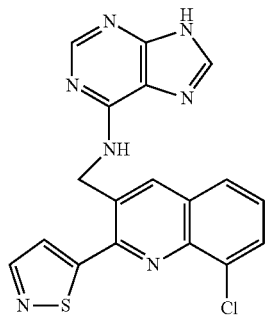 [SMILES: Clc1cccc2cc(CNc3ncnc4[nH]cnc34)c(-c3ccns3)nc12]

N-((8-chloro-2-(isothiazol-5-yl)quinolin-3-yl)methyl)-9H-purin-6-amine, $^1$H NMR (DMSO-d$_6$) δ ppm 8.72 (1H, s), 8.45 (1H, br), 8.17 (2H, br), 8.08 (1H, s), 7.96-8.02 (2H, m), 7.58 (1H, t, J=8.0 Hz), Mass Spectrum (ESI) m/e=394.1 (M+1).

Example 75

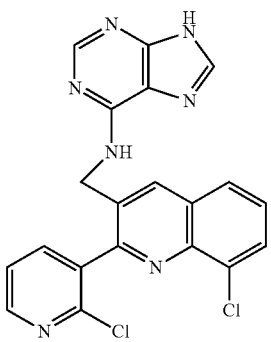 [SMILES: Clc1ncccc1-c1nc2c(Cl)cccc2cc1CNc1ncnc2[nH]cnc12]

N-((8-Chloro-2-(2-chloropyridin-3-yl)quinolin-3-yl)methyl)-9H-purin-6-amine, $^1$H NMR (DMSO-d$_6$) δ ppm 8.49 (1H, s), 8.37 (1H, d, J=8.0 Hz), 8.09 (1H, s), 8.08 (1H, br), 7.90-7.98 (3H, m), 7.59 (1H, t, J=8.0 Hz), 7.36 (1H, dd, J=8.0, 8.0 Hz), Mass Spectrum (ESI) m/e=422.0 (M+1).

Example 76

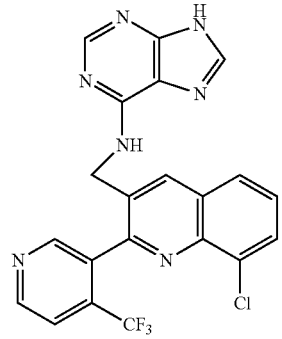 [SMILES: FC(F)(F)c1ccncc1-c1nc2c(Cl)cccc2cc1CNc1ncnc2[nH]cnc12]

N-((8-Chloro-2-(4-(trifluoromethyl)pyridin-3-yl)quinolin-3-yl)methyl)-9H-purin-6-amine, ¹H NMR (MeOD) δ ppm 8.75 (1H, s), 8.69 (1H, d, J=8.0 Hz), 8.41 (1H, s), 7.98 (1H, s), 7.95 (1H, br), 7.84 (1H, d, J=8.0 Hz), 7.81 (1H, d, J=8.0 Hz), 7.67 (1H, d, J=8.0 Hz), 7.50 (1H, t, J=8.0 Hz), Mass Spectrum (ESI) m/e=456.1 (M+1).

Example 77

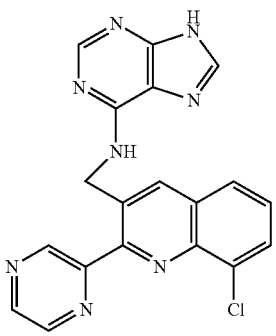 [SMILES: Clc1cccc2cc(CNc3ncnc4[nH]cnc34)c(-c3cnccn3)nc12]

N-((8-Chloro-2-(pyrazin-2-yl)quinolin-3-yl)methyl)-9H-purin-6-amine, ¹H NMR (DMSO-d₆) δ ppm 9.43 (1H, s), 8.80-8.85 (2H, m), 8.49 (1H, s), 8.08 (2H, br), 8.01 (1H, d, J=8.0 Hz), 7.98 (1H, d, J=8.0 Hz), 7.61 (1H, t, J=8.0 Hz), Mass Spectrum (ESI) m/e=389.0 (M+1).

Using the same or analogous synthetic techniques and substituting with appropriate reagents as in example 109, with additional two different steps as shown below, following compounds were prepared:

Example 78

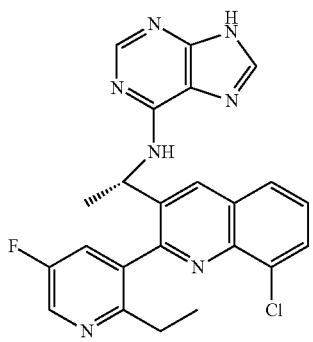 [SMILES: CCc1ncc(F)cc1-c1nc2c(Cl)cccc2cc1[C@H](C)Nc1ncnc2[nH]cnc12]

N—((S)-1-(8-Chloro-2-(2-ethyl-5-fluoropyridin-3-yl)quinolin-3-yl)ethyl)-9H-purin-6-amine, ¹H NMR (MeOD) δ ppm 8.71 (1H, s), 8.28-8.57 (3H, m), 7.85-8.07 (3H, m), 7.64 (1H, t, J=8.0 Hz), 1.84 (1.5H, br), 1.69 (1.5H, br), 1.28 (1.5H, br), 1.16 (1.5H, br), Mass Spectrum (ESI) m/e=448.1 (M+1).

Example 79

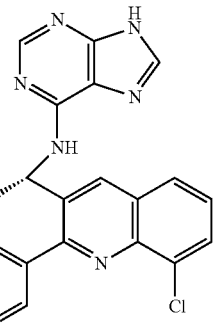

N—((S)-1-(8-Chloro-2-(5-fluoropyridin-3-yl)quinolin-3-yl)ethyl)-9H-purin-6-amine, ¹H NMR (MeOD) δ ppm 8.80 (1H, s), 8.67 (1H, s), 8.58 (1H, br), 8.48 (1H, br), 8.43 (1H, br), 8.11 (1H, br), 7.97 (1H, d, J=8.0 Hz), 7.94 (1H, d, J=8.0 Hz), 7.61 (1H, t, J=8.0 Hz), 1.76 (3H, d, J=8.0 Hz), Mass Spectrum (ESI) m/e=420.1 (M+1).

Example 80

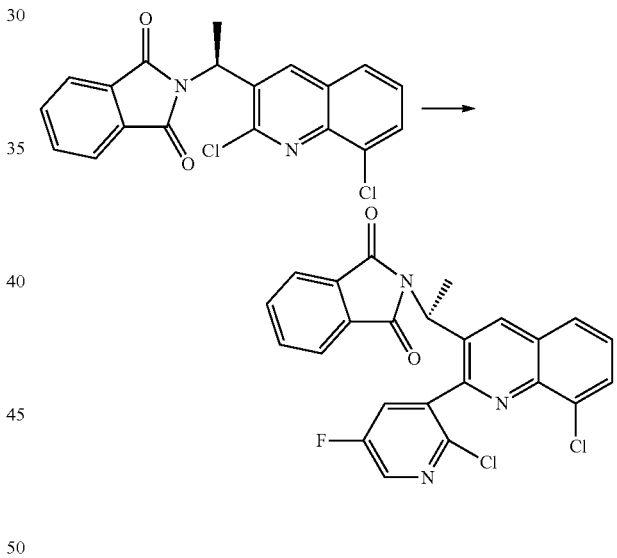

A mixture of (S)-2-(1-(2,8-dichloroquinolin-3-yl)ethyl)isoindoline-1,3-dione (120.0 mg, 323 μmol), 2-chloro-5-fluoropyridin-3-ylboronic acid (57 mg, 323 μmol), tetrakis(triphenylphosphine)palladium (37 mg, 32 μmol), cesium fluoride (147 mg, 970 μmol) and copper(I) iodide (12 mg, 65 μmol) in 1,2-ethanediol, dimethyl ether (3.0 mL, 323 μmol) was subjected to microwave at 100° C. for 1 h, cooled to room temperature. Filtration of the resultant mixture and rinsed with EtOAc, the filtrates were collected and concentrated. Purification of the residue by flash chromatography over silica gel, gradient elution, 0-100% EtOAc in hexane, gave 2-((S)-1-(8-chloro-2-(2-chloro-5-fluoropyridin-3-yl)quinolin-3-yl)-ethyl)isoindoline-1,3-dione, Mass Spectrum (ESI) m/e=466.0 (M+1).

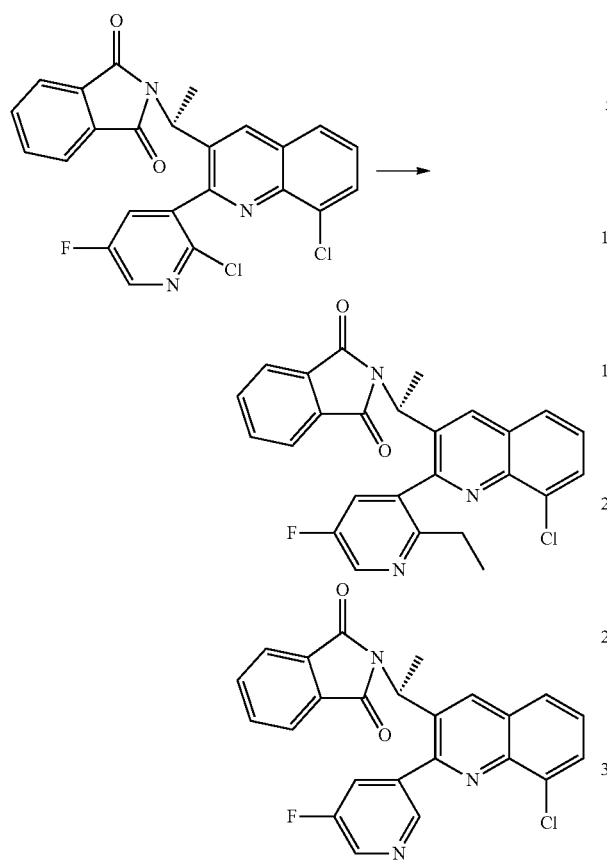

A mixture of 2-((S)-1-(8-chloro-2-(2-chloro-5-fluoropyridin-3-yl)quinolin-3-yl)-ethyl)isoindoline-1,3-dione (192.7 mg, 413 μmol), dioxan (15 mL, 175989 μmol)-, triethylaluminum (236 mg, 2066 μmol) and tetrakis(triphenylphosphine)-palladium (96 mg, 83 μmol) was refluxed for 4 hs under $N_2$, cooled to room temperature. The reaction mixture was acidified with HCl (2N) and the solvent was evaporated. The residue was diluted with water, basified with NaOH (20%), and the mixture was extracted with EtOAc. The combined extracts were washed with water, brine, dried and concentrated. Purification of the residue by flash chromatography over silica gel, gradient elution, 0-100% EtOAc in hexane, gave 2-((S)-1-(8-chloro-2-(2-ethyl-5-fluoropyridin-3-yl)quinolin-3-yl)ethyl)isoindoline-1,3-dione, Mass Spectrum (ESI) m/e=460.1 (M+1). And 2-((S)-1-(8-chloro-2-(5-fluoropyridin-3-yl)quinolin-3-yl)ethyl)isoindoline-1,3-dione, Mass Spectrum (ESI) m/e=432.1 (M+1).

Example 81: Preparation of N-((5-Chloro-3-(2-chlorophenyl)quinoxalin-2-yl)methyl)-9H-purin-6-amine 3-Chlorobenzene-1,2-diamine

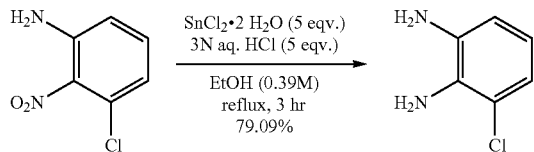 [SMILES: Nc1cccc(Cl)c1[N+](=O)[O-] ; Nc1cccc(Cl)c1N]

To a solution of 3-chloro-2-nitroaniline (10.00 g, 57.95 mmol), 3 N aq. HCl (96.58 mL, 289.7 mmol), and ethyl alcohol (148.6 mL, 57.95 mmol) was added Tin(II) chloride dihydrate (65.96 g, 289.7 mmol) and the mixture was heated under reflux with stirring. After 3 h, the mixture was cooled to room temperature and concentrated under reduced pressure to give a brown syrup. The mixture was cautiously treated with an excess of 10 M KOH (115.9 mL, 1159 mmol, 20 eqv.). The mixture was diluted with EtOAc (200 mL), filtered through Celite™ pad, and washed the pad well with EtOAc (100 mL×2). The filtrate was extracted with EtOAc (100 mL×2). The combined organic layers were washed with water (100 mL×1), dried over $MgSO_4$, filtered, and concentrated under reduced pressure to give 3-chlorobenzene-1,2-diamine as a red oil: $^1$H NMR (400 MHz, DMSO-$d_6$) δ ppm 6.43-6.53 (2H, m), 6.38 (1H, t, J=7.8 Hz), 4.80 (2H, s), 4.60 (2H, s); LC-MS (ESI) m/z 142.9 [M+H]$^+$. The crude product was carried on crude without purification for the next step.

1-(2-Chlorophenyl)propane-1,2-dione

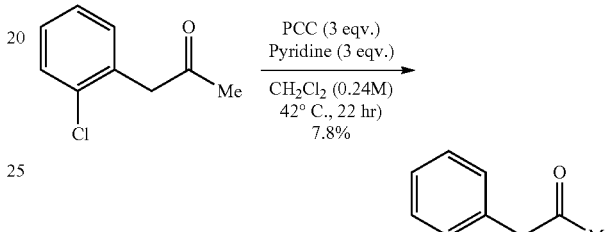

To a solution of 2-chlorophenylacetone (10.800 g, 64.049 mmol) in 279 mL of $CH_2Cl_2$, pyridinium chlorochromate (41.418 g, 192.15 mmol), and pyidine (16 mL) in three portions were added over 2.5 hours and the mixture was refluxed under vigorous stirring. After 22 h, he mixture was removed from heat. The mixture was concentrated in vacuo to give a dark red syrup. The crude mixture was purified by column chromatography on a 120 g of Redi-Sep™ column using 0-10% gradient of EtOAc in hexane over 28 min as eluent to give 1-(2-chlorophenyl)propane-1,2-dione as yellow liquid: $^1$H NMR (400 MHz, choroform-d) δ ppm 7.66 (1H, dd, J=7.6, 1.8 Hz), 7.49-7.54 (1H, m), 7.38-7.45 (2H, m), 2.58 (3H, s); LC-MS: m/z 182.9 [M+H]$^+$.

3-Bromo-1-(2-chlorophenyl)propane-1,2-dione

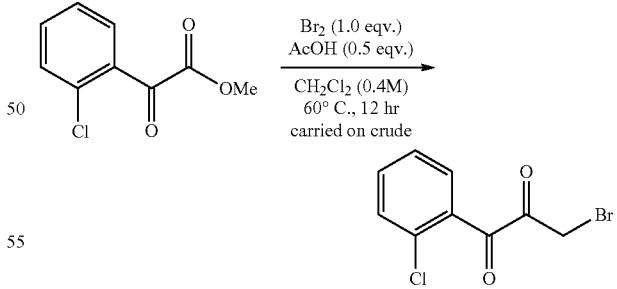

A mixture of 1-(2-chlorophenyl)propane-1,2-dione (4.2379 g, 23.208 mmol), bromine (1.1891 mL, 23.208 mmol), and glacial acetic acid (0.67005 mL, 11.604 mmol) in chloroform (58.020 mL, 23.208 mmol) was heated at 60° C. After 17 h of stirring at 60° C., the mixture was removed from heat and concentrated under reduced pressure to give 3-bromo-1-(2-chlorophenyl)propane-1,2-dione as an orange liquid: LC-MS: a peak of m/z 261.0 [M+H($^{79}$Br)]$^+$ and 262.9 [M+H ($^{81}$Br)—]$^+$. The orange liquid was carried on crude without purification for the next step.

3-(Bromomethyl)-5-chloro-2-(2-chlorophenyl)quinoxaline and 2-(Bromomethyl)-5-chloro-3-(2-chlorophenyl)quinoxaline

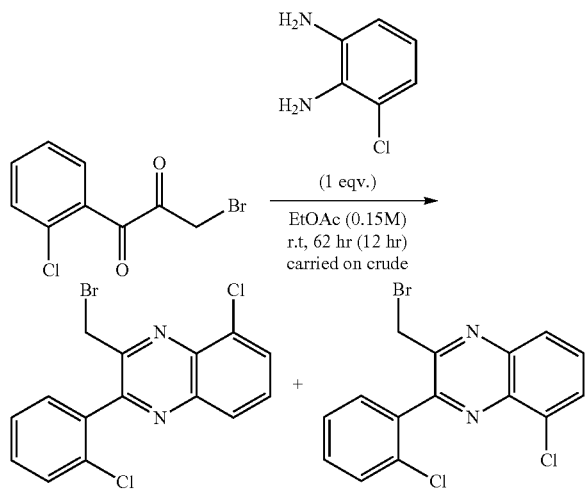

To a solution of 3-bromo-1-(2-chlorophenyl)propane-1,2-dione (6.0689 g, 23.208 mmol) in 100 mL of EtOAc was added a solution of 3-chlorobenzene-1,2-diamine (3.3091 g, 23.208 mmol) in 54.7 mL of EtOAc at room temperature and the resulting red mixture was stirred at room temperature. After 6 h of stirring at room temperature, the mixture was concentrated under reduced pressure to give a mixture of 3-(bromomethyl)-5-chloro-2-(2-chlorophenyl)quinoxaline and 2-(bromomethyl)-5-chloro-3-(2-chlorophenyl)quinoxaline as a red syrup: LC-MS (ESI) m/z 369.0 [M+H]$^+$. The crude product was carried on crude without purification for the next step.

(8-Chloro-3-(2-chlorophenyl)quinoxalin-2-yl)methanamine and (5-Chloro-3-(2-chlorophenyl)quinoxalin-2-yl)methanamine

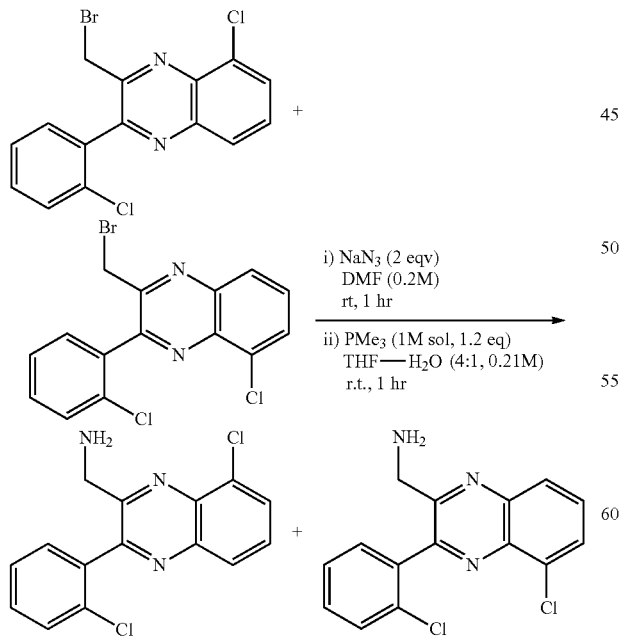

To a stirring solution of a mixture of 3-(bromomethyl)-5-chloro-2-(2-chlorophenyl)quinoxaline and 2-(bromomethyl)-5-chloro-3-(2-chlorophenyl)-quinoxaline (8.5418 g, 23.21 mmol) in DMF (100.0 mL, 23.21 mmol) was added sodium azide (3.017 g, 46.42 mmol) at room temperature and the mixture was stirred at room temperature. After 40 min, the mixture was partitioned between EtOAc (200 mL) and H$_2$O (100 mL). The organic layer was washed with brine (100 mL×1), dried over Na$_2$SO$_4$, filtered, and concentrated under reduced pressure to give 2-(azidomethyl)-5-chloro-3-(2-chlorophenyl)quinoxaline as a brown liquid: LC-MS (ESI) major peak of m/z 330.1 [M+H]$^+$. The crude product was carried on crude without purification for the next step.

To a stirring solution of 2-(azidomethyl)-5-chloro-3-(2-chlorophenyl)quinoxaline (7.6630 g, 23.21 mmol) in 100 mL of THF—H$_2$O (4:1) was added dropwise trimethylphosphine, 1.0 M solution in THF (27.85 mL, 27.85 mmol) at room temperature and the mixture was stirred at room temperature. After 1 h, the mixture was diluted with ice-cold 1 N NaOH (100 mL) and extracted with EtOAc (100 mL×3). The combined organic layers were washed with brine (100 mL×3), dried over Na$_2$SO$_4$, and concentrated under the reduced pressure to give green syrup. The green syrup was purified by column chromatography on a 120 g of Redi-Sep™ column using 3% isocratic of CH$_2$Cl$_2$:MeOH:NH$_4$OH (89:9:1) in CH$_2$Cl$_2$ for 42 min, then 3% to 100% gradient of CH$_2$Cl$_2$:MeOH:NH$_4$OH (89:9:1) in CH$_2$Cl$_2$ over 27 min, and then 100% isocratic of CH$_2$Cl$_2$:MeOH:NH$_4$OH (89:9:1) in CH$_2$Cl$_2$ for 5 min as eluent to give two separated regiosiomers: (8-chloro-3-(2-chlorophenyl)quinoxalin-2-yl)methanamine as a dark brown syrup: $^1$H NMR (400 MHz, DMSO-d$_6$) δ ppm 8.07-8.15 (2H, m), 7.81-7.90 (1H, m), 7.65-7.71 (1H, m), 7.52-7.66 (3H, m), 3.85 (2H, s), 2.23 (2H, br. s.); LC-MS (ESI) m/z 304.0 and 306.0 [M+H]$^+$ and (5-chloro-3-(2-chlorophenyl)-quinoxalin-2-yl)methanamine as a reddish-brown syrupy solid: $^1$H NMR (400 MHz, DMSO-d$_6$) δ ppm 8.15 (1H, dd, J=8.2, 1.2 Hz), 8.05 (1H, dd, J=7.8, 1.2 Hz), 7.85-7.93 (1H, m), 7.67-7.72 (1H, m), 7.53-7.66 (3H, m), 3.83 (2H, s), 2.07 (2H, br. s.); LC-MS (ESI) m/z 304.0 and 306.0 [M+H]$^+$. The structures of two regiosiomers were confirmed by NOESY experiment.

N-((5-Chloro-3-(2-chlorophenyl)quinoxalin-2-yl)methyl)-9H-purin-6-amine

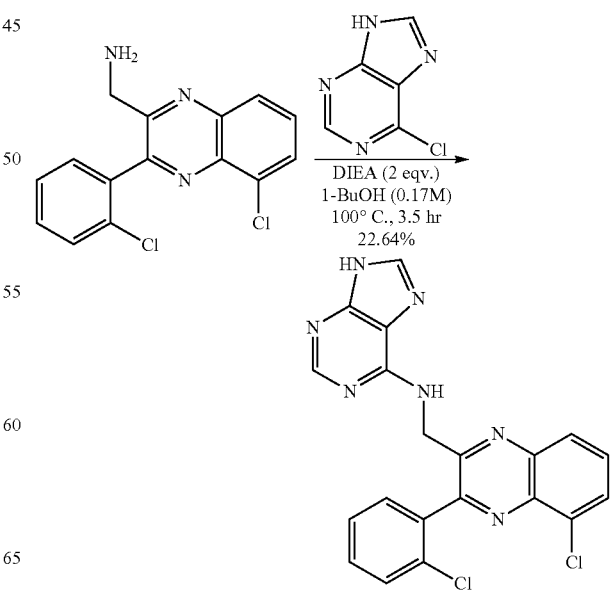

A mixture of 6-bromopurine (0.4553 g, 2.288 mmol), (5-chloro-3-(2-chlorophenyl)quinoxalin-2-yl)methanamine (0.6959 g, 2.288 mmol), and N,N-diisopropylethylamine (0.7970 mL, 4.576 mmol) in 1-butanol (13.46 mL, 2.288 mmol) was stirred at 100° C. After 3.5 h, the mixture was removed from the heat and concentrated under reduced pressure. The residue was purified by flash column chromatography on a silica gel column using 50% of $CH_2Cl_2$:MeOH:$NH_4OH$ (89:9:1) in $CH_2Cl_2$ as eluent to give a light-yellow solid. The light-yellow solid was suspended in $CH_2Cl_2$-Hexane (1:1) and filtered to give N-((5-chloro-3-(2-chlorophenyl)quinoxalin-2-yl)methyl)-9H-purin-6-amine as a light-yellow solid: $^1$H NMR (400 MHz, DMSO-$d_6$) δ ppm 12.93 (1H, s), 8.02-8.16 (4H, m), 7.95 (1H, br. s.), 7.83-7.90 (1H, m), 7.61-7.72 (2H, m), 7.53-7.59 (1H, m), 7.47-7.53 (1H, m), 4.72-4.98 (2H, m), 89676-20-1-1H-NMR; LC-MS (ESI) m/z 422.0 and 424.0 [M+H]$^+$.

Example 82: Preparation of N-((8-Chloro-2-(2-chlorophenyl)quinolin-3-yl)-methyl)morpholin-4-amine

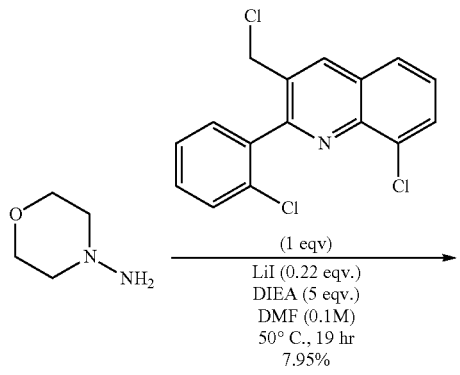

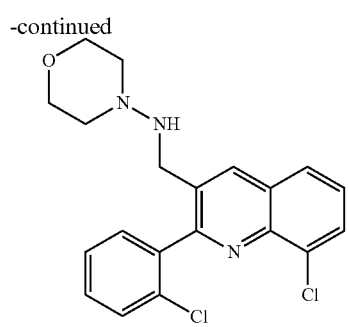

To a mixture of 8-chloro-3-(chloromethyl)-2-(2-chlorophenyl)quinoline (Prepared in Example 2), N,N-diisopropylethylamine (0.584 mL, 3.35 mmol), and lithium iodide (0.00566 mL, 0.148 mmol) in 7 mL of DMF was added 4-aminomorpholine (0.0647 mL, 0.670 mmol) and the mixture was stirred at 50° C. After 19 h, the mixture was concentrated under reduced pressure to give an yellow oil. The crude mixture was purified by column chromatography on a 40 g of Redi-Sep™ column using 0-100% gradient of EtOAc in hexane over 14 min and then 100% isocratic of EtOAc for 10 min as eluent to give N-((8-chloro-2-(2-chlorophenyl)-quinolin-3-yl)methyl)morpholin-4-amine as a light yellow foam (syrup): $^1$H NMR (400 MHz, choroform-d) δ ppm 8.39 (1H, s), 7.73-7.88 (2H, m), 7.37-7.53 (5H, m), 3.78-4.07 (2H, m), 3.64 (4H, t, J=4.7 Hz), 2.53 (4H, s); LC-MS (ESI) m/z 388.0 and 390.1 [M+H]$^+$.

Example 83: Preparation of N-((3-(2-Chlorophenyl)-8-methylquinoxalin-2-yl)methyl)thieno[3,2-d]pyrimidin-4-amine as a TFA salt and N-((3-(2-chlorophenyl)-5-methylquinoxalin-2-yl)methyl)thieno[3,2-d]pyrimidin-4-amine as a TFA Salt

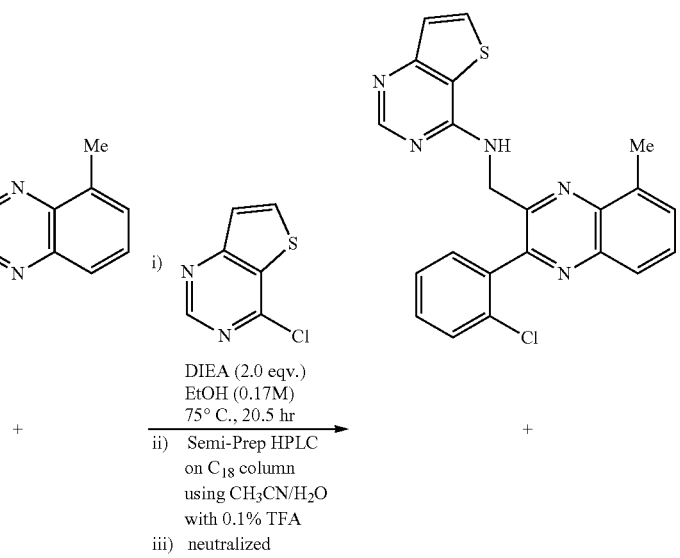

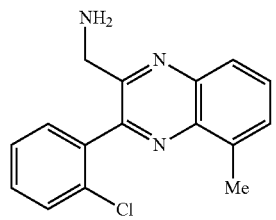

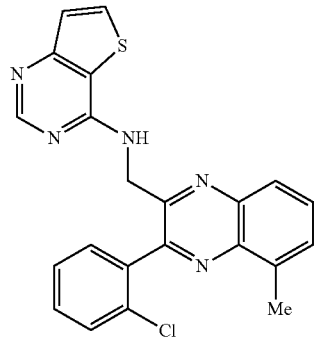

A mixture of 4-chlorothieno[3,2-d]pyrimidine (0.1200 g, 0.7033 mmol), a mixture of (3-(2-chlorophenyl)-8-methylquinoxalin-2-yl)methanamine and (3-(2-chloro-phenyl)-5-methylquinoxalin-2-yl)methanamine (Prepared in Examples 18 and 19, 0.2276 g, 0.8018 mmol), and N,N-diisopropylethylamine (0.2450 mL, 1.407 mmol) in 4 mL of EtOH was stirred at 75° C. After 20.5 h, the mixture was removed from the heat and concentrated in vacuo to give a brown syrup. The brown syrup was purified by column chromatography on a 40 g of Redi-Sep™ column using 0 to 100% gradient of EtOAc in hexane over 14 min and then 100% isocratic of EtOAc for 5 min as eluent to give a mixture of two regioisomers as a brown foam type syrup. The brown foam type syrup (0.1333 g) was purified by semi-prep-HPLC on a Gemini™ 10μ C18 column (250×21.2 mm, 10 μm) using 20-50% gradient of CH$_3$CN (0.1% of TFA) in water (0.1% of TFA) over 40 min as eluent to give two separated regioisomers: N-((3-(2-chlorophenyl)-8-methylquinoxalin-2-yl)methyl)thieno[3,2-d]pyrimidin-4-amine as a TFA salt as a white solid: $^1$H NMR (400 MHz, DMSO-d$_6$) δ ppm 9.58 (1H, s), 8.56 (1H, s), 8.37 (1H, d, J=5.5 Hz), 7.93-7.98 (1H, m), 7.76-7.80 (1H, m), 7.72-7.76 (1 H, m), 7.54-7.62 (2H, m), 7.44-7.50 (2H, m), 7.37-7.43 (1H, m), 5.00 (2H, br. s.), 2.59 (3H, s); LC-MS (ESI) m/z 418.0 [M+H]$^+$ and N-((3-(2-chlorophenyl)-5-methylquinoxalin-2-yl)methyl)thieno[3,2-d]pyrimidin-4-amine as a TFA salt as an off-white solid: $^1$H NMR (400 MHz, DMSO-d$_6$) δ ppm 9.77 (1H, br. s.), 8.55 (1H, s), 8.37 (1H, d, J=5.5 Hz), 7.89-7.95 (1H, m), 7.77-7.82 (1H, m), 7.73-7.76 (1H, m), 7.63 (1H, dd, J=7.4, 1.6 Hz), 7.54-7.58 (2H, m), 7.43-7.49 (2H, m), 7.37-7.42 (1H, m), 4.99 (2H, br. s.), 2.69 (3H, s); LC-MS (ESI) m/z 418.0 [M+H]$^+$ at 1.498 min, (Exact Mass of neutral form: 417.081).

Example 84: Preparation of N-((3-(2-Chlorophenyl)-8-fluoroquinoxalin-2-yl)-methyl)-9H-purin-6-amine as a TFA salt and N-((3-(2-chlorophenyl)-5-fluoroquinoxalin-2-yl)methyl)-9H-purin-6-amine as a TFA Salt 3-(Bromomethyl)-2-(2-chlorophenyl)-5-fluoroquinoxaline and 2-(Bromomethyl)-3-(2-chlorophenyl)-5-fluoroquinoxaline

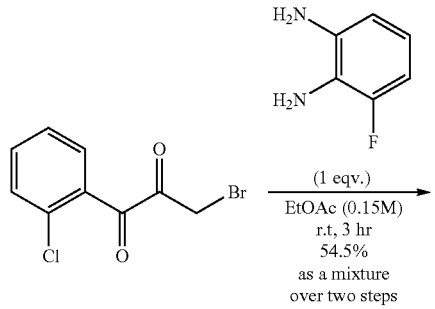

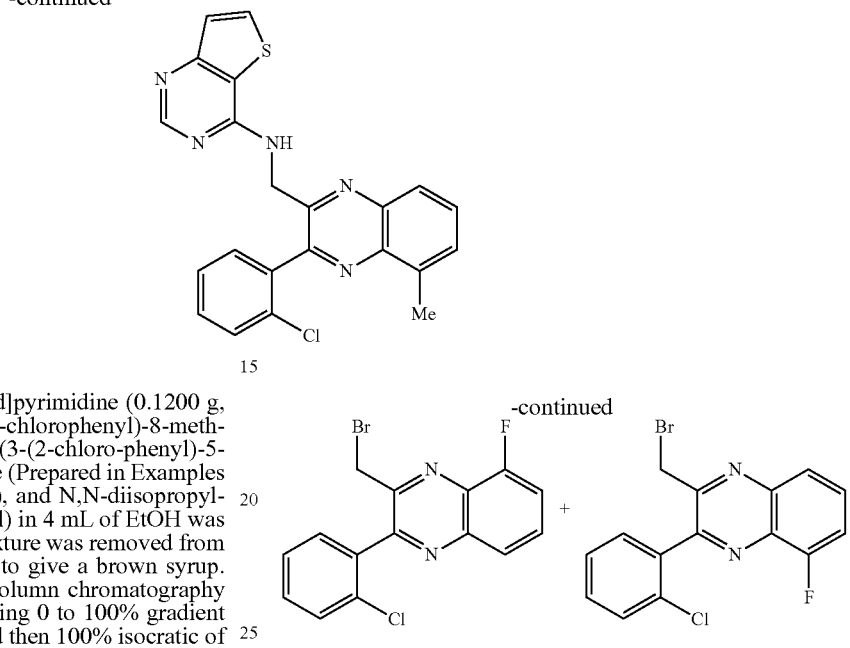

To a solution of 3-bromo-1-(2-chlorophenyl)propane-1,2-dione (Prepared in Example 81, 2.3832 g, 9.114 mmol) in 61 mL of EtOAc was added a solution of 3-fluorobenzene-1,2-diamine (1.150 g, 9.114 mmol) at room temperature and the resulting red mixture was stirred at room temperature. After 3 h, the mixture was concentrated in vacuo to give a mixture of two regioisomers as a black syrup. The black syrup was purified by column chromatography on a 80 g of Redi-Sep™ column using 0 to 50% gradient of EtOAc in hexane over 25 min and then 100% isocratic of EtOAc for 4 min as eluent to give a mixture of 3-(bromomethyl)-2-(2-chlorophenyl)-5-fluoroquinoxaline and 2-(bromomethyl)-3-(2-chlorophenyl)-5-fluoroquinoxaline as a red syrup; LC-MS (ESI) two peaks of m/z 351.0 [M+H ($^{79}$Br)]$^+$ and 352.9 [M+H ($^{81}$Br)]$^+$. The crude product was used without further purification in the next step.

3-(2-Chlorophenyl)-8-fluoroquinoxalin-2-yl)methanamine and (3-(2-Chlorophenyl)-5-fluoroquinoxalin-2-yl)methanamine

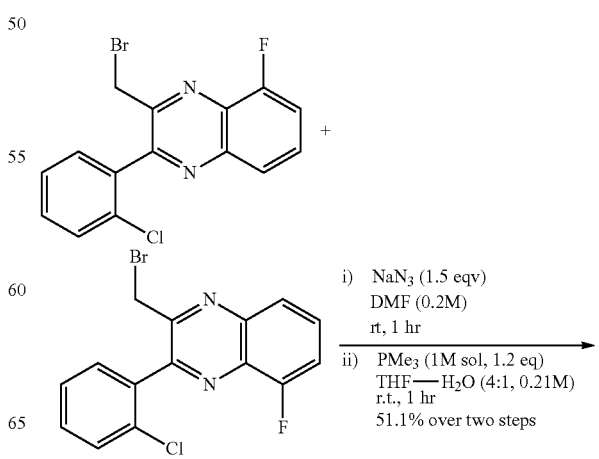

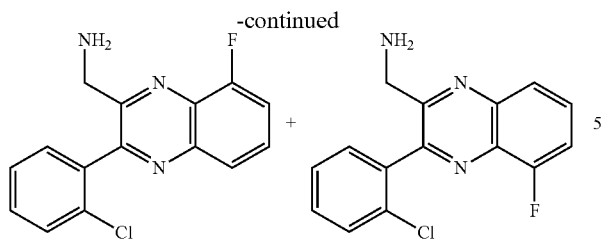

To a stirring solution of a mixture of 3-(bromomethyl)-2-(2-chlorophenyl)-5-fluoroquinoxaline and 2-(bromomethyl)-3-(2-chlorophenyl)-5-fluoroquinoxaline (0.7617 g, 2.166 mmol) in 11 mL of DMF was added sodium azide (0.2113 g, 3.250 mmol) at room temperature and the mixture was stirred at room temperature. After 50 min, the mixture was partitioned between EtOAc (100 mL) and $H_2O$ (100 mL). The organic layer was washed with brine (50 mL×1), dried over $MgSO_4$, filtered, and concentrated under reduced pressure to give a mixture of 3-(azidomethyl)-2-(2-chlorophenyl)-5-fluoroquinoxaline and 2-(azidomethyl)-3-(2-chlorophenyl)-5-fluoroquinoxaline as a dark red syrup: LC-MS (ESI) m/z 314.0 [M+H]$^+$. The crude product was carried on crude without purification for the next step.

To a stirring solution of a mixture of 3-(azidomethyl)-2-(2-chlorophenyl)-5-fluoroquinoxaline and 2-(azidomethyl)-3-(2-chlorophenyl)-5-fluoroquinoxaline (0.6796 g, 2.166 mmol) in 10 mL of THF—$H_2O$ (4:1) was added dropwise trimethylphosphine, 1.0 m solution in thf (2.600 mL, 2.600 mmol) at room temperature and the mixture was stirred at room temperature. After 1 h, to the mixture was added EtOAc (100 mL) was added and the mixture was extracted with 1 N HCl (3×60 mL). The combined extracts were neutralized with solid sodium bicarbonate, and extracted with EtOAc (50 mL×2). The combined organic extracts were washed with brine (50 mL×2), dried over MgSO4, filtered, and concentrated in vacuo to give the crude product as a violet syrup (0.3319 g). The violet syrup was purified by column chromatography on a 40 g of Redi-Sep™ column using 0 to 15% gradient of $CH_2Cl_2$:MeOH:$NH_4OH$ (89:9:1) in $CH_2Cl_2$ over 2 min, 15% isocratic of $CH_2Cl_2$:MeOH:$NH_4OH$ (89:9:1) in $CH_2Cl_2$ for 5 min, then 15% to 100% gradient of $CH_2Cl_2$:MeOH:$NH_4OH$ (89:9:1) in $CH_2Cl_2$ over 3 min, 30% isocratic of $CH_2Cl_2$:MeOH:$NH_4OH$ (89:9:1) in $CH_2Cl_2$ for 5 min, and then 30% to 100% gradient of $CH_2Cl_2$:MeOH:$NH_4OH$ (89:9:1) in $CH_2Cl_2$ over 9 min, and then 100% isocratic of $CH_2Cl_2$:MeOH:$NH_4OH$ (89:9:1) for 3 min as eluent to give a mixture of 3-(2-chlorophenyl)-8-fluoroquinoxalin-2-yl)methanamine and (3-(2-chlorophenyl)-5-fluoroquinoxalin-2-yl)methanamine as a dark green syrup: LC-MS (ES) m/z 288.1 [M+H]$^+$. A mixture of the two regioisomers was used without further purification for the next step.

N-((3-(2-Chlorophenyl)-8-fluoroquinoxalin-2-yl)methyl)-9H-purin-6-amine as a TFA salt and N-((3-(2-Chlorophenyl)-5-fluoroquinoxalin-2-yl)methyl)-9H-purin-6-amine as a TFA Salt

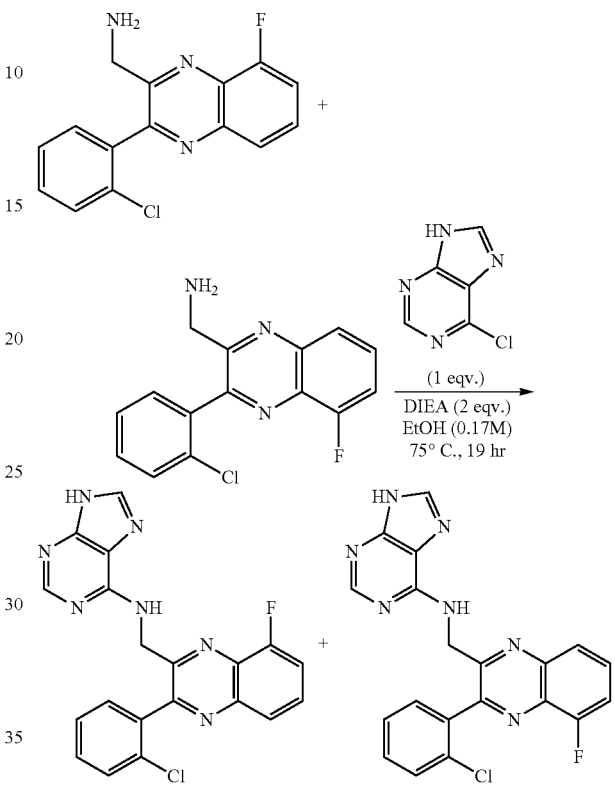

A mixture of 6-chloropurine (0.171 g, 1.11 mmol), a mixture of ((3-(2-chlorophenyl)-8-fluoroquinoxalin-2-yl)methanamine and (3-(2-chlorophenyl)-5-fluoroquinoxalin-2-yl)methanamine) (0.3186 g, 1.11 mmol), and N,N-diisopropylethylamine (0.386 mL, 2.21 mmol) in 6.5 mL of EtOH was stirred at 75° C. After 19 h, the mixture was removed from the heat and concentrated under reduced pressure to give an ornage syrup. The orange syrup was chromatographed on a 40 g of Redi-Sep™ column using 0 to 100% gradient of $CH_2Cl_2$:MeOH:$NH_4OH$ (89:9:1) in $CH_2Cl_2$ over 14 min and 100% isocratic of $CH_2Cl_2$:MeOH:$NH_4OH$ (89:9:1) for 5 min as eluent to give a mixture of two regioisomers as a brown solid. The brown solid (0.0635 g) was purified (1.0 mL (~20 mg)×3 injections) by semi-prep-HPLC on a Gemini™ 10μ C18 column (250×21.2 mm, 10 μm) using 20-50% gradient of $CH_3CN$ (0.1% of TFA) in water (0.1% of TFA) over 40 min as eluent to give two separated regiosiomers: N-((3-(2-chlorophenyl)-8-fluoroquinoxalin-2-yl)methyl)-9H-purin-6-amine as a TFA salt as a white solid: $^1H$ NMR (400 MHz, DMSO-d$_6$) δ ppm 8.55 (1H, br. s.), 8.25 (2H, d, J=20.7 Hz), 7.99 (1H, d, J=8.2 Hz), 7.84-7.92 (1H, m), 7.72-7.80 (1H, m), 7.67 (1H, dd, J=7.2, 1.8 Hz), 7.63 (1H, dd, J=8.0, 1.0 Hz), 7.51-7.57 (1H, m), 7.46-7.51 (1H, m), 4.90 (2H, s); LC-MS (ESI) m/z 406.0 [M+H]$^+$ (Exact Mass of neutral form: 405.09) and N-((3-(2-chlorophenyl)-5-fluoroquinoxalin-2-yl)methyl)-9H-purin-6-amine as a TFA salt as a off-white solid: $^1H$ NMR (400 MHz, DMSO-d$_6$) δ ppm 8.44 (1H, br. s.), 8.17-8.30 (2H, m), 7.93-7.99 (1H, m), 7.85-7.93 (1H, m), 7.71-7.78 (1H, m), 7.68 (1H, dd, J=7.2, 1.8 Hz), 7.62-7.66 (1H, m), 7.53-7.59 (1H, m), 7.48-7.53 (1H, m), 4.88 (2H, br. s.); LC-MS (ESI) m/z 406.0 [M+H]⁺ (Exact Mass of neutral form: 405.09).

Example 85: Preparation of N-((5-Chloro-3-(2-(trifluoromethyl)phenyl)-quinoxalin-2-yl)methyl)-9H-purin-6-amine 8-Chloro-3-methylquinoxalin-2 (1H)-one and 5-chloro-3-methylquinoxalin-2 (1H)-one

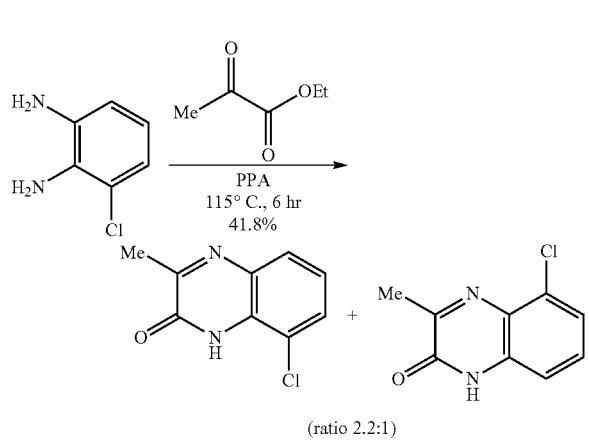

(ratio 2.2:1)

A mixture of ethyl pyruvate (11.523 mL, 103.70 mmol) and 3-chlorobenzene-1,2-diamine (Prepared in Example 81, 14.7866 g, 103.70 mmol) in polyphosphoric acid (100.00 g) was stirred and heated at 115° C. After 6 h, the mixture was cooled to room temperature, thoroughly mixed with water (500 mL), and neutralized with 10 N NaOH (180 mL). The resulting precipitate was collected by filtration and the solid was washed with water (1000 mL) and dried to give a dark brown solid as a mixture of chloro-3-methylquinoxalin-2 (1H)-one and 5-chloro-3-methylquinoxalin-2 (1H)-one as a dark brown solid. The dark brown solid was purified by silica gel column chromatography on a 330 g of Redi-Sep™ column using 100% of Hexane for 5 min, then 0 to 18% gradient of EtOAc in hexane over 9.5 min, then 18% isocratic of EtOAc in hexane for 23.2 min, then 18% to 100% gradient of EtOAc in hexane over 48 min, and then 100% isocratic of EtOAc for 10 min as eluent to give two separated regiosiomers: 8-chloro-3-methylquinoxalin-2 (1H)-one as an orange solid: ¹H NMR (400 MHz, DMSO-d₆) δ ppm 11.88 (1H, s), 7.68 (1H, dd, J=7.8, 1.2 Hz), 7.58-7.63 (1H, m), 7.28 (1H, t, J=8.0 Hz), 2.43 (3H, s); LC-MS (ESI) m/z 195.1 [M+H]⁺ and 5-chloro-3-methylquinoxalin-2 (1H)-one as an orange solid: ¹H NMR (400 MHz, DMSO-d₆) δ ppm 12.48 (1H, s), 7.37-7.47 (2H, m), 7.23 (1H, dd, J=7.8, 1.6 Hz), 2.44 (3H, s); LC-MS (ESI) m/z 195.1 [M+H]⁺.

3,5-Dichloro-2-methylquinoxaline

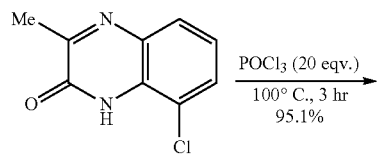

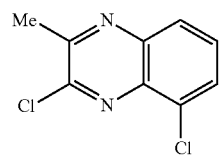

A mixture of 8-chloro-3-methylquinoxalin-2-ol (1.0765 g, 5.5314 mmol) and phosphorous oxychloride (10.127 mL, 110.63 mmol) was stirred at 100° C. After 3 h, the mixture was cooled to room temperature. The mixture was poured into ice (~100 mL) with stirring and neutralized with NH₄OH (30 mL) and ice with stirring. The resulting precipitate was collected by filtration, rinsed with water (200 mL), and dried to give 3,5-dichloro-2-methylquinoxaline as a pink solid: ¹H NMR (400 MHz, DMSO-d₆) δ ppm 7.98-8.07 (2H, m), 7.84 (1H, dd, J=8.3, 7.7 Hz), 2.79 (3H, s); LC-MS (ESI) m/z 213.0 [M+H]⁺. The pink solid was carried on crude without purification for the next step.

5-Chloro-2-methyl-3-(2-(trifluoromethyl)phenyl)quinoxaline

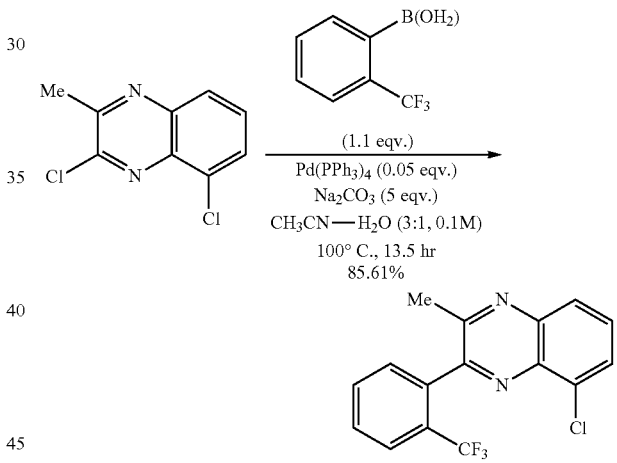

A mixture of 3,5-dichloro-2-methylquinoxaline (1.1209 g, 5.261 mmol), 2-(trifluoromethyl)phenylboronic acid (1.099 g, 5.787 mmol), tetrakis(triphenyl-phosphine)palladium (0.3040 g, 0.2630 mmol), and sodium carbonate anhydrous (2.788 g, 26.30 mmol) in 53 mL of CH₃CN—H₂O (3:1) was stirred at 100° C. After 13.5 h, the mixture was cooled to room temperature and partitioned between EtOAc (100 mL) and water (100 mL). The organic layer was washed with brine (50 mL×3), dried over Na₂SO₄, filtered, and concentrated under reduced pressure to give a red syrup. The red syrup was purified by silica gel column chromatography on a 80 g of Redi-Sep™ column using 0 to 50% gradient of EtOAc in hexane over 25 min and then 50% isocratic of EtOAc for 20 min as eluent to give 5-chloro-2-methyl-3-(2-(trifluoromethyl)phenyl)quinoxaline as a red solid: ¹H NMR (400 MHz, DMSO-d₆) δ ppm 8.09 (1H, dd, J=8.4, 1.4 Hz), 8.02 (1H, dd, J=7.6, 1.2 Hz), 7.98 (1H, d, J=7.8 Hz), 7.73-7.92 (4H, m), 2.47 (3H, s); LC-MS (ESI) m/z 323.0 [M+H]⁺.

2-(Bromomethyl)-5-chloro-3-(2-(trifluoromethyl)phenyl)quinoxaline

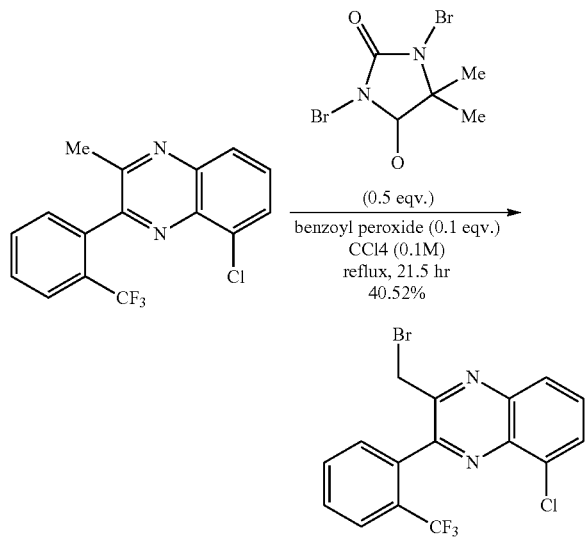

5-Chloro-2-methyl-3-(2-(trifluoromethyl)phenyl)quinoxaline (1.4455 g, 4.479 mmol) and 1,3-dibromo-5,5-dimethylhydantoin (0.6404 g, 2.240 mmol) were suspended in carbon tetrachloride (44.79 mL, 4.479 mmol). To the mixture was added benzoyl peroxide (0.1447 g, 0.4479 mmol) and the mixture was heated at reflux. After 21.5 h, the mixture was cooled to room temperature and concentrated under reduced pressure. The residue was purified by silica gel column chromatography on a 80 g of Redi-Sep™ column using 0 to 9% gradient of EtOAc in hexane over 2 min, then 9% isocratic of EtOAc for 13 min, then 9 to 100% gradient of EtOAc in hexane over 23 min, then 100% isocratic of EtOAc for 4 min as eluent to give 2-(bromomethyl)-5-chloro-3-(2-(trifluoromethyl)-phenyl)quinoxaline as a yellow solid: $^1$H NMR (400 MHz, DMSO-$d_6$) δ ppm 8.18 (1H, dd, J=8.4, 1.4 Hz), 8.13 (1H, dd, J=7.8, 1.2 Hz), 7.81-8.03 (5H, m), 4.69 (2H, dd, J=88.4, 10.2 Hz); LC-MS (ESI) m/z 400.9 and 403.0 [M+H]$^+$.

(5-Chloro-3-(2-(trifluoromethyl)phenyl)quinoxalin-2-yl)methanamine

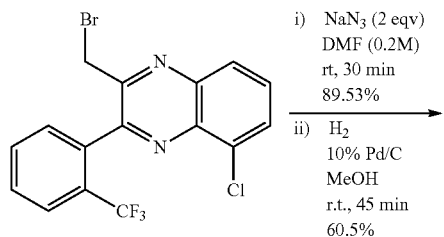

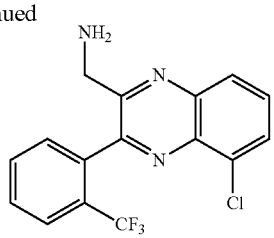

To a stirring solution of 2-(bromomethyl)-5-chloro-3-(2-(trifluoromethyl)phenyl)-quinoxaline (0.7173 g, 1.786 mmol) in DMF (8.930 mL, 1.786 mmol) was added sodium azide (0.2322 g, 3.572 mmol) at room temperature and the mixture was stirred at room temperature. After 30 min, the mixture was partitioned between EtOAc (100 mL) and H$_2$O (100 mL). The organic layer was washed with brine (50 mL×1), dried over Na$_2$SO$_4$, filtered, and concentrated under reduced pressure to give bluish-brown syrup. The bluish-brown syrup was purified by silica gel column chromatography on a 40 g of Redi-Sep™ column using 0 to 50% gradient of EtOAc in hexane over 14 min, then 50% isocratic of EtOAc for 5 min as eluent to give 2-(azidomethyl)-5-chloro-3-(2-(trifluoromethyl)phenyl)quinoxaline: $^1$H NMR (400 MHz, DMSO-$d_6$) δ ppm 8.20 (1H, dd, J=8.6, 1.2 Hz), 8.10-8.14 (1H, m), 7.99 (1H, d, J=7.8 Hz), 7.95 (1H, dd, J=8.4, 7.6 Hz), 7.79-7.91 (3H, m), 4.41-4.67 (2H, m); LC-MS (ESI) major peak of m/z 364.0 [M+H]$^+$. The crude product was carried on crude without purification for the next step.

To a solution of 2-(azidomethyl)-5-chloro-3-(2-(trifluoromethyl)phenyl)-quinoxaline (0.5736 g, 1.58 mmol) in methanol (17.500 mL, 1.58 mmol) was added palladium, 10 wt. % on activated carbon (0.0839 g, 0.0789 mmol). After repeating three times of evacuation of air in the flask by house vacuum and filling the flask with H$_2$, the mixture was stirred under H$_2$. After 45 min, the mixture was filtered through a pad of Celite™ and rinsed the pad with MeOH. The filtrate was concentrated under reduced pressure to give blue syrup. The blue syrup was purified by column chromatography on a 80 g of Redi-Sep™ column using 0 to 12% gradient of CH$_2$Cl$_2$:MeOH:NH$_4$OH (89:9:1) in CH$_2$Cl$_2$ over 3 min, 12% isocratic of CH$_2$Cl$_2$:MeOH:NH$_4$OH (89:9:1) in CH$_2$Cl$_2$ for 4 min, 12% to 100% gradient of CH$_2$Cl$_2$:MeOH:NH$_4$OH (89:9:1) in CH$_2$Cl$_2$ over 22 min as eluent to give (5-chloro-3-(2-(trifluoromethyl)phenyl)quinoxalin-2-yl)methanamine as a blue syrupy solid: $^1$H NMR (500 MHz, DMSO-$d_6$) δ ppm 8.15 (1H, dd, J=8.6, 1.2 Hz), 8.04 (1H, dd, J=7.6, 1.2 Hz), 7.97 (1H, d, J=7.6 Hz), 7.74-7.92 (4H, m), 3.62-3.91 (2H, m), 1.98 (2H, br. s.); LC-MS (ESI) m/z 338.0 [M+H]$^+$.

N-((5-Chloro-3-(2-(trifluoromethyl)phenyl)quinoxalin-2-yl)methyl)-9H-purin-6-amine

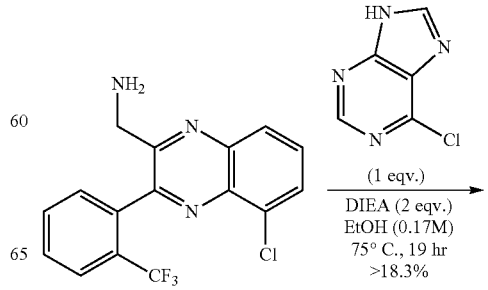

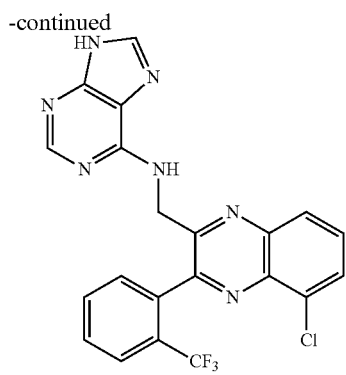

A mixture of 6-chloropurine (0.147 g, 0.954 mmol), (5-chloro-3-(2-(trifluoro-methyl)phenyl)quinoxalin-2-yl)methanamine (0.3223 g, 0.954 mmol), and N,N-diisopropylethylamine (0.332 mL, 1.91 mmol) in ethanol (5.61 mL, 0.954 mmol) was stirred at 75° C. After 19 h, the mixture was removed from the heat and concentrated under reduced pressure. The residue was purified by column chromatography on a 40 g of Redi-Sep™ column using 0 to 100% gradient of EtOAc in hexane over 14 min, then 100% isocratic of EtOAc for 10 min, then 0 to 65% gradient of $CH_2Cl_2$:MeOH:$NH_4OH$ (89:9:1) in $CH_2Cl_2$ over 10 min, then 65% isocratic of $CH_2Cl_2$:MeOH:$NH_4OH$ (89:9:1) in $CH_2Cl_2$ for 10 min, then 65% to 100% gradient of $CH_2Cl_2$:MeOH:$NH_4OH$ (89:9:1) in $CH_2Cl_2$ over 4 min, and then 100% isocratic of $CH_2Cl_2$:MeOH:$NH_4OH$ (89:9:1) for 4 min as eluent to give the desired product as a brown solid. The brown solid was suspended in $CH_2Cl_2$ filtered to give N-((5-chloro-3-(2-(trifluoromethyl)phenyl)quinoxalin-2-yl)methyl)-9H-purin-6-amine as an off-white solid: 1H NMR (400 MHz, DMSO-$d_6$) δ ppm 12.94 (1H, s), 7.57-8.34 (10H, m), 4.76 (2H, d, J=55.9 Hz); LC-MS (ESI) m/z 456.1 $[M+H]^+$.

Example 86: Preparation of N-((8-Chloro-2-(2-(trifluoromethoxy)phenyl)-quinolin-3-yl)methyl)-9H-purin-6-amine 8-Chloro-2-(2-(trifluoromethoxy)phenyl)quinoline-3-carbaldehyde

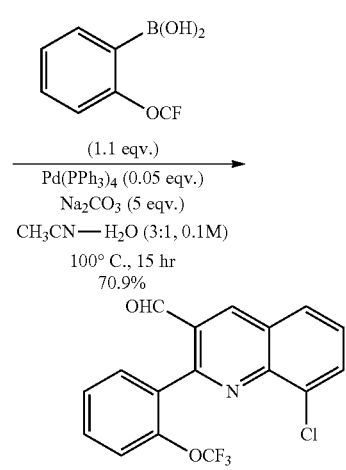

A mixture of 2,8-dichloroquinoline-3-carbaldehyde (Prepared in Example 2, 0.5000 g, 2.212 mmol), 2-(trifluoromethoxyphenyl)boronic acid (0.5010 g, 2.433 mmol), tetrakis(triphenylphosphine)palladium (0.1278 g, 0.1106 mmol), and sodium carbonate anhydrous (1.172 g, 11.06 mmol) in 90 mL of $CH_3CN$—$H_2O$ (3:1) was stirred at 100° C. After 15 h, the mixture was cooled to room temperature and partitioned between EtOAc (100 mL) and water (100 mL). The organic layer was washed with brine (50 mL×2), dried over $Na_2SO_4$, filtered, and concentrated under reduced pressure and purified by silica gel column chromatography on a 40 g of Redi-Sep™ column using 0 to 50% gradient of EtOAc in hexane over 14 min and then 50% isocratic of EtOAc for 5 min as eluent to give 8-chloro-2-(2-(trifluoromethoxy)phenyl)quinoline-3-carbaldehyde: 1H NMR (500 MHz, DMSO-$d_6$) δ ppm 9.98 (1H, s), 9.14 (1H, s), 8.31 (1H, dd, J=8.1, 1.0 Hz), 8.18 (1H, dd, J=7.5, 1.3 Hz), 7.70-7.82 (3H, m), 7.62-7.67 (1H, m), 7.57 (1H, d, J=8.3 Hz); LC-MS (ESI) m/z 352.0 $[M+H]^+$.

(8-Chloro-2-(2-(trifluoromethoxy)phenyl)quinolin-3-yl)methanol

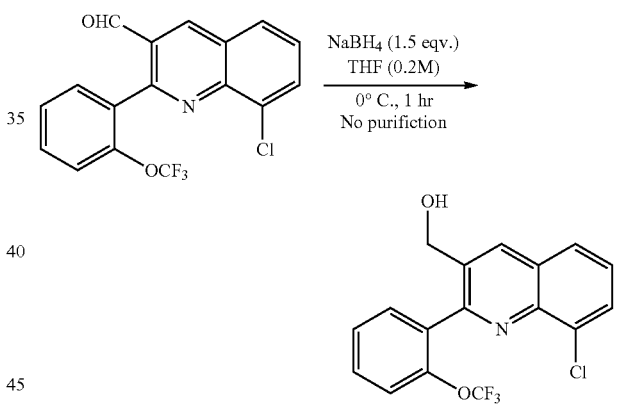

To a solution of 8-chloro-2-(2-(trifluoromethoxy)phenyl)quinoline-3-carbaldehyde (0.5427 g, 1.543 mmol) in tetrahydrofuran (7.715 mL, 1.543 mmol) at 0° C. was added SODIUM BOROHYDRIDE (0.08757 g, 2.315 mmol) and the mixture was stirred at 0° C. and allowed to warm to room temperature over 1 hour. After 1 h of stirring at 0° C., the mixture was partitioned between EtOAc (100 mL) and $H_2O$ (100 mL), and the organic layer was washed with brine (50 mL×2), dried over $Na_2SO_4$, filtered, and concentrated under reduced pressure to give (8-chloro-2-(2-(trifluoromethoxy)phenyl)quinolin-3-yl)methanol as a light-yellow solid: 1H NMR (400 MHz, DMSO-$d_6$) δ ppm 8.58 (1H, s), 8.10 (1H, dd, J=8.3, 1.3 Hz), 7.95 (1H, dd, J=7.5, 1.3 Hz), 7.51-7.72 (5H, m), 5.54 (1H, s), 4.44 (2H, s); LC-MS (ESI) m/z 354.0 $[M+H]^+$. The product was carried on crude without purification for the next step.

8-Chloro-3-(chloromethyl)-2-(2-(trifluoromethoxy)phenyl)quinoline hydrochloride

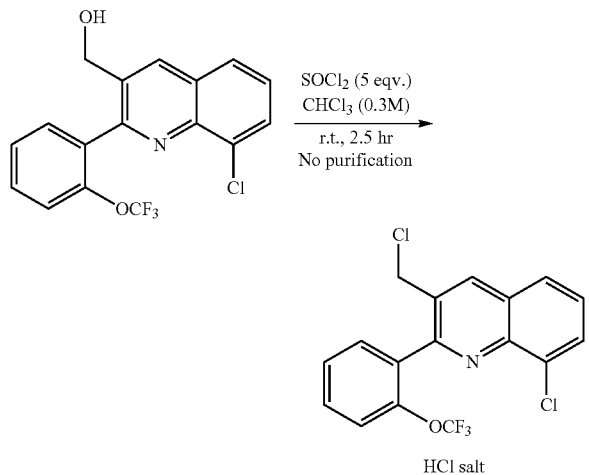

A solution of (8-chloro-2-(2-(trifluoromethoxy)phenyl) quinolin-3-yl)methanol (0.5470 g, 1.546 mmol) in chloroform (5.155 mL, 1.546 mmol) was treated with thionyl chloride (0.5626 mL, 7.732 mmol) dropwise, and the reaction mixture was stirred at room temperature. After 2.5 h, the mixture was concentrated under reduced pressure and co-evaporated three times with $CH_2Cl_2$ to give 8-chloro-3-(chloromethyl)-2-(2-(trifluoromethoxy)phenyl)quinoline hydrochloride as a yellow syrup: $^1$H NMR (400 MHz, DMSO-$d_6$) δ ppm 8.75 (1H, s), 8.10 (1H, dd, J=8.2, 1.2 Hz), 8.03 (1H, dd, J=7.5, 1.3 Hz), 7.64-7.74 (3H, m), 7.53-7.63 (2H, m), 4.75 (2H, br. s.), 89676-3-1-1H-NMR; LC-MS (ESI) m/z 372.0 [M+H]$^+$ (Exact Mass of neutral form: 371.009). The yellow syrup was carried on crude without purification for the next step.

(8-Chloro-2-(2-(trifluoromethoxy)phenyl)quinolin-3-yl)methanamine

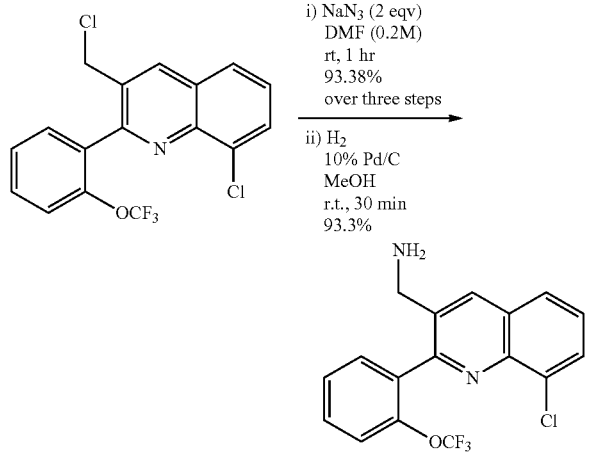

To a stirring solution of 8-chloro-3-(chloromethyl)-2-(2-(trifluoromethoxy)-phenyl)quinoline hydrochloride (0.6319 g, 1.546 mmol) in DMF (7.732 mL, 1.546 mmol) was added sodium azide (0.2011 g, 3.093 mmol) at room temperature and the mixture was stirred at room temperature. After 1 h, the mixture was partitioned between EtOAc (100 mL) and $H_2O$ (100 mL). The organic layer was washed with brine (50 mL×1), dried over $Na_2SO_4$, filtered, and concentrated under reduced pressure. The residue was purified by silica gel column chromatography on a 40 g of Redi-Sep™ column using 0 to 50% gradient of EtOAc in hexane over 14 min, then 50% isocratic of EtOAc for 5 min as eluent to give 3-(azidomethyl)-8-chloro-2-(2-(trifluoromethoxy)phenyl) quinoline as a colorless syrup: $^1$H NMR (400 MHz, DMSO-$d_6$) δ ppm 8.66 (1H, s), 8.11 (1H, dd, J=8.2, 1.2 Hz), 8.02 (1H, dd, J=7.6, 1.4 Hz), 7.54-7.74 (5H, m), 4.52 (2H, br. s.); LC-MS (ESI) m/z 379.0 [M+H]$^+$.

To a solution of 3-(azidomethyl)-8-chloro-2-(2-(trifluoromethoxy)phenyl)-quinoline (0.5374 g, 1.42 mmol) in methanol (14.2 mL, 1.42 mmol) was added palladium, 10 wt. % on activated carbon (0.0755 g, 0.0709 mmol). After repeating three times of evacuation of air in the flask by house vacuum and filling the flask with $H_2$, the mixture was stirred under $H_2$. After 30 min, the mixture was filtered through a pad of Celite™ and rinsed the pad with MeOH. The filtrate was concentrated under reduced pressure to give dark green syrup. The dark green syrup was purified by column chromatography on a 40 g of Redi-Sep™ column using 0% to 20% gradient of $CH_2Cl_2$:MeOH:$NH_4OH$ (89:9:1) in $CH_2Cl_2$ over 14 min, and then 20% isocratic of $CH_2Cl_2$:MeOH:$NH_4OH$ (89:9:1) for 15 min as eluent to give (8-chloro-2-(2-(trifluoromethoxy)phenyl)quinolin-3-yl)-methanamine. $^1$H NMR (400 MHz, DMSO-$d_6$) δ ppm 8.62 (1H, s), 8.03 (1H, dd, J=8.2, 1.2 Hz), 7.93 (1H, dd, J=7.4, 1.2 Hz), 7.50-7.70 (5H, m), 3.66 (2H, s), 1.97 (2H, br. s.); LC-MS (ESI) m/z 353.0 [M+H]$^+$.

N-((8-Chloro-2-(2-(trifluoromethoxy)phenyl)quinolin-3-yl)methyl)-9H-purin-6-amine

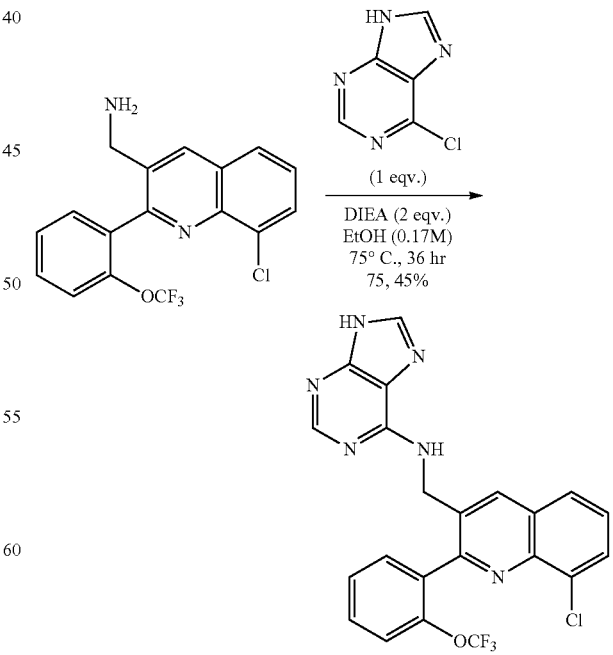

A mixture of 6-chloropurine (0.1109 g, 0.7175 mmol), (8-chloro-2-(2-(trifluoro-methoxy)phenyl)quinolin-3-yl)

methanamine (0.2531 g, 0.7175 mmol), and N,N-diisopropylethylamine (0.2500 mL, 1.435 mmol) in ethanol (4.221 mL, 0.7175 mmol) was stirred at 75° C. After 36 h, the mixture was removed from the heat and concentrated under reduced pressure. The residue was purified by flash column chromatography on a silica gel column using 50% of CH$_2$Cl$_2$:MeOH:NH$_4$OH (89:9:1) in CH$_2$Cl$_2$ as eluent to give N-((8-chloro-2-(2-(trifluoromethoxy)phenyl)quinolin-3-yl)methyl)-9H-purin-6-amine as a white solid: $^1$H NMR (400 MHz, DMSO-d$_6$) δ ppm 12.94 (1H, s), 8.38 (1H, s), 8.03-8.32 (3H, m), 7.96-8.02 (1H, m), 7.93 (1H, dd, J=7.5, 0.9 Hz), 7.51-7.75 (5H, m), 4.69 (2H, br. s.); LC-MS (ESI) m/z 471.1 [M+H]$^+$.

Example 87: Preparation of N-((8-Chloro-2-(5-fluoro-2-(trifluoromethyl)-phenyl)quinolin-3-yl)methyl)-9H-purin-6-amine 8-Chloro-2-(5-fluoro-2-(trifluoromethyl)phenyl)quinoline-3-carbaldehyde

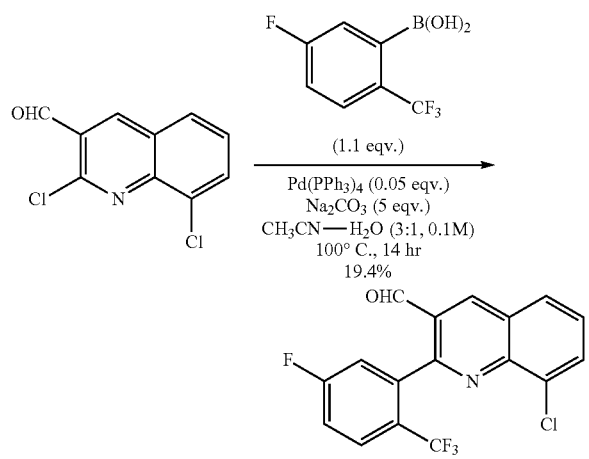

A mixture of 2,8-dichloroquinoline-3-carbaldehyde (Prepared in Example 2, 1.0000 g, 4.424 mmol), 5-fluoro-2-(trifluoromethyl)phenylboronic acid (1.012 g, 4.866 mmol), tetrakis(triphenylphosphine)palladium (0.2556 g, 0.2212 mmol), and sodium carbonate anhydrous (2.344 g, 22.12 mmol) in 40 mL of CH$_3$CN—H$_2$O (3:1) was stirred at 100° C. After 14 h, the mixture was cooled to room temperature and partitioned between EtOAc (100 mL) and water (100 mL). The organic layer was washed with brine (50 mL×2), dried over Na$_2$SO$_4$, filtered, and concentrated under reduced pressure to give a brown solid. The brown solid was purified by silica gel column chromatography on a 80 g of Redi-Sep™ column using 0 to 50% gradient of EtOAc in hexane over 25 min and then 50% isocratic of EtOAc for 10 min as eluent to give 8-chloro-2-(5-fluoro-2-(trifluoromethyl)-phenyl)quinoline-3-carbaldehyde as a yellow solid: $^1$H NMR (400 MHz, DMSO-d$_6$) δ ppm 10.00 (1H, s), 9.21 (1H, s), 8.32 (1H, dd, J=8.3, 1.1 Hz), 8.20 (1H, dd, J=7.6, 1.4 Hz), 8.01 (1H, dd, J=8.7, 5.4 Hz), 7.76-7.84 (1H, m), 7.55-7.66 (2H, m); LC-MS (ESI) m/z 354.0 [M+H]$^+$.

(8-Chloro-2-(5-fluoro-2-(trifluoromethyl)phenyl)quinolin-3-yl)methanol

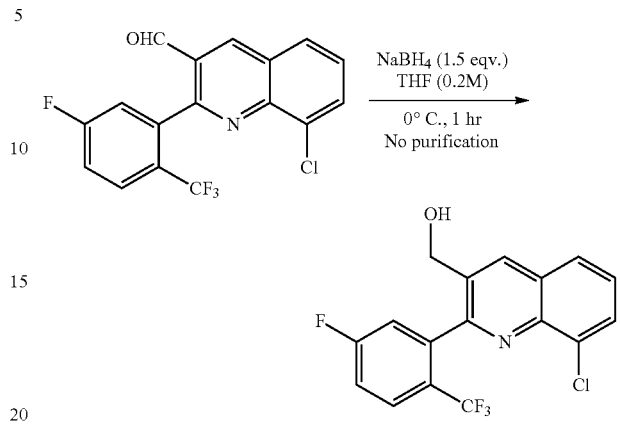

To a solution of 8-chloro-2-(5-fluoro-2-(trifluoromethyl)phenyl)quinoline-3-carbaldehyde (0.3036 g, 0.8584 mmol) in tetrahydrofuran (4.292 mL, 0.8584 mmol) at 0° C. was added sodium borohydride (0.04871 g, 1.288 mmol) and the mixture was stirred at 0° C. After 1 h of stirring at 0° C., the mixture was partitioned between EtOAc (100 mL) and H$_2$O (100 mL), and the organic layer was washed with brine (50 mL×2), dried over Na$_2$SO$_4$, filtered, and concentrated under reduced pressure to give (8-chloro-2-(5-fluoro-2-(trifluoromethyl)phenyl)-quinolin-3-yl)methanol as a light-yellow syrupy solid: $^1$H NMR (400 MHz, DMSO-d$_6$) δ ppm 8.57 (1H, s), 8.10 (1H, dd, J=8.2, 1.2 Hz), 8.01 (1H, dd, J=8.8, 5.3 Hz), 7.95 (1H, dd, J=7.6, 1.4 Hz), 7.53-7.69 (3H, m), 5.55 (1H, br. s.), 4.25-4.56 (2H, m); LC-MS (ESI) m/z 356.0 [M+H]$^+$. The light-yellow syrupy solid was carried on crude without purification for the next step.

8-Chloro-3-(chloromethyl)-2-(5-fluoro-2-(trifluoromethyl)phenyl)quinoline hydrochloride

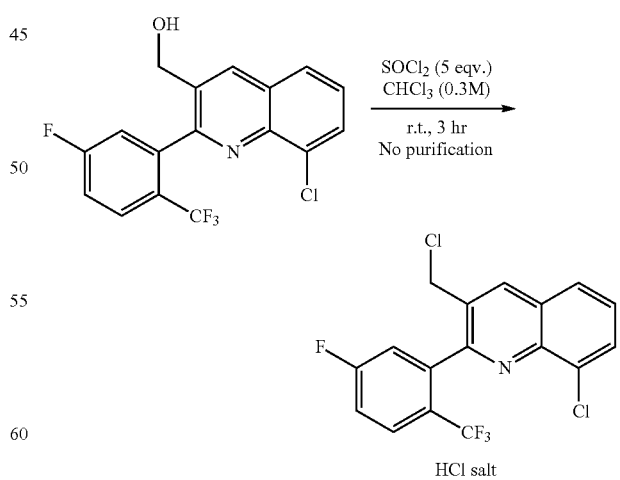

A solution of (8-chloro-2-(5-fluoro-2-(trifluoromethyl)phenyl)quinolin-3-yl)-methanol (0.3016 g, 0.8479 mmol) in chloroform (2.826 mL, 0.8479 mmol) was treated with thionyl chloride (0.3085 mL, 4.239 mmol) dropwise, and the reaction mixture was stirred at room temperature. After 3 h, the mixture was concentrated under reduced pressure and co-evaporated three times with CH$_2$Cl$_2$ to give 8-chloro-3-(chloromethyl)-2-(5-fluoro-2-(trifluoromethyl)phenyl)quinoline hydrochloride as a yellow syrup: $^1$H NMR (400 MHz, DMSO-d$_6$) δ ppm 8.76 (1H, s), 8.11 (1H, dd, J=8.2, 1.2 Hz), 7.99-8.07 (2H, m), 7.60-7.75 (3H, m), 4.63-4.90 (2H, m); LC-MS (ESI) m/z [M+H]$^+$ (Exact Mass of neutral form: 373.005). The yellow syrup was carried on crude without purification for the next step.

(8-Chloro-2-(5-fluoro-2-(trifluoromethyl)phenyl)quinolin-3-yl)methanamine

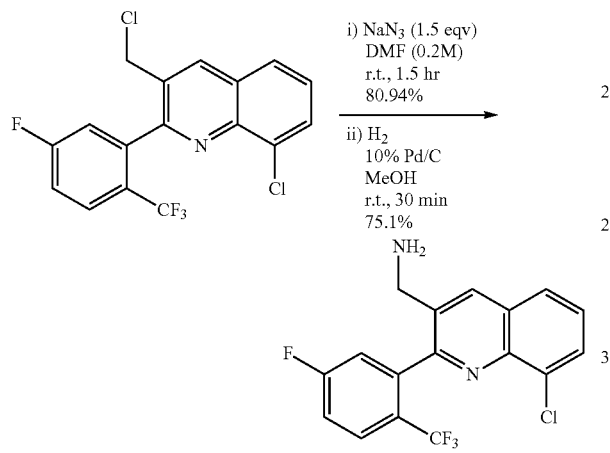

To a stirring solution of 8-chloro-3-(chloromethyl)-2-(5-fluoro-2-(trifluoro-methyl)phenyl)quinoline hydrochloride (0.3482 g, 0.8480 mmol) in DMF (4.240 mL, 0.8480 mmol) was added sodium azide (0.1103 g, 1.696 mmol) at room temperature and the mixture was stirred at room temperature. After 1.5 h, the mixture was partitioned between EtOAc (100 mL) and H$_2$O (100 mL). The organic layer was washed with brine (50 mL×1), dried over Na$_2$SO$_4$, filtered, and concentrated under reduced pressure. The residue was purified by silica gel column chromatography on a 40 g of Redi-Sep™ column using 0 to 50% gradient of EtOAc in hexane over 14 min, then 50% isocratic of EtOAc for 5 min as eluent to give 3-(azidomethyl)-8-chloro-2-(5-fluoro-2-(trifluoromethyl)phenyl)quinoline as a colorless syrup: $^1$H NMR (400 MHz, DMSO-d$_6$) δ ppm 8.65 (1H, s), 8.12 (1H, dd, J=8.3, 1.3 Hz), 7.99-8.06 (2H, m), 7.69 (1H, dd, J=8.1, 7.5 Hz), 7.58-7.66 (2H, m), 4.44-4.59 (2H, m); LC-MS (ESI) m/z 381.1 [M+H]$^+$. To a solution of 3-(azidomethyl)-8-chloro-2-(5-fluoro-2-(trifluoromethyl)phenyl)-quinoline (0.2573 g, 0.676 mmol) in methanol (6.76 mL, 0.676 mmol) was added palladium, 10 wt. % on activated carbon (0.0360 g, 0.0338 mmol). After repeating three times of evacuation of air in the flask by house vacuum and filling the flask with H$_2$, the mixture was stirred under H$_2$. After 30 min, the mixture was filtered through a pad of Celite™ and rinsed the pad with MeOH. The filtrate was concentrated under reduced pressure to give green syrup. The green syrup was purified by column chromatography on a 40 g of Redi-Sep™ column using 0% to 20% gradient of CH$_2$Cl$_2$:MeOH:NH$_4$OH (89:9:1) in CH$_2$Cl$_2$ over 14 min, and then 20% isocratic of CH$_2$Cl$_2$:MeOH:NH$_4$OH (89:9:1) for 20 min as eluent to give (8-chloro-2-(5-fluoro-2-(trifluoromethyl)phenyl)quinolin-3-yl)methanamine as a yellow syrup: $^1$H NMR (400 MHz, DMSO-d$_6$) δ ppm 8.62 (1H, s), 8.04 (1H, dd, J=8.4, 1.2 Hz), 8.01 (1H, dd, J=8.5, 5.4 Hz), 7.93 (1H, dd, J=7.4, 1.4 Hz), 7.54-7.67 (3H, m), 3.48-3.74 (2H, m), 1.96 (2H, br. s.); LC-MS (ESI) m/z 355.1 [M+H]$^+$.

N-((8-Chloro-2-(5-fluoro-2-(trifluoromethyl)phenyl)quinolin-3-yl)methyl)-9H-purin-6-amine

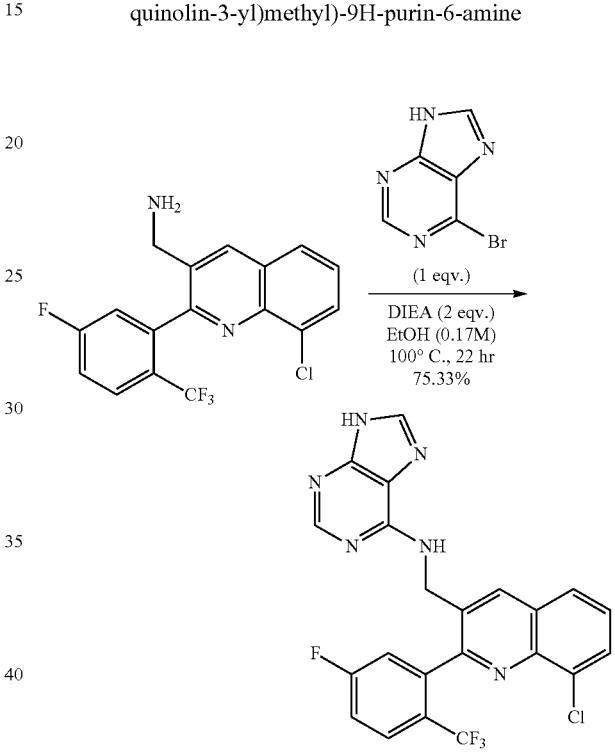

A mixture of 6-bromopurine (0.09706 g, 0.4877 mmol), (8-chloro-2-(5-fluoro-2-(trifluoromethyl)phenyl)quinolin-3-yl)methanamine (0.1730 g, 0.4877 mmol), and N,N-diisopropylethylamine (0.1699 mL, 0.9754 mmol) in 2.8 mL of 1-butanol was stirred at 100° C. After 22 h, the mixture was removed from the heat and concentrated under reduced pressure to give a yellow syrupy solid. The yellow syrupy solid was purified by column chromatography on a 40 g of Redi-Sep™ column using 0 to 20% gradient of CH$_2$Cl$_2$:MeOH:NH$_4$OH (89:9:1) in CH$_2$Cl$_2$ over 14 min, then 20% isocratic of CH$_2$Cl$_2$:MeOH:NH$_4$OH (89:9:1) in CH$_2$Cl$_2$ for 10 min, then 20 to 50% gradient of CH$_2$Cl$_2$:MeOH:NH$_4$OH (89:9:1) in CH$_2$Cl$_2$ over 10 min, and then 50% isocratic of CH$_2$Cl$_2$:MeOH:NH$_4$OH (89:9:1) in CH$_2$Cl$_2$ for 10 min as eluent to give N-((8-chloro-2-(5-fluoro-2-(trifluoromethyl)-phenyl)quinolin-3-yl)methyl)-9H-purin-6-amine as an off-white solid: YS-89676-13-1. The off white solid was suspended in CH$_2$Cl$_2$ and filtered to give N-((8-chloro-2-(5-fluoro-2-(trifluoromethyl)phenyl)quinolin-3-yl)methyl)-9H-purin-6-amine. $^1$H NMR (400 MHz, DMSO-d$_6$) δ ppm 12.93 (1H, s), 8.46 (1H, s), 8.05-8.24 (3H, m), 8.02 (1H, d, J=8.0 Hz), 7.90-7.98 (2H, m), 7.56-7.64 (2H, m), 7.52 (1H, t, J=8.7 Hz), 4.64 (2H, s); LC-MS (ESI) m/z 473.2 [M+H]$^+$.

Example 88: Preparation of N-((2-(3-Fluorophenyl)-8-methoxyquinolin-3-yl)-methyl)-9H-purin-6-amine

2-Chloro-8-methoxyquinoline-3-carbaldehyde

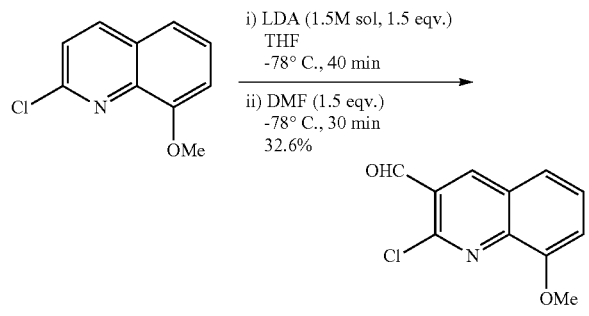

To a cooled solution of lithium diisopropylamide mono (tetrahydrofuran), 1.5 M sol. in cyclohexane (25.82 mL, 38.73 mmol) in 72 mL of THF at −75° C. was added a solution of 2-chloro-8-methoxyquinoline (5.0000 g, 25.82 mmol) in 26 mL of THF dropwise over 35 min (10:00 am~10:35 am) with stirring and keeping the temperature below −65° C. After 40 min, to the cooled mixture was added DMF (2.999 mL, 38.73 mmol) dropwise and the mixture was stirred at −72° C. for 30 min. After 30 min, the reaction was quenched with NH$_4$Cl (20 mL) and partitioned between EtOAc (150 mL) and water (100 mL). The combined organic layers were washed with water (100 mL×1), brine (100 mL×2), dried over Na$_2$SO$_4$, filtered, and concentrated under reduced pressure to give a yellow solid.

The yellow solid was purified by flash column chromatography on a silica gel column using 20% of EtOAc in hexane as eluent to give 2-chloro-8-methoxyquinoline-3-carbaldehyde as a yellow solid: $^1$H NMR (400 MHz, DMSO-d6) δ ppm 10.38 (1H, s), 8.92 (1H, s), 7.79 (1H, dd, J=8.4, 1.0 Hz), 7.67 (1H, t, J=8.0 Hz), 7.44 (1H, dd, J=7.8, 1.2 Hz), 4.00 (3H, s); LC-MS (ESI) m/z 222.1 [M+H]$^+$.

2-(3-Fluorophenyl)-8-methoxyquinoline-3-carbaldehyde

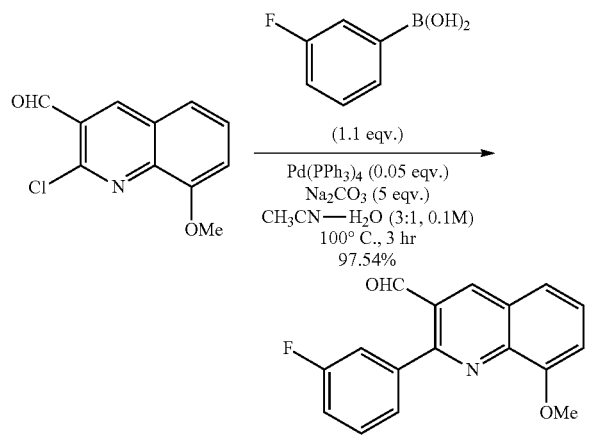

A mixture of 2-chloro-8-methoxyquinoline-3-carbaldehyde (1.8583 g, 8.384 mmol), 3-fluorobenzeneboronic acid (1.290 g, 9.223 mmol), tetrakis(tri-phenylphosphine)palladium (0.4844 g, 0.4192 mmol), and sodium carbonate anhydrous (4.443 g, 41.92 mmol) in 76 mL of CH$_3$CN—H$_2$O (3:1) was stirred at 100° C. After 3 h, the mixture was cooled to room temperature and partitioned between EtOAc (200 mL) and water (100 mL). The organic layer was washed with brine (100 mL×2), dried over Na$_2$SO$_4$, filtered, and concentrated under reduced pressure to give an orange solid. The orange solid was purified by silica gel column chromatography on a 80 g of Redi-Sep™ column using 0 to 50% gradient of EtOAc in hexane over 25 min and then 50% isocratic of EtOAc for 25 min as eluent to give 2-(3-fluorophenyl)-8-methoxyquinoline-3-carbaldehyde as a light-yellow solid: $^1$H NMR (400 MHz, DMSO-d$_6$) δ ppm 10.09 (1H, s), 8.94 (1H, s), 7.80 (1H, dd, J=8.2, 1.2 Hz), 7.66 (1H, t, J=8.0 Hz), 7.53-7.64 (2H, m), 7.47-7.53 (1H, m), 7.36-7.44 (2H, m), 4.00 (3H, s); LC-MS (ESI) m/z 282.1 [M+H]$^+$.

3-(Chloromethyl)-2-(3-fluorophenyl)-8-methoxyquinoline hydrochloride

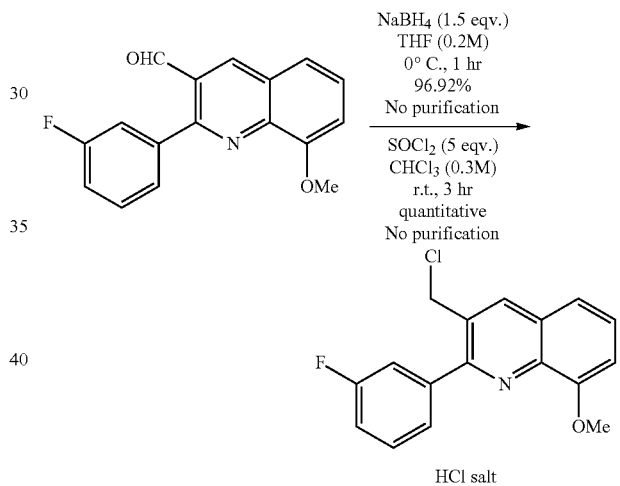

To a solution of 2-(3-fluorophenyl)-8-methoxyquinoline-3-carbaldehyde (2.2967 g, 8.165 mmol) in tetrahydrofuran (40.83 mL, 8.165 mmol) at 0° C. was added sodium borohydride (0.4634 g, 12.25 mmol) and the mixture was stirred at 0° C.

After 1 h of stirring at 0° C., the mixture was partitioned between EtOAc (100 mL) and H$_2$O (100 mL), and the organic layer was washed with brine (100 mL×2), dried over Na$_2$SO$_4$, filtered, and concentrated under reduced pressure to give (2-(3-fluorophenyl)-8-methoxyquinolin-3-yl)methanol as a brown solid: $^1$H NMR (400 MHz, DMSO-d$_6$) δ ppm 8.43 (1H, s), 7.46-7.60 (5H, m), 7.29-7.36 (1H, m), 7.19 (1H, dd, J=7.4, 1.6 Hz), 5.50 (1H, t, J=5.3 Hz), 4.61 (2H, dd, J=5.5, 0.8 Hz), 3.96 (3H, s); LC-MS (ESI) m/z 284.0 [M+H]$^+$. The brown solid was carried on crude without purification for the next step.

A solution of (2-(3-fluorophenyl)-8-methoxyquinolin-3-yl)methanol (2.2330 g, 7.882 mmol) in chloroform (26.27 mL, 7.882 mmol) was treated with thionyl chloride (2.868 mL, 39.41 mmol) dropwise, and the reaction mixture was stirred at room temperature. After 3 h, the mixture was concentrated under reduced pressure and co-evaporated three times with CH$_2$Cl$_2$ to give 3-(chloromethyl)-2-(3-fluorophenyl)-8-methoxyquinoline hydrochloride as a yellow solid: $^1$H NMR (400 MHz, DMSO-d$_6$) δ ppm 8.59 (1H, s), 7.55-7.65 (3H, m), 7.44-7.52 (2H, m), 7.33-7.41 (1H, m), 7.23-7.30 (1H, m), 4.91 (2H, s); LC-MS (ESI) m/z 302.0 [M+H]$^+$ (Exact Mass of neutral form: 301.067). The yellow solid was carried on crude without purification for the next step.

(2-(3-Fluorophenyl)-8-methoxyquinolin-3-yl)methanamine

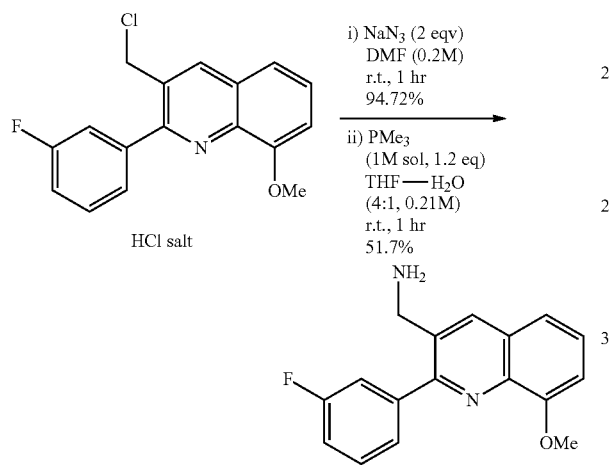

To a stirring solution of 3-(chloromethyl)-2-(3-fluorophenyl)-8-methoxyquinoline hydrochloride (0.9601 g, 2.839 mmol) in DMF (14.19 mL, 2.839 mmol) was added sodium azide (0.3691 g, 5.678 mmol) at room temperature and the mixture was stirred at room temperature After 1 h, the mixture was partitioned between EtOAc (100 mL) and H$_2$O (100 mL). The organic layer was washed with brine (100 mL×1), dried over Na$_2$SO$_4$, filtered, and concentrated under reduced pressure to give 3-(azidomethyl)-2-(3-fluorophenyl)-8-methoxyquinoline as a yellow solid: $^1$H NMR (400 MHz, DMSO-d$_6$) δ ppm 8.48 (1H, s), 7.54-7.62 (3H, m), 7.43-7.49 (2H, m), 7.32-7.39 (1H, m), 7.21-7.28 (1H, m), 4.68 (2H, s), 3.97 (3H, s); LC-MS (ESI) m/z 309.1 [M+H]$^+$. The yellow solid was carried on crude without purification for the next step.

To a stirring solution of 3-(azidomethyl)-2-(3-fluorophenyl)-8-methoxyquinoline (0.8163 g, 2.65 mmol) in 12 mL of THF—H$_2$O (4:1) was added dropwise trimethylphosphine, 1.0 M solution in THF (3.18 mL, 3.18 mmol) at room temperature and the mixture was stirred at room temperature. After 1.5 h, the mixture was diluted with ice-cold 1 N NaOH (100 mL) and extracted with EtOAc (100 mL×2). The combined organic layers were washed with brine (100 mL×3), dried over Na$_2$SO$_4$, and concentrated under reduced pressure of give a yellow solid (0.8054 g). The yellow solid (0.8054 g) was purified by column chromatography on a 80 g of Redi-Sep™ column using 0-100% gradient of EtOAc in hexane over 25 min, then 100% isocratic of EtOAc for 10 min, then 0% to 50% gradient of CH$_2$Cl$_2$:MeOH:NH$_4$OH (89:9:1) in CH$_2$Cl$_2$ over 25 min, and then 50% isocratic of CH$_2$Cl$_2$:MeOH:NH$_4$OH (89:9:1) for 10 min as eluent to give (2-(3-fluorophenyl)-8-methoxyquinolin-3-yl)methanamine as a yellow syrupy solid: $^1$H NMR (400 MHz, DMSO-d$_6$) δ ppm 8.45 (1H, s), 7.44-7.59 (5H, m), 7.28-7.36 (1H, m), 7.13-7.19 (1H, m), 3.95 (3H, s), 3.83 (2H, d, J=0.8 Hz), 1.98 (2H, br. s.); LC-MS (ESI) m/z 283.1 [M+H]$^+$.

N-((2-(3-Fluorophenyl)-8-methoxyquinolin-3-yl)methyl)-9H-purin-6-amine

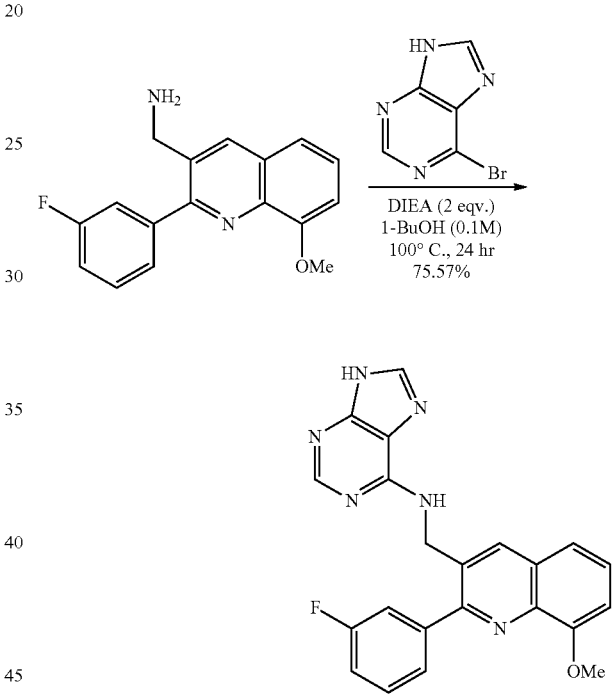

A mixture of 6-bromopurine (0.1418 g, 0.7125 mmol), (2-(3-fluorophenyl)-8-methoxyquinolin-3-yl)methanamine (0.2213 g, 0.7838 mmol), and N,N-diisopropylethylamine (0.2482 mL, 1.425 mmol) in 1-butanol (7.125 mL, 0.7125 mmol) was stirred at 100° C. After 24 h, the mixture was removed from the heat and concentrated under reduced pressure. The residue was purified by flash column chromatography on a silica gel column using 50% of CH$_2$Cl$_2$:MeOH:NH$_4$OH (89:9:1) in CH$_2$Cl$_2$ as eluent to give an off-white solid. The off-white solid was suspended in EtOAc and filtered to give N-((2-(3-fluoro-phenyl)-8-methoxyquinolin-3-yl)methyl)-9H-purin-6-amine as a white solid: $^1$H NMR (400 MHz, DMSO-d$_6$) δ ppm 12.95 (1H, s), 8.18-8.30 (2H, m), 8.11 (2H, s), 7.42-7.61 (5H, m), 7.28-7.36 (1H, m), 7.16 (1H, dd, J=7.1, 1.7 Hz), 4.71-4.95 (2H, m), 3.95 (3H, s); LC-MS (ESI) m/z 401.2 [M+H]$^+$.

Example 89: Preparation of N—((S)-1-(8-Chloro-2-(2-fluorophenyl)quinolin-3-yl)ethyl)-9H-purin-6-amine 2-((S)-1-(8-Chloro-2-(2-fluorophenyl)quinolin-3-yl)ethyl)carbamoyl)benzoic acid

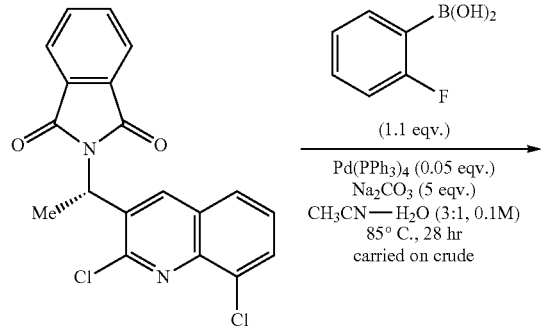

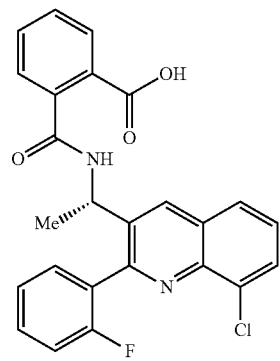

A mixture of (S)-2-(1-(2,8-dichloroquinolin-3-yl)ethyl)isoindoline-1,3-dione (0.5000 g, 1.347 mmol), 2-fluorobenzeneboronic acid (0.2073 g, 1.482 mmol), tetrakis(triphenylphosphine)palladium (0.07782 g, 0.06735 mmol), and sodium carbonate anhydrous (0.7138 g, 6.735 mmol) in acetonitrile-water (3:1) (12.00 mL, 1.346 mmol) was stirred at 85° C. After 28 h, the mixture was cooled to room temperature. The mixture was concentrated under reduced pressure to remove acetonitrile. The mixture was partitioned between CH$_2$Cl$_2$ (50 mL) and water (50 mL). The aqueous layer (pH 1011) was washed with CH$_2$Cl$_2$ (50 mL×2) to remove byproducts. The aqueous layer was treated with 2 N HCl (50 mL) and extracted with CH$_2$Cl$_2$ (50 mL×2). The combined organic layers were washed with water (50 mL×1), brine (50 mL×1), dried over Na$_2$SO$_4$, filtered, and concentrated under reduced pressure to give 2-(((S)-1-(8-chloro-2-(2-fluoro-phenyl)quinolin-3-yl)ethyl)carbamoyl) benzoic acid as a solid: LC-MS (ESI) m/z 448.9 [M+H]$^+$. The crude product was carried on crude without purification for the next step.

(1S)-1-(8-Chloro-2-(2-fluorophenyl)quinolin-3-yl) ethanamine

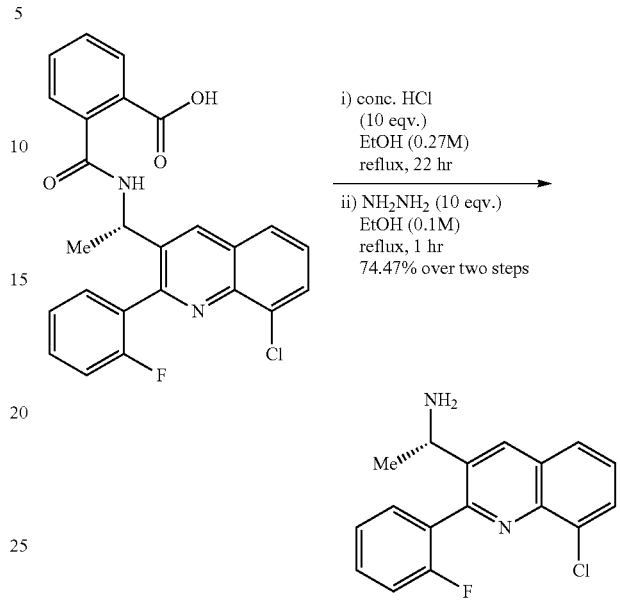

To a suspension of 2-(((S)-1-(8-chloro-2-(2-fluorophenyl)quinolin-3-yl)ethyl)-carbamoyl)benzoic acid (0.6046 g, 1.347 mmol) in ethanol (5.000 mL, 1.347 mmol) was added 12 N HCl (1.123 mL, 13.47 mmol), and the mixture was stirred under reflux. After 22 h, the mixture was poured into ice water (100 mL). The mixture was basified with 10 N NaOH (0.4 mL) to pH ~10 and extracted with CH$_2$Cl$_2$ (50 mL×2). The combined organic layers were washed with water (50 mL×2) and brine (50 mL×3), dried over Na$_2$SO$_4$, filtered, and concentrated under reduced pressure to give a mixture of 2-((S)-1-(8-chloro-2-(2-fluoro-phenyl)quinolin-3-yl)ethyl)isoindoline-1,3-dione and (1S)-1-(8-chloro-2-(2-fluorophenyl)quinolin-3-yl)ethanamine as a yellow syrup. To a mixture of 2-((S)-1-(8-chloro-2-(2-fluorophenyl)quinolin-3-yl)ethyl)isoindoline-1,3-dione and (1S)-1-(8-chloro-2-(2-fluorophenyl)quinolin-3-yl)ethanamine in ethanol (12.50 mL, 1.347 mmol) was added hydrazine monohydrate (0.4183 mL, 13.47 mmol), and the mixture was stirred under reflux. After 1 h, the mixture was cooled to room temperature and concentrated under reduced pressure to give a green solid. The green solid was purified by column chromatography on a 80 g of Redi-Sep™ column using 0% to 50% gradient of CH$_2$Cl$_2$:MeOH:NH$_4$OH (89:9:1) in CH$_2$Cl$_2$ over 25 min and then 50% isocratic of CH$_2$Cl$_2$:MeOH:NH$_4$OH (89:9:1) in CH$_2$Cl$_2$ for 25 min as eluent to give (1S)-1-(8-chloro-2-(2-fluorophenyl)quinolin-3-yl)-ethanamine as a light yellow syrup: $^1$H NMR (400 MHz, DMSO-d$_6$) δ ppm 8.74 (1H, s), 8.03 (1H, dd, J=8.3, 1.3 Hz), 7.93 (1H, dd, J=7.5, 1.3 Hz), 7.50-7.65 (3H, m), 7.33-7.43 (2H, m), 4.03 (1H, q, J=6.3 Hz), 1.98 (2H, s), 1.16 (3H, d, J=5.5 Hz); LC-MS (ESI) m/z 301.0 [M+H]$^+$.

N—((S)-1-(8-chloro-2-(2-fluorophenyl)quinolin-3-yl)ethyl)-9H-purin-6-amine

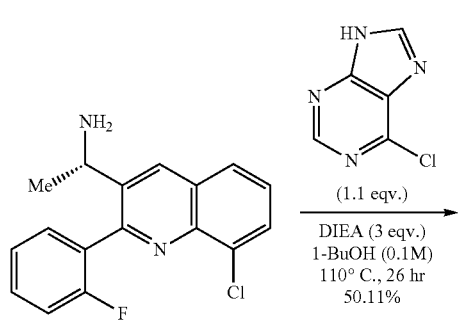

Example 90: Preparation of N-((6-Chloro-2-(2-chlorophenyl)quinolin-3-yl)-methyl)-9H-purin-6-amine

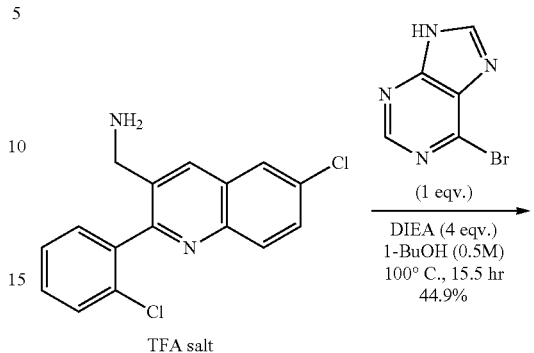

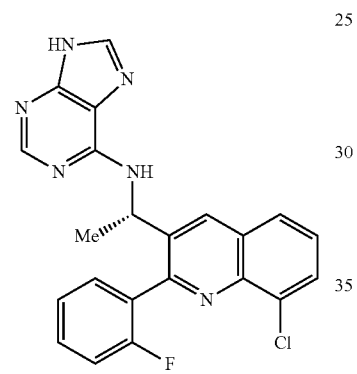

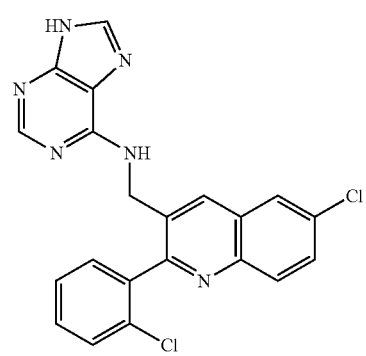

A mixture of 6-chloropurine (0.1680 g, 1.087 mmol), (1S)-1-(8-chloro-2-(2-fluorophenyl)quinolin-3-yl)ethanamine (0.2972 g, 0.9882 mmol), and N,N-diisopropylethylamine (0.5164 mL, 2.965 mmol) in 1-butanol (9.882 mL, 0.9882 mmol) was stirred at 110° C. After 26 h, the mixture was cooled to room temperature and concentrated under reduced pressure to give a yellow syrup. The yellow syrup was dissolved in CH$_2$Cl$_2$ (50 mL) and washed with water (30 mL×1). The organic layer was dried over Na$_2$SO$_4$, filtered, and concentrated under reduced pressure. The residue was purified by column chromatography on a 40 g of Redi-Sep™ column using 0 to 35% gradient of CH$_2$Cl$_2$:MeOH:NH$_4$OH (89:9:1) in CH$_2$Cl$_2$ over 14 min and then 35% isocratic of CH$_2$Cl$_2$:MeOH:NH$_4$OH (89:9:1) in CH$_2$Cl$_2$ for 25 min as eluent to give a tan solid. The tan solid was suspended in CH$_2$Cl$_2$ and filtered to give N—((S)-1-(8-chloro-2-(2-fluorophenyl)-quinolin-3-yl)ethyl)-9H-purin-6-amine as a solid: $^1$H NMR (400 MHz, DMSO-d$_6$) δ ppm 12.86 (1H, s), 8.67 (1H, s), 8.20 (1H, s), 8.09 (1H, s), 7.95-8.03 (2H, m), 7.93 (1H, dd, J=7.6, 1.0 Hz), 7.69 (1H, s), 7.58 (1H, t, J=7.8 Hz), 7.46-7.55 (1H, m), 7.25-7.39 (2H, m), 5.38 (1H, s), 1.55 (3H, d, J=7.0 Hz); LC-MS (ESI) m/z 418.9 [M+H]$^+$.

A mixture of 6-bromopurine (0.1000 g, 0.5025 mmol), (6-chloro-2-(2-chlorophenyl)quinolin-3-yl)methanamine as a TFA salt (0.2138 g, 0.5125 mmol), and N,N-diisopropylethylamine (0.3501 mL, 2.010 mmol) in 1-butanol (1.005 mL, 0.5025 mmol) was stirred at 100° C. After 15.5 h, the mixture was cooled to room temperature and concentrated under reduced pressure. The residue was purified by column chromatography on a 40 g of Redi-Sep™ column using 0 to 50% gradient of CH$_2$Cl$_2$:MeOH:NH$_4$OH (89:9:1) in CH$_2$Cl$_2$ over 14 min and then 50% isocratic of CH$_2$Cl$_2$:MeOH:NH$_4$OH (89:9:1) in CH$_2$Cl$_2$ for 10 min as eluent to give a tan solid (0.0939 g). The tan solid was suspended in EtOAc and filtered to give N-((6-chloro-2-(2-chlorophenyl)quinolin-3-yl)methyl)-9H-purin-6-amine as a tan solid: $^1$H NMR (400 MHz, DMSO-d$_6$) δ ppm 12.94 (1H, s), 8.28 (1H, s), 8.06-8.24 (4H, m), 8.03 (1H, d, J=9.0 Hz), 7.75 (1H, dd, J=9.0, 2.3 Hz), 7.61 (1H, d, J=7.4 Hz), 7.42-7.57 (3H, m), 4.49-4.77 (2H, m); LC-MS (ESI) miz 421.0 [M+H]$^+$.

Example 91: Preparation of N-((8-chloro-2-(2-fluorophenyl)quinolin-3-yl)-methyl)-9H-purin-6-amine 8-Chloro-2-(2-fluorophenyl)quinoline-3-carbaldehyde

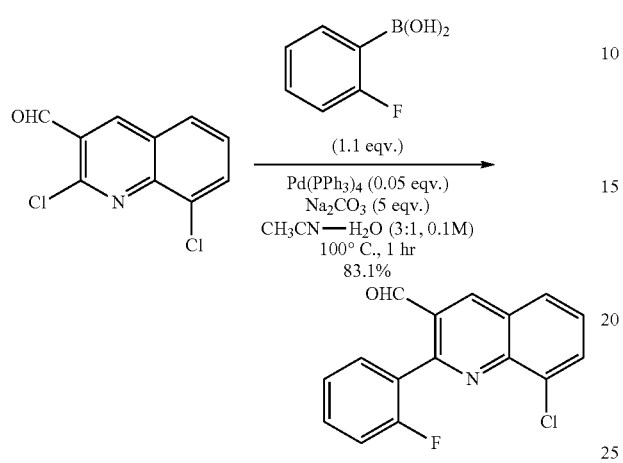

2,8-Dichloroquinoline-3-carbaldehyde (Prepared in Example 2, 1.000 g, 4.42 mmol), 2-fluorophenylboronic acid (0.681 g, 4.87 mmol), tetrakis(triphenyl-phosphine) palladium (0.256 g, 0.221 mmol), and sodium carbonate (2.34 g, 22.1 mmol) were stirred in 3:1 acetonitrile-water (48 mL) at 100° C. After 1 h, the mixture was partitioned between EtOAc and water. The organic layer was washed with brine, dried over $MgSO_4$, filtered, and concentrated under reduced pressure. The crude product was purified by column chromatography on a 40 g of Redi-Sep™ column using 0% to 100% gradient of EtOAc in hexane as eluent to give 8-chloro-2-(2-fluorophenyl)quinoline-3-carbaldehyde: LC-MS (ESI) m/z 286.0 $[M+H]^+$.

(8-Chloro-2-(2-fluorophenyl)quinolin-3-yl)methanol

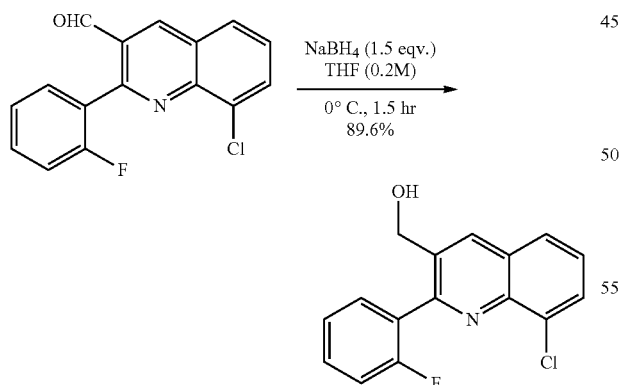

Sodium borohydride (0.159 g, 4.20 mmol) was added portion wise to a stirring solution of 8-chloro-2-(2-fluorophenyl)quinoline-3-carbaldehyde (0.800 g, 2.80 mmol) in 15 mL of THF. The reaction stirred at room temperature. After 1.5 h, the mixture was partitioned between water and EtOAc. The organic layer was dried over $MgSO_4$, filtered, and concentrated under reduced pressure: LC-MS (ESI) m/z 288.1 $[M+H]^+$. The crude product was carried on crude without purification for the next step.

8-Chloro-3-(chloromethyl)-2-(2-fluorophenyl)quinoline

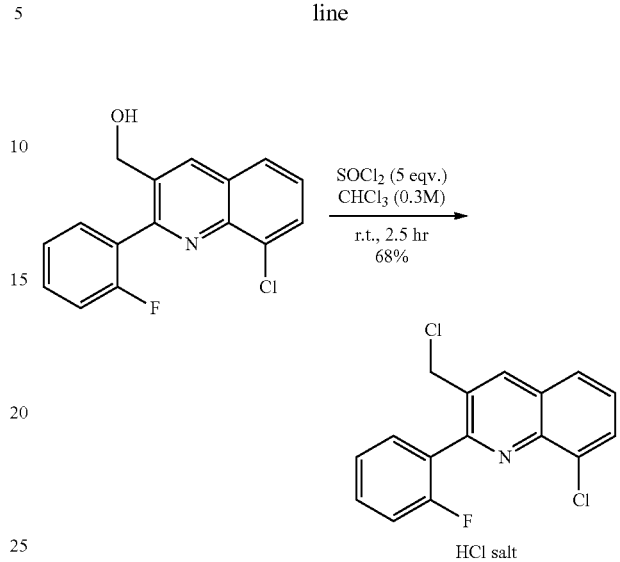

Thionyl chloride (0.850 mL, 11.6 mmol) was added to a stirring solution of (8-chloro-2-(2-fluorophenyl)quinolin-3-yl)methanol (0.670 g, 2.33 mmol) in $CH_2Cl_2$. The reaction mixture was stirred at room temperature. After 2.5 h, the crude product was purified by column chromatography on a 40 g Redi-Sep™ column using 0% to 100% gradient of $CH_2Cl_2$-MeOH—$NH_4OH$ (89:9:1) in $CH_2Cl_2$ to give 8-chloro-3-(chloromethyl)-2-(2-fluorophenyl)quinoline: LC-MS (ESI) m/z 306.0 $[M+H]^+$.

3-(Azidomethyl)-8-chloro-2-(2-fluorophenyl)quinoline

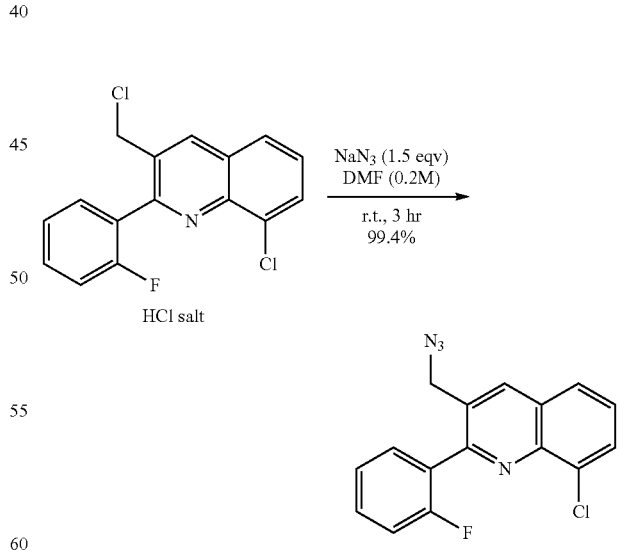

To stirring solution of 8-chloro-3-(chloromethyl)-2-(2-fluorophenyl)quinoline (0.330 g, 1.08 mmol) in DMF was added sodium azide (0.561 g, 8.62 mmol), and the mixture stirred at room temperature. After 3 hours, the mixture was partitioned between $CH_2Cl_2$ and $H_2O$. The organic layer was dried over $MgSO_4$, filtered and concentrated under reduced pressure: LC-MS (ESI) m/z 313.0 [M+H]⁺. The crude product was carried on crude without purification for the next step.

(8-Chloro-2-(2-fluorophenyl)quinolin-3-yl)methanamine

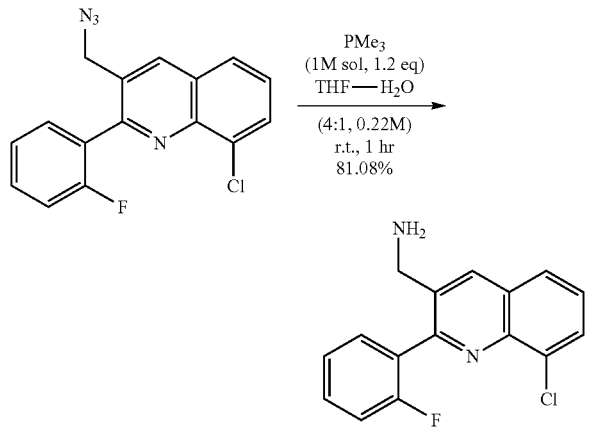

To a stirring solution of 3-(azidomethyl)-8-chloro-2-(2-fluorophenyl)quinoline (0.3083 g, 0.9858 mmol) in THF—H₂O (4:1) (12.000 mL) was added dropwise trimethylphosphine, 1.0 M solution in THF (1.183 mL, 1.183 mmol) at room temperature and the mixture was stirred at room temperature. After 1 h, the mixture was diluted with ice-cold 1 N NaOH (60 mL) and extracted with EtOAc (50 mL×2). The combined organic layers were washed with brine (50 mL×2), dried over Na₂SO₄, and concentrated under the reduced pressure to give a yellow syrup. The yellow syrup was purified by column chromatography on a 40 g of Redi-Sep™ column using 0-100% gradient of EtOAc in hexane over 14 min, then 100% isocratic of EtOAc for 10 min, then 0% to 50% gradient of CH₂Cl₂:MeOH:NH₄OH (89:9:1) in CH₂Cl₂ over 14 min, and then 50% isocratic of CH₂Cl₂:MeOH:NH₄OH (89:9:1) for 10 min as eluent to give (8-chloro-2-(2-fluorophenyl)quinolin-3-yl)methanamine ¹H NMR (500 MHz, DMSO-d₆) δ ppm 8.62 (1H, s), 8.03 (1H, dd, J=8.2, 1.1 Hz), 7.93 (1H, dd, J=7.3, 1.2 Hz), 7.55-7.66 (2H, m), 7.49-7.55 (1H, m), 7.34-7.43 (2H, m), 3.72 (2H, s), 1.94 (2H, br. s.); LC-MS (ESI) m/z 287.2 [M+H]⁺.

N-((8-Chloro-2-(2-fluorophenyl)quinolin-3-yl)methyl)-9H-purin-6-amine

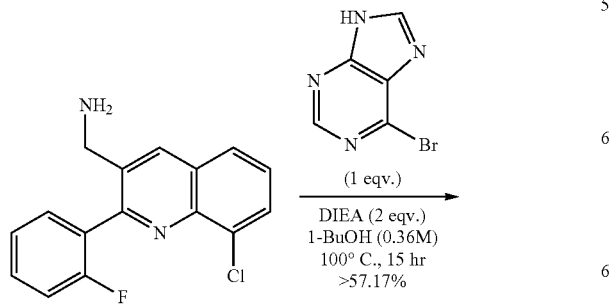

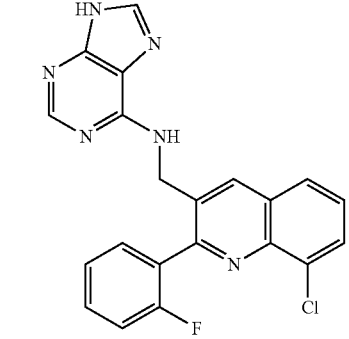

A mixture of 6-bromopurine (0.1456 g, 0.7317 mmol), (8-chloro-2-(2-fluoro-phenyl)quinolin-3-yl)methanamine (0.2203 g, 0.7683 mmol), and N,N-diisopropylethylamine (0.3824 mL, 2.195 mmol) in 1-butanol (2.000 mL, 0.7317 mmol) was stirred at 100° C. After 15 h, the mixture was removed from the heat and cooled to room temperature. The resulting precipitate was collected by filtration and washed with MeOH to give a yellow solid. The yellow solid was purified by column chromatography on a 40 g of Redi-Sep™ column using 0 to 50% gradient of CH₂Cl₂:MeOH:NH₄OH (89:9:1) in CH₂Cl₂ over 14 min and then 50% isocratic of CH₂Cl₂:MeOH:NH₄OH (89:9:1) in CH₂Cl₂ for 10 min as eluent to give an off-white solid. The off-white solid was suspended in EtOAc-Hexane (1:1) and filtered to give N-((8-chloro-2-(2-fluorophenyl)quinolin-3-yl)methyl)-9H-purin-6-amine as an off-white solid: ¹H NMR (500 MHz, DMSO-d₆) δ ppm 12.95 (1H, s), 8.35 (1H, s), 8.03-8.29 (3H, m), 7.99 (1H, dd, J=8.2, 1.1 Hz), 7.93 (1H, dd, J=7.5, 1.1 Hz), 7.53-7.65 (3H, m), 7.36-7.44 (2H, m), 4.63-4.82 (2H, m); LC-MS (ESI) m/z 405.1 [M+H]⁺.

Example 92: Preparation of N-((3-(2-Chlorophenyl)-5,6-difluoroquinoxalin-2-yl)methyl)-9H-purin-6-amine 3-(Bromomethyl)-2-(2-chlorophenyl)-5,6-difluoroquinoxaline and 2-(Bromomethyl)-3-(2-chlorophenyl)-5,6-difluoroquinoxaline

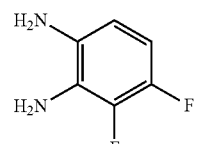
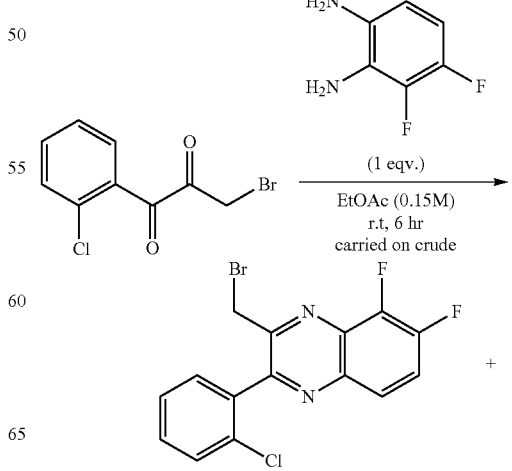

-continued

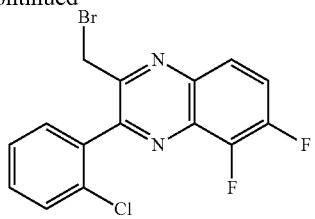

To a solution of 3-bromo-1-(2-chlorophenyl)propane-1,2-dione (Prepared in Example 81, 1.4324 g, 5.4775 mmol) in ethyl acetate (36.517 mL, 5.4775 mmol) was added 1,2-diamino-3,4-difluorobenzene (0.78943 g, 5.4775 mmol) at room temperature and the resulting red mixture was stirred at room temperature. After 26 h of stirring at room temperature, the mixture was concentrated under reduced pressure to give a mixture of 3-(bromomethyl)-2-(2-chlorophenyl)-5,6-difluoroquinoxaline and 2-(bromomethyl)-3-(2-chlorophenyl)-5,6-difluoroquinoxaline as a brown syrup: LC-MS (ESI) m/z 369.0 and 370.9 [M+H]$^+$. The crude product as a brown syrup was carried on crude without purification for the next step.

(3-(2-Chlorophenyl)-7,8-difluoroquinoxalin-2-yl)methanamine and (3-(2-Chlorophenyl)-5,6-difluoroquinoxalin-2-yl)methanamine

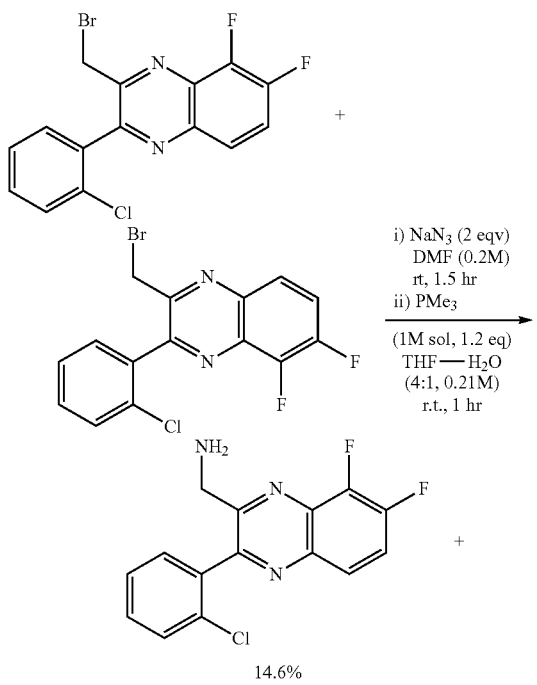

To a stirring solution of a mixture of 3-(bromomethyl)-2-(2-chlorophenyl)-5,6-difluoroquinoxaline and 2-(bromomethyl)-3-(2-chlorophenyl)-5,6-difluoroquinoxaline (2.0244 g, 5.477 mmol) in DMF (20.00 mL, 5.477 mmol) was added sodium azide (0.7122 g, 10.95 mmol) at room temperature and the mixture was stirred at room temperature. After 1.5 h, the mixture was partitioned between EtOAc (100 mL) and H$_2$O (100 mL). The organic layer was washed with brine (100 mL×1), dried over Na$_2$SO$_4$, filtered, and concentrated under reduced pressure to give a mixture of 3-(azidomethyl)-2-(2-chlorophenyl)-5,6-difluoroquinoxaline and 2-(azidomethyl)-3-(2-chlorophenyl)-5,6-difluoroquinoxaline as a dark red syrup: LC-MS (ESI) m/z 332.0 [M+H]$^+$. The crude product was carried on crude without purification for the next step.

To a stirring solution of 3-(azidomethyl)-2-(2-chlorophenyl)-5,6-difluoroquinoxaline and 2-(azidomethyl)-3-(2-chlorophenyl)-5,6-difluoroquinoxaline (1.8170 g, 5.478 mmol) in 25 mL of THF—H$_2$O (4:1) was added dropwise trimethylphosphine, 1.0 M solution in THF (6.573 mL, 6.573 mmol) at room temperature and the mixture was stirred at room temperature. After 1 h, the mixture was diluted with ice-cold 1 N NaOH (25 mL) and extracted with EtOAc (50 mL×3). The combined organic layers were washed with brine (50 mL×3), dried over Na$_2$SO$_4$, and concentrated under the reduced pressure to give a green syrup. The green syrup was purified by column chromatography on a 120 g of Redi-Sep™ column using 0% to 20% gradient of CH$_2$Cl$_2$:MeOH:NH$_4$OH (89:9:1) in CH$_2$Cl$_2$ over 15 min, then 20% isocratic of CH$_2$Cl$_2$:MeOH:NH$_4$OH (89:9:1) in CH$_2$Cl$_2$ for 15 min, then 20% to 50% gradient of CH$_2$Cl$_2$:MeOH:NH$_4$OH (89:9:1) in CH$_2$Cl$_2$ over 5 min, and then 50% isocratic of CH$_2$Cl$_2$:MeOH:NH$_4$OH (89:9:1) in CH$_2$Cl$_2$ for 15 min as eluent to give two separated regioisomers: (3-(2-chlorophenyl)-7,8-difluoroquinoxalin-2-yl)methanamine as a brown-green syrupy solid: $^1$H NMR (400 MHz, DMSO-d$_6$) δ ppm 7.94-8.10 (2H, m), 7.50-7.73 (4H, m), 3.84 (2H, br. s.), 2.03 (2H, br. s.); LC-MS (ESI) m/z 306.1 [M+H]$^+$ and (3-(2-chlorophenyl)-5,6-difluoroquinoxalin-2-yl)methanamine as a blue syrupy solid: $^1$H NMR (400 MHz, DMSO-d$_6$) δ ppm 7.97-8.13 (2H, m), 7.45-7.74 (4H, m), 3.82 (2H, s), 2.10 (2H, br. s.); LC-MS (ESI) m/z 306.1 [M+H]$^+$. The structures of two separated isomers were confirmed by $^1$H-$^{15}$N HMBC experiment.

N-((3-(2-Chlorophenyl)-5,6-difluoroquinoxalin-2-yl)methyl)-9H-purin-6-amine

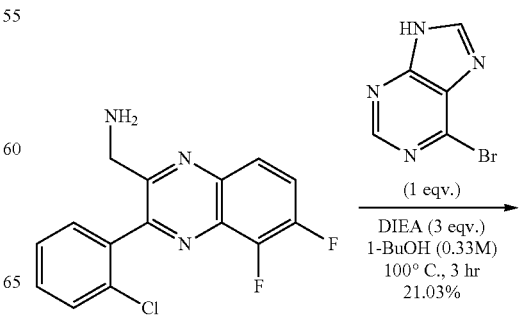

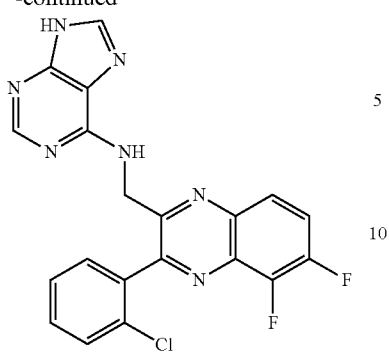

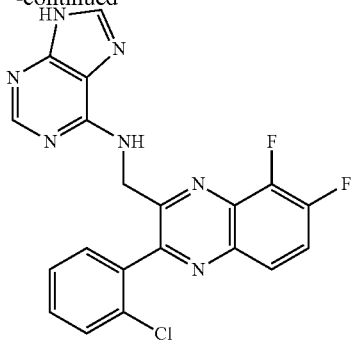

A mixture of 6-bromopurine (0.1978 g, 0.9938 mmol), (3-(2-chlorophenyl)-5,6-difluoroquinoxalin-2-yl)methanamine (0.3342 g, 1.093 mmol), and N,N-diisopropylethylamine (0.5193 mL, 2.981 mmol) in 1-butanol (3.000 mL, 0.9938 mmol) was stirred at 100° C. After 3 h, the mixture was removed from the heat and concentrated under reduced pressure. The residue was suspended in MeOH and the resulting precipitate was collected by filtration, and washed with MeOH to give a yellow solid. The yellow solid (0.1232 g) was purified by column chromatography on a 40 g of Redi-Sep™ column using 0 to 50% gradient of CH$_2$Cl$_2$: MeOH:NH$_4$OH (89:9:1) in CH$_2$Cl$_2$ over 14 min and then 50% isocratic of CH$_2$Cl$_2$:MeOH:NH$_4$OH (89:9:1) in CH$_2$Cl$_2$ for 14 min as eluent to give an off-white solid (0.1014 g). The off white solid was suspended in CH$_2$Cl$_2$ and filtered to give N-((3-(2-chlorophenyl)-5,6-difluoroquinoxalin-2-yl)methyl)-9H-purin-6-amine as an off-white solid: 1H NMR (400 MHz, DMSO-d$_6$) δ ppm 12.93 (1H, s), 7.81-8.16 (5H, m), 7.61-7.72 (2H, m), 7.53-7.58 (1H, m), 7.46-7.52 (1H, m), 4.71-4.97 (2H, m); LC-MS (ESI) m/z 424.0 [M+H]$^+$.

Example 93: Preparation of N-((3-(2-Chlorophenyl)-7,8-difluoroquinoxalin-2-yl)methyl)-9H-purin-6-amine A mixture of 6-bromopurine (0.1359 g, 0.6828 mmol), (3-(2-chlorophenyl)-7,8-difluoroquinoxalin-2-yl)methanamine (Prepared in Example 92, 0.2296 g, 0.7510 mmol), and N,N-diisopropylethylamine (0.3568 mL, 2.048 mmol) in 1-butanol (3.000 mL, 0.6828 mmol) was stirred at 100° C. After 3 h, the mixture was removed from the heat and concentrated under reduced pressure. The residue was suspended in MeOH and the insoluble solid was removed by filtration. The filtrate was concentrated under reduced pressure and purified by column chromatography on a 40 g of Redi-Sep™ column using 0 to 50% gradient of CH$_2$Cl$_2$: MeOH:NH$_4$OH (89:9:1) in CH$_2$Cl$_2$ over 14 min and then 50% isocratic of CH$_2$Cl$_2$:MeOH:NH$_4$OH (89:9:1) in CH$_2$Cl$_2$ for 14 min as eluent to give a yellow solid. The yellow solid was suspended in CH$_2$Cl$_2$ and filtered to give N-((3-(2-chlorophenyl)-7,8-difluoroquinoxalin-2-yl)methyl)-9H-purin-6-amine as a yellow solid: $^1$H NMR (400 MHz, DMSO-d$_6$) δ ppm 12.92 (1H, br. s.), 7.93-8.15 (4H, m), 7.60-7.69 (2H, m), 7.51-7.57 (1H, m), 7.45-7.50 (1H, m), 4.83 (2H, br. s.); LC-MS (ESI) m/z 424.1 [M+H]$^+$.

Example 94: Preparation of 34 (9H-Purin-6-ylamino)methyl)-2-(3-fluoro-phenyl)quinolin-8-ol

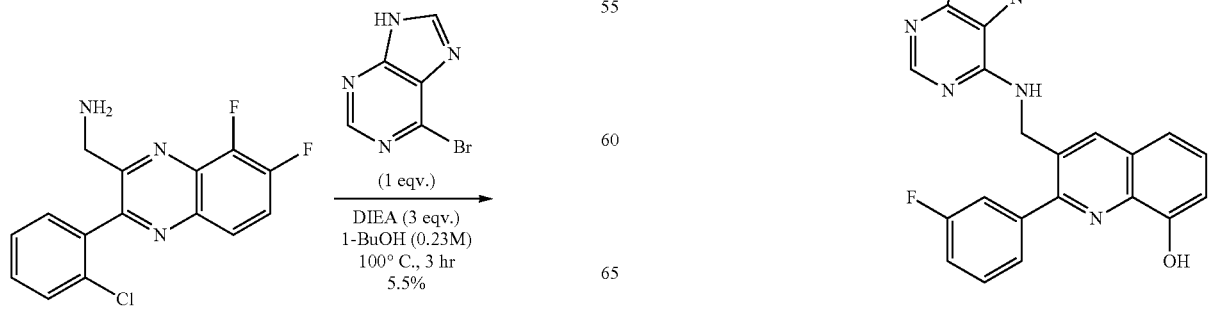

To a solution of N-((2-(3-fluorophenyl)-8-methoxyquinolin-3-yl)methyl)-9H-purin-6-amine (0.1500 g, 0.3746 mmol) in DCM (3.746 mL, 0.3746 mmol) at 0° C., boron tribromide, 1.0 M sol. in DCM (1.498 mL, 1.498 mmol) was added dropwise and the mixture was cooling bath was removed and stirred at room temperature. After 29 h, the mixture was cooled to 0° C. and to the cooled mixture, ice-water (50 mL) was added with stirring. The mixture was neutralized with 10 N NaOH (~5 mL) to pH 8 and the resulting precipitate was collected by filtration to give a yellow solid. yellow solid (YS-90942-4-1) was purified by column chromatography on a 40 g of Redi-Sep™ column using 0 to 100% gradient of $CH_2Cl_2$:MeOH:$NH_4OH$ (89:9:1) in $CH_2Cl_2$ over 14 min and then 100% isocratic of $CH_2Cl_2$:MeOH:$NH_4OH$ (89:9:1) in $CH_2Cl_2$ for 10 min as eluent to give an off-white solid. The off-white solid was suspended in $CH_2Cl_2$ and filtered to give 3-((9H-purin-6-ylamino)methyl)-2-(3-fluorophenyl)quinolin-8-ol as an off-white solid: $^1$H NMR (400 MHz, DMSO-$d_6$) δ ppm 12.95 (1H, s), 9.58 (1H, s), 8.18 (4H, d, J=50.5 Hz), 7.26-7.71 (6H, m), 7.06 (1H, d, J=6.7 Hz), 4.88 (2H, br. s.); LC-MS (ESI) m/z 387.1 [M+H]$^+$.

Example 95: Preparation of N-((5-Chloro-3-(3-fluorophenyl)quinoxalin-2-yl)-methyl)-9H-purin-6-amine 5-Chloro-3-(3-fluorophenyl)-2-methylquinoxaline

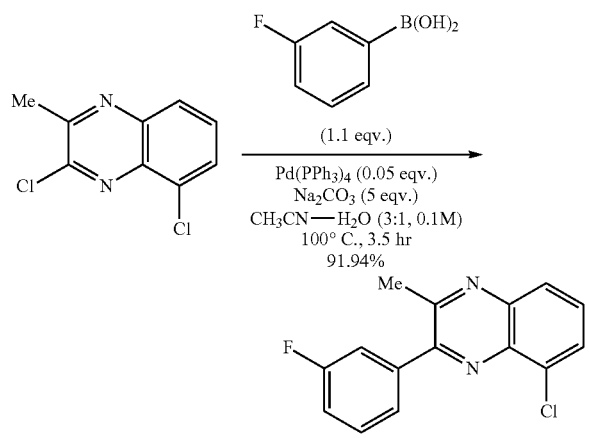

A mixture of 3,5-dichloro-2-methylquinoxaline (Prepared in Example 85, 0.3361 g, 1.577 mmol), 3-fluorobenzeneboronic acid (0.2428 g, 1.735 mmol), tetrakis(triphenylphosphine)palladium (0.09114 g, 0.07887 mmol), and sodium carbonate anhydrous (0.8360 g, 7.887 mmol) in CH3CN—H2O (3:1) (16.00 mL) was stirred at 100° C. After 3.5 h, the mixture was cooled to room temperature and partitioned between EtOAc (100 mL) and water (100 mL). The organic layer was washed with brine (50 mL×2), dried over $Na_2SO_4$, filtered, and concentrated under reduced pressure to give red syrup. The red syrup was purified by silica gel column chromatography on a 40 g of Redi-Sep™ column using 0 to 50% gradient of EtOAc in hexane over 14 min and then 50% isocratic of EtOAc for 10 min as eluent to give 5-chloro-3-(3-fluorophenyl)-2-methylquinoxaline as a solid: $^1$H NMR (400 MHz, DMF) δ ppm 8.05 (1H, dd, J=8.4, 1.4 Hz), 8.00 (1H, dd, J=7.6, 1.4 Hz), 7.83 (1H, dd, J=8.4, 7.6 Hz), 7.60-7.67 (3H, m), 7.38-7.46 (1H, m), 2.74 (3H, s); LC-MS (ESI) m/z 273.1 [M+H]$^+$.

2-(Bromomethyl)-5-chloro-3-(3-fluorophenyl)quinoxaline

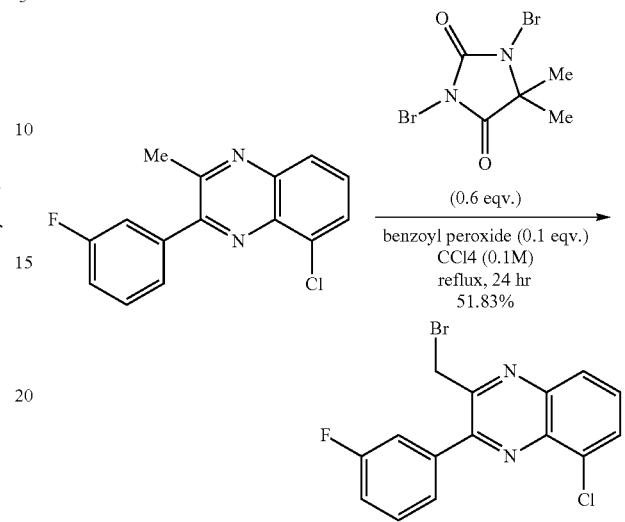

5-chloro-3-(3-fluorophenyl)-2-methylquinoxaline (0.3907 g, 1.433 mmol) and 1,3-dibromo-5,5-dimethylhydantoin (0.2458 g, 0.8596 mmol) were suspended in carbon tetrachloride (14.33 mL, 1.433 mmol). To the mixture was added benzoyl peroxide (0.04627 g, 0.1433 mmol) and the mixture was heated at reflux. After 24 h, the mixture was cooled to room temperature and concentrated under reduced pressure. The residue was purified by silica gel column chromatography on a 40 g of Redi-Sep™ column using 0 to 9% gradient of EtOAc in hexane over 1.3 min, then 9% isocratic of EtOAc for 7.6 min, then 9 to 100% gradient of EtOAc in hexane over 12.7 min, then 100% isocratic of EtOAc for 10 min as eluent to give 2-(bromomethyl)-5-chloro-3-(3-fluorophenyl)quinoxaline as an off-white solid: $^1$H NMR (400 MHz, DMSO-$d_6$) δ ppm 8.14 (1H, dd, J=8.4, 1.2 Hz), 8.12 (1H, dd, J=7.6, 1.4 Hz), 7.92 (1H, dd, J=8.4, 7.8 Hz), 7.64-7.70 (3H, m), 7.43-7.50 (1H, m), 4.91 (2H, s); LC-MS (ESI) m/z 351.0 and 352.9 [M+H]$^+$.

2-((5-Chloro-3-(3-fluorophenyl)quinoxalin-2-yl)methyl)isoindoline-1,3-dione

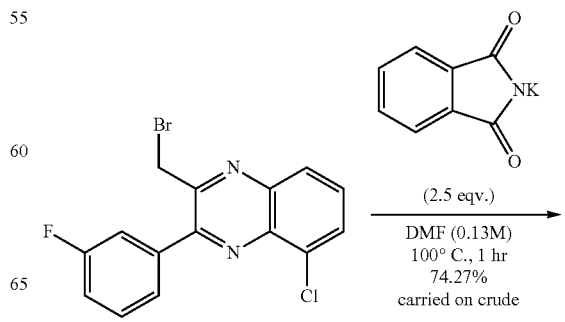

-continued

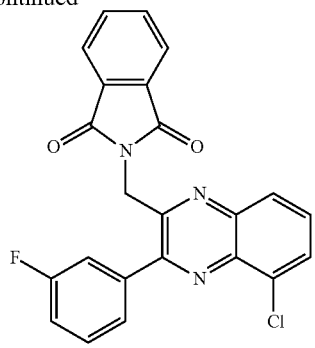

To a heterogeneous mixture of 2-(bromomethyl)-5-chloro-3-(3-fluorophenyl)-quinoxaline (0.2401 g, 0.6829 mmol) in DMF (5.003 mL, 0.6829 mmol) was added potassium phthalimide (0.3162 g, 1.707 mmol) and the heterogeneous mixture was stirred at 100° C. After stirring at 100° C. for 1 h, the mixture was concentrated under reduced pressure and triturated with water (30 mL). The precipitate was collected by filtration. The solid was washed with water (50 mL), then MeOH (100 mL), and dried to give 2-((5-chloro-3-(3-fluorophenyl)-quinoxalin-2-yl)methyl)isoindoline-1,3-dione as an off-white solid: $^1$H NMR (400 MHz, DMSO-$d_6$) δ ppm 8.04 (1H, dd, J=7.6, 1.4 Hz), 7.84-7.92 (5H, m), 7.60-7.81 (4H, m), 7.38-7.46 (1H, m), 5.22 (2H, s); LC-MS (ESI) m/z 418.1 [M+H]$^+$. The crude product was carried on crude without purification for the next step.

(5-Chloro-3-(3-fluorophenyl)quinoxalin-2-yl)methanamine

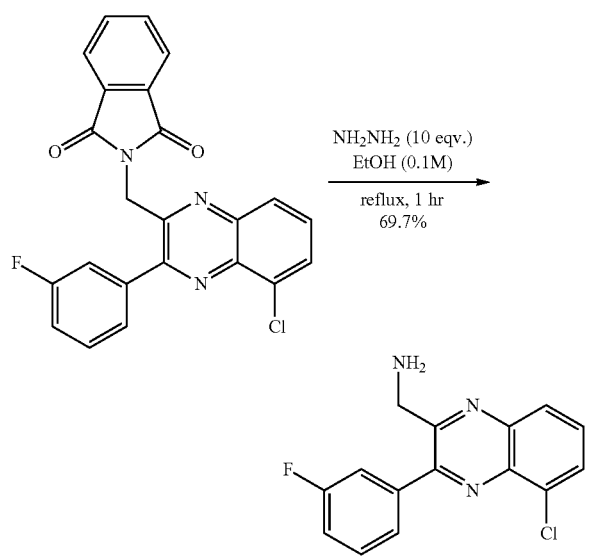

To a suspension of 2-((5-chloro-3-(3-fluorophenyl)quinoxalin-2-yl)methyl)-isoindoline-1,3-dione (0.2061 g, 0.493 mmol) in ethanol (5.00 mL, 0.493 mmol) was added hydrazine, anhydrous (0.155 mL, 4.93 mmol), and the mixture was stirred under reflux. After 1 h, the mixture was cooled to room temperature. The by product was filtered off and washed with MeOH. The filtrate was concentrated under reduced pressure to give a yellow solid (0.2012 g). The yellow solid (0.2012 g) was purified by column chromatography on a 40 g of Redi-Sep™ column using 0% to 100% gradient of CH$_2$Cl$_2$:MeOH:NH$_4$OH (89:9:1) in CH$_2$Cl$_2$ over 14 min, and then 100% isocratic of CH$_2$Cl$_2$:MeOH:NH$_4$OH (89:9:1) in CH$_2$Cl$_2$ for 3 min as eluent to give (5-chloro-3-(3-fluorophenyl)quinoxalin-2-yl)-methanamine as a green solid: $^1$H NMR (400 MHz, DMSO-$d_6$) δ ppm 8.12 (1H, dd, J=8.4, 1.4 Hz), 8.03 (1H, dd, J=7.6, 1.4 Hz), 7.86 (1H, dd, J=8.4, 7.6 Hz), 7.59-7.71 (3H, m), 7.39-7.47 (1H, m), 4.06 (2H, s); LC-MS (ESI) m/z 288.1 [M+H]$^+$.

N-((5-Chloro-3-(3-fluorophenyl)quinoxalin-2-yl)methyl)-9H-purin-6-amine

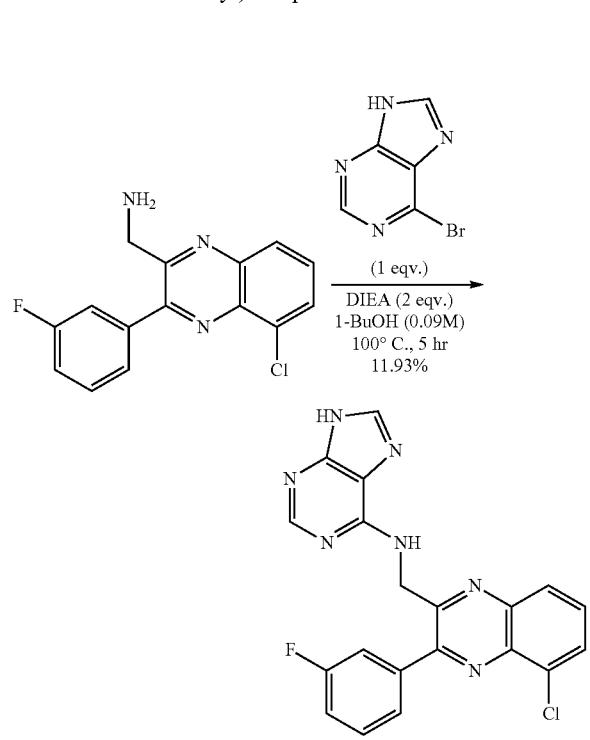

A mixture of 6-bromopurine (0.05568 g, 0.2798 mmol), (5-chloro-3-(3-fluoro-phenyl)quinoxalin-2-yl)methanamine (0.09660 g, 0.3357 mmol), and N,N-diisopropylethylamine (0.1462 mL, 0.8394 mmol) in 1-butanol (3.000 mL, 0.2798 mmol) was stirred at 100° C. After 5 h, the mixture was removed from the heat and concentrated under reduced pressure. The residue was suspended in MeOH and the resulting precipitate was collected by filtration, and washed with MeOH to give a green solid. The green solid (0.0542 g) was purified by column chromatography on a 40 g of Redi-Sep™ column using 0 to 100% gradient of CH$_2$Cl$_2$:MeOH:NH$_4$OH (89:9:1) in CH$_2$Cl$_2$ over 14 min and then 100% isocratic of CH$_2$Cl$_2$:MeOH:NH$_4$OH (89:9:1) in CH$_2$Cl$_2$ for 14 min as eluent to give N-((5-chloro-3-(3-fluorophenyl)quinoxalin-2-yl)methyl)-9H-purin-6-amine as a green solid: $^1$H NMR (400 MHz, DMSO-$d_6$) δ ppm 12.94 (1H, s), 7.93-8.20 (5H, m), 7.83 (1H, t, J=8.0 Hz), 7.57-7.73 (3H, m), 7.34-7.45 (1H, m), 5.04 (2H, br. s.); LC-MS (ESI) m/z 406.1 [M+H]$^+$.

Example 96: Preparation of N—((S)-1-(8-Chloro-2-(2-methylpyridin-3-yl)-quinolin-3-yl)ethyl)-9H-purin-6-amine and N—((R)-1-(8-chloro-2-(2-methylpyridin-3-yl)quinolin-3-yl)ethyl)-9H-purin-6-amine 8-Chloro-2-(2-methylpyridin-3-yl)quinoline-3-carbaldehyde

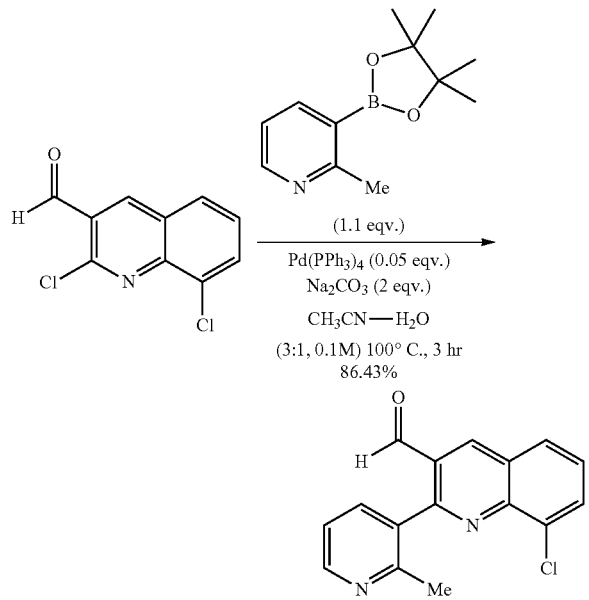

A mixture of 2,8-dichloroquinoline-3-carbaldehyde (Prepared in Example 2, 1.0000 g, 4.424 mmol), tetrakis(triphenylphosphine)palladium (0.2556 g, 0.2212 mmol), and sodium carbonate anhydrous (2.344 g, 22.12 mmol) in 90 mL of CH$_3$CN—H$_2$O (3:1) was stirred at 100° C. After 3 h, the mixture was cooled to room temperature and partitioned between EtOAc (150 mL) and water (150 mL). The organic layer was washed with brine (100 mL×2), dried over Na$_2$SO$_4$, filtered, and concentrated under reduced pressure to give a yellow solid. The yellow solid was purified by silica gel column chromatography on a 80 g of Redi-Sep™ column using 0 to 100% gradient of EtOAc in hexane over 25 min and then 100% isocratic of EtOAc for 10 min as eluent to give 8-chloro-2-(2-methylpyridin-3-yl)quinoline-3-carbaldehyde as an off-white solid: $^1$H NMR (400 MHz, DMSO-d$_6$) δ ppm 9.96 (1H, s), 9.16 (1H, s), 8.62 (1H, dd, J=4.9, 1.8 Hz), 8.31 (1H, dd, J=8.2, 1.2 Hz), 8.18 (1H, dd, J=7.4, 1.2 Hz), 7.80 (1H, dd, J=7.6, 1.8 Hz), 7.76 (1H, dd, J=8.2, 7.4 Hz), 7.40 (1H, dd, J=7.4, 4.7 Hz), 2.35 (3H, s); LC-MS (ESI) m/z 283.0 [M+H]$^+$.

1-(8-Chloro-2-(2-methylpyridin-3-yl)quinolin-3-yl)ethanol

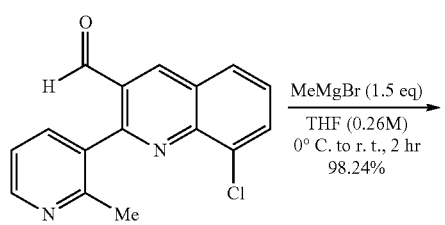

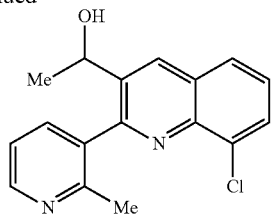

To a stirring heterogeneous mixture of 8-chloro-2-(2-methylpyridin-3-yl)-quinoline-3-carbaldehyde (1.0741 g, 3.799 mmol) in THF (14.61 mL, 3.799 mmol) was added methylmagnesium bromide 3 M in diethyl ether (1.900 mL, 5.699 mmol) dropwise at 0° C., and the mixture was allowed to warm to room temperature over 2 h. The reaction was quenched with NH$_4$Cl (50 mL) and extracted with EtOAc (50 mL×2). The combined organics were washed with water (50 mL×1), brine (50 mL×1), dried over Na$_2$SO$_4$, filtered, and concentrated under reduced pressure to give an orange syrup (1.4409 g). The orange syrup (1.4409 g) was purified by silica gel column chromatography on a 80 g of Redi-Sep™ column using 0 to 100% gradient of EtOAc in hexane over 25 min and then 100% isocratic of EtOAc for 30 min as eluent to give 1-(8-chloro-2-(2-methylpyridin-3-yl)quinolin-3-yl)ethanol as a solid: $^1$H NMR (400 MHz, DMSO-d$_6$) δ ppm 8.68 (1H, s), 8.59 (1H, dd, J=4.9, 1.8 Hz), 8.10 (1H, dd, J=8.2, 1.2 Hz), 7.94 (1H, dd, J=7.6, 1.4 Hz), 7.74 (1H, dd, J=7.8, 1.6 Hz), 7.58-7.65 (1H, m), 7.39 (1H, dd, J=7.6, 4.9 Hz), 5.47 (1H, d, J=4.3 Hz), 4.64 (1H, br. s.), 2.25 (3H, s), 1.20 (3H, d, J=7.4 Hz); LC-MS (ESI) m/z 299.0 [M+H]$^+$.

8-Chloro-3-(1-chloroethyl)-2-(2-methylpyridin-3-yl)quinoline hydrochloride

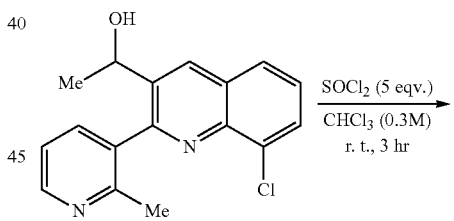

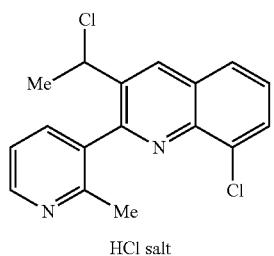

HCl salt

A solution of 1-(8-chloro-2-(2-methylpyridin-3-yl)quinolin-3-yl)ethanol (1.1090 g, 3.712 mmol) in chloroform (12.37 mL, 3.712 mmol) was treated with thionyl chloride (1.350 mL, 18.56 mmol) dropwise, and the reaction mixture was stirred at room temperature. After 3 h, the mixture was concentrated under reduced pressure and co-evaporated three times with CH$_2$Cl$_2$ to give 8-chloro-3-(1-chloroethyl)-2-(2-methylpyridin-3-yl)quinoline hydrochloride as an off-white syrupy solid: $^1$H NMR (400 MHz, DMSO-d$_6$) δ ppm 9.04 (1H, s), 8.94 (1H, dd, J=5.7, 1.4 Hz), 8.56 (1H, d, J=7.4 Hz), 8.19 (1H, dd, J=8.2, 1.2 Hz), 8.07 (1H, dd, J=7.4, 1.2 Hz), 8.02 (1H, dd, J=7.6, 5.7 Hz), 7.71-7.77 (1H, m), 5.25 (1H, d, J=6.3 Hz), 2.52 (3H, s), 1.92 (3H, d, J=6.7 Hz); LC-MS (ESI) m/z 317.0 [M+H]+ (Exact Mass of neutral form: 316.053). The crude product was carried on crude without purification for the next step.

2-(1-(8-Chloro-2-(2-methylpyridin-3-yl)quinolin-3-yl)ethyl)isoindoline-1,3-dione

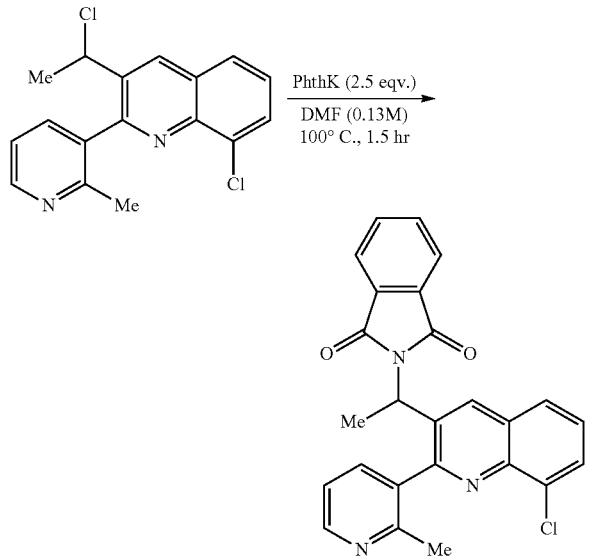

To a stirring solution of 8-chloro-3-(1-chloroethyl)-2-(2-methylpyridin-3-yl)-quinoline hydrochloride (1.3130 g, 3.712 mmol) in DMF (18.56 mL, 3.712 mmol) at 100° C. was added potassium phthalimide (1.719 g, 9.281 mmol) at 100° C. and the mixture was stirred at 100° C. After 1.5 h, the mixture was concentrated under reduced pressure and triturated with water (50 mL). The resulting solid was filtered and washed with 2 N NaOH (50 mL) and then with water (500 mL), and air-dried to give 2-(1-(8-chloro-2-(2-methylpyridin-3-yl)quinolin-3-yl)ethyl)-isoindoline-1,3-dione as a tan solid: LC-MS (ESI) m/z 428.0 [M+H]+. The impure product was carried on crude without purification for the next step.

1-(8-Chloro-2-(2-methylpyridin-3-yl)quinolin-3-yl)ethanamine

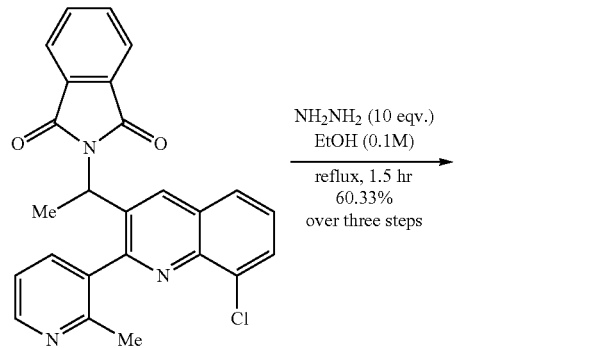

To a suspension of 2-(1-(8-chloro-2-(2-methylpyridin-3-yl)quinolin-3-yl)ethyl)-isoindoline-1,3-dione (1.5831 g, 3.700 mmol) in ethanol (37.00 mL, 3.700 mmol) was added hydrazine, anhydrous (1.161 mL, 37.00 mmol), and the mixture was stirred under reflux. After 1.5 h, the mixture was cooled to room temperature. The by product was filtered off and washed with MeOH (~100 mL). The filtrate was concentrated under reduced pressure to give a yellow solid. The yellow solid was purified by column chromatography on a 80 g of Redi-Sep™ column using 0% to 100% gradient of $CH_2Cl_2$:MeOH:$NH_4OH$ (89:9:1) in $CH_2Cl_2$ over 25 min, and then 100% isocratic of $CH_2Cl_2$:MeOH:$NH_4OH$ (89:9:1) in $CH_2Cl_2$ for 10 min as eluent to give 1-(8-chloro-2-(2-methylpyridin-3-yl)quinolin-3-yl)ethanamine as a yellow syrup: $^1$H NMR (400 MHz, DMSO-$d_6$) δ ppm 8.75 (1H, s), 8.58 (1H, dd, J=4.9, 1.8 Hz), 8.04 (1H, dd, J=8.2, 1.2 Hz), 7.92 (1H, dd, J=7.4, 1.2 Hz), 7.77 (1H, s), 7.60 (1H, dd, J=8.2, 7.4 Hz), 7.34-7.44 (1H, m), 4.09 (1H, d, J=4.7 Hz), 2.25 (3H, s), 2.05 (2H, br. s.), 1.13 (3H, d, J=6.7 Hz): LC-MS (ESI) m/z 298.1 [M+H]+.

N—((S)-1-(8-Chloro-2-(2-methylpyridin-3-yl)quinolin-3-yl)ethyl)-9H-purin-6-amine and N—((R)-1-(8-chloro-2-(2-methylpyridin-3-yl)quinolin-3-yl)ethyl)-9H-purin-6-amine

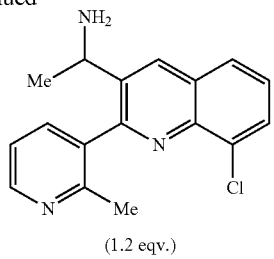

-continued

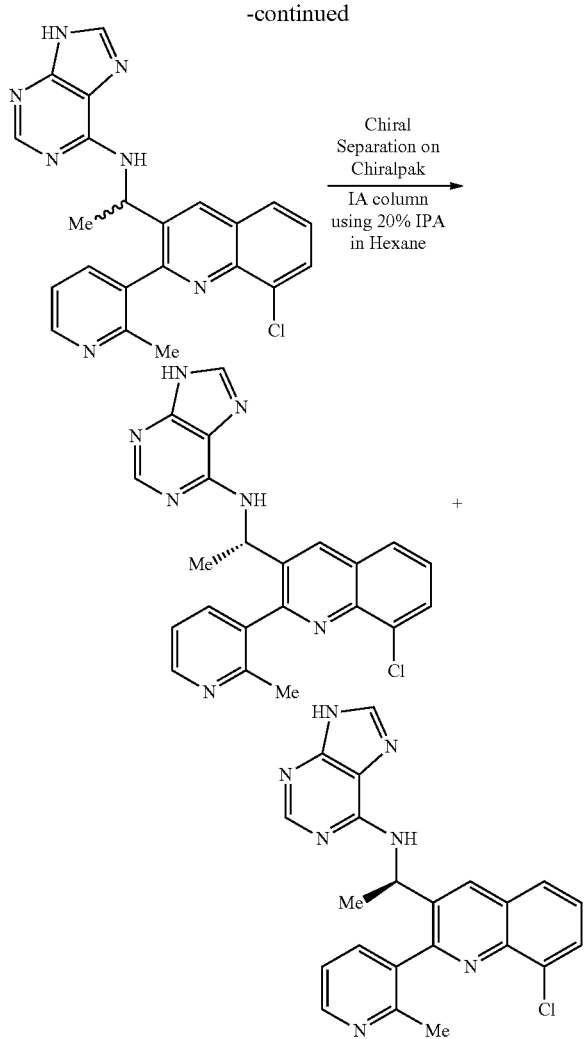

A mixture of 6-bromopurine (0.4148 g, 2.084 mmol), 1-(8-chloro-2-(2-methylpyridin-3-yl)quinolin-3-yl)ethanamine (0.6827 g, 2.293 mmol), and N,N-diisopropylethylamine (1.089 mL, 6.253 mmol) in 1-butanol (5.698 mL, 2.084 mmol) was heated under reflux with stirring. After 18 h, the mixture was removed from the heat and concentrated under reduced pressure. The residue was purified by column chromatography on a 80 g of Redi-Sep™ column using 0 to 50% gradient of CH$_2$Cl$_2$:MeOH:NH$_4$OH (89:9:1) in CH$_2$Cl$_2$ over 20 min, then 50% isocratic of CH$_2$Cl$_2$:MeOH:NH$_4$OH (89:9:1) in CH$_2$Cl$_2$ for 20 min, then 50 to 100% gradient of CH$_2$Cl$_2$:MeOH:NH$_4$OH (89:9:1) in CH$_2$Cl$_2$ over 20 min, and then 100% isocratic of CH$_2$Cl$_2$:MeOH:NH$_4$OH (89:9:1) in CH$_2$Cl$_2$ for 10 min as eluent to give a yellow solid. The yellow solid was suspended in MeOH and filtered to give N-(1-(8-chloro-2-(2-methylpyridin-3-yl)quinolin-3-yl)ethyl)-9H-purin-6-amine as an off-white solid. The 0.1505 g of racemic mixture was dissolved in MeOH—CH$_2$Cl$_2$ (1:4, 5 mL), filtered, and separated on a Chiralpak™ IA column (30×250 mm, 5 μm) using 20% isocratic of isopropanol in hexane for 40 min as eluent to give two separated isomers: N—((S)-1-(8-chloro-2-(2-methylpyridin-3-yl)quinolin-3-yl)ethyl)-9H-purin-6-amine as a white solid: $^1$H NMR (400 MHz, DMSO-d$_6$) δ ppm 12.90 (1H, s), 8.59 (2H, d, J=61.6 Hz), 7.70-8.37 (6H, m), 7.58 (1H, t, J=7.8 Hz), 7.32 (1H, s), 5.34 (1H, br. s.), 2.32 (3H, s), 1.53 (3H, br. s.); LC-MS (ESI) m/z 416.2 [M+H]$^+$ and N—((R)-1-(8-chloro-2-(2-methylpyridin-3-yl)quinolin-3-yl)ethyl)-9H-purin-6-amine as a white solid: $^1$H NMR (400 MHz, DMSO-d$_6$) δ ppm 12.90 (1H, s), 8.59 (2H, d, J=56.5 Hz), 7.69-8.34 (6H, m), 7.58 (1H, t, J=7.7 Hz), 7.32 (1H, s), 5.32 (1H, s), 2.32 (3H, d, J=1.8 Hz), 1.54 (3H, br. s.); LC-MS (ESI) m/z 416.2 [M+H]$^+$.

Example 97: Preparation of N-((3-(2-Chlorophenyl)-8-iodoquinoxalin-2-yl)-methyl)-9H-purin-6-amine 2-(Bromomethyl)-3-(2-chlorophenyl)-5-nitroquinoxaline and 3-(Bromomethyl)-2-(2-chlorophenyl)-5-nitroquinoxaline

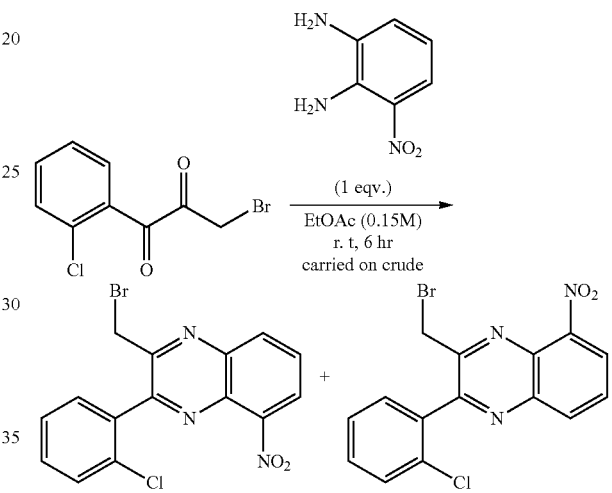

To a solution of 3-bromo-1-(2-chlorophenyl)propane-1,2-dione (Prepared in Example 81, 4.2971 g, 16.4325 mmol) in ethyl acetate (109.55 mL, 16.433 mmol) was added 3-nitro-1,2-phenylenediamine (2.5165 g, 16.433 mmol) at room temperature and the resulting red mixture was stirred at room temperature. After 26 h of stirring at room temperature, the mixture was concentrated under reduced pressure to give 2-(bromomethyl)-3-(2-chlorophenyl)-5-nitroquinoxaline including its regioisomer as a red syrup: LC-MS (ESI) m/z 378.0 and 379.9 [M+H]$^+$. The crude product as a red syrup was carried on crude without purification for the next step.

2-((3-(2-Chlorophenyl)-5-nitroquinoxalin-2-yl)methyl)isoindoline-1,3-dione and 2-((3-(2-Chlorophenyl)-8-nitroquinoxalin-2-yl)methyl)isoindoline-1,3-dione

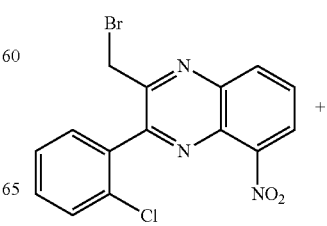

178

2-((5-Amino-3-(2-chlorophenyl)quinoxalin-2-yl)methyl)isoindoline-1,3-dione and 2-((8-Amino-3-(2-chlorophenyl)quinoxalin-2-yl)methyl)isoindoline-1,3-dione

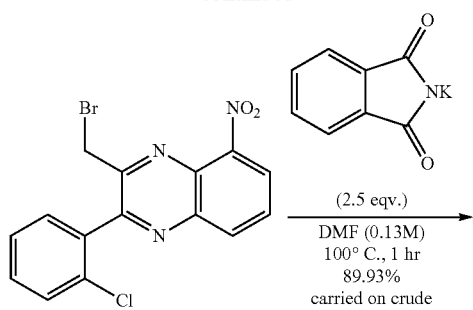

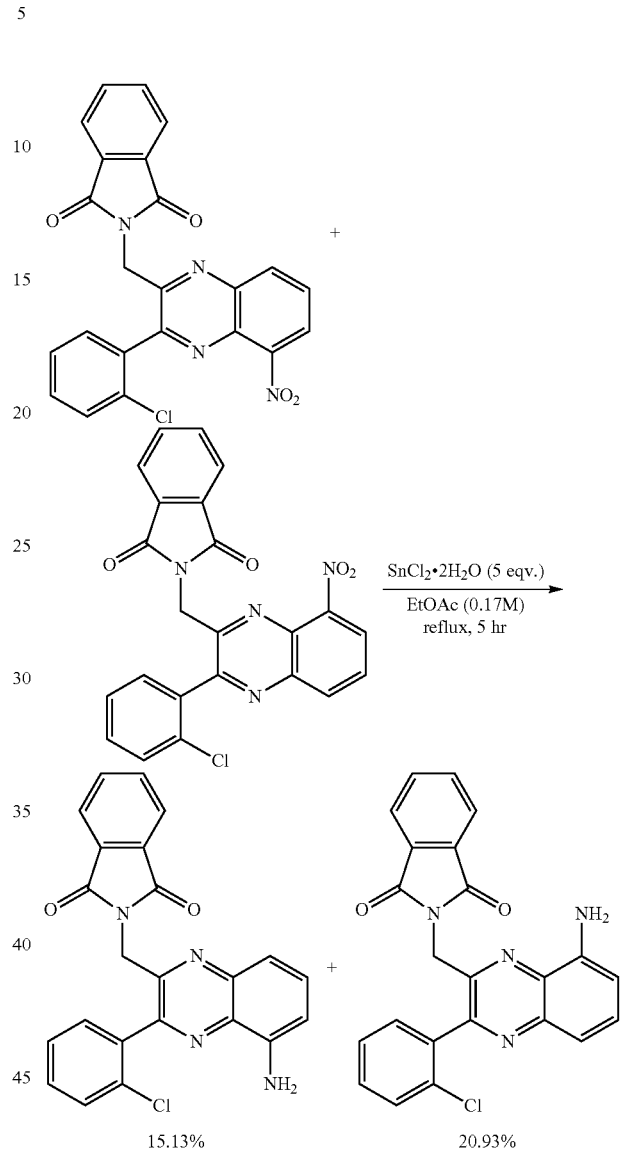

To a stirring solution of a mixture of 2-(bromomethyl)-3-(2-chlorophenyl)-5-nitroquinoxaline and 3-(bromomethyl)-2-(2-chlorophenyl)-5-nitroquinoxaline (6.2215 g, 16.43 mmol) in DMF (82.16 mL, 16.43 mmol) was added potassium phthalimide (7.609 g, 41.08 mmol) and the mixture was stirred at 100° C. After 2 h, the mixture was concentrated under reduced pressure and triturated with water (150 mL). The resulting solid was filtered and washed with 2 N NaOH (150 mL) and then with water (500 mL), and dried to give a mixture of 2-((3-(2-chlorophenyl)-5-nitroquinoxalin-2-yl)methyl)isoindoline-1,3-dione and 2-((3-(2-chlorophenyl)-8-nitroquinoxalin-2-yl)methyl)isoindoline-1,3-dione as a dark brown solid: $^1$H NMR (400 MHz, DMSO-$d_6$); LC-MS (ESI) m/z 445.1 [M+H]$^+$. The crude product was carried on crude without purification for the next step.

To a solution of 2-((3-(2-chlorophenyl)-5-nitroquinoxalin-2-yl)methyl)-isoindoline-1,3-dione and 2-((3-(2-chlorophenyl)-8-nitroquinoxalin-2-yl)methyl)-isoindoline-1,3-dione (5.9271 g, 13.32 mmol) in EtOAc (78.38 mL, 13.32 mmol) was added tin(II) chloride dihydrate (15.17 g, 66.62 mmol) and the mixture was heated under reflux. After 5 h, the mixture was concentrated under reduced pressure to remove EtOAc. To the residue was added aqueous saturated NaHCO$_3$ (300 mL). The resulting precipitate was collected by filtration and washed with water (300 mL) to give a brown solid. The brown solid was suspended in CH$_2$Cl$_2$ (200 mL) and filtered off through Celite™ pad and washed the solid well with CH$_2$Cl$_2$ (100 mL). The filtrate was concentrated under reduced pressure to give a dark brown syrup (0.7 g). The dark brown syrup (0.7 g) was purified by silica gel column chromatography on a 120 g of Redi-Sep™ column using 0 to 26% gradient of EtOAc in hexane over 7 min, then 26% isocratic of EtOAc in hexane for 10 min, then 26 to 100% gradient of EtOAc in hexane over 20 min, and then 100% isocratic of EtOAc in hexane for 15 min as eluent to give two separated regioisomers: 2-((5-amino-3-(2-chlorophenyl)quinoxalin-2-yl)methyl)-isoindoline-1,3-dione as a solid: $^1$H NMR (400 MHz, DMSO-$d_6$) δ ppm 7.83-7.91 (4H, m), 7.62-7.68 (2H, m), 7.45-7.59 (3H, m), 6.97 (1H, dd, J=8.4, 1.0 Hz), 6.91 (1H, dd, J=7.6, 1.0 Hz), 6.11 (2H, s), 4.87 (2H, br. s.), 90942-16-2-1H-NMR; LC-MS (ESI) m/z 415.1 [M+H]$^+$ and 2-((8-amino-3-(2-chlorophenyl)-quinoxalin-2-yl)methyl)isoindoline-1,3-dione as a solid: $^1$H NMR (400 MHz, DMSO-$d_6$) δ ppm 7.83-7.91 (4H, m), 7.59-7.66 (2H, m), 7.46-7.58 (3H, m), 7.21 (1H, dd, J=8.2, 1.2 Hz), 6.92 (1H, dd, J=7.8, 1.2 Hz), 5.74 (2H, s), 4.90 (2H, d, J=31.7 Hz); LC-MS (ESI) m/z 415.1 [M+H]$^+$. The structures of two regioisomers were confirmed by $^1$H-$^{15}$N HMBC and 1D NOE experiment. 2-((3-(2-Chlorophenyl)-8-iodoquinoxalin-2-yl)methyl)isoindoline-1,3-dione

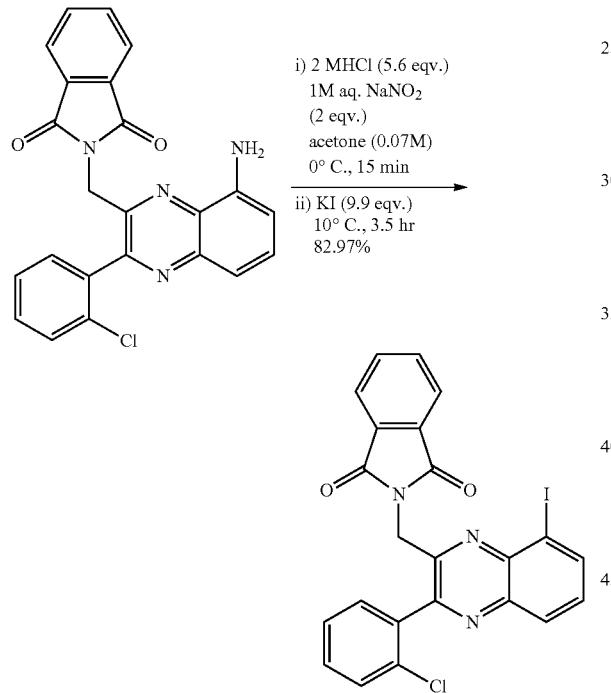

2-((8-amino-3-(2-chlorophenyl)quinoxalin-2-yl)methyl) isoindoline-1,3-dione (1.1337 g, 2.733 mmol) was dissolved in acetone (39.04 mL, 2.733 mmol) and cooled to 0° C. While being stirred, the solution was treated first with 2 M hydrochloric acid (7.652 mL, 15.30 mmol) and then dropwise with 1 M aq. sodium nitrite (5.466 mL, 5.466 mmol) while maintaining the temperature of the mixture at 0° C. After the additions were complete, the mixture was stirred for 15 min and then treated with 5 M aq. potassium iodide (5.411 mL, 27.06 mmol) maintaining the temperature below 5° C. The mixture was then allowed to warm to 15° C. over 3.5 h. The acetone was removed under reduced pressure, and the residue was partitioned between water (100 mL) and ethyl acetate (100 mL). The organic solution was washed with 10% aqueous sodium bisulfate (100 mL×1) and saturated aqueous sodium bicarbonate (100 mL×1), brine (100 mL×1), dried over MgSO$_4$, filtered, and concentrated under reduced pressure to give a dark violet syrupy solid. The dark violet syrupy solid was purified by silica gel column chromatography on a 80 g of Redi-Sep™ column using 0 to 50% gradient of EtOAc in hexane over 15 min and then 50% isocratic of EtOAc in hexane for 25 min as eluent to give 2-((3-(2-chlorophenyl)-8-iodoquinoxalin-2-yl)methyl)-isoindoline-1,3-dione as a solid: LC-MS (ESI) m/z 526.0 [M+H]$^+$.

(3-(2-Chlorophenyl)-8-iodoquinoxalin-2-yl)methanamine

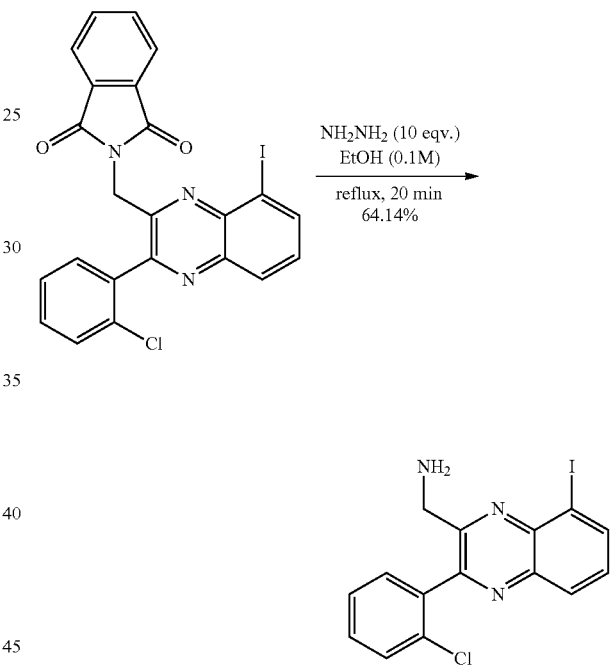

To a suspension of 2-((3-(2-chlorophenyl)-8-iodoquinoxalin-2-yl)methyl)-isoindoline-1,3-dione (0.5530 g, 1.052 mmol) in ethanol (10.00 mL, 1.052 mmol) was added hydrazine, anhydrous (0.3301 mL, 10.52 mmol), and the mixture was stirred under reflux. After 20 min, the mixture was cooled to room temperature. The mixture was concentrated under reduced pressure. The residue was purified by column chromatography on a 80 g of Redi-Sep™ column using 0% to 50% gradient of CH$_2$Cl$_2$:MeOH:NH$_4$OH (89:9:1) in CH$_2$Cl$_2$ over 25 min, and then 50% isocratic of CH$_2$Cl$_2$:MeOH:NH$_4$OH (89:9:1) in CH$_2$Cl$_2$ for 5 min as eluent to give (3-(2-chlorophenyl)-8-iodoquinoxalin-2-yl)methanamine: $^1$H NMR (400 MHz, DMSO-$d_6$) δ ppm 8.50 (1H, dd, J=7.4, 1.2 Hz), 8.14 (1H, dd, J=8.4, 1.4 Hz), 7.52-7.71 (5H, m), 3.84 (2H, s), 2.15 (2H, s); LC-MS (ESI) m/z 396.0 [M+H]$^+$.

181

N-((3-(2-Chlorophenyl)-8-iodoquinoxalin-2-yl)methyl)-9H-purin-6-amine

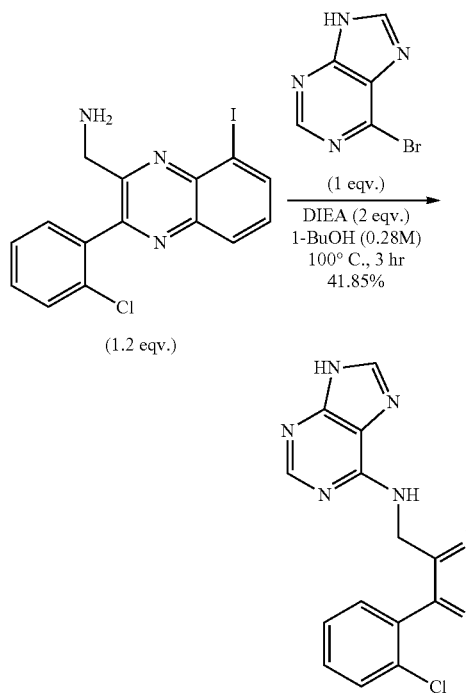

(1.2 eqv.)

A mixture of 6-bromopurine (0.1119 g, 0.5622 mmol), (3-(2-chlorophenyl)-8-iodoquinoxalin-2-yl)methanamine (0.2669 g, 0.6746 mmol), and N,N-diisopropylethylamine (0.2938 mL, 1.687 mmol) in 1-butanol (2.000 mL, 0.5622 mmol) was stirred at 100° C. After 3 h, the mixture was removed from the heat and the green precipitate was collected by filtration and washed the solid with MeOH to give a green solid. The green solid was purified by column chromatography on a 40 g of Redi-Sep™ column using 0 to 100% gradient of $CH_2Cl_2$:MeOH:$NH_4OH$ (89:9:1) in $CH_2Cl_2$ over 14 min and then 100% isocratic of $CH_2Cl_2$:MeOH:$NH_4OH$ (89:9:1) for 5 min as eluent to give a yellow solid. The yellow solid was suspended in $CH_2Cl_2$ and filtered to give N-((3-(2-chloro-phenyl)-8-iodoquinoxalin-2-yl)methyl)-9H-purin-6-amine as a yellow solid: $^1$H NMR (400 MHz, DMSO-$d_6$) δ ppm 12.93 (1H, s), 8.48 (1H, d, J=7.4 Hz), 8.03-8.20 (3H, m), 7.43-7.88 (6H, m), 4.84 (2H, s); LC-MS (ESI) m/z 514.0 [M+H]$^+$.

Example 98: Preparation of N-((3-(2-Chlorophenyl)-8-(methylsulfonyl)-quinoxalin-2-yl)methyl)-9H-purin-6-amine as a TFA Salt

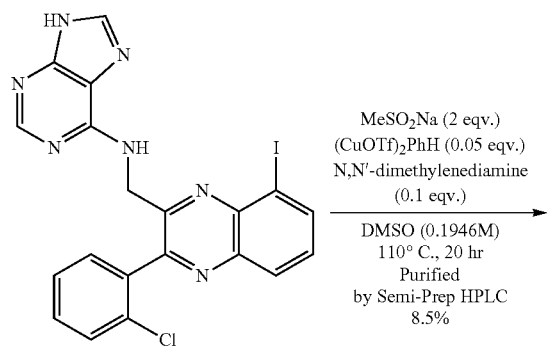

182

-continued

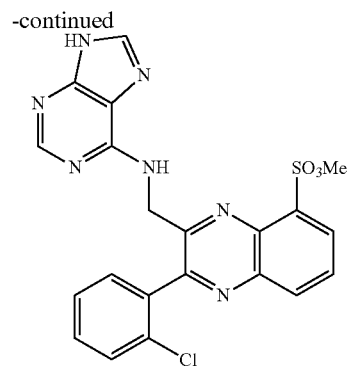

To a Schelnk tube with a stirrer bar was added N-((3-(2-chlorophenyl)-8-iodoquinoxalin-2-yl)methyl)-9H-purin-6-amine (Prepared in Example 97, 0.1000 g, 0.19 mmol), copper (I) trifluoromethanesulfonate toluene complex (2 to 1) (0.0050 g, 0.0097 mmol), and sodium methanesulfinate (0.047 g, 0.39 mmol) under an argon atmosphere. The aperture of the tube was then covered with a rubber septum and an argon atmosphere was established. N,N'-dimethylethyl-enediamine (0.0021 mL, 0.019 mmol) and DMSO (1.0 mL, 0.19 mmol) were added via syringe. The septum was replaced by a teflon coated screw cap and the reaction vessel was placed in a 110° C. After stirring for 20 h, the reaction mixture was cooled to room temperature, diluted with $CH_2Cl_2$ (50 mL), filtered through a pad of silica gel, washed the pad with $CH_2Cl_2$ (100 mL). The filtrate was washed with water (50 mL×2) and brine (50 mL×1), dried over $Na_2SO_4$, filtered, and concentrated under reduced pressure to give a green syrup. The green syrup was purified by column chromatography on a 40 g of Redi-Sep™ column using 0 to 100% gradient of $CH_2Cl_2$:MeOH:$NH_4OH$ (89:9:1) in $CH_2Cl_2$ over 14 min and then 100% isocratic of $CH_2Cl_2$:MeOH:$NH_4OH$ (89:9:1) for 3 min as eluent to give a red syrupy solid (0.0172 g). The dark red syrup (0.0172 g) was purified by semi-prep-HPLC on C18 column using 20-70% gradient of $CH_3CN$ (0.1% of TFA) in water (0.1% of TFA) over 40 min as eluent to give N-((3-(2-chlorophenyl)-8-(methylsulfonyl)quinoxalin-2-yl)methyl)-9H-purin-6-amine as a TFA salt as a light-yellow solid: LC-MS (ESI) m/z 466.1 [M+H]$^+$ (Exact Mass of neutral form: 465.077).

Example 99: Preparation of N-((3-(2-Chlorophenyl)-5-iodoquinoxalin-2-yl)-methyl)-9H-purin-6-amine 2-((3-(2-Chlorophenyl)-5-iodoquinoxalin-2-yl)methyl)isoindoline-1,3-dione

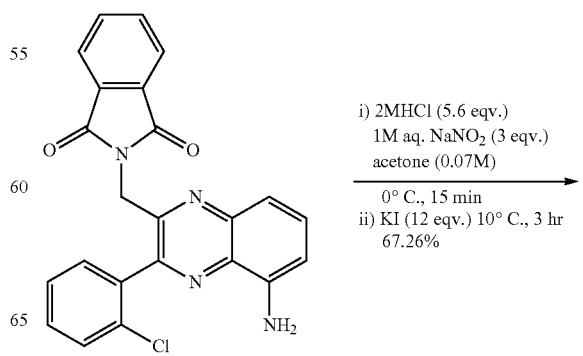

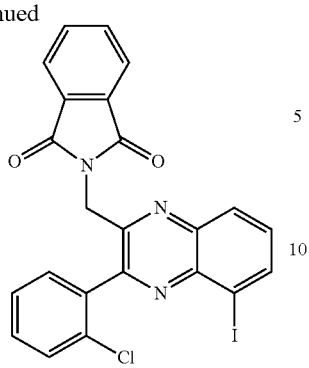

2-((5-amino-3-(2-chlorophenyl)quinoxalin-2-yl)methyl)isoindoline-1,3-dione (Prepared in Example 97, 0.8364 g, 2.016 mmol) was dissolved in acetone (28.80 mL, 2.016 mmol) and cooled to 0° C. While being stirred, the solution was treated first with 2 M hydrochloric acid (5.645 mL, 11.29 mmol) and then dropwise with 1 M aq. sodium nitrite (6.049 mL, 6.049 mmol) while maintaining the temperature of the mixture at 0° C. After the additions were complete, the mixture was stirred for 15 min and then treated with 5 M aq. potassium iodide (4.839 mL, 24.19 mmol) maintaining the temperature below 5° C. The mixture was then allowed to warm to 15° C. over 3 h. The acetone was removed under reduced pressure, and the residue was partitioned between water (100 mL) and ethyl acetate (100 mL). The organic solution was washed with 10% aqueous sodium bisulfate (100 mL×3) and saturated aqueous sodium bicarbonate (100 mL×1), brine (100 mL×1), dried over MgSO$_4$, filtered, and concentrated under reduced pressure to give a red solid. The red solid was purified by silica gel column chromatography on a 80 g of Redi-Sep™ column using 0 to 50% gradient of EtOAc in hexane over 25 min and then 50% isocratic of EtOAc in hexane for 25 min as eluent to give 2-((3-(2-chlorophenyl)-5-iodoquinoxalin-2-yl)methyl)-isoindoline-1,3-dione as a solid: $^1$H NMR (400 MHz, DMSO-d$_6$) δ ppm 8.48 (1H, dd, J=7.4, 1.2 Hz), 7.97 (1H, dd, J=8.2, 1.2 Hz), 7.83-7.91 (4H, m), 7.51-7.75 (5H, m), 4.96 (2H, d, J=21.9 Hz); LC-MS (ESI) m/z 526.0 [M+H]$^+$.

(3-(2-Chlorophenyl)-5-iodoquinoxalin-2-yl)methanamine

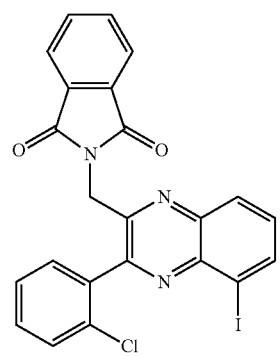

NH$_2$NH$_2$ (10 eqv.)
EtOH (0.1M)
reflux, 30 min
86.3%

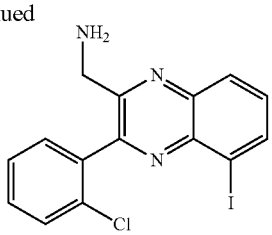

To a suspension of 2-((3-(2-chlorophenyl)-5-iodoquinoxalin-2-yl)methyl)-isoindoline-1,3-dione (0.7028 g, 1.337 mmol) in ethanol (12.00 mL, 1.337 mmol) was added hydrazine, anhydrous (0.4196 mL, 13.37 mmol), and the mixture was stirred under reflux. After 30 min, the mixture was cooled to room temperature. The mixture was concentrated under reduced pressure. The residue was purified by column chromatography on a 80 g of Redi-Sep™ column using 0% to 50% gradient of CH$_2$Cl$_2$:MeOH:NH$_4$OH (89:9:1) in CH$_2$Cl$_2$ over 25 min, and then 50% isocratic of CH$_2$Cl$_2$:MeOH:NH$_4$OH (89:9:1) in CH$_2$Cl$_2$ for 5 min as eluent to give (3-(2-chlorophenyl)-5-iodoquinoxalin-2-yl)methanamine as a green syrupy solid: $^1$H NMR (400 MHz, DMSO-d$_6$) δ ppm 8.45 (1H, dd, J=7.4, 1.0 Hz), 8.17 (1H, dd, J=8.4, 1.2 Hz), 7.52-7.74 (5H, m), 3.83 (2H, br. s.), 1.97 (2H, br. s.); LC-MS (ESI) m/z 396.0 [M+H]$^+$.

N-((3-(2-Chlorophenyl)-5-iodoquinoxalin-2-yl)methyl)-9H-purin-6-amine

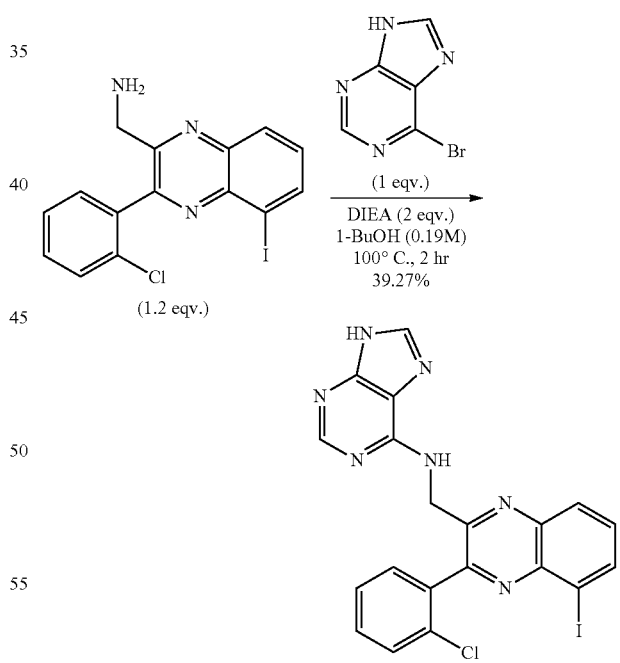

A mixture of 6-bromopurine (0.1859 g, 0.9340 mmol), (3-(2-chlorophenyl)-5-iodoquinoxalin-2-yl)methanamine (0.4434 g, 1.121 mmol), and N,N-diisopropylethylamine (0.4880 mL, 2.802 mmol) in 1-butanol (5.000 mL, 0.9340 mmol) was stirred at 100° C. After 2 h, the mixture was cooled to room temperature and concentrated under reduced pressure. The residue was purified by flash column chromatography on a silica gel column using 50% of CH$_2$Cl$_2$:

MeOH:NH₄OH (89:9:1) in CH₂Cl₂ as eluent to give a yellow solid (0.2120 g). The yellow solid was suspended in CH₂Cl₂ and filtered to give N-((3-(2-chlorophenyl)-5-iodo-quinoxalin-2-yl)methyl)-9H-purin-6-amine as a light yellow solid: ¹H NMR (400 MHz, DMSO-d₆) δ ppm 12.88 (1H, br. s.), 8.46 (1H, dd, J=7.4, 1.2 Hz), 8.12 (2H, d, J=7.2 Hz), 8.06 (1H, s), 7.93 (1H, s), 7.69 (1H, dd, J=7.4, 1.8 Hz), 7.64 (2H, t, J=8.0 Hz), 7.53-7.59 (1H, m), 7.48-7.53 (1H, m), 4.83 (2H, br. s.); LC-MS (ESI) m/z 514.0 [M+H]⁺.

Example 100: Preparation of N-((5-chloro-3-(2-chloro-5-fluorophenyl)-quinoxalin-2-yl)methyl)-9H-purin-6-amine 5-Chloro-3-(2-chloro-5-fluorophenyl)-2-methylquinoxaline

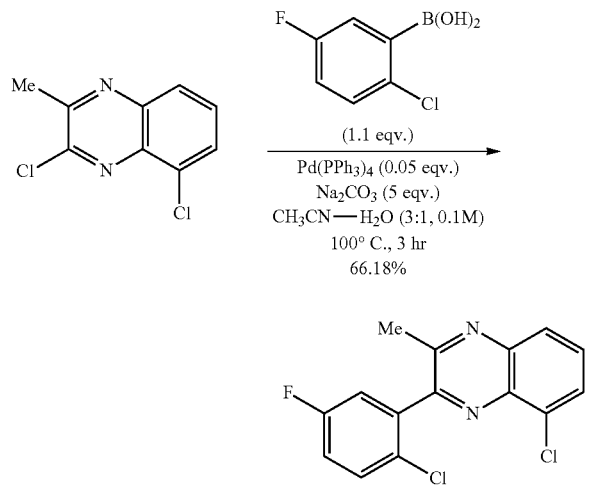

A mixture of 3,5-dichloro-2-methylquinoxaline (Prepared in Example 85, 1.0000 g, 4.693 mmol), 2-chloro-5-fluorophenylboronic acid (0.9002 g, 5.163 mmol), tetrakis(triphenylphosphine)palladium (0.2712 g, 0.2347 mmol), and sodium carbonate anhydrous (2.487 g, 23.47 mmol) in acetonitrile-water (3:1) (47.00 mL) was stirred at 100° C. After 3 hs, the mixture was cooled to room temperature and partitioned between EtOAc (100 mL) and water (100 mL). The organic layer was washed with brine (50 mL×2), dried over Na₂SO₄, filtered, and concentrated under reduced pressure. The residue was purified by silica gel column chromatography on a 80 g of Redi-Sep™ column using 0 to 50% gradient of EtOAc in hexane over 25 min and then 50% isocratic of EtOAc for 10 min as eluent to give 5-chloro-3-(2-chloro-5-fluorophenyl)-2-methylquinoxaline as a red syrupy solid: ¹H NMR (400 MHz, DMSO-d₆) δ ppm 8.09 (1H, dd, J=8.4, 1.4 Hz), 8.03 (1H, dd, J=7.6, 1.4 Hz), 7.88 (1H, dd, J=8.4, 7.6 Hz), 7.75 (1H, dd, J=9.0, 5.1 Hz), 7.61 (1H, dd, J=8.6, 3.1 Hz), 7.46-7.53 (1H, m), 2.54 (3H, s); LC-MS (ESI) m/z 307.0 [M+H]⁺.

2-(Bromomethyl)-5-chloro-3-(2-chloro-5-fluorophenyl)quinoxaline

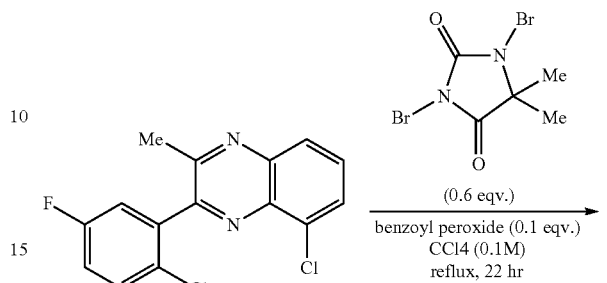

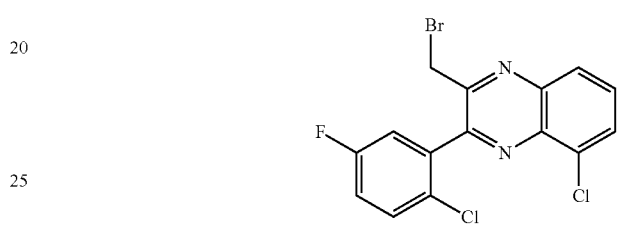

5-chloro-3-(2-chloro-5-fluorophenyl)-2-methylquinoxaline (0.3013 g, 0.981 mmol) and 1,3-dibromo-5,5-dimethylhydantoin (0.280 g, 0.981 mmol) were suspended in carbon tetrachloride (9.81 mL, 0.981 mmol). To the mixture was added benzoyl peroxide (0.0317 g, 0.0981 mmol) and the mixture was heated at reflux. After 22 h, the mixture was cooled to room temperature and concentrated under reduced pressure. The residue was purified by silica gel column chromatography on a 80 g of Redi-Sep™ column using 0 to 5% gradient of EtOAc in hexane over 10 min, then 5% isocratic of EtOAc for 25 min, then 5 to 20% gradient of EtOAc in hexane over 20 min, then 20% isocratic of EtOAc for 4 min as eluent to give 2-(bromomethyl)-5-chloro-3-(2-chloro-5-fluorophenyl)-quinoxaline as a light yellow syrupy solid: ¹H NMR (400 MHz, DMSO-d₆) δ ppm 8.12-8.21 (2H, m), 7.92-8.00 (1H, m), 7.76 (1H, dd, J=9.0, 5.1 Hz), 7.71 (1H, dd, J=8.6, 3.1 Hz), 7.49-7.58 (1H, m), 4.74 (2H, br. s.); LC-MS (ESI) m/z 387.0 [M+H]⁺.

2-((5-Chloro-3-(2-chloro-5-fluorophenyl)quinoxalin-2-yl)methyl)isoindoline-1,3-dione

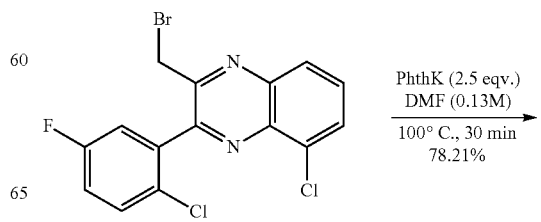

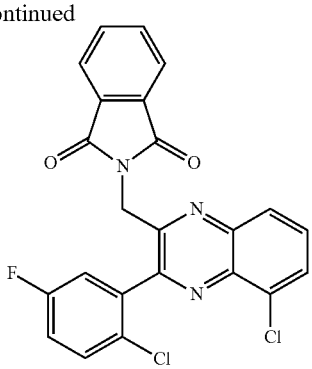

To a heterogeneous mixture of 2-(bromomethyl)-5-chloro-3-(2-chloro-5-fluoro-phenyl)quinoxaline (0.1815 g, 0.4702 mmol) in DMF (3.444 mL, 0.4702 mmol) was added potassium phthalimide (0.2177 g, 1.175 mmol) and the heterogeneous mixture was stirred at 100° C. After stirring at 100° C. for 30 min, the mixture was concentrated under reduced pressure and triturated with water (30 mL). The precipitate was collected by filtration. The resulting solid was filtered and washed with 2 N NaOH (30 mL) and then with water (100 mL), and air-dried to give 2-((5-chloro-3-(2-chloro-5-fluorophenyl)quinoxalin-2-yl)methyl)isoindoline-1,3-dione as an off-white solid: $^1$H NMR (400 MHz, DMSO-$d_6$) δ ppm 8.09 (1H, dd, J=7.6, 1.4 Hz), 7.95-8.01 (1H, m), 7.82-7.91 (5H, m), 7.65-7.75 (2H, m), 7.43-7.52 (1H, m), 4.99 (2H, br. s.); LC-MS (ESI) m/z 452.0 [M+H]$^+$. The crude product was carried on crude without purification for the next step.

(5-Chloro-3-(2-chloro-5-fluorophenyl)quinoxalin-2-yl)methanamine

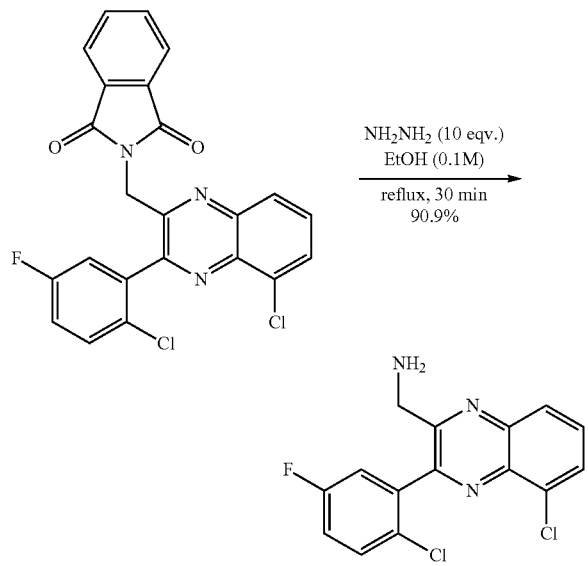

To a suspension of 2-((5-chloro-3-(2-chloro-5-fluorophenyl)quinoxalin-2-yl)-methyl)isoindoline-1,3-dione (0.1607 g, 0.355 mmol) in ethanol (3.60 mL, 0.355 mmol) was added hydrazine, anhydrous (0.112 mL, 3.55 mmol), and the mixture was stirred under reflux. After 30 min, the mixture was cooled to room temperature. The byproduct was filtered off and washed with MeOH. The filtrate was concentrated under reduced pressure. The residue was purified by column chromatography on a 40 g of Redi-Sep™ column using 0% to 100% gradient of CH$_2$Cl$_2$:MeOH:NH$_4$OH (89:9:1) in CH$_2$Cl$_2$ over 14 min, and then 100% isocratic of CH$_2$Cl$_2$:MeOH:NH$_4$OH (89:9:1) for 10 min as eluent to give (5-chloro-3-(2-chloro-5-fluorophenyl)quinoxalin-2-yl)methanamine as a green syrupy solid: $^1$H NMR (400 MHz, DMSO-$d_6$) δ ppm 8.16 (1H, dd, J=8.4, 1.4 Hz), 8.06 (1H, dd, J=7.8, 1.2 Hz), 7.87-7.95 (1H, m), 7.74 (1H, dd, J=9.0, 5.1 Hz), 7.61 (1H, dd, J=8.6, 3.1 Hz), 7.46-7.54 (1H, m), 3.85 (2H, s), 2.11 (2H, br. s.); LC-MS (ESI) m/z 322.0 [M+H]$^+$.

N-((5-Chloro-3-(2-chloro-5-fluorophenyl)quinoxalin-2-yl)methyl)-9H-purin-6-amine

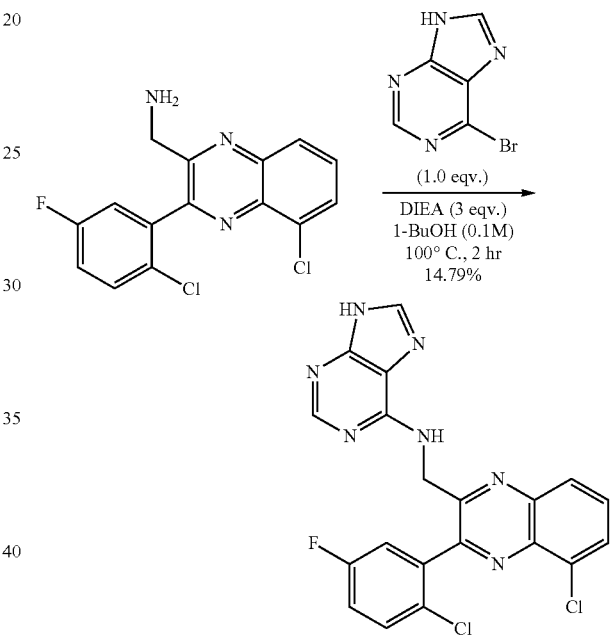

A mixture of 6-bromopurine (0.07531 g, 0.3784 mmol), (5-chloro-3-(2-chloro-5-fluorophenyl)quinoxalin-2-yl)methanamine (0.1016 g, 0.3154 mmol), and N,N-diisopropylethylamine (0.1648 mL, 0.9461 mmol) in 1-butanol (3.000 mL, 0.3154 mmol) was stirred at 100° C. After 2 h, the mixture was removed from the heat and concentrated under reduced pressure. The residue was purified by column chromatography on a 40 g of Redi-Sep™ column using 0 to 20% gradient of CH$_2$Cl$_2$:MeOH:NH$_4$OH (89:9:1) in CH$_2$Cl$_2$ over 14 min, then 20% isocratic of CH$_2$Cl$_2$:MeOH:NH$_4$OH (89:9:1) in CH$_2$Cl$_2$ for 14 min, then 20 to 50% gradient of CH$_2$Cl$_2$:MeOH:NH$_4$OH (89:9:1) in CH$_2$Cl$_2$ over 10 min and then 50% isocratic of CH$_2$Cl$_2$:MeOH:NH$_4$OH (89:9:1) in CH$_2$Cl$_2$ for 10 min as eluent to give a light yellow solid (0.0622 g). The yellow solid (0.0622 g) was suspended in MeOH and filtered to give N-((5-chloro-3-(2-chloro-5-fluorophenyl)quinoxalin-2-yl)methyl)-9H-purin-6-amine as a light yellow solid: $^1$H NMR (400 MHz, DMSO-$d_6$) δ ppm 12.92 (1H, s), 8.03-8.19 (4H, m), 7.82-8.01 (2H, m), 7.63 (1H, dd, J=9.0, 5.1 Hz), 7.55 (1H, dd, J=8.6, 3.1 Hz), 7.29-7.44 (1H, m), 4.89 (2H, s); LC-MS (ESI) m/z 440.0 [M+H]$^+$.

Example 101: Preparation of N—((S)-1-(5-chloro-3-(2-chloro-5-fluorophenyl)-quinoxalin-2-yl)ethyl)-9H-purin-6-amine and N—((R)-1-(5-chloro-3-(2-chloro-5-fluorophenyl)quinoxalin-2-yl)ethyl)-9H-purin-6-amine 5-Chloro-3-(2-chloro-5-fluorophenyl)quinoxaline-2-carbaldehyde

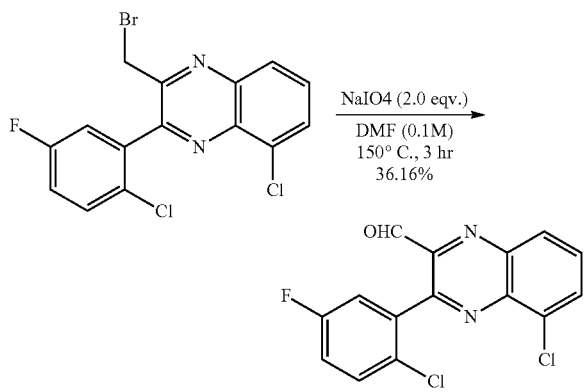

A mixture of 2-(bromomethyl)-5-chloro-3-(2-chloro-5-fluorophenyl)quinoxaline (Prepared in Example 100, 0.5625 g, 1.457 mmol) and sodium metaperiodate (0.1613 mL, 2.914 mmol) in DMF (9.714 mL, 1.457 mmol) was heated at 150° C. with stirring. After 3 h, the mixture was cooled to room temperature, diluted with EtOAc (100 mL), washed with brine (50 mL×2), dried over Na$_2$SO$_4$, filtered, and concentrated under reduced pressure. The residue was purified by silica gel column chromatography on a 80 g of Redi-Sep™ column using 0 to 10% gradient of EtOAc in hexane over 10 min, then 10% isocratic of EtOAc for 20 min, then 10 to 20% gradient of EtOAc in hexane over 20 min, then 20% isocratic of EtOAc for 3 min as eluent to give 5-chloro-3-(2-chloro-5-fluorophenyl)quinoxaline-2-carbaldehyde as an off-white solid: $^1$H NMR (400 MHz, DMSO-d$_6$) δ ppm 10.16 (1H, s), 8.35-8.41 (1H, m), 8.29-8.34 (1H, m), 8.07 (1H, dd, J=8.4, 7.6 Hz), 7.68 (1H, dd, J=8.8, 4.9 Hz), 7.44-7.58 (2H, m); LC-MS (ESI) m/z 321.0 [M+H]$^+$.

1-(5-Chloro-3-(2-chloro-5-fluorophenyl)quinoxalin-2-yl)ethanol

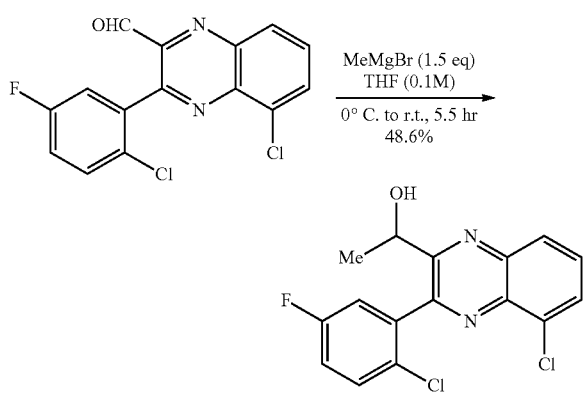

To a stirring heterogeneous mixture of 5-chloro-3-(2-chloro-5-fluorophenyl)-quinoxaline-2-carbaldehyde (0.1650 g, 0.514 mmol) in THF (5.00 mL, 0.514 mmol) was added methylmagnesium bromide 3 M in diethyl ether (0.257 mL, 0.771 mmol) dropwise at 0° C., and the mixture was then allowed to warm to room temperature and stirred at room temperature. After 5.5 h, the reaction was quenched with NH$_4$Cl (50 mL) and extracted with EtOAc (50 mL×2). The combined organic layers were washed with water (50 mL×1), brine (50 mL×1), dried over Na$_2$SO$_4$, filtered, and concentrated under reduced pressure. The residue was purified by silica gel column chromatography on a 40 g of Redi-Sep™ column using 0 to 50% gradient of EtOAc in hexane over 14 min and then 50% isocratic of EtOAc for 10 min as eluent to give 1-(5-chloro-3-(2-chloro-5-fluorophenyl)quinoxalin-2-yl)ethanol as a solid: $^1$H NMR (400 MHz, DMSO-d$_6$) δ ppm 8.17 (1H, dd, J=8.4, 1.4 Hz), 8.09 (1H, dd, J=7.8, 1.2 Hz), 7.88-7.96 (1H, m), 7.72 (1H, dd, J=9.0, 5.1 Hz), 7.61 (1H, br. s.), 7.44-7.53 (1H, m), 5.36 (1H, d, J=6.3 Hz), 4.83 (1H, br. s.), 1.49 (3H, br. s.); LC-MS (ESI) m/z 337.0 [M+H]$^+$.

2-(1-(5-Chloro-3-(2-chloro-5-fluorophenyl)quinoxalin-2-yl)ethyl)isoindoline-1,3-dione

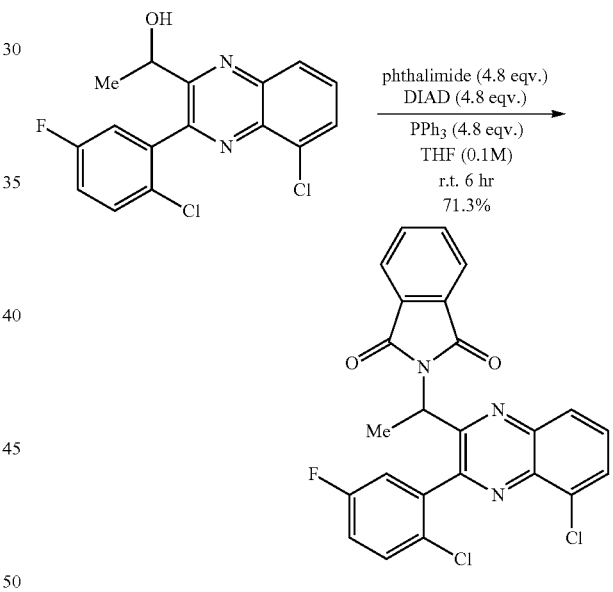

To a solution of 1-(5-chloro-3-(2-chloro-5-fluorophenyl)quinoxalin-2-yl)ethanol (0.08320 g, 0.2468 mmol) in tetrahydrofuran (2.468 mL, 0.2468 mmol) were added triphenylphosphine (0.07766 g, 0.2961 mmol), phthalimide (0.04357 g, 0.2961 mmol), and diisopropyl azodicarboxylate (0.05735 mL, 0.2961 mmol). The reaction mixture was stirred at room temperature. After 6 h, the mixture was concentrated under reduced pressure and partitioned between EtOAc (100 mL) and brine (100 mL). The combined organic layers were dried over Na$_2$SO$_4$, filtered, and concentrated under reduced pressure. The residue was purified by silica gel column chromatography on a 40 g of Redi-Sep™ column using 0 to 10% gradient of EtOAc in hexane over 10 min, then 10% isocratic of EtOAc for 20 min, then 10 to 50% gradient of EtOAc in hexane over 20 min, then 50% isocratic of EtOAc for 3 min as eluent to give 2-(1-(5-chloro-3-(2-chloro-5-fluorophenyl)quinoxalin-2-yl)ethyl)isoindoline-1,3-dione as a tan solid: LC-MS (ESI) m/z 466.0 [M+H]⁺.

1-(5-Chloro-3-(2-chloro-5-fluorophenyl)quinoxalin-2-yl)ethanamine

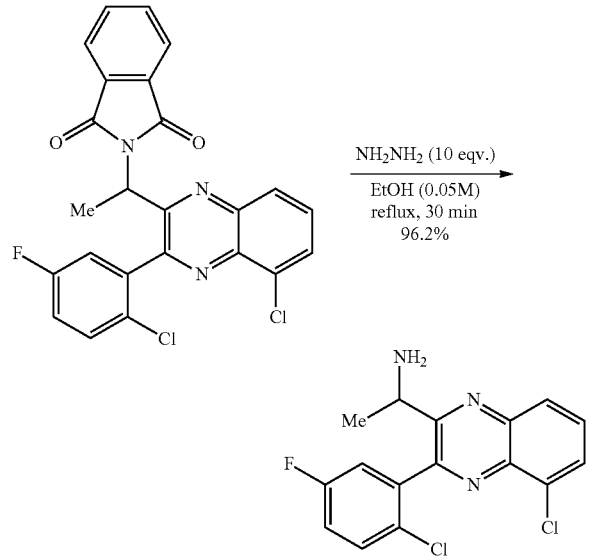

To a suspension of 2-(1-(5-chloro-3-(2-chloro-5-fluorophenyl)quinoxalin-2-yl)-ethyl)isoindoline-1,3-dione (0.0802 g, 0.172 mmol) in ethanol (3.44 mL, 0.172 mmol) was added hydrazine, anhydrous (0.0540 mL, 1.72 mmol), and the mixture was stirred under reflux. After 30 min, the mixture was cooled to room temperature. The mixture was concentrated under reduced pressure. The residue was purified by column chromatography on a 40 g of Redi-Sep™ column using 0% to 100% gradient of CH₂Cl₂:MeOH:NH₄OH (89:9:1) in CH₂Cl₂ over 14 min, and then 100% isocratic of CH₂Cl₂:MeOH:NH₄OH (89:9:1) for 5 min as eluent to give 1-(5-chloro-3-(2-chloro-5-fluorophenyl)quinoxalin-2-yl)ethanamine as a light yellow solid: ¹H NMR (400 MHz, DMSO-d₆) δ ppm 8.11-8.17 (1H, m), 8.06 (1H, dd, J=7.6, 1.4 Hz), 7.87-7.94 (1H, m), 7.74 (1H, dd, J=9.0, 5.1 Hz), 7.67 (1H, dd, J=8.8, 2.9 Hz), 7.46-7.55 (1H, m), 3.99 (1H, q, J=6.7 Hz), 2.24 (2H, br. s.), 1.12-1.43 (3H, m); LC-MS (ESI) m/z 336.1 [M+H]⁺.

N—((S)-1-(5-Chloro-3-(2-chloro-5-fluorophenyl)quinoxalin-2-yl)ethyl)-9H-purin-6-amine and
N—((R)-1-(5-Chloro-3-(2-chloro-5-fluorophenyl)quinoxalin-2-yl)ethyl)-9H-purin-6-amine

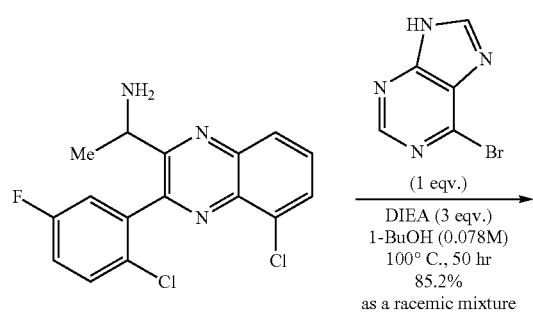

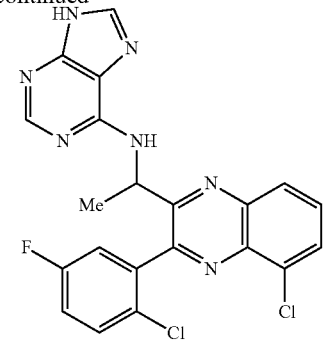

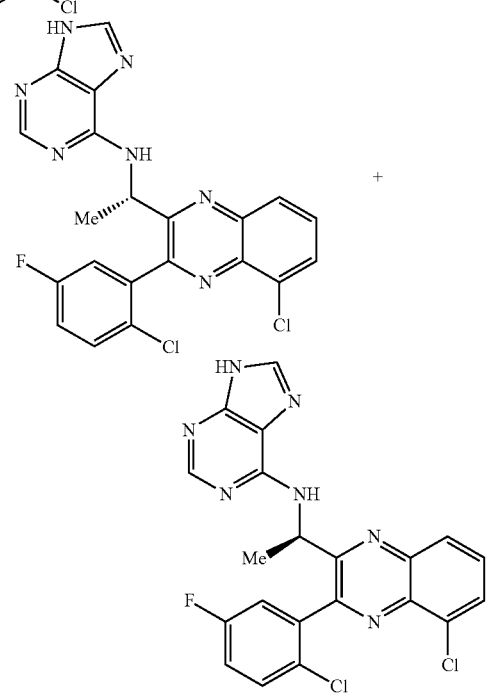

A mixture of 6-bromopurine (0.0309 g, 0.155 mmol), 1-(5-chloro-3-(2-chloro-5-fluorophenyl)quinoxalin-2-yl)ethanamine (0.0522 g, 0.155 mmol), and N,N-diisopropylethylamine (0.0811 mL, 0.466 mmol) in 1-butanol (2.00 mL, 0.155 mmol) was stirred at 100° C. After 50 h, the mixture was removed from the heat and concentrated under reduced pressure. The residue was purified by column chromatography on a 40 g of Redi-Sep™ column using 0% to 100% gradient of CH₂Cl₂:MeOH:NH₄OH (89:9:1) in CH₂Cl₂ over 14 min and then 100% isocratic of CH₂Cl₂:MeOH:NH₄OH (89:9:1) for 20 min as eluent to give a racemic mixture as a yellow solid (0.0601 g, 85.2%). The racemic mixture (0.0601 g) was dissolved in MeOH—CH₂Cl₂ (1:3, 4 mL), filtered, and separated on a Chiralpak™ IA column (30×250 mm, 5 μm) using 10% isocratic of isopropanol in hexane for 40 min as eluent to give two separated isomers: N—((S)-1-(5-chloro-3-(2-chloro-5-fluorophenyl)quinoxalin-2-yl)ethyl)-9H-purin-6-amine as an off-white solid: $^1$H NMR (400 MHz, DMSO-d$_6$) δ ppm 12.87 (1H, s), 7.12-8.29 (9H, m), 5.59 (1H, br. s.), 1.63 (3H, d, J=5.9 Hz); LC-MS (ESI) m/z 454.1 [M+H]$^+$ and N—((R)-1-(5-chloro-3-(2-chloro-5-fluorophenyl)quinoxalin-2-yl)ethyl)-9H-purin-6-amine as an off-white solid: $^1$H NMR (400 MHz, DMSO-d$_6$) δ ppm 12.89 (1H, s), 7.04-8.40 (9H, m), 5.56 (1H, br. s.), 1.63 (3H, d, J=6.8 Hz); LC-MS (ESI) m/z 454.1 [M+H]$^+$.

Example 102: Preparation of N-((8-chloro-2-(1-methyl-1H-imidazol-5-yl)-quinolin-3-yl)methyl)-9H-purin-6-amine dihydrochloride 2-((8-Chloro-2-(1-methyl-1H-imidazol-5-yl)quinolin-3-yl)methyl)isoindoline-1,3-dione

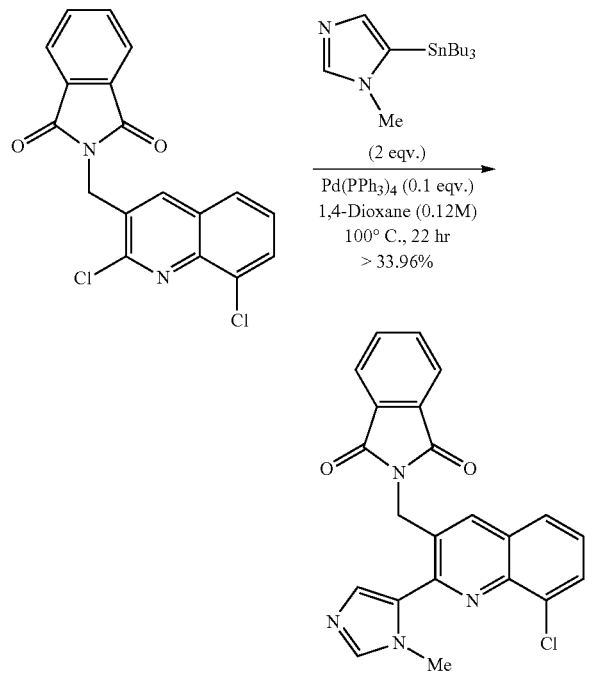

A solution of 2-((2,8-dichloroquinolin-3-yl)methyl)isoindoline-1,3-dione (0.5000 g, 1.400 mmol), 1-methyl-5-(tributylstannyl)-1H-imidazole (crude) (1.039 g, 2.800 mmol), and tetrakis(triphenylphosphine)palladium(0) (0.1618 g, 0.1400 mmol) in 1,4-Dioxane (11.67 mL, 1.400 mmol) was stirred at 100° C. After 22 h, the mixture was cooled to room temperature and concentrated under reduced pressure. The residue was mixed with Et$_2$O (20 mL) and sonicated, and filtered. The solid was washed with Et$_2$O (20 mL) and then hexane (40 mL) to give an off-white solid. The off-white solid was purified by column chromatography on a 40 g of Redi-Sep™ column using 0 to 100% gradient of CH$_2$Cl$_2$:MeOH:NH$_4$OH (89:9:1) in CH$_2$Cl$_2$ over 14 min and then 100% isocratic of CH$_2$Cl$_2$:MeOH:NH$_4$OH (89:9:1) for 5 min as eluent to give 2-((8-chloro-2-(1-methyl-1H-imidazol-5-yl)quinolin-3-yl)methyl)isoindoline-1,3-dione as an off-white solid: $^1$H NMR (400 MHz, DMSO-d$_6$) δ ppm 8.36 (1H, s), 7.86-7.97 (7H, m), 7.62 (1H, d, J=1.2 Hz), 7.53 (1H, t, J=8.0 Hz), 5.13 (2H, s), 4.00 (3H, s); LC-MS (ESI) m/z 403.1 [M+H]$^+$.

(8-Chloro-2-(1-methyl-1H-imidazol-5-yl)quinolin-3-yl)methanamine

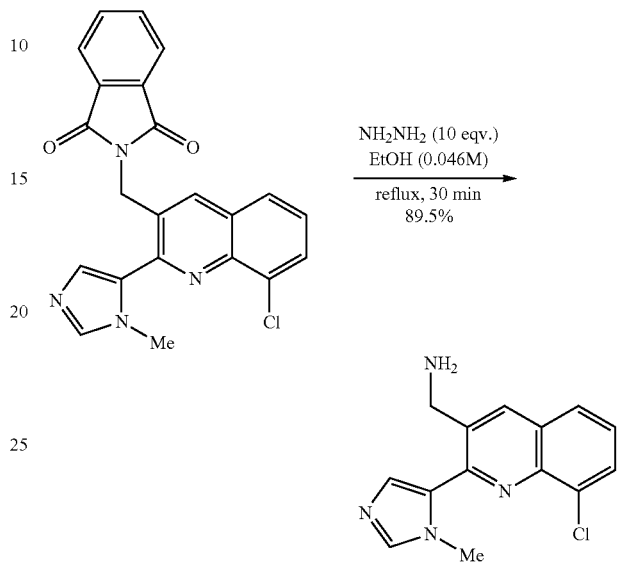

To a suspension of 2-((8-chloro-2-(1-methyl-1H-imidazol-5-yl)quinolin-3-yl)-methyl)isoindoline-1,3-dione (0.1841 g, 0.457 mmol) in ethanol (10.0 mL, 0.457 mmol) was added hydrazine, anhydrous (0.143 mL, 4.57 mmol), and the mixture was stirred under reflux for 30 min. After 30 min, the mixture was cooled to room temperature. The mixture was concentrated under reduced pressure. The residue was purified by column chromatography on a 40 g of Redi-Sep™ column using 0% to 100% gradient of CH$_2$Cl$_2$:MeOH:NH$_4$OH (89:9:1) in CH$_2$Cl$_2$ over 14 min, and then 100% isocratic of CH$_2$Cl$_2$:MeOH:NH$_4$OH (89:9:1) for 20 min as eluent to give (8-chloro-2-(1-methyl-1H-imidazol-5-yl)quinolin-3-yl)-methanamine as a white solid: $^1$H NMR (400 MHz, DMSO-d$_6$) δ ppm 8.60 (1H, s), 7.96 (1H, dd, J=8.2, 1.2 Hz), 7.91 (1H, dd, J=7.4, 1.2 Hz), 7.87 (1H, s), 7.52-7.61 (2H, m), 4.05 (2H, d, J=0.8 Hz), 3.97 (3H, s), 2.06 (2H, br. s.); LC-MS (ESI) m/z 273.1 [M+H]$^+$.

N-((8-Chloro-2-(1-methyl-1H-imidazol-5-yl)quinolin-3-yl)methyl)-9H-purin-6-amine dihydrochloride

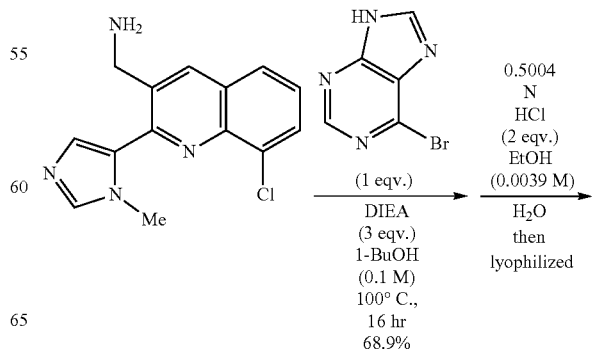

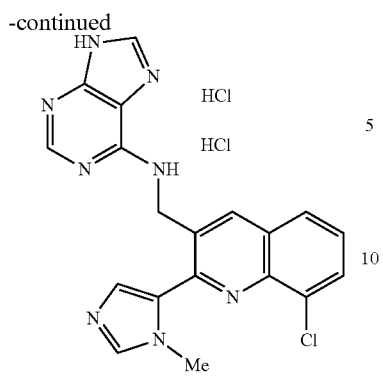

A mixture of 6-bromopurine (0.07844 g, 0.3942 mmol), (8-chloro-2-(1-methyl-1H-imidazol-5-yl)quinolin-3-yl) methanamine (0.1075 g, 0.3942 mmol), and N,N-diisopropylethylamine (0.2060 mL, 1.182 mmol) in 1-butanol (3.942 mL, 0.3942 mmol) was stirred at 100° C. After 16 h, the mixture was removed from the heat. The precipitate was filtered and the solid was washed with MeOH to give an off-white solid and filtrate. The off-white solid was purified by column chromatography on a 40 g of Redi-Sep™ column using 0 to 100% gradient of CH$_2$Cl$_2$:MeOH:NH$_4$OH (89:9:1) in CH$_2$Cl$_2$ over 14 min and then 100% isocratic of CH$_2$Cl$_2$:MeOH:NH$_4$OH (89:9:1) for 20 min as eluent to give an off-white solid. The off-white solid was suspended in MeOH and filtered to give N-((8-chloro-2-(1-methyl-1H-imidazol-5-yl)quinolin-3-yl)methyl)-9H-purin-6-amine as a white solid. A suspension of in N-((8-chloro-2-(1-methyl-1H-imidazol-5-yl)quinolin-3-yl)methyl)-9H-purin-6-amine (0.10596 g) in ethanol absolute (7 mL) was treated with hydrochloric acid volumetric standard, 0.5004 N solution in water (1.084 mL, 0.54322 mmol, 2 eqv.). The mixture was stirred at 95° C. oil bath for 5 min. After 5 min, the mixture became clear solution and cooled to room temperature. The cooed mixture was concentrated under reduced pressure to give a light yellow solid. The light yellow solid was dissolved in 3 mL of water, frozen, and dried on lyophilizer to give N-((8-chloro-2-(1-methyl-1H-imidazol-5-yl)quinolin-3-yl)-methyl)-9H-purin-6-amine dihydrochloride as an off-white solid: $^1$H NMR (400 MHz, DMSO-d$_6$) δ ppm 9.99 (1H, br. s.), 9.34 (1H, s), 8.66 (1H, s), 8.42-8.62 (2H, m), 8.37 (1H, s), 7.99-8.07 (2H, m), 7.67 (1H, t, J=8.0 Hz), 5.19 (2H, br. s.), 4.08 (3H, s); LC-MS (ESI) m/z 391.1 [M+H]$^+$ (Exact Mass of neutral form: 390.111).

Example 103: Preparation of N-(2-(5-Chloro-3-(3-fluorophenyl)quinoxalin-2-yl)propan-2-yl)-9H-purin-6-amine 5-Chloro-3-isopropylquinoxalin-2(1H)-one and 8-Chloro-3-isopropylquinoxalin-2(1H)-one

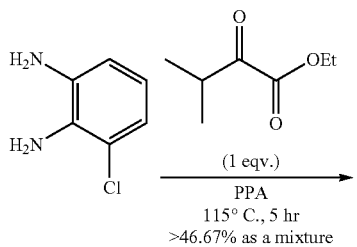

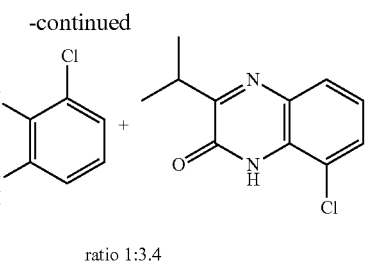

ratio 1:3.4

A mixture of 3-chlorobenzene-1,2-diamine (Prepared in Example 81, 10.000 g, 70.13 mmol) and ethyl 3-methyl-2-oxobutyrate (10.22 mL, 70.13 mmol) in polyphosphoric acid (100.00 g) was stirred and heated at 115° C. After 5 h, the mixture was cooled to room temperature, thoroughly mixed with water (300 mL), and neutralized with 10 N NaOH (100 mL). The resulting precipitate was collected by filtration, washed with water (1 L), and dried to give a mixture of two resiosiomers as a brown solid. The brown solid was suspended in MeOH (100 mL), filtered, and washed with MeOH (150 mL) to give a mixture of 5-chloro-3-isopropylquinoxalin-2 (1H)-one and 8-chloro-3-isopropylquinoxalin-2 (1H)-one as a tan solid: LC-MS (ESI) m/z 223.1 [M+H]$^+$. The crude product was carried on crude without purification for the next step.

2,5-Dichloro-3-isopropylquinoxaline and 3,5-Dichloro-2-isopropylquinoxaline

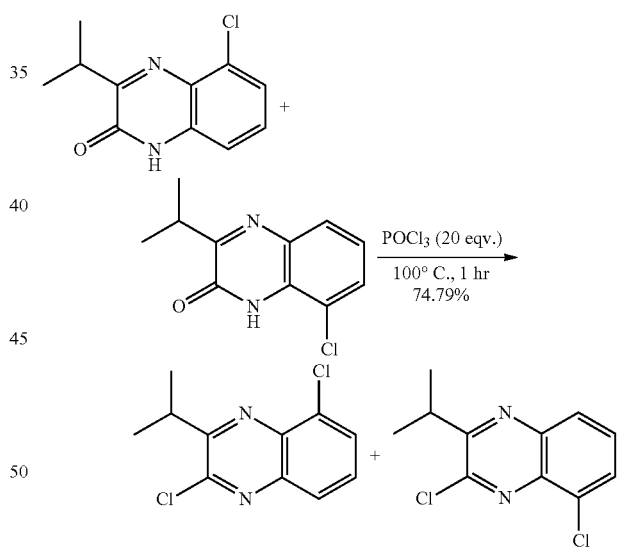

A mixture of 5-chloro-3-isopropylquinoxalin-2 (1H)-one and 8-chloro-3-isopropylquinoxalin-2 (1H)-one (3.3933 g, 15.239 mmol) and phosphoryl trichloride (27.900 mL, 304.78 mmol) was stirred at 100° C. After 1 h, the mixture was cooled to room temperature. The mixture was poured into ice (~200 mL) with stirring and neutralized with NH$_4$OH (100 mL) and ice (~400 mL) with stirring. The resulting precipitate was collected by filtration, rinsed with water (200 mL), and dried to give a mixture of 2,5-dichloro-3-isopropylquinoxaline and 3,5-dichloro-2-isopropylquinoxaline as a red solid: LC-MS (ESI) m/z 241.0 [M+H]$^+$. The crude product was carried on crude without purification for the next step.

5-Chloro-3-(3-fluorophenyl)-2-isopropylquinoxaline and 5-Chloro-2-(3-fluorophenyl)-3-isopropylquinoxaline

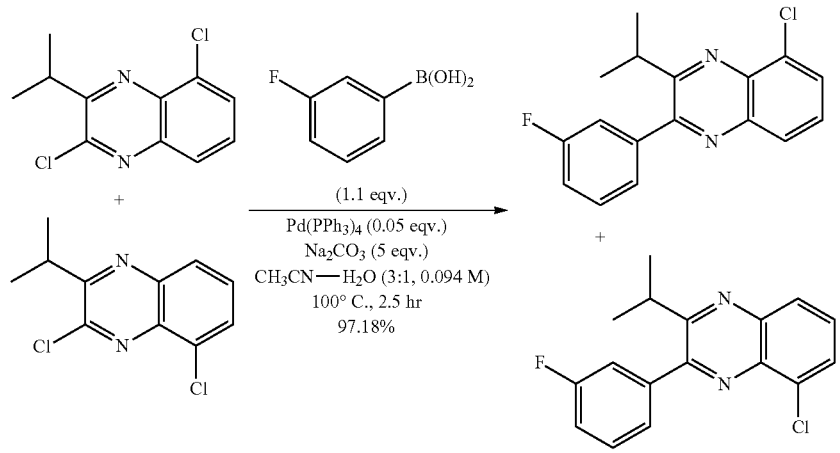

A mixture of 2,5-dichloro-3-isopropylquinoxaline and 3,5-dichloro-2-isopropylquinoxaline (2.7397 g, 11.36 mmol), 3-fluorophenylboronic acid (1.749 g, 12.50 mmol), tetrakis(triphenylphosphine)palladium (0.6565 g, 0.5681 mmol), and sodium carbonate anhydrous (6.021 g, 56.81 mmol) in acetonitrile-water (3:1) (120.00 mL) was stirred at 100° C. After 2.5 h, the mixture was cooled to room temperature and partitioned between EtOAc (100 mL) and water (100 mL). The organic layer was washed with brine (50 mL×2), dried over Na$_2$SO$_4$, filtered, and concentrated under reduced pressure. The residue was purified by silica gel column chromatography on a 80 g of Redi-Sep™ column using 0 to 20% gradient of EtOAc in hexane over 25 min and then 20% isocratic of EtOAc for 10 min as eluent to give a mixture of 5-chloro-3-(3-fluorophenyl)-2-isopropylquinoxaline and 5-chloro-2-(3-fluorophenyl)-3-isopropylquinoxaline as a light yellow syrupy solid: LC-MS (ESI) m/z 301.1 [M+H]$^+$. The mixture of two regioisomers was carried as a mixture without further purification for the next step.

3-(2-Bromopropan-2-yl)-5-chloro-2-(3-fluorophenyl)quinoxaline and 2-(2-bromopropan-2-yl)-5-chloro-3-(3-fluorophenyl)quinoxaline

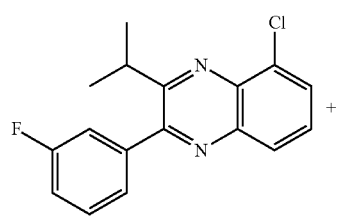

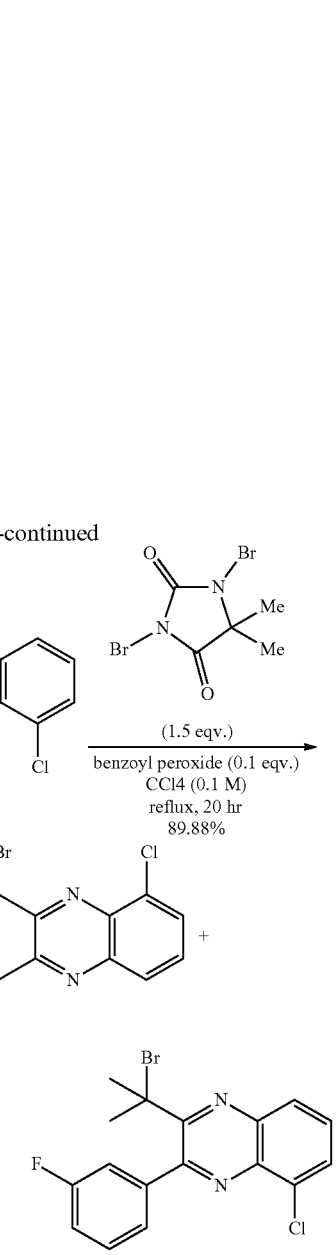

A mixture of 5-chloro-2-(3-fluorophenyl)-3-isopropylquinoxaline and 5-chloro-3-(3-fluorophenyl)-2-isopropylquinoxaline (3.3042 g, 10.99 mmol) and 1,3-dibromo-5,5-dimethylhydantoin (4.712 g, 16.48 mmol) were suspended in carbon tetrachloride (109.9 mL, 10.99 mmol). To the mixture was added benzoyl peroxide (0.3548 g, 1.099 mmol) and the mixture was heated at reflux. After 20 h, the mixture was cooled to room temperature and concentrated under reduced pressure. The residue was purified by silica gel column chromatography on a 120 g of Redi-Sep™ column using 0 to 10% gradient of EtOAc in hexane over 15 min and then 10% isocratic of EtOAc for 30 min as eluent to give 3-(2-bromopropan-2-yl)-5-chloro-2-(3-fluorophenyl)quinoxaline and 2-(2-bromopropan-2-yl)-5-chloro-3-(3-fluorophenyl)quinoxaline as a yellow solid: LC-MS (ESI) m/z 379.0 and 381.0 [M+H]$^+$. The mixture of two regioisomers was carried as a mixture without further purification for the next step.

2-(8-Chloro-3-(3-fluorophenyl)quinoxalin-2-yl)propan-2-amine and 2-(5-Chloro-3-(3-fluorophenyl)quinoxalin-2-yl)propan-2-amine 2-(2-Azidopropan-2-yl)-5-chloro-3-(3-fluorophenyl)quinoxaline and 3-(2-Azidopropan-2-yl)-5-chloro-2-(3-fluorophenyl)quinoxaline

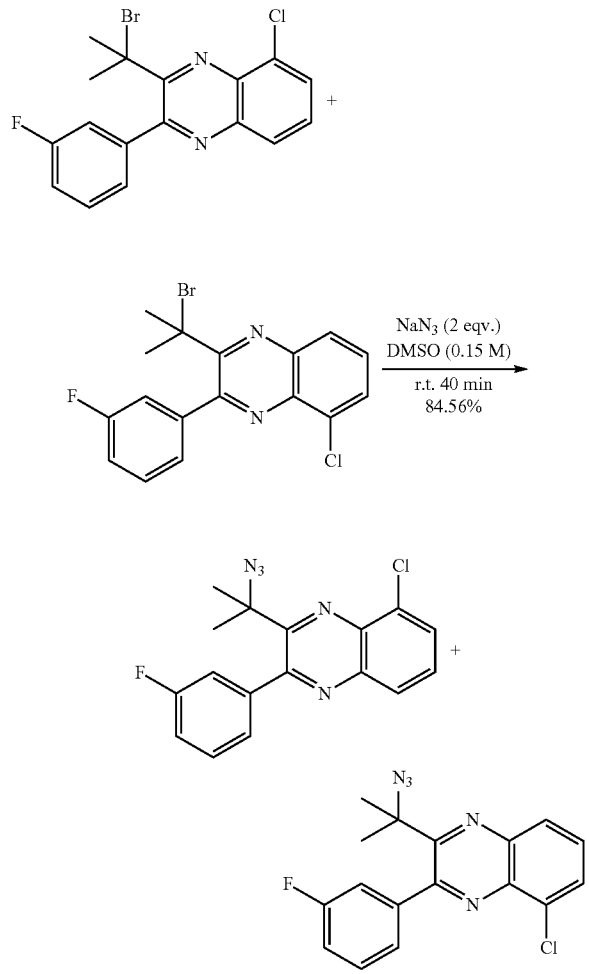

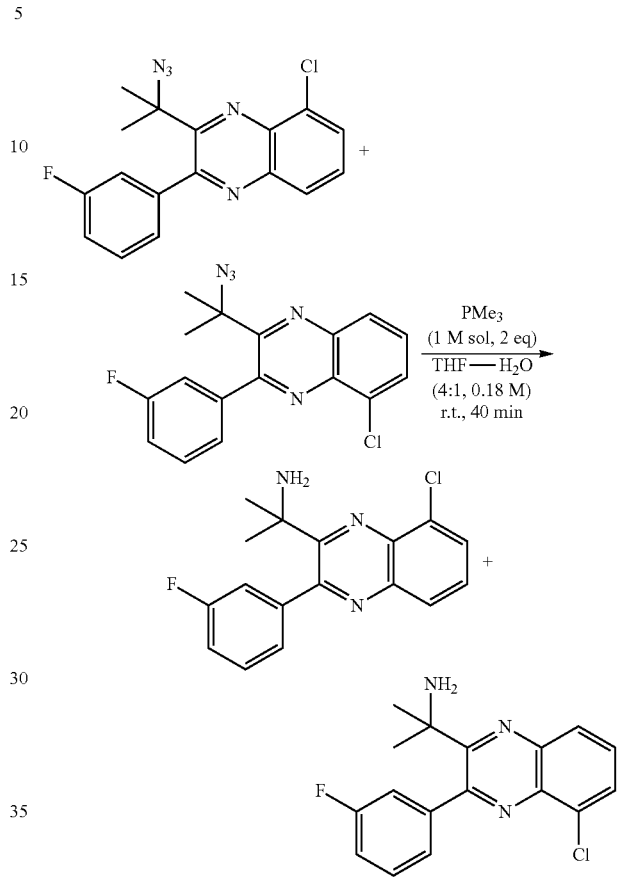

To a solution of 3-(2-bromopropan-2-yl)-5-chloro-2-(3-fluorophenyl)quinoxaline and 2-(2-bromopropan-2-yl)-5-chloro-3-(3-fluorophenyl)quinoxaline (1.0000 g, 2.634 mmol) in methyl sulfoxide (17.56 mL, 2.634 mmol) was added sodium azide (0.3425 g, 5.268 mmol), and the mixture was stirred at room temperature. After 40 min, the mixture was partitioned between EtOAc (100 mL) and H$_2$O (100 mL). The organic layer was washed with brine (100 mL×1), dried over Na$_2$SO$_4$, filtered, and concentrated under reduced pressure to give a mixture of 2-(2-azidopropan-2-yl)-5-chloro-3-(3-fluorophenyl)quinoxaline and 3-(2-azidopropan-2-yl)-5-chloro-2-(3-fluorophenyl)quinoxaline as a yellow solid: LC-MS (ESI) m/z 342.1 [M+H]$^+$. The crude product was carried on crude without purification for the next step.

To a stirring solution of a mixture of 2-(2-azidopropan-2-yl)-5-chloro-3-(3-fluoro-phenyl)quinoxaline and 3-(2-azidopropan-2-yl)-5-chloro-2-(3-fluorophenyl)-quinoxaline (0.9002 g, 2.634 mmol) in THF—H$_2$O (4:1) (15.00 mL, 2.634 mmol) was added dropwise trimethylphosphine, 1.0 M solution in THF (5.268 mL, 5.268 mmol) at room temperature and the mixture was stirred at room temperature. After 40 min, the mixture was diluted with ice-cold 2 N NaOH (25 mL) and extracted with EtOAc (50 mL×3). The combined organic layers were washed with brine (50 mL×3), dried over MgSO$_4$, and concentrated under the reduced pressure to give a green syrup. The green syrup was purified by column chromatography on a 120 g of RediSep™ column using 0% to 20% gradient of CH$_2$Cl$_2$:MeOH:NH$_4$OH (89:9:1) in CH$_2$Cl$_2$ over 15 min, then 20% isocratic of CH$_2$Cl$_2$:MeOH:NH$_4$OH (89:9:1) in CH$_2$Cl$_2$ for 15 min, then 20% to 50% gradient of CH$_2$Cl$_2$:MeOH:NH$_4$OH (89:9:1) in CH$_2$Cl$_2$ over 15 min, and then 50% isocratic of CH$_2$Cl$_2$:MeOH:NH$_4$OH (89:9:1) in CH$_2$Cl$_2$ for 20 min as eluent to give two separated regiosiomers: 2-(8-chloro-3-(3-fluorophenyl)quinoxalin-2-yl)propan-2-amine: $^1$H NMR (400 MHz, DMSO-d$_6$) δ ppm 8.01-8.08 (2H, m), 7.79-7.85 (1H, m), 7.47-7.58 (2H, m), 7.31-7.46 (2H, m), 1.99 (2H, br. s.), 1.41 (6H, s); LC-MS (ESI) m/z 316.1 [M+H]$^+$ and 2-(5-chloro-3-(3-fluoro-phenyl)quinoxalin-2-yl)propan-2-amine: $^1$H NMR (400 MHz, DMSO-d$_6$) δ ppm 8.08 (1H, dd, J=8.4, 1.4 Hz), 8.02 (1H, dd, J=7.6, 1.4 Hz), 7.85 (1H, dd, J=8.4, 7.6 Hz), 7.48-7.59 (2H, m), 7.40-7.44 (1H, m), 7.33-7.39 (1H, m), 1.93 (2H, s), 1.39 (6H, s); LC-MS (ESI) m/z 316.1 [M+H]⁺ at 1.100 min.

N-(2-(5-Chloro-3-(3-fluorophenyl)quinoxalin-2-yl)propan-2-yl)-9H-purin-6-amine

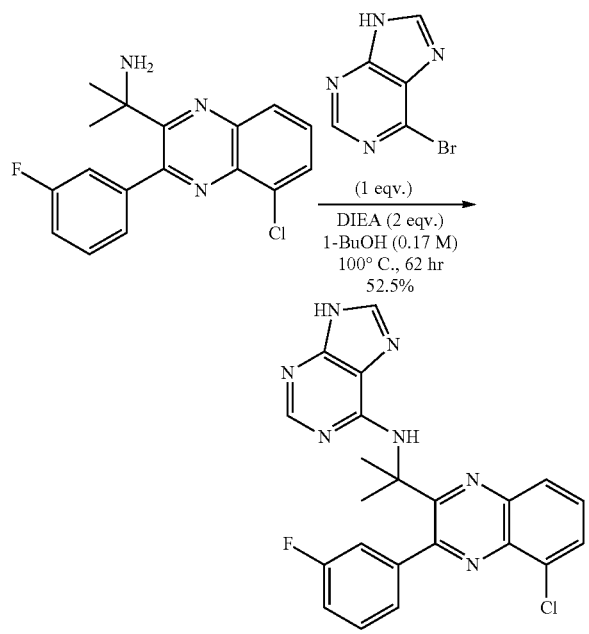

A mixture of 6-bromopurine (0.2423 g, 1.218 mmol), 2-(5-chloro-3-(3-fluoro-phenyl)quinoxalin-2-yl)propan-2-amine (0.3845 g, 1.218 mmol), and N,N-diisopropylethylamine (0.6363 mL, 3.653 mmol) in 1-butanol (7.000 mL, 1.218 mmol) was stirred at 100° C. After 62 h, the mixture was removed from the heat and concentrated under reduced pressure. The residue was purified by flash chromatography on a silica gel column using 30% of CH₂Cl₂:MeOH:NH₄OH (89:9:1) in CH₂Cl₂ as eluent to give N-(2-(5-chloro-3-(3-fluorophenyl)quinoxalin-2-yl)propan-2-yl)-9H-purin-6-amine as a white solid: ¹H NMR (400 MHz, DMSO-d₆) δ ppm 12.84 (1H, s), 8.12 (1H, dd, J=8.4, 1.0 Hz), 8.00 (2H, dd, J=7.5, 1.1 Hz), 7.80-7.91 (1H, m), 7.78 (1H, s), 6.88-7.19 (3H, m), 6.75 (1H, s), 6.41 (1H, s), 1.94 (6H, s); LC-MS (ESI) m/z 434.2 [M+H]⁺.

Example 104: Preparation of N-(2-(8-Chloro-3-(3-fluorophenyl)quinoxalin-2-yl)propan-2-yl)-9H-purin-6-amine as a TFA Salt

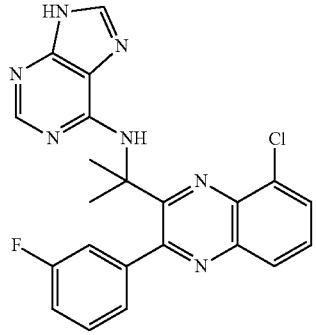

A mixture of 6-bromopurine (0.0195 g, 0.0982 mmol), 2-(8-chloro-3-(3-fluoro-phenyl)quinoxalin-2-yl)propan-2-amine (Prepared in Example 103, 0.0310 g, 0.0982 mmol), and N,N-diisopropylethylamine (0.0513 mL, 0.295 mmol) in 1-butanol (1.00 mL, 0.0982 mmol) was stirred at 100° C. for 62 h and then the mixture was irradiated at 300 W at 140° C. in a microwave reactor. The mixture was removed from the heat and concentrated under reduced pressure. The mixture was dissolved in DMSO (1.5 mL) and purified by semi-prep-HPLC on a Gemini™ 10μ C18 column (250× 21.2 mm, 10 μm) using 20-70% gradient of CH₃CN (0.1% of TFA) in water (0.1% of TFA) over 40 min as eluent to give N-(2-(8-chloro-3-(3-fluorophenyl)quinoxalin-2-yl)propan-2-yl)-9H-purin-6-amine as a TFA salt as a yellow solid: ¹H NMR (400 MHz, DMSO-d₆) δ ppm 8.26 (1H, s), 7.99-8.12 (3H, m), 7.76-7.96 (2H, m), 6.94-7.08 (2H, m), 6.76 (1H, d, J=7.0 Hz), 6.64 (1H, d, J=9.0 Hz), 2.01 (6H, s); LC-MS (ESI) m/z 434.2 [M+H]⁺ (Exact Mass of neutral form: 433.122).

Example 105: Preparation of N—((S)-1-(8-Chloro-2-(3-(trifluoromethyl)-1H-pyrazol-1-yl)quinolin-3-yl)ethyl)-9H-purin-6-amine as a TFA Salt 2-((S)-1-(8-Chloro-2-(3-(trifluoromethyl)-1H-pyrazol-1-yl)quinolin-3-yl)-ethyl)isoindoline-1,3-dione

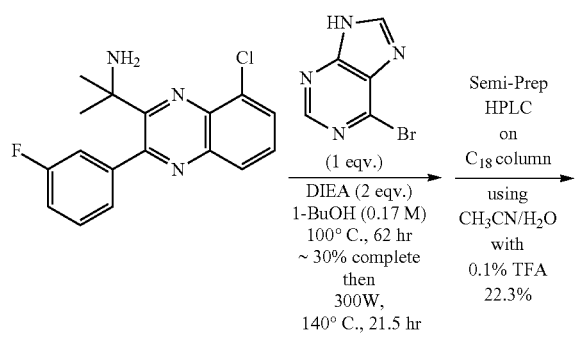

-continued

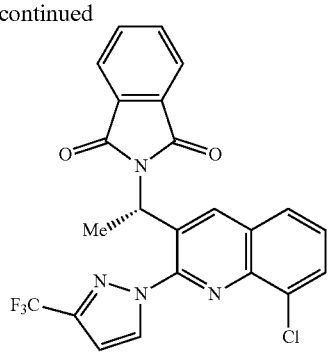

A mixture of (S)-2-(1-(2,8-dichloroquinolin-3-yl)ethyl)isoindoline-1,3-dione (0.2000 g, 0.539 mmol), 3-(trifluoromethyl)pyrazole (0.0733 g, 0.539 mmol), cesium carbonate (0.351 g, 1.08 mmol) and in DMF (1.80 mL, 0.539 mmol) was stirred at 100° C. After 2 h, The mixture was cooled to room temperature. To the cooled mixture was added water (30 mL). The mixture was extracted with EtOAc (50 mL×2). The combined organic layers were washed with brine (50 mL×1), dried over MgSO$_4$, filtered, and concentrated under reduced pressure. The residue was purified by silica gel column chromatography on a 40 g of Redi-Sep™ column using 0 to 10% gradient of EtOAc in hexane over 10 min, then 10% isocratic of EtOAc for 10 min, then 10 to 50% gradient of EtOAc in hexane over 20 min, then 50% isocratic of EtOAc for 10 min as eluent to give 2-((S)-1-(8-chloro-2-(3-(trifluoromethyl)-1H-pyrazol-1-yl)quinolin-3-yl)ethyl)isoindoline-1,3-dione as a yellow syrup: $^1$H NMR (400 MHz, DMSO-d$_6$) δ ppm 9.05 (1H, s), 8.51 (1H, d, J=2.2 Hz), 8.25 (1H, dd, J=8.4, 1.0 Hz), 8.08 (1H, dd, J=7.7, 0.9 Hz), 7.63-7.85 (5H, m), 6.92 (1H, d, J=2.7 Hz), 5.94-6.05 (1H, m), 1.83 (3H, d, J=7.0 Hz); LC-MS (ESI) m/z 471.1 [M+H]$^+$.

(1S)-1-(8-Chloro-2-(3-(trifluoromethyl)-1H-pyrazol-1-yl)quinolin-3-yl)-ethanamine

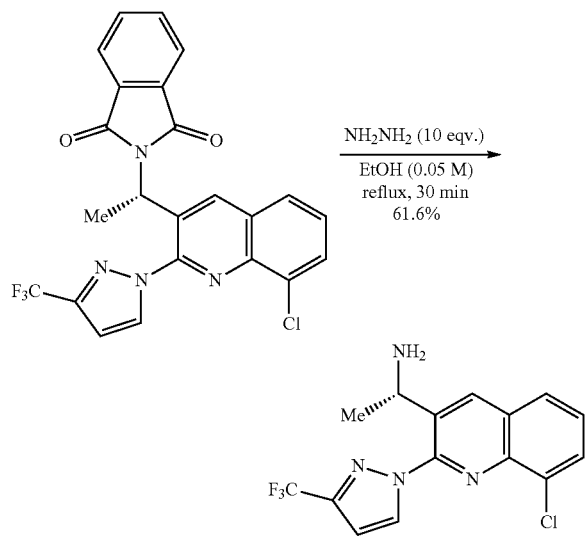

To a suspension of 2-((S)-1-(8-chloro-2-(3-(trifluoromethyl)-1H-pyrazol-1-yl)-quinolin-3-yl)ethyl)isoindoline-1,3-dione (0.0435 g, 0.0924 mmol) in ethanol (1.85 mL, 0.0924 mmol) was added hydrazine, anhydrous (0.0290 mL, 0.924 mmol), and the mixture was stirred under reflux. After 30 min, the mixture was cooled to room temperature. The mixture was concentrated under reduced pressure. The residue was purified by column chromatography on a 40 g of Redi-Sep™ column using 0% to 100% gradient of CH$_2$Cl$_2$: MeOH:NH$_4$OH (89:9:1) in CH$_2$Cl$_2$ over 14 min, and then 100% isocratic of CH$_2$Cl$_2$:MeOH:NH$_4$OH (89:9:1) for 5 min as eluent to give (1S)-1-(8-chloro-2-(3-(trifluoromethyl)-1H-pyrazol-1-yl)quinolin-3-yl)ethanamine as a yellow syrup: $^1$H NMR (400 MHz, DMSO-d$_6$) δ ppm 8.98 (1H, s), 8.65-8.70 (1H, m), 8.11 (1H, dd, J=8.2, 1.2 Hz), 8.02 (1H, dd, J=7.4, 1.2 Hz), 7.65-7.72 (1H, m), 7.12 (1H, d, J=2.7 Hz), 4.53 (1H, q, J=6.8 Hz), 2.26 (2H, br. s.), 1.24 (3H, d, J=6.7 Hz); LC-MS (ESI) m/z 341.0 [M+H]$^+$.

N—((S)-1-(8-Chloro-2-(3-(trifluoromethyl)-1H-pyrazol-1-yl)quinolin-3-yl)-ethyl)-9H-purin-6-amine as a TFA Salt

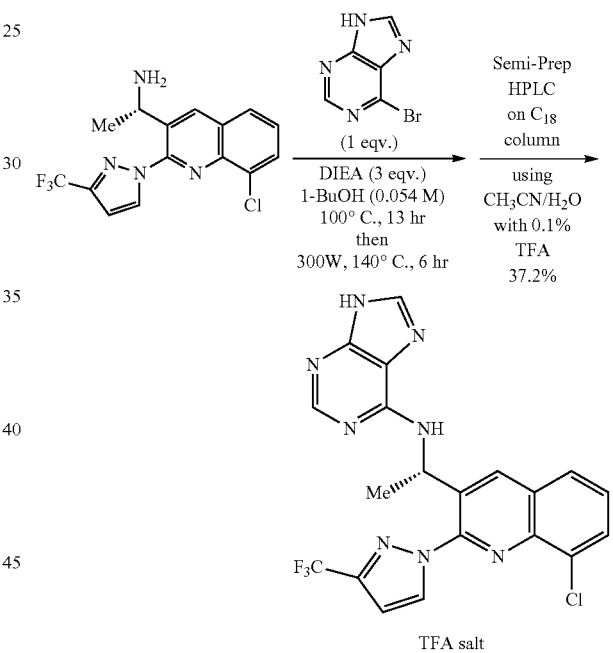

A mixture of 6-bromopurine (0.0107 g, 0.0540 mmol), (1S)-1-(8-chloro-2-(3-(trifluoromethyl)-1H-pyrazol-1-yl)quinolin-3-yl)ethanamine (0.0184 g, 0.0540 mmol), and N,N-diisopropylethylamine (0.0282 mL, 0.162 mmol) in 1-butanol (1.00 mL, 0.0540 mmol) was stirred at 100° C. After 13 h at 100° C. and then 6 h at 140° C. in microwave reactor, the mixture was removed from the heat and concentrated under reduced pressure. The crude mixture was dissolved in DMSO (1.5 mL) and purified (1.5 mL (30.9 mg)×1 injection) by semi-prep-HPLC on a Gemini™ 10μ C18 column (250×21.2 mm, 10 μm) using 20-70% gradient of CH$_3$CN (0.1% of TFA) in water (0.1% of TFA) over 40 min as eluent, and dried on the lyophilizer to give N—((S)-1-(8-chloro-2-(3-(trifluoromethyl)-1H-pyrazol-1-yl)quinolin-3-yl)ethyl)-9H-purin-6-amine as a TFA salt as a white solid: $^1$H NMR (400 MHz, DMSO-d$_6$) δ ppm 8.73-8.93 (3H, m), 8.15-8.41 (2H, m), 7.98-8.09 (2H, m), 7.60-7.71 (1H, m), 7.11 (1H, d, J=2.3 Hz), 5.85 (1H, br. s.), 1.71 (3H, br. s.); LC-MS (ESI) m/z 459.1 [M+H]⁺ (Exact Mass of neutral form: 458.098).

Example 106: Preparation of N—((S)-1-(5-Chloro-3-(3-fluorophenyl)-quinoxalin-2-yl)ethyl)-9H-purin-6-amine and N—((R)-1-(5-Chloro-3-(3-fluoro-phenyl)quinoxalin-2-yl)ethyl)-9H-purin-6-amine 5-Chloro-3-(3-fluorophenyl)quinoxaline-2-carbaldehyde

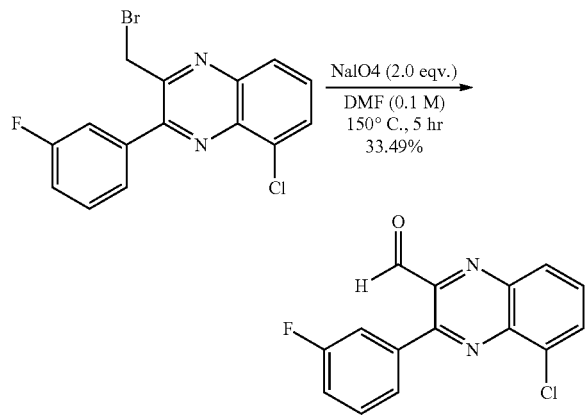

A mixture of 2-(bromomethyl)-5-chloro-3-(3-fluorophenyl)quinoxaline (Prepared in Example 95, 0.8089 g, 2.301 mmol) and sodium metaperiodate (0.9842 g, 4.601 mmol) in DMF (15.34 mL, 2.301 mmol) was heated at 150° C. with stirring. After 5 h, the mixture was cooled to room temperature, diluted with EtOAc (100 mL), washed with sat'd Na₂S₂O₃ (50 mL×1) and brine (50 mL×2), dried over Na₂SO₄, filtered, and concentrated under reduced pressure. The residue was purified by silica gel column chromatography on a 80 g of Redi-Sep™ column using 0 to 10% gradient of EtOAc in hexane over 10 min, then 10% isocratic of EtOAc for 20 min, then 10 to 20% gradient of EtOAc in hexane over 20 min, then 20% isocratic of EtOAc for 20 min as eluent to give 5-chloro-3-(3-fluorophenyl)quinoxaline-2-carbaldehyde as a solid: ¹H NMR (400 MHz, DMSO-d₆) δ ppm 10.18 (1H, s), 8.31 (1H, dd, J=8.2, 1.2 Hz), 8.25 (1H, dd, J=7.4, 1.2 Hz), 7.99 (1H, dd, J=8.4, 7.6 Hz), 7.56-7.70 (3H, m), 7.38-7.46 (1H, m); LC-MS (ESI) m/z 287.0 [M+H]⁺.

1-(5-Chloro-3-(3-fluorophenyl)quinoxalin-2-yl)ethanol

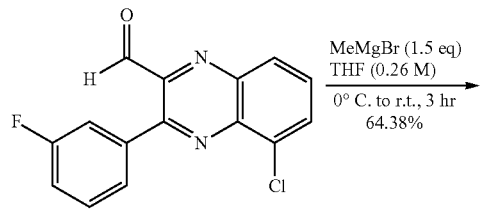

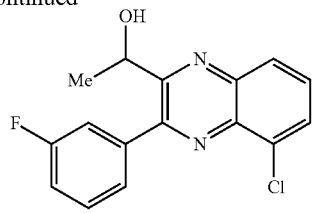

To a stirring heterogeneous mixture of 5-chloro-3-(3-fluorophenyl)quinoxaline-2-carbaldehyde (0.4405 g, 1.537 mmol) in THF (14.95 mL, 1.537 mmol) was added methylmagnesium bromide 3 M in diethyl ether (1.024 mL, 3.073 mmol) dropwise at 0° C. and the mixture was then allowed to warm to room temperature. After 3 h, the reaction was quenched with saturated aq. NH₄Cl (50 mL) and extracted with EtOAc (50 mL×2). The combined organic layers were washed with water (50 mL×1), brine (50 mL×1), dried over Na₂SO₄, filtered, and concentrated under reduced pressure. The residue was purified by silica gel column chromatography on a 40 g of Redi-Sep™ column using 0 to 50% gradient of EtOAc in hexane over 14 min and then 50% isocratic of EtOAc for 10 min as eluent to give 1-(5-chloro-3-(3-fluorophenyl)quinoxalin-2-yl)ethanol as a solid: ¹H NMR (400 MHz, DMSO-d₆) δ ppm 8.14 (1H, dd, J=8.4, 1.2 Hz), 8.06 (1H, dd, J=7.6, 1.4 Hz), 7.87 (1H, dd, J=8.4, 7.6 Hz), 7.56-7.71 (3H, m), 7.37-7.46 (1H, m), 5.50 (1H, d, J=6.1 Hz), 5.04-5.13 (1H, m), 1.48 (3H, d, J=6.3 Hz); LC-MS (ESI) m/z 303.1 [M+H]⁺.

2-(1-(5-Chloro-3-(3-fluorophenyl)quinoxalin-2-yl)ethyl)isoindoline-1,3-dione

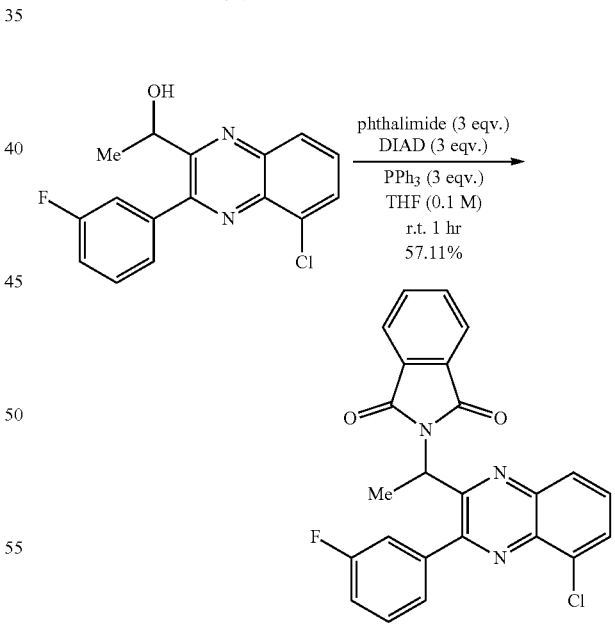

To a solution of 1-(5-chloro-3-(3-fluorophenyl)quinoxalin-2-yl)ethanol (0.2875 g, 0.9497 mmol) in tetrahydrofuran (9.497 mL, 0.9497 mmol) were added triphenyl-phosphine (0.7473 g, 2.849 mmol), phthalimide (0.4192 g, 2.849 mmol), and diisopropyl azodicarboxylate (0.5518 mL, 2.849 mmol). The reaction mixture was stirred at room temperature. After 1 h, the mixture was concentrated under reduced pressure and partitioned between EtOAc (100 mL) and brine (100 mL). The organic layer was dried over Na$_2$SO$_4$, filtered, and concentrated under reduced pressure. The residue was purified by silica gel column chromatography on a 40 g of Redi-Sep™ column using 0 to 50% gradient of EtOAc in hexane over 20 min and 50% isocratic of EtOAc for 5 min as eluent to give 2-(1-(5-chloro-3-(3-fluorophenyl)quinoxalin-2-yl)ethyl)isoindoline-1,3-dione as a yellow solid: $^1$H NMR (400 MHz, DMSO-d$_6$) δ ppm 8.19 (1H, dd, J=8.4, 1.4 Hz), 8.09 (1H, dd, J=7.6, 1.4 Hz), 7.91 (1H, dd, J=8.4, 7.6 Hz), 7.73-7.80 (2H, m), 7.60-7.68 (2H, m), 7.31-7.38 (1H, m), 7.14-7.24 (2H, m), 7.00-7.09 (1H, m), 6.04-6.13 (1H, m), 1.77 (3H, d, J=6.7 Hz); LC-MS (ESI) m/z 432.1 [M+H]$^+$.

1-(5-Chloro-3-(3-fluorophenyl)quinoxalin-2-yl)ethanamine

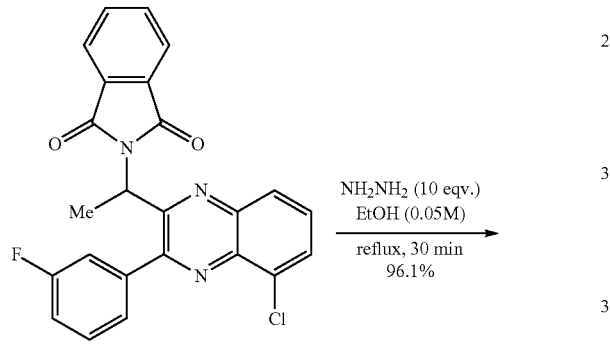

To a suspension of 2-(1-(5-chloro-3-(3-fluorophenyl)quinoxalin-2-yl)ethyl)-isoindoline-1,3-dione (0.2272 g, 0.526 mmol) in ethanol (10.5 mL, 0.526 mmol) was added hydrazine, anhydrous (0.165 mL, 5.26 mmol), and the mixture was stirred under reflux. After 30 min, the mixture was cooled to room temperature. The mixture was concentrated under reduced pressure. The residue was purified by column chromatography on a 40 g of Redi-Sep™ column using 0% to 100% gradient of CH$_2$Cl$_2$:MeOH:NH$_4$OH (89:9:1) in CH$_2$Cl$_2$ over 14 min, and then 100% isocratic of CH$_2$Cl$_2$:MeOH:NH$_4$OH (89:9:1) for 3 min as eluent to give 1-(5-chloro-3-(3-fluorophenyl)quinoxalin-2-yl)ethanamine as a yellow syrup: $^1$H NMR (400 MHz, DMSO-d$_6$) δ ppm 8.11 (1H, dd, J=8.4, 1.4 Hz), 8.00-8.05 (1H, m), 7.86 (1H, dd, J=8.4, 7.6 Hz), 7.57-7.69 (3H, m), 7.38-7.47 (1H, m), 4.32 (1H, q, J=6.7 Hz), 2.12 (2H, br. s.), 1.31 (3H, d, J=6.7 Hz); LC-MS (ESI) M/z 302.0 [M+H]$^+$.

N—((S)-1-(5-Chloro-3-(3-fluorophenyl)quinoxalin-2-yl)ethyl)-9H-purin-6-amine and N—((R)-1-(5-Chloro-3-(3-fluorophenyl)quinoxalin-2-yl)ethyl)-9H-purin-6-amine

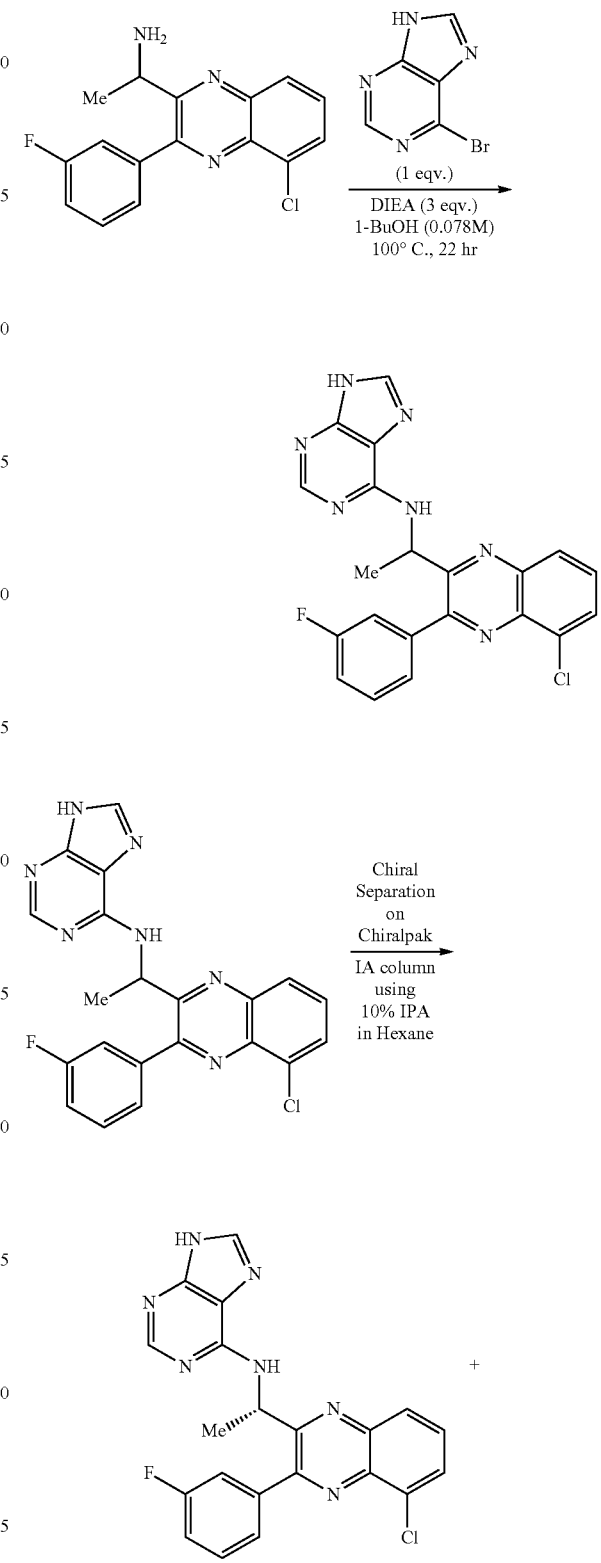

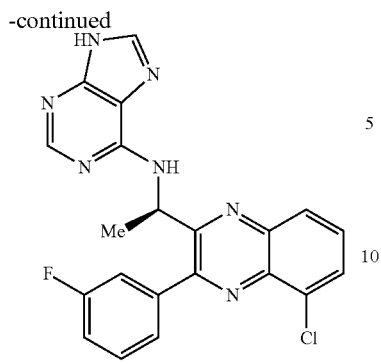

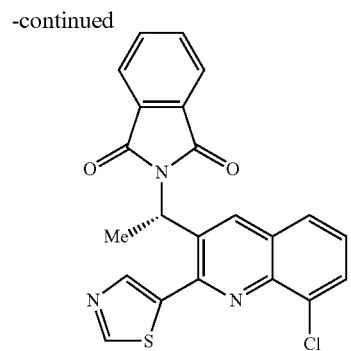

A mixture of 6-bromopurine (0.09794 g, 0.4921 mmol), 1-(5-chloro-3-(3-fluoro-phenyl)quinoxalin-2-yl)ethanamine (0.1485 g, 0.4921 mmol), and N,N-diisopropylethylamine (0.2572 mL, 1.476 mmol) in 1-butanol (6.340 mL, 0.4921 mmol) was stirred at 100° C. After 22 h, the mixture was removed from the heat and concentrated under reduced pressure. The residue was purified by column chromatography on a 40 g of Redi-Sep™ column using 0% to 100% gradient of CH$_2$Cl$_2$:MeOH:NH$_4$OH (89:9:1) in CH$_2$Cl$_2$ over 14 min and then 100% isocratic of CH$_2$Cl$_2$:MeOH:NH$_4$OH (89:9:1) for 10 min as eluent to give the desired product as a racemic mixture as a yellow solid (0.2806 g). The yellow solid was suspended in CH$_2$Cl$_2$-MeOH (2:1) and filtered to give N-(1-(5-chloro-3-(3-fluoro-phenyl)quinoxalin-2-yl)ethyl)-9H-purin-6-amine as a white solid. The racemic mixture was separated (5 injections of ~40 mg in 1 mL) on a Chiralpak™ IA column (30×250 mm, 5 µm) using 10% isocratic of isopropanol in hexane for 40 min as eluent to give two separated isomers: N—((S)-1-(5-chloro-3-(3-fluoro-phenyl)quinoxalin-2-yl)ethyl)-9H-purin-6-amine as a yellow solid: $^1$H NMR (400 MHz, DMSO-d$_6$) δ ppm 12.90 (1H, s), 7.92-8.28 (5H, m), 7.78-7.88 (1H, m), 7.61-7.75 (2H, m), 7.55 (1H, s), 7.32 (1H, s), 5.72 (1H, s), 1.55 (3H, d, J=6.3 Hz); LC-MS (ESI) m/z 420.1 [M+H]$^+$ and N—((R)-1-(5-chloro-3-(3-fluoro-phenyl)quinoxalin-2-yl)ethyl)-9H-purin-6-amine as a yellow solid: $^1$H NMR (400 MHz, DMSO-d$_6$) δ ppm 12.91 (1H, s), 7.96-8.30 (5H, m), 7.82 (1H, t, J=8.0 Hz), 7.62-7.75 (2H, m), 7.54 (1H, s), 7.32 (1H, s), 5.72 (1H, s), 1.55 (3H, d, J=5.1 Hz); LC-MS (ESI) m/z 420.1 [M+H]$^+$.

Example 107: Preparation of N—((S)-1-(8-Chloro-2-(thiazol-5-yl)quinolin-3-yl)ethyl)-9H-purin-6-amine as a TFA Salt 2-((S)-1-(8-Chloro-2-(thiazol-5-yl)quinolin-3-yl)ethyl)isoindoline-1,3-dione

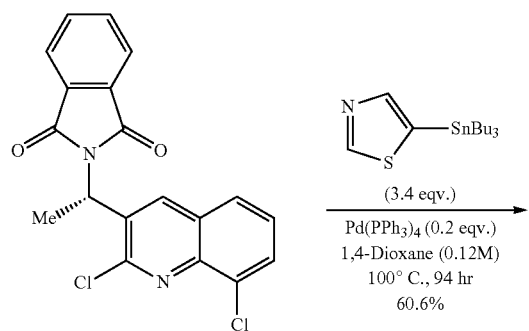

A solution of (S)-2-(1-(2,8-dichloroquinolin-3-yl)ethyl) isoindoline-1,3-dione (0.2000 g, 0.5388 mmol), 5-(tributyl-stannyl)thiazole (0.4032 g, 1.078 mmol), and tetrakis(triphenylphosphine)palladium(0) (0.06226 g, 0.05388 mmol) in 1,4-dioxane (4.490 mL, 0.5388 mmol) was stirred at 100° C. After 94 h, the mixture was cooled to room temperature and concentrated under reduced pressure. The residue was purified by column chromatography on a 40 g of Redi-Sep™ column using 0 to 100% gradient of EtOAc in hexane over 14 min and then 100% isocratic of EtOAc for 7 min as eluent to give 2-((S)-1-(8-chloro-2-(thiazol-5-yl)-quinolin-3-yl) ethyl)isoindoline-1,3-dione as a light yellow solid: 1H NMR (400 MHz, DMSO-d$_6$) δ ppm 9.10 (1H, s), 8.83 (1H, s), 8.30 (1H, d, J=0.8 Hz), 8.13 (1H, dd, J=8.2, 1.2 Hz), 7.99 (1H, dd, J=7.6, 1.4 Hz), 7.71-7.82 (4H, m), 7.60-7.69 (1H, m), 6.03 (1H, q, J=7.2 Hz), 1.88 (3H, d, J=7.0 Hz); LC-MS (ESI) m/z 420.1 [M+H]$^+$.

(1S)-1-(8-Chloro-2-(thiazol-5-yl)quinolin-3-yl) ethanamine

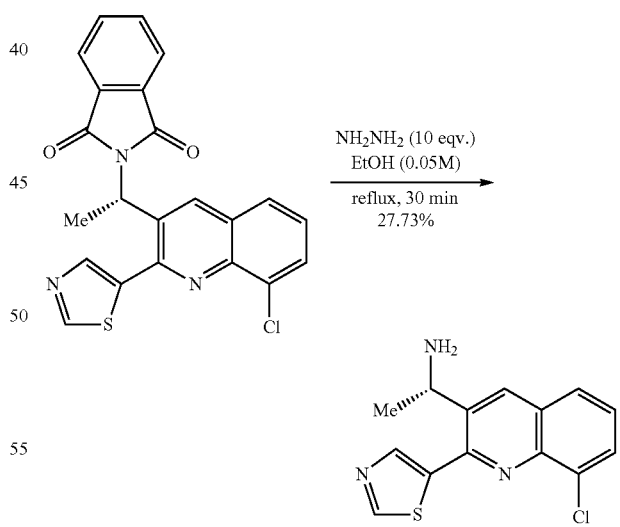

To a suspension of 2-((S)-1-(8-chloro-2-(thiazol-5-yl)quinolin-3-yl)ethyl)-isoindoline-1,3-dione (0.1280 g, 0.3048 mmol) in ethanol (6.097 mL, 0.3048 mmol) was added hydrazine, anhydrous (0.09568 mL, 3.048 mmol), and the mixture was stirred under reflux. After 30 min, the mixture was cooled to room temperature. The mixture was concentrated under reduced pressure. The residue was purified by column chromatography on a 40 g of Redi-Sep™ column using 0% to 100% gradient of CH₂Cl₂:MeOH:NH₄OH (89:9:1) in CH₂Cl₂ over 14 min and then 100% isocratic of CH₂Cl₂:MeOH:NH₄OH (89:9:1) in CH₂Cl₂ for 5 min as eluent to give (1S)-1-(8-chloro-2-(thiazol-5-yl)quinolin-3-yl)ethanamine as a solid: ¹H NMR (400 MHz, DMSO-d₆) δ ppm 9.26 (1H, s), 8.77 (1H, s), 8.49 (1H, s), 8.00 (1H, dd, J=8.2, 1.2 Hz), 7.93 (1H, dd, J=7.4, 1.2 Hz), 7.58 (1H, dd, J=8.2, 7.4 Hz), 4.63 (1H, q, J=6.4 Hz), 1.42 (3H, d, J=6.7 Hz); LC-MS (ESI) m/z 290.0 [M+H]⁺.

N—((S)-1-(8-Chloro-2-(thiazol-5-yl)quinolin-3-yl)ethyl)-9H-purin-6-amine as a TFA Salt

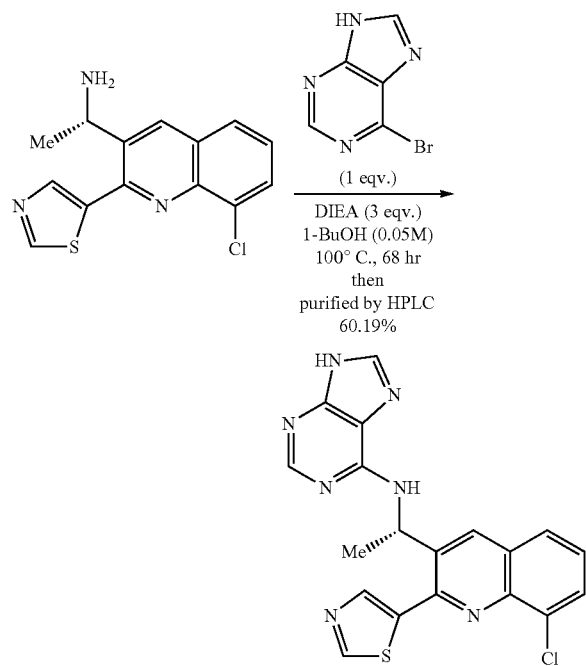

A mixture of 6-bromopurine (0.01634 g, 0.08213 mmol), (1S)-1-(8-chloro-2-(thiazol-5-yl)quinolin-3-yl)ethanamine (0.02380 g, 0.08213 mmol), and N,N-diisopropylethylamine (0.04292 mL, 0.2464 mmol) in 1-butanol (1.521 mL, 0.08213 mmol) was stirred at 100° C. After 68 h, the mixture was removed from the heat and concentrated under reduced pressure. The crude mixture was purified (1.5 mL (42.86 mg)×1 injection) by semi-prep-HPLC on a Gemini™ 10µ C18 column (250×21.2 mm, 10 µm) using 20-70% gradient of CH₃CN (0.1% of TFA) in water (0.1% of TFA) over 40 min as eluent, and dried on the lyophilizer to give N—((S)-1-(8-chloro-2-(thiazol-5-yl)quinolin-3-yl)ethyl)-9H-purin-6-amine as a TFA salt as a light yellow solid: ¹H NMR (400 MHz, DMSO-d₆) δ ppm 9.27 (1H, s), 8.92 (1H, s), 8.67 (1H, s), 8.54 (1H, s), 8.25-8.40 (2H, m), 7.95 (2H, d, J=7.8 Hz), 7.53-7.62 (1H, m), 5.97 (1H, s), 1.70 (3H, d, J=5.5 Hz); LC-MS (ESI) m/z 408.1 [M+H]⁺ (Exact Mass of neutral form: 407.072).

Example 108: Preparation of N—((S)-1-(5-Chloro-2-(3-fluorophenyl)quinolin-3-yl)ethyl)-9H-purin-6-amine and N—((R)-1-(5-Chloro-2-(3-fluorophenyl)-quinolin-3-yl)ethyl)-9H-purin-6-amine 5-Chloro-2-(3-fluorophenyl)quinoline-3-carbaldehyde

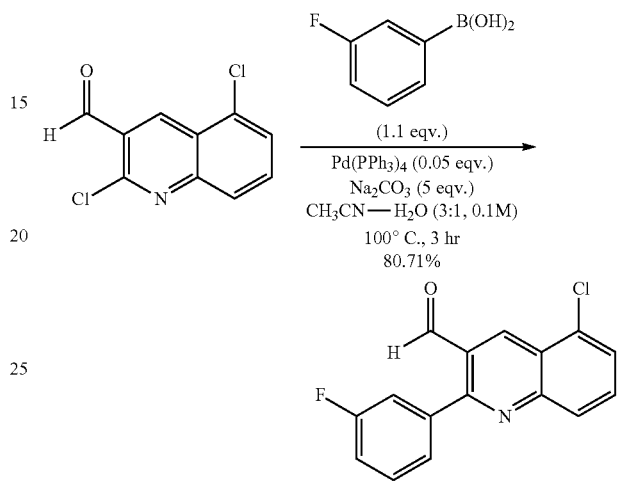

A mixture of 2,5-dichloroquinoline-3-carbaldehyde (1.0000 g, 4.424 mmol), 3-fluorophenylboronic acid (0.6808 g, 4.866 mmol), tetrakis(triphenylphosphine)-palladium (0.2556 g, 0.2212 mmol), and sodium carbonate anhydrous (2.344 g, 22.12 mmol) in acetonitrile-water (3:1) (0.04000 mL) was stirred at 100° C. After 3 h, the mixture was cooled to room temperature and partitioned between EtOAc (100 mL) and water (100 mL). The organic layer was washed with brine (50 mL×2), dried over Na₂SO₄, filtered, and concentrated under reduced pressure. The residue was purified by silica gel column chromatography on a 80 g of Redi-Sep™ column using 0 to 50% gradient of EtOAc in hexane over 25 min and then 50% isocratic of EtOAc for 10 min as eluent to give 5-chloro-2-(3-fluorophenyl)-quinoline-3-carbaldehyde as a yellow solid: ¹H NMR (400 MHz, DMSO-d₆) δ ppm 10.14 (1H, s), 9.06 (1H, d, J=0.8 Hz), 8.13-8.18 (1H, m), 7.92-8.00 (2H, m), 7.59-7.67 (2H, m), 7.53-7.58 (1H, m), 7.39-7.47 (1H, m); LC-MS (ESI) m/z 286.0 [M+H]⁺.

1-(5-Chloro-2-(3-fluorophenyl)quinolin-3-yl)ethanol

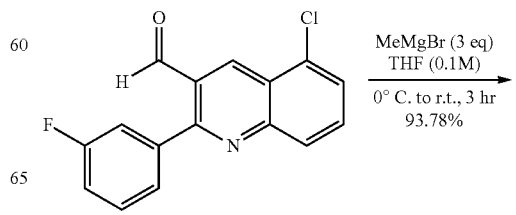

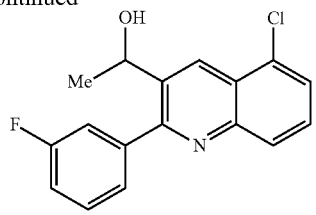

To a stirring heterogeneous mixture of 5-chloro-2-(3-fluorophenyl)quinoline-3-carbaldehyde (1.0120 g, 3.542 mmol) in tetrahydrofuran (35.42 mL, 3.542 mmol) was added methylmagnesium bromide 3 M in diethyl ether (3.542 mL, 10.63 mmol) dropwise at 0° C. (started at 11:10 am), and the mixture was then stirred at room temperature. After 3 h, the reaction was quenched with saturated aq. NH$_4$Cl (50 mL) and extracted with EtOAc (50 mL×2). The combined organic layers were washed with water (50 mL×1), brine (50 mL×1), dried over Na$_2$SO$_4$, filtered, and concentrated under reduced pressure. The residue was purified by silica gel column chromatography on a 80 g of Redi-Sep™ column using 0 to 50% gradient of EtOAc in hexane over 25 min and then 50% isocratic of EtOAc for 10 min as eluent to give 1-(5-chloro-2-(3-fluorophenyl)quinolin-3-yl)ethanol as a yellow solid: $^1$H NMR (400 MHz, DMSO-d$_6$) δ ppm 8.79 (1H, s), 8.00-8.05 (1H, m), 7.73-7.85 (2H, m), 7.54-7.63 (1H, m), 7.41-7.47 (2H, m), 7.33-7.40 (1H, m), 5.56 (1H, d, J=4.3 Hz), 4.98-5.06 (1H, m), 1.27 (3H, d, J=6.7 Hz); LC-MS (ESI) m/z 302.0 [M+H]$^+$.

2-(1-(5-Chloro-2-(3-fluorophenyl)quinolin-3-yl)ethyl)isoindoline-1,3-dione

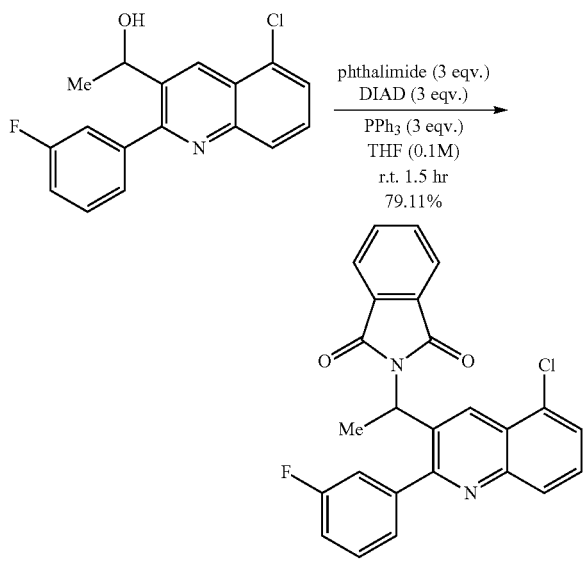

To a solution of 1-(5-chloro-2-(3-fluorophenyl)quinolin-3-yl)ethanol (0.9927 g, 3.290 mmol) in tetrahydrofuran (32.90 mL, 3.290 mmol) were added triphenylphosphine (2.589 g, 9.870 mmol), phthalimide (1.452 g, 9.870 mmol), and diisopropyl azodicarboxylate (1.943 mL, 9.870 mmol). The reaction mixture was stirred at room temperature. After 1.5 h, the mixture was concentrated under reduced pressure and partitioned between EtOAc (100 mL) and brine (100 mL). The organic layer was dried over Na$_2$SO$_4$, filtered, and concentrated under reduced pressure. The residue was purified by silica gel column chromatography on a 80 g of Redi-Sep™ column using 0 to 50% gradient of EtOAc in hexane over 25 min and 50% isocratic of EtOAc for 10 min as eluent to give 2-(1-(5-chloro-2-(3-fluorophenyl)quinolin-3-yl)ethyl)isoindoline-1,3-dione as a light yellow solid: $^1$H NMR (400 MHz, DMSO-d$_6$) δ ppm 8.84 (1H, s), 7.98-8.04 (1H, m), 7.85-7.90 (1H, m), 7.82 (1H, s), 7.74-7.81 (2H, m), 7.65-7.71 (2H, m), 7.21-7.33 (2H, m), 7.12-7.19 (2H, m), 5.76-5.82 (1H, m), 1.83 (3H, d, J=6.7 Hz); LC-MS (ESI) m/z 431.0 [M+H]$^+$.

1-(5-Chloro-2-(3-fluorophenyl)quinolin-3-yl)ethanamine

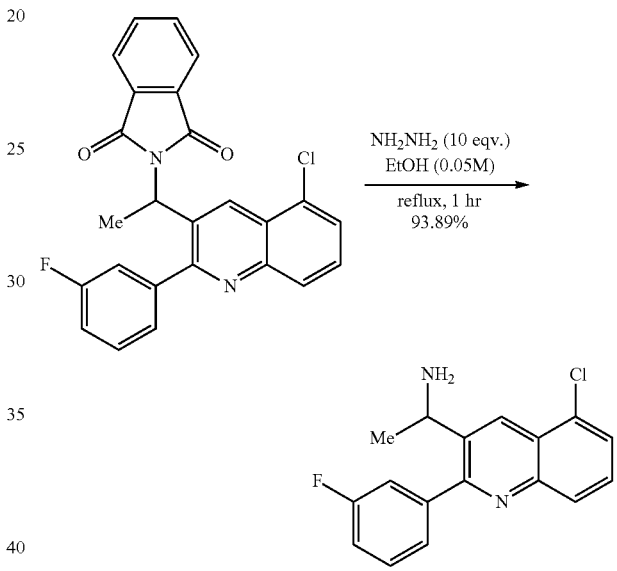

To a suspension of 2-(1-(5-chloro-2-(3-fluorophenyl)quinolin-3-yl)ethyl)-isoindoline-1,3-dione (1.1115 g, 2.580 mmol) in ethanol (51.59 mL, 2.580 mmol) was added hydrazine, anhydrous (0.8097 mL, 25.80 mmol), and the mixture was stirred under reflux. After 1 h, the mixture was cooled to room temperature. The mixture was diluted with CH$_2$Cl$_2$ (50 mL), filtered to removed the precipitated byproduct, and washed the filtered solid with CH$_2$Cl$_2$ (50 mL). The filtrate containing the desired product was concentrated under reduced pressure. The residue was purified by column chromatography on a 80 g of Redi-Sep™ column using 0% to 100% gradient of CH$_2$Cl$_2$:MeOH:NH$_4$OH (89:9:1) in CH$_2$Cl$_2$ over 25 min, and then 100% isocratic of CH$_2$Cl$_2$:MeOH:NH$_4$OH (89:9:1) for 4 min as eluent to give 1-(5-chloro-2-(3-fluorophenyl)quinolin-3-yl)ethanamine as a yellow syrup: $^1$H NMR (400 MHz, DMSO-d$_6$) δ ppm 8.87 (1H, s), 7.97-8.02 (1H, m), 7.78-7.82 (1H, m), 7.73 (1H, dd, J=8.4, 7.6 Hz), 7.52-7.61 (1H, m), 7.41-7.50 (2H, m), 7.31-7.39 (1H, m), 4.29 (1H, q, J=6.7 Hz), 2.10 (2H, br. s.), 1.19 (3H, d, J=6.7 Hz); LC-MS (ESI) m/z 301.1 [M+H]$^+$.

215

N—((S)-1-(5-Chloro-2-(3-fluorophenyl)quinolin-3-yl)ethyl)-9H-purin-6-amine and N—((R)-1-(5-Chloro-2-(3-fluorophenyl)quinolin-3-yl)ethyl)-9H-purin-6-amine

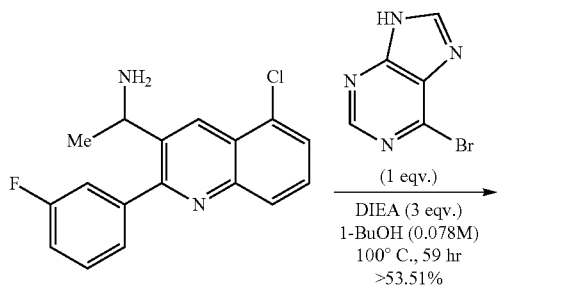

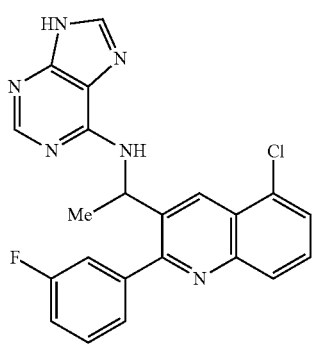

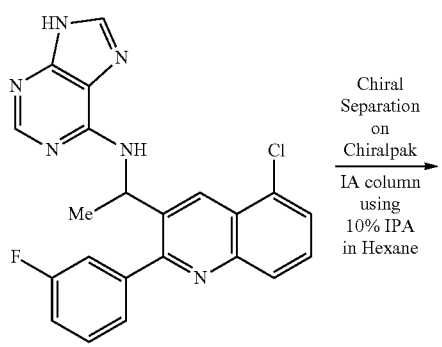

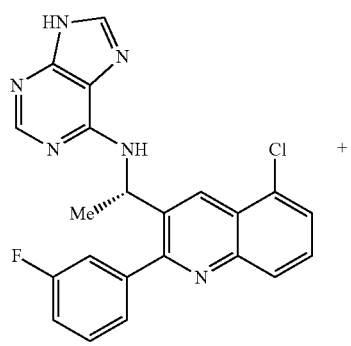

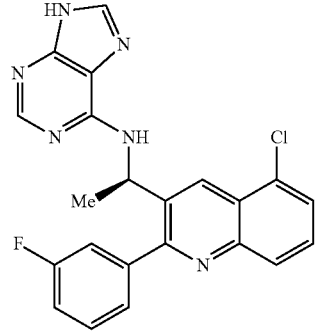

A mixture of 6-bromopurine (0.4753 g, 2.388 mmol), 1-(5-chloro-2-(3-fluoro-phenyl)quinolin-3-yl)ethanamine (0.7183 g, 2.388 mmol), and N,N-diisopropylethylamine (1.248 mL, 7.165 mmol) in 1-butanol (20.00 mL, 2.388 mmol) was stirred at 110° C. After 59 h, the mixture was removed from the heat and concentrated under reduced pressure. The residue was purified by column chromatography on a 80 g of Redi-Sep™ column using 0% to 50% gradient of $CH_2Cl_2$:MeOH:$NH_4OH$ (89:9:1) in $CH_2Cl_2$ over 20 min and then 50% isocratic of $CH_2Cl_2$:MeOH:$NH_4OH$ (89:9:1) in $CH_2Cl_2$ for 20 min as eluent to give the desired product as a racemic mixture as a tan solid (0.7361 g,). The tan solid was suspended in MeOH, sonicated, and filtered to give N-(1-(5-chloro-2-(3-fluorophenyl)quinolin-3-yl)ethyl)-9H-purin-6-amine as a racemic mixture as a white solid. The racemic mixture (0.1486 g) was separated (3 injections of ~50 mg in 1.5 mL) on a Chiralpak™ IA column (30×250 mm, 5 μm) using 10% isocratic of isopropanol in hexane for 40 min as eluent to give two separated isomers: N—((S)-1-(5-chloro-2-(3-fluorophenyl)quinolin-3-yl)ethyl)-9H-purin-6-amine as a light yellow solid: $^1$H NMR (400 MHz, DMF) δ ppm 12.92 (1H, br. s.), 8.83 (1H, br. s.), 8.63 (1H, br. s.), 8.11 (2H, d, J=18.4 Hz), 8.00 (1H, d, J=8.2 Hz), 7.53-7.81 (5H, m), 7.29-7.39 (1H, m), 5.61 (1H, br. s.), 1.47 (3H, br. s.); LC-MS (ESI) m/z 419.2 [M+H]$^+$ and N—((R)-1-(5-chloro-2-(3-fluoro-phenyl)quinolin-3-yl)ethyl)-9H-purin-6-amine as a light yellow solid: $^1$H NMR (400 MHz, DMSO-d$_6$) δ ppm 12.93 (1H, s), 8.84 (1H, s), 8.63 (1H, s), 8.10 (2H, d, J=18.0 Hz), 8.00 (1H, d, J=8.2 Hz), 7.52-7.81 (5H, m), 7.28-7.39 (1H, m), 5.62 (1H, br. s.), 1.47 (3H, br. s.); LC-MS (ESI) m/z 419.2 [M+H]$^+$.

Example 109: Preparation of N—((S)-1-(8-Chloro-2-(2,3-difluorophenyl)-quinolin-3-yl)ethyl)-9H-purin-6-amine 2-((S)-1-(8-Chloro-2-(2,3-difluorophenyl)quinolin-3-yl)ethyl)carbamoyl)-benzoic acid

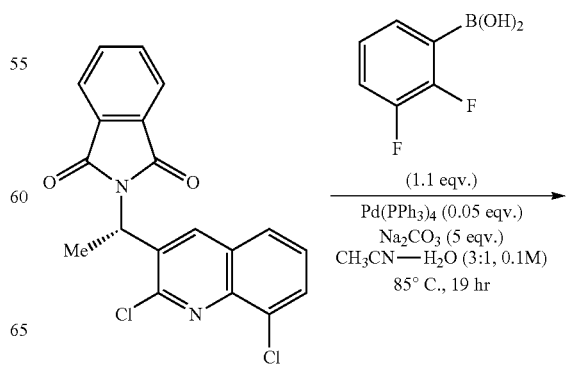

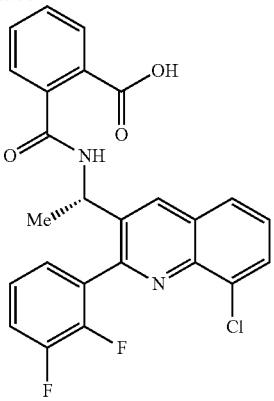

A mixture of (S)-2-(1-(2,8-dichloroquinolin-3-yl)ethyl)isoindoline-1,3-dione (0.2000 g, 0.5388 mmol), 2,3-difluorobenzeneboronic acid (0.09358 g, 0.5926 mmol), tetrakis(triphenylphosphine)palladium (0.03113 g, 0.02694 mmol), and sodium carbonate anhydrous (0.2855 g, 2.694 mmol) in acetonitrile-water (3:1) (5.200 mL, 0.5387 mmol) was stirred at 85° C. After 19 h, the mixture was cooled to room temperature and partitioned between CH$_2$Cl$_2$ (30 mL) and 2 N HCl (30 mL). The organic layer was washed with brine (50 mL×2), dried over Na$_2$SO$_4$, filtered, and concentrated under reduced pressure to give 2-(((S)-1-(8-chloro-2-(2,3-difluorophenyl)quinolin-3-yl)ethyl)carbamoyl)benzoic acid as a yellow foam type solid: LC-MS (ESI) m/z 467.0 [M+H]$^+$.

(1S)-1-(8-Chloro-2-(2,3-difluorophenyl)quinolin-3-yl)ethanamine

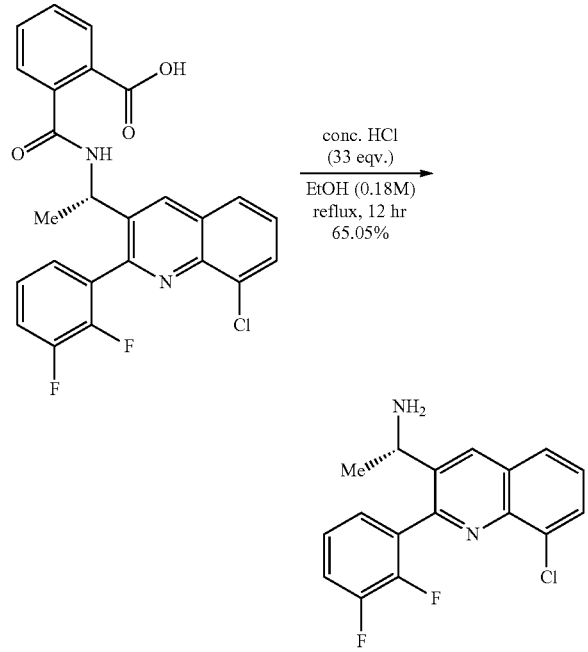

To a suspension of 2-(((S)-1-(8-chloro-2-(2,3-difluorophenyl)quinolin-3-yl)ethyl)-carbamoyl)benzoic acid (0.2515 g, 0.5387 mmol) in ethanol (3.000 mL, 0.5387 mmol) was added 12 N HCl (1.500 mL, 18.00 mmol), and the mixture was stirred under reflux. After 12 h, the mixture was poured into ice water (50 mL). The mixture was neutralized with NaHCO$_3$ and extracted with CH$_2$Cl$_2$ (50 mL×3). The combined organic layers were washed with brine (50 mL×3), dried over Na$_2$SO$_4$, filtered, and concentrated under reduced pressure. The residue was purified by column chromatography on a 40 g of Redi-Sep™ column using 0% to 50% gradient of CH$_2$Cl$_2$:MeOH:NH$_4$OH (89:9:1) in CH$_2$Cl$_2$ over 14 min and then 50% isocratic of CH$_2$Cl$_2$:MeOH:NH$_4$OH (89:9:1) in CH$_2$Cl$_2$ for 5 min as eluent to give (1S)-1-(8-chloro-2-(2,3-difluorophenyl)quinolin-3-yl)ethanamine as a light green syrup: LC-MS (ESI) m/z 319.1 [M+H]$^+$.

N—((S)-1-(8-Chloro-2-(2,3-difluorophenyl)quinolin-3-yl)ethyl)-9H-purin-6-amine

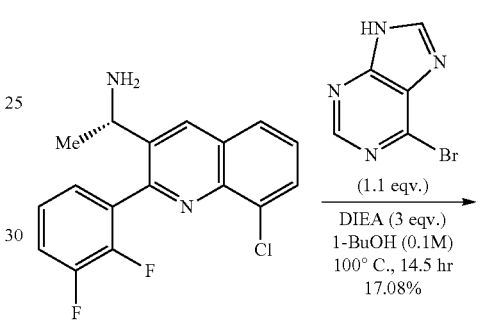

A mixture of 6-bromopurine (0.07479 g, 0.3758 mmol), (1S)-1-(8-chloro-2-(2,3-difluorophenyl)quinolin-3-yl)ethanamine (0.1089 g, 0.3416 mmol), and N,N-diisopropylethylamine (0.1785 mL, 1.025 mmol) in 1-butanol (3.416 mL, 0.3416 mmol) was stirred at 110° C. After 14.5 h, the mixture was removed from the heat and concentrated under reduced pressure. The residue was purified by column chromatography on a 40 g of Redi-Sep™ column using 0 to 50% gradient of CH$_2$Cl$_2$:MeOH:NH$_4$OH (89:9:1) in CH$_2$Cl$_2$ over 14 min and then 50% isocratic of CH$_2$Cl$_2$:MeOH:NH$_4$OH (89:9:1) in CH$_2$Cl$_2$ for 20 min as eluent to give N—((S)-1-(8-chloro-2-(2,3-difluorophenyl)quinolin-3-yl)ethyl)-9H-purin-6-amine as a light yellow solid: $^1$H NMR (400 MHz, DMSO-d$_6$) δ ppm 12.86 (1H, s), 8.71 (1H, s), 7.91-8.28 (5H, m), 7.61 (1H, t, J=7.8 Hz), 7.47 (2H, br. s.), 7.29 (1H, br. s.), 5.42 (1H, br. s.), 1.58 (3H, d, J=7.0 Hz); LC-MS (ESI) m/z 437.2 [M+H]+.

Example 110: Preparation of N—((S)-1-(3-(2-chlorophenyl)-5-(trifluoro-methyl)quinoxalin-2-yl)ethyl)-9H-purin-6-amine and N—((R)-1-(3-(2-chlorophenyl)-5-(trifluoromethyl)quinoxalin-2-yl)ethyl)-9H-purin-6-amine

3-Methyl-8-(trifluoromethyl)quinoxalin-2-ol and 3-Methyl-5-(trifluoro-methyl)quinoxalin-2-ol

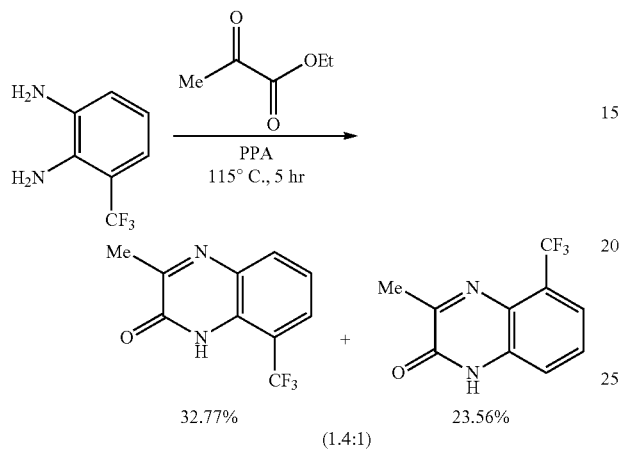

A mixture of ethyl pyruvate (1.262 mL, 11.35 mmol) and 3-(trifluoromethyl)-benzene-1,2-diamine (2.0000 g, 11.35 mmol) in polyphosphoric acid (16.000 g) was stirred and heated at 115° C. After 5 h, the mixture was cooled to room temperature, thoroughly mixed with water (100 mL), and neutralized with 2 N NaOH (160 mL). The resulting precipitate was collected by filtration and the solid was washed with water (250 mL) and dried to give a dark brown solid as a mixture of two regioisomers. The dark brown solid was purified by flash column chromatography on a silica gel column (~400 mL volume of $SiO_2$) using 30% of EtOAc in hexane and then 50% of EtOAc in hexane to give two separated regioisomers: 3-methyl-8-(trifluoromethyl)quinoxalin-2-ol as an orange solid: $^1$H NMR (400 MHz, DMSO-$d_6$) δ ppm 11.73 (1H, s), 8.00 (1H, s), 7.86 (1H, s), 7.45 (1H, s), 2.45 (3H, s); LC-MS (ESI) m/z 229.0 [M+H]$^+$ and 3-methyl-5-(trifluoromethyl)quinoxalin-2-ol as an orange solid: $^1$H NMR (400 MHz, DMSO-$d_6$) δ ppm 12.58 (1H, s), 7.58-7.64 (2H, m), 7.51-7.57 (1H, m), 2.44 (3H, s); LC-MS (ESI) m/z 229.0 [M+H]$^+$.

3-Chloro-2-methyl-5-(trifluoromethyl)quinoxaline

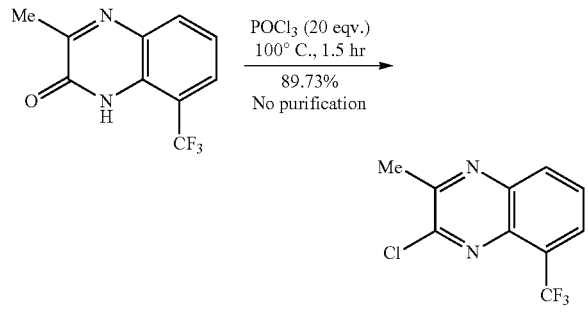

A mixture of 3-methyl-8-(trifluoromethyl)quinoxalin-2-ol (0.8292 g, 3.634 mmol) and phosphorous oxychloride (6.653 mL, 72.68 mmol) was stirred at 100° C. After 1.5 h, the mixture was cooled to room temperature. The mixture was poured into ice (~50 mL) with stirring and neutralized with $NH_4OH$ (30 mL) and ice with stirring. The resulting precipitate was collected by filtration, rinsed with water (100 mL), and dried to give 3-chloro-2-methyl-5-(trifluoromethyl)-quinoxaline as a pink solid: $^1$H NMR (400 MHz, DMF) δ ppm 8.35 (1H, d, J=8.4 Hz), 8.25 (1H, d, J=7.4 Hz), 7.94-8.02 (1H, m), 2.80 (3H, s); LC-MS (ESI) m/z 247.0 [M+H]$^+$. The pink solid was carried on crude without purification for the next step.

3-(2-Chlorophenyl)-2-methyl-5-(trifluoromethyl)quinoxaline

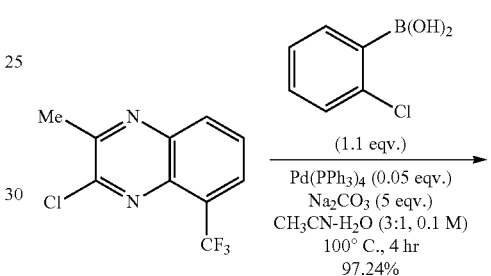

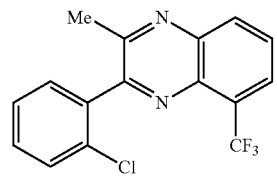

A mixture of 3-chloro-2-methyl-5-(trifluoromethyl)quinoxaline (0.7939 g, 3.219 mmol), [Reactants], tetrakis(triphenylphosphine)palladium (0.1860 g, 0.1610 mmol), and sodium carbonate anhydrous (1.706 g, 16.10 mmol) in $CH_3CN$—$H_2O$ (3:1) (32.00 mL) was stirred at 100° C. After 4 h, the mixture was cooled to room temperature and partitioned between EtOAc (100 mL) and water (100 mL). The organic layer was washed with brine (50 mL×2), dried over $Na_2SO_4$, filtered, and concentrated under reduced pressure. The residue was purified by silica gel column chromatography on a 80 g of Redi-Sep™ column using 0 to 50% gradient of EtOAc in hexane over 15 min and then 50% isocratic of EtOAc for 4 min as eluent to give 3-(2-chlorophenyl)-2-methyl-5-(trifluoromethyl)quinoxaline as an orange syrup: $^1$H NMR (400 MHz, DMSO-$d_6$) δ ppm 8.36-8.41 (1H, m), 8.25 (1H, d, J=7.4 Hz), 8.01 (1H, t, J=7.8 Hz), 7.66-7.71 (1H, m), 7.54-7.65 (3H, m), 2.54 (3H, s); LC-MS (ESI) m/z 323.0 [M+H]$^+$.

2-(Bromomethyl)-3-(2-chlorophenyl)-5-(trifluoromethyl)quinoxaline

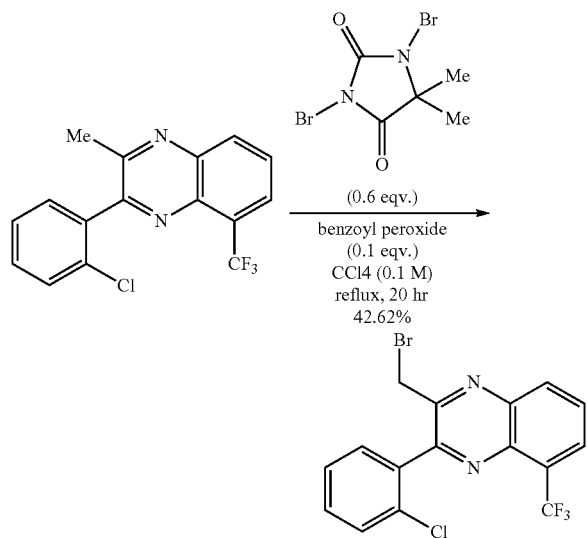

3-(2-Chlorophenyl)-2-methyl-5-(trifluoromethyl)quinoxaline (0.9969 g, 3.089 mmol) and 1,3-dibromo-5,5-dimethylhydantoin (0.5299 g, 1.853 mmol) were suspended in carbon tetrachloride (30.89 mL, 3.089 mmol). To the mixture was added benzoyl peroxide (0.09977 g, 0.3089 mmol) and the mixture was heated at reflux. After 20 h, the mixture was cooled to room temperature and concentrated under reduced pressure. The residue was purified by silica gel column chromatography on a 80 g of Redi-Sep™ column using 0 to 5% gradient of EtOAc in hexane over 10 min, then 5% isocratic of EtOAc for 30 min, then 5 to 20% gradient of EtOAc in hexane over 20 min, then 20% isocratic of EtOAc for 4 min as eluent to give 2-(bromomethyl)-3-(2-chlorophenyl)-5-(trifluoromethyl)-quinoxaline as an off-white syrupy solid: $^1$H NMR (400 MHz, DMSO-$d_6$) δ ppm 8.48 (1H, dd, J=8.6, 0.8 Hz), 8.37 (1H, d, J=6.7 Hz), 8.09 (1H, t, J=7.8 Hz), 7.55-7.77 (4H, m), 4.73 (2H, d, J=61.8 Hz); LC-MS (ESI) m/z 403.0 [M+H]$^+$.

3-(2-Chlorophenyl)-5-(trifluoromethyl)quinoxaline-2-carbaldehyde

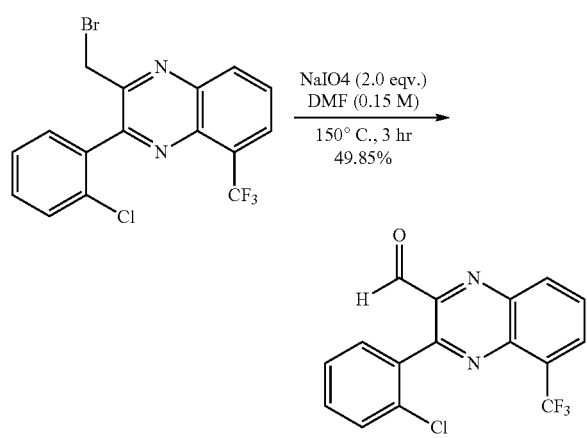

A mixture of 2-(bromomethyl)-3-(2-chlorophenyl)-5-(trifluoromethyl)quinoxaline (0.5137 g, 1.279 mmol) and sodium metaperiodate (0.1416 mL, 2.558 mmol) in DMF (8.527 mL, 1.279 mmol) was heated at 150° C. with stirring. After 3 h, the mixture was cooled to room temperature, diluted with EtOAc (100 mL), washed with brine (50 mL×2), dried over Na$_2$SO$_4$, filtered, and concentrated under reduced pressure. The residue was purified by silica gel column chromatography on a 80 g of Redi-Sep™ column using 0 to 10% gradient of EtOAc in hexane over 10 min, then 10% isocratic of EtOAc for 20 min, then 10 to 40% gradient of EtOAc in hexane over 20 min, then 40% isocratic of EtOAc for 5 min as eluent to give 3-(2-chlorophenyl)-5-(trifluoromethyl)quinoxaline-2-carbaldehyde as a yellow syrup: $^1$H NMR (400 MHz, DMSO-$d_6$) δ ppm 10.15 (1H, s), 8.66 (1H, dd, J=8.6, 1.2 Hz), 8.52 (1H, d, J=7.0 Hz), 8.18 (1H, t, J=8.0 Hz), 7.53-7.67 (4H, m); LC-MS (ESI) m/z 337.0 [M+H]$^+$.

1-(3-(2-Chlorophenyl)-5-(trifluoromethyl)quinoxalin-2-yl)ethanol

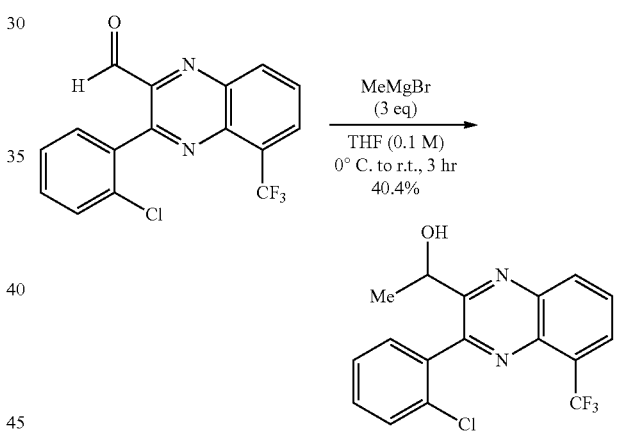

To a stirring heterogeneous mixture of 3-(2-chlorophenyl)-5-(trifluoromethyl)-quinoxaline-2-carbaldehyde (0.2129 g, 0.632 mmol) in tetrahydrofuran (6.32 mL, 0.632 mmol) was added methylmagnesium bromide 3 M in diethyl ether (0.632 mL, 1.90 mmol) dropwise at 0° C. (started at 11:20 am), and the mixture was then stirred at room temperature. After 3 h, the reaction was quenched with saturated aq. NH$_4$Cl (50 mL) and extracted with EtOAc (50 mL×2). The combined organic layers were washed with water (50 mL×1), brine (50 mL×1), dried over Na$_2$SO$_4$, filtered, and concentrated under reduced pressure to give a brown syrup. The brown syrup was purified by silica gel column chromatography on a 80 g of Redi-Sep™ column using 0 to 50% gradient of EtOAc in hexane over 25 min and then 50% isocratic of EtOAc for 10 min as eluent to give 1-(3-(2-chlorophenyl)-5-(trifluoromethyl)quinoxalin-2-yl)ethanol as a solid: $^1$H NMR (400 MHz, DMSO-$d_6$) δ ppm 8.47 (1H, d, J=8.6 Hz), 8.31 (1H, d, J=7.0 Hz), 8.05 (1H, t, J=8.0 Hz), 7.48-7.71 (4H, m), 5.33 (1H, br. s.), 4.84 (1H, br. s.), 1.28-1.55 (3H, m); LC-MS (ESI) m/z 353.0 [M+H]$^+$.

2-(1-(3-(2-Chlorophenyl)-5-(trifluoromethyl)quinoxalin-2-yl)ethyl)-isoindoline-1,3-dione

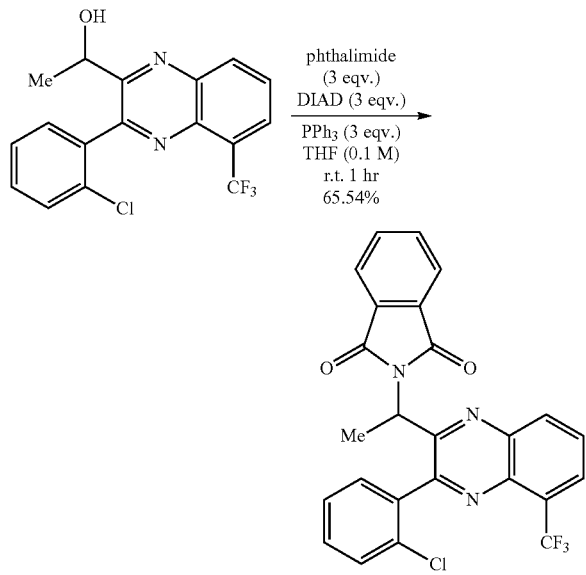

To a solution of 1-(3-(2-chlorophenyl)-5-(trifluoromethyl)quinoxalin-2-yl)ethanol (0.08980 g, 0.2546 mmol) in tetrahydrofuran (2.546 mL, 0.2546 mmol) were added triphenylphosphine (0.2003 g, 0.7637 mmol), phthalimide (0.1124 g, 0.7637 mmol), and diisopropyl azodicarboxylate (0.1504 mL, 0.7637 mmol). The reaction mixture was stirred at room temperature. After 1 h, the mixture was concentrated under reduced pressure and partitioned between EtOAc (100 mL) and brine (100 mL). The organic layer was dried over Na$_2$SO$_4$, filtered, and concentrated under reduced pressure. The residue was purified by silica gel column chromatography on a 40 g of Redi-Sep™ column using 0 to 50% gradient of EtOAc in hexane over 20 min and 50% isocratic of EtOAc for 10 min as eluent to give 2-(1-(3-(2-chlorophenyl)-5-(trifluoromethyl)quinoxalin-2-yl)ethyl)-isoindoline-1,3-dione as a yellow solid: LC-MS (ESI) m/z 482.0 [M+H]$^+$.

1-(3-(2-Chlorophenyl)-5-(trifluoromethyl)quinoxalin-2-yl)ethanamine

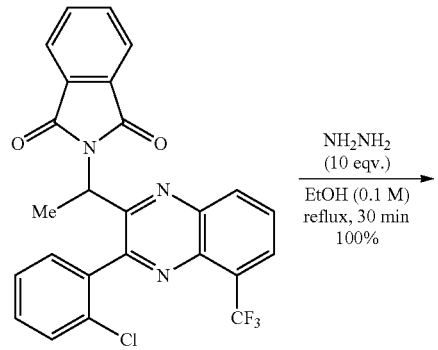

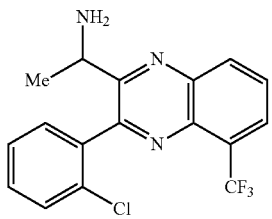

To a suspension of 2-(1-(3-(2-chlorophenyl)-5-(trifluoromethyl)quinoxalin-2-yl)-ethyl)isoindoline-1,3-dione (0.07720 g, 0.160 mmol) in ethanol (3.20 mL, 0.160 mmol) was added hydrazine hydrate (0.0499 mL, 1.60 mmol), and the mixture was stirred under reflux. After 30 min, the mixture was cooled to room temperature. The mixture was concentrated under reduced pressure. The residue was purified by column chromatography on a 40 g of Redi-Sep™ column using 0% to 100% gradient of CH$_2$Cl$_2$:MeOH:NH$_4$OH (89:9:1) in CH$_2$Cl$_2$ over 14 min, and then 100% isocratic of CH$_2$Cl$_2$:MeOH:NH$_4$OH (89:9:1) for 3 min as eluent to give 1-(3-(2-chlorophenyl)-5-(trifluoromethyl)quinoxalin-2-yl)ethanamine as a yellow syrup: LC-MS (ESI) m/z 352.1 [M+H]$^+$.

N—((S)-1-(3-(2-Chlorophenyl)-5-(trifluoromethyl)quinoxalin-2-yl)ethyl)-9H-purin-6-amine and N—((R)-1-(3-(2-Chlorophenyl)-5-(trifluoromethyl)-quinoxalin-2-yl)ethyl)-9H-purin-6-amine

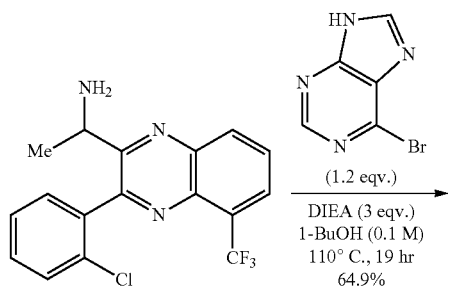

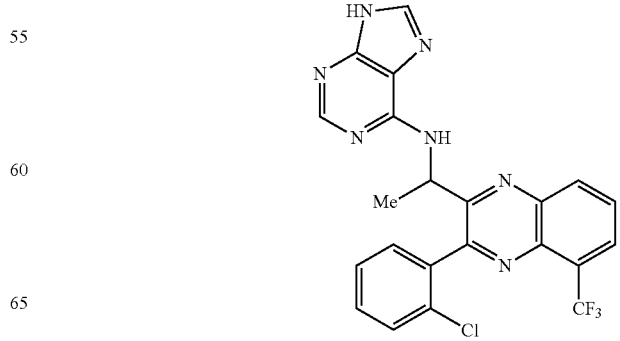

-continued

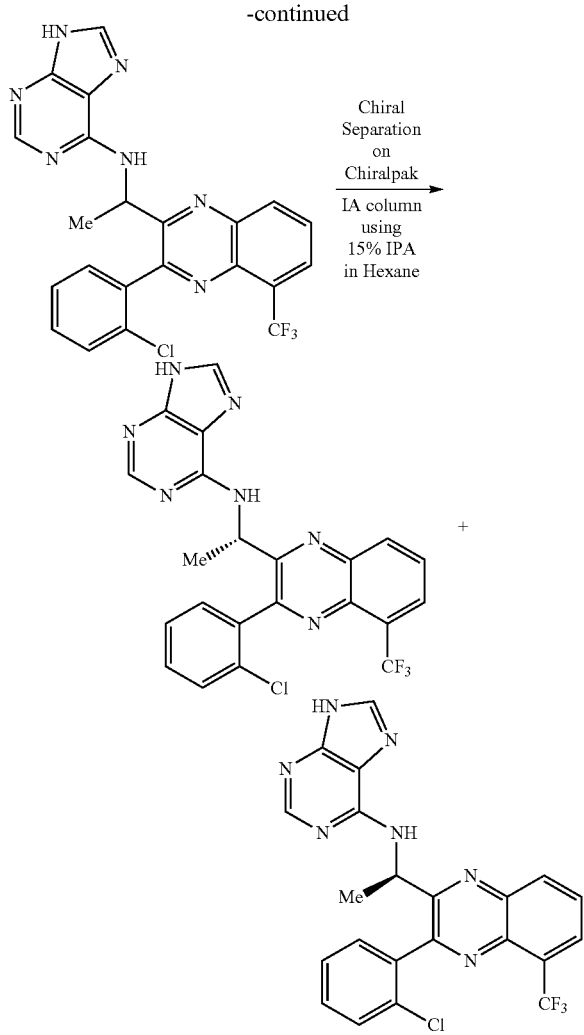

A mixture of 6-bromopurine (0.0383 g, 0.192 mmol), 1-(3-(2-chlorophenyl)-5-(trifluoromethyl)quinoxalin-2-yl)ethanamine (0.0564 g, 0.160 mmol), and N,N-diisopropylethylamine (0.0838 mL, 0.481 mmol) in 1-butanol (1.60 mL, 0.160 mmol) was stirred at 110° C. After 19 h, the mixture was removed from the heat and concentrated under reduced pressure. The residue was purified by column chromatography on a 40 g of Redi-Sep™ column using 0 to 50% gradient of $CH_2Cl_2$:MeOH:$NH_4OH$ (89:9:1) in $CH_2Cl_2$ over 14 min and then 50% isocratic of $CH_2Cl_2$:MeOH:$NH_4OH$ (89:9:1) in $CH_2Cl_2$ for 20 min as eluent to give N-(1-(3-(2-chlorophenyl)-5-(trifluoromethyl)quinoxalin-2-yl)ethyl)-9H-purin-6-amine as a light yellow solid. The racemic mixture (0.0372 g) was separated on a Chiralpak™ IA column (30×250 mm, 5 μm) using 15% isocratic of isopropanol in hexane for 40 min as eluent to give two separated isomers: N—((S)-1-(3-(2-chlorophenyl)-5-(trifluoromethyl)quinoxalin-2-yl)ethyl)-9H-purin-6-amine as an off-white solid: $^1$H NMR (400 MHz, choroform-d) δ ppm 8.23-8.51 (2H, m), 8.06-8.19 (1H, m), 7.78-8.04 (2H, m), 7.32-7.67 (4H, m), 5.87 (1H, br. s.), 1.57 (3H, dd, J=67.4, 6.4 Hz); LC-MS (ESI) m/z 470.2 [M+H]$^+$ and N—((R)-1-(3-(2-chlorophenyl)-5-(trifluoromethyl)quinoxalin-2-yl)ethyl)-9H-purin-6-amine as an off-white solid: $^1$H NMR (400 MHz, choroform-d) δ ppm 8.23-8.49 (2H, m), 8.13 (1H, t, J=8.6 Hz), 7.78-8.04 (2H, m), 7.35-7.69 (4H, m), 5.86 (1H, br. s.), 1.44-1.70 (3H, m); LC-MS (ESI) m/z 470.2 [M+H]$^+$.

Example 111: Preparation of N—((S)-1-(2-(2-Chlorophenyl)-7-fluoroquinolin-3-yl)ethyl)-9H-purin-6-amine and N—((R)-1-(2-(2-Chlorophenyl)-7-fluoroquinolin-3-yl)ethyl)-9H-purin-6-amine 2-(2-Chlorophenyl)-7-fluoroquinoline-3-carbaldehyde

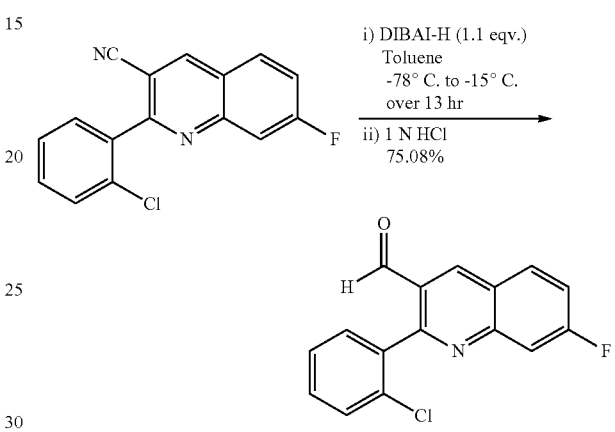

To a solution of 2-(2-chlorophenyl)-7-fluoroquinoline-3-carbonitrile (1.000 g, 3.537 mmol) in toluene (3.537 mL, 3.537 mmol) at −78° C. was added with stirring, DIBAL-H, 1 M sol. in Toluene (3.891 mL, 3.891 mmol) and the mixture was allowed to warm to −15° C. with stirring over 13 h. The mixture was cooled in ice water bath, quenched by addition of 1 N aq. HCl (14.15 mL, 14.15 mmol), and stirred for 2 h. To the mixture was added potassium acetate (3 g, 30.56 mmol, 8.6 eqv) and the mixture extracted with ethyl acetate (50 mL×2). The combined organic layers were washed saturated $NaHCO_3$ (50 mL×1), brine (50 mL×), filtered, and concentrated at reduced pressure to give a yellow solid. The yellow solid was purified by silica gel column chromatography on a 80 g of Redi-Sep™ column using 0 to 50% gradient of EtOAc in hexane over 25 min and then 50% isocratic of EtOAc for 10 min as eluent to give 2-(2-chlorophenyl)-7-fluoroquinoline-3-carbaldehyde as a light yellow solid: $^1$H NMR (400 MHz, DMSO-d$_6$) δ ppm 9.88 (1H, s), 9.11 (1H, s), 8.44 (1H, dd, J=9.1, 6.4 Hz), 7.92 (1H, dd, J=10.3, 2.6 Hz), 7.72-7.78 (1H, m), 7.50-7.66 (4H, m); LC-MS (ESI) m/z 286.1 [M+H]$^+$.

1-(2-(2-Chlorophenyl)-7-fluoroquinolin-3-yl)ethanol

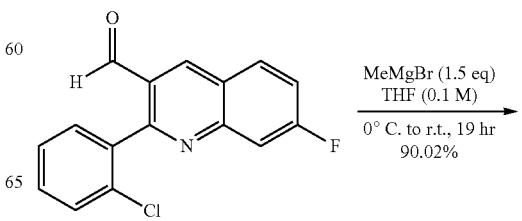

-continued

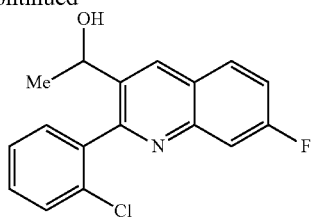

To a stirring mixture of 2-(2-chlorophenyl)-7-fluoroquinoline-3-carbaldehyde (0.7588 g, 2.656 mmol) in tetrahydrofuran (26.56 mL, 2.656 mmol) was added methylmagnesium bromide 3 M in diethyl ether (1.328 mL, 3.984 mmol) dropwise at 0° C. (started at 4:00 μm), and the mixture was allowed to warm to room temperature with stirring over 19 h. The reaction was quenched with saturated aq. NH$_4$Cl (50 mL) and extracted with EtOAc (50 mL×1). The combined organic layers were washed with water (50 mL×1), brine (50 mL×1), dried over Na$_2$SO$_4$, filtered, and concentrated under reduced pressure. The residue was purified by silica gel column chromatography on a 80 g of Redi-Sep™ column using 0 to 50% gradient of EtOAc in hexane over 25 min and then 50% isocratic of EtOAc for 10 min as eluent to give 1-(2-(2-chlorophenyl)-7-fluoroquinolin-3-yl)ethanol as a yellow syrup: $^1$H NMR (400 MHz, DMSO-d$_6$) δ ppm 8.63 (1H, d, J=11.0 Hz), 8.20 (1H, dd, J=8.6, 6.7 Hz), 7.75 (1H, dd, J=10.6, 2.7 Hz), 7.42-7.66 (5H, m), 5.39 (1H, dd, J=57.5, 3.9 Hz), 4.59-4.69 (1H, m), 1.20 (3H, dd, J=58.7, 6.3 Hz); LC-MS (ESI) m/z 302.0 [M+H]$^+$.

2-(1-(2-(2-Chlorophenyl)-7-fluoroquinolin-3-yl)ethyl)isoindoline-1,3-dione

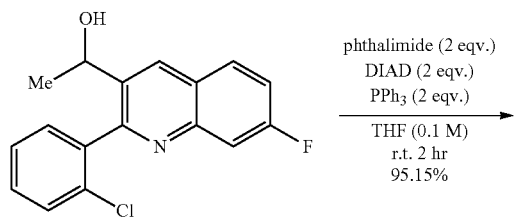

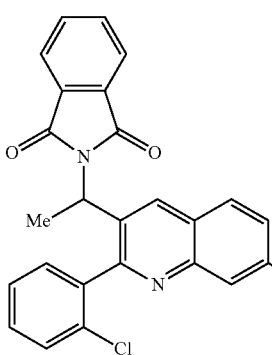

To a solution of 1-(2-(2-chlorophenyl)-7-fluoroquinolin-3-yl)ethanol (0.7018 g, 2.326 mmol) in tetrahydrofuran (23.26 mL, 2.326 mmol) were added triphenylphosphine (1.220 g, 4.652 mmol), phthalimide (0.6844 g, 4.652 mmol), and diisopropyl azodicarboxylate (0.9159 mL, 4.652 mmol). The reaction mixture was stirred at room temperature. After 2 h, the mixture was concentrated under reduced pressure and partitioned between EtOAc (100 mL) and brine (100 mL). The organic layer was dried over Na$_2$SO$_4$, filtered, and concentrated under reduced pressure. The residue was purified by silica gel column chromatography on a 80 g of Redi-Sep™ column using 0 to 50% gradient of EtOAc in hexane over 25 min and 50% isocratic of EtOAc in hexane for 10 min as eluent to 2-(1-(2-(2-chlorophenyl)-7-fluoroquinolin-3-yl)ethyl)isoindoline-1,3-dione as an off-white solid: LC-MS (ESI) m/z 431.0 [M+H]$^+$.

1-(2-(2-Chlorophenyl)-7-fluoroquinolin-3-yl)ethanamine

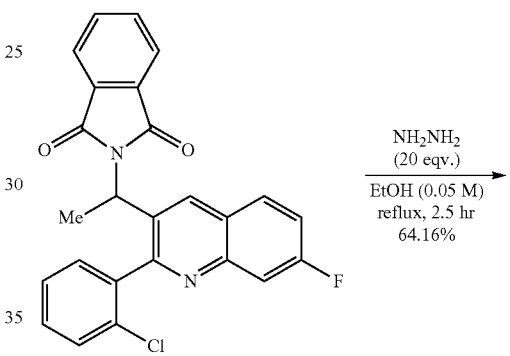

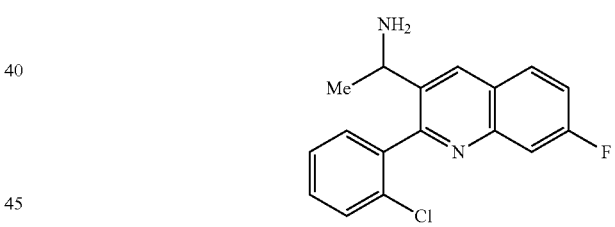

To a suspension of 2-(1-(2-(2-chlorophenyl)-7-fluoroquinolin-3-yl)ethyl)-isoindoline-1,3-dione (impure) (0.9331 g, 2.166 mmol) in ethanol (43.31 mL, 2.166 mmol) was added hydrazine hydrate (1.349 mL, 43.31 mmol), and the mixture was stirred under reflux. After 2.5 h, the mixture was cooled to room temperature. The mixture was diluted with CH$_2$Cl$_2$ (50 mL), filtered to removed the precipitated byproduct, and washed the filtered solid with CH$_2$Cl$_2$ (50 mL). The filtrate containing the desired product was concentrated under reduced pressure. The residue was purified by column chromatography on a 80 g of Redi-Sep™ column using 0% to 50% gradient of CH$_2$Cl$_2$:MeOH:NH$_4$OH (89:9:1) in CH$_2$Cl$_2$ over 25 min, and then 50% isocratic of CH$_2$Cl$_2$:MeOH:NH$_4$OH (89:9:1) in CH$_2$Cl$_2$ for 5 min as eluent to give 1-(2-(2-chlorophenyl)-7-fluoroquinolin-3-yl)-ethanamine as a yellow syrup: LC-MS (ESI) m/z 301.1 [M+H]$^+$.

229

N—((S)-1-(2-(2-Chlorophenyl)-7-fluoroquinolin-3-yl)ethyl)-9H-purin-6-amine and N—((R)-1-(2-(2-Chlorophenyl)-7-fluoroquinolin-3-yl)ethyl)-9H-purin-6-amine

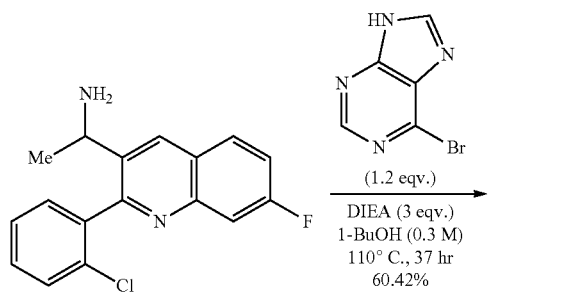

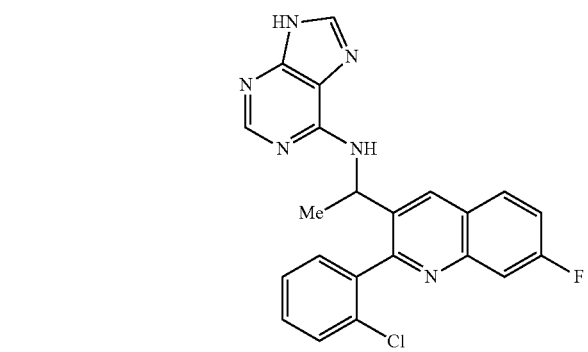

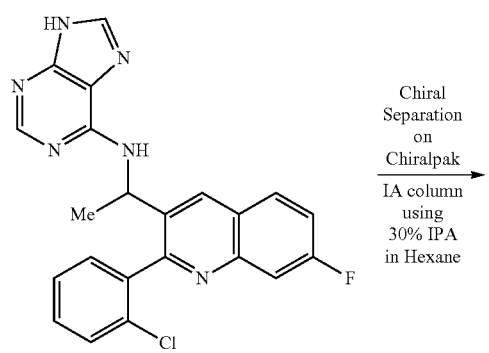

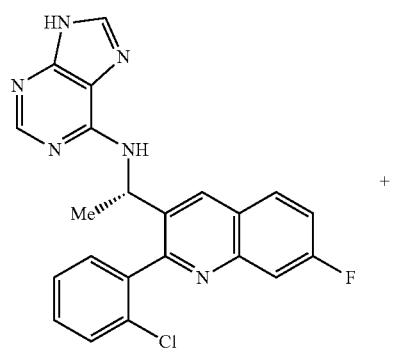

-continued

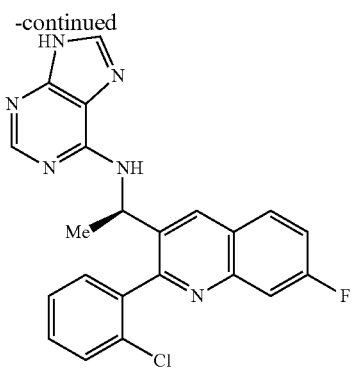

A mixture of 6-bromopurine (0.3221 g, 1.618 mmol), 1-(2-(2-chlorophenyl)-7-fluoroquinolin-3-yl)ethanamine (0.4056 g, 1.349 mmol), and N,N-diisopropylethylamine (0.7047 mL, 4.046 mmol) in 1-butanol (4.495 mL, 1.349 mmol) was stirred at 110° C. After 37 h, the mixture was removed from the heat and concentrated under reduced pressure. The residue was purified by column chromatography on a 80 g of Redi-Sep™ column using 0% to 50% gradient of $CH_2Cl_2$:MeOH:$NH_4OH$ (89:9:1) in $CH_2Cl_2$ over 20 min and then 50% isocratic of $CH_2Cl_2$:MeOH:$NH_4OH$ (89:9:1) in $CH_2Cl_2$ for 20 min as eluent to give the desired product as a racemic mixture as a solid. The solid was suspended in MeOH, sonicated, and filtered to give N-(1-(2-(2-chlorophenyl)-7-fluoroquinolin-3-yl)ethyl)-9H-purin-6-amine as a yellow syrupy solid. The racemic mixture was dissolved in $CH_2Cl_2$ (7.5 mL), filtered, and separated on a Chiralpak™ IA column (30×250 mm, 5 μm) using 30% isocratic of isopropanol in hexane for 40 min as eluent to give two separated isomers: N—((S)-1-(2-(2-chlorophenyl)-7-fluoroquinolin-3-yl)ethyl)-9H-purin-6-amine as an off-white solid: $^1$H NMR (400 MHz, DMSO-$d_6$) δ ppm 12.86 (1H, s), 8.52-8.80 (1H, m), 7.91-8.26 (4H, m), 7.26-7.82 (6H, m), 5.28 (1H, d, J=47.7 Hz), 1.52 (3H, d, J=6.7 Hz) LC-MS (ESI) m/z 419.2 [M+H]$^+$ and N—((R)-1-(2-(2-chlorophenyl)-7-fluoroquinolin-3-yl)ethyl)-9H-purin-6-amine as an off-white solid: $^1$H NMR (400 MHz, DMSO-$d_6$) δ ppm 12.86 (1H, s), 8.56-8.81 (1H, m), 7.91-8.28 (4H, m), 7.25-7.82 (6H, m), 5.15-5.44 (1H, m), 1.52 (3H, d, J=6.8 Hz); LC-MS (ESI) m/z 419.2 [M+H]$^+$.

BIOLOGICAL ASSAYS

Recombinant Expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with poly-His tag, was expressed with Baculo virus in Hi5 insect cells. The γ isozyme was purified by sequential Ni-NTA, Superdex-200, Q-HP chromatography. The γ isozyme was stored frozen at −80° C. in $NaH_2PO_4$, pH 8, 0.2M NaCl, 1% ethylene glycol, 2 mM β-mercaptoethanol.

|  | Alpha | Beta | Delta | gamma |
| --- | --- | --- | --- | --- |
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |

-continued

|      | Alpha | Beta | Delta | gamma |
|------|-------|------|-------|-------|
| ATP  | 1 uM  | 0.5 uM | 0.5 uM | 1 uM |
| PIP2 | none  | 2.5 uM | 2.5 uM | none |
| time | 1 h   | 2 h  | 2 h   | 1 h   |
| [Enzyme] | 15 nM | 40 nM | 15 nM | 50 nM |

In Vitro Enzyme Assays.

Assays were performed in 25 µL with the above final concentrations of components in white polyproplyene plates (Costar 3355). Phospatidyl inositol phosphoacceptor, PtdIns (4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 µL) was added per test well, and the inhibition relative to reactions containing no compound, with and without enzyme was determined After assay incubation at room temperature, the reaction was stopped and residual ATP determined by addition of an equal volume of a commercial ATP bioluminescence kit (Perkin Elmer Easy-Lite) according to the manufacturer's instructions, and detected using a AnalystGT luminometer.

Human B Cells Proliferation Stimulate by Anti-IgM
Isolate Human B Cells:

Isolate PBMCs from Leukopac or from human fresh blood. Isolate human B cells by using Miltenyi protocol and B cell isolation kit II. —human B cells were Purified by using autoMACS® column.

Activation of Human B Cells

Use 96 well Flat bottom plate, plate 50000/well purified B cells in B cell proliferation medium (DMEM+5% FCS, 10 mM Hepes, 50 µM 2-mercaptoethanol); 150 µL medium contain 250 ng/mL CD40L-LZ recombinant protein (Amgen) and 2 µg/mL anti-Human IgM antibody (Jackson ImmunoReseach Lab. #109-006-129), mixed with 50 µL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

| Compound | IC50 |
|----------|------|
| (3S)-3-(8-chloro-2-(2-chlorophenyl)-3-quinolinyl)-3-(9H-purin-6-ylamino)-1-propanol | 0.013138 |
| 1-(8-chloro-3-((9H-purin-6-ylamino)methyl)-2-quinolinyl)-3-piperidinol | 0.098845 |
| 2-(3-fluorophenyl)-3-((1S)-1-(9H-purin-6-ylamino)ethyl)-8-quinolinecarbonitrile | 0.003383 |
| 2-(3-fluorophenyl)-3-((9H-purin-6-ylamino)methyl)-8-quinolinecarbonitrile | 0.300015 |
| 2-(8-chloro-3-((9H-purin-6-ylamino)methyl)-2-quinolinyl)-4-fluorophenol | 0.818604 |
| 2-(8-chloro-3-((9H-purin-6-ylamino)methyl)-2-quinolinyl)benzonitrile | 0.055087 |
| 3-((1S)-1-(9H-purin-6-ylamino)ethyl)-2-(2-pyridinyl)-8-quinolinecarbonitrile | 0.046694 |
| 3-(8-chloro-3-((1S)-1-(9H-purin-6-ylamino)ethyl)-2-quinolinyl)-4-pyridinecarboxamide | 4.635 |
| 8-chloro-2-phenyl-3-((1S)-1-(7H-pyrrolo[2,3-d]pyrimidin-4-yloxy)ethyl)quinoline | 0.003035 |
| 8-chloro-2-phenyl-3-((9H-purin-6-yloxy)methyl)quinoline | 0.081441 |
| N-((1R)-1-(3-(2-chlorophenyl)-5-(trifluoromethyl)-2-quinoxalinyl)ethyl)-9H-purin-6-amine | 0.053372 |
| N-((1R)-1-(5-chloro-2-(3-fluorophenyl)-3-quinolinyl)ethyl)-9H-purin-6-amine | 0.03363 |
| N-((1R)-1-(5-chloro-3-(3-fluorophenyl)-2-quinolinyl)ethyl)-9H-purin-6-amine | 0.02103 |
| N-((1R)-1-(5-chloro-3-(3-fluorophenyl)-2-quinoxalinyl)ethyl)-9H-purin-6-amine | 0.013869 |
| N-((1R)-1-(8-chloro-2-(1,3-thiazol-2-yl)-3-quinolinyl)ethyl)-9H-purin-6-amine | 0.181889 |
| N-((1R)-1-(8-chloro-2-(3-fluorophenyl)-3-quinolinyl)propyl)-9H-purin-6-amine | 0.003757 |
| N-((1R)-1-(8-chloro-2-(3-fluorophenyl)-3-quinolinyl)propyl)-9H-purin-6-amine | 1.243545 |
| N-((1S)-1-(2-(2-(benzyloxy)-5-fluorophenyl)-8-chloro-3-quinolinyl)ethyl)-9H-purin-6-amine | 0.016795 |
| N-((1S)-1-(2-(2,5-difluorophenyl)-8-fluoro-3-quinolinyl)ethyl)-7H-purin-6-amine | 0.012659 |
| N-((1S)-1-(2-(2-chloro-5-fluorophenyl)-7-fluoro-3-quinolinyl)ethyl)-9H-purin-6-amine | 0.019962 |
| N-((1S)-1-(2-(2-chloro-5-fluorophenyl)-8-fluoro-3-quinolinyl)ethyl)-7H-purin-6-amine | 0.03373 |
| N-((1S)-1-(2-(2-chlorophenyl)-7-fluoro-3-quinolinyl)ethyl)-9H-purin-6-amine | 0.028993 |
| N-((1S)-1-(2-(2-chlorophenyl)-7-fluoro-3-quinolinyl)ethyl)-9H-purin-6-amine | 0.028993 |
| N-((1S)-1-(2-(2-chlorophenyl)-8-fluoro-3-quinolinyl)ethyl)-7H-purin-6-amine | 0.01137 |
| N-((1S)-1-(2-(2-pyridinyl)-3-quinolinyl)ethyl)-9H-purin-6-amine | 0.005602 |
| N-((1S)-1-(2-(3,5-difluorophenyl)-7-fluoro-3-quinolinyl)ethyl)-9H-purin-6-amine | 0.005149 |
| N-((1S)-1-(2-(3,5-difluorophenyl)-8-fluoro-3-quinolinyl)ethyl)-7H-purin-6-amine | 0.00707 |
| N-((1S)-1-(2-(3-chloro-5-fluorophenyl)-8-fluoro-3-quinolinyl)ethyl)-7H-purin-6-amine | 0.008089 |
| N-((1S)-1-(2,8-bis(3-fluorophenyl)-3-quinolinyl)ethyl)-9H-purin-6-amine | 0.001062 |
| N-((1S)-1-(2,8-di-2-pyridinyl-3-quinolinyl)ethyl)-9H-purin-6-amine | 0.067391 |

| Compound | IC50 |
|---|---|
| N-((1S)-1-(2,8-diphenyl-3-quinolinyl)ethyl)-9H-purin-6-amine | 0.018823 |
| N-((1S)-1-(3-(2-chlorophenyl)-5-(trifluoromethyl)-2-quinoxalinyl)ethyl)-9H-purin-6-amine | 0.010401 |
| N-((1S)-1-(5-chloro-2-(3-fluorophenyl)-3-quinolinyl)ethyl)-9H-purin-6-amine | 0.014192 |
| N-((1S)-1-(5-chloro-3-(2-chloro-5-fluorophenyl)-2-quinoxalinyl)ethyl)-9H-purin-6-amine | 0.089326 |
| N-((1S)-1-(5-chloro-3-(3-fluorophenyl)-2-quinolinyl)ethyl)-9H-purin-6-amine | 0.008779 |
| N-((1S)-1-(5-chloro-3-(3-fluorophenyl)-2-quinoxalinyl)ethyl)-9H-purin-6-amine | 0.008554 |
| N-((1S)-1-(7-fluoro-1-oxido-2-phenyl-3-quinolinyl)ethyl)-9H-purin-6-amine | 0.004638 |
| N-((1S)-1-(7-fluoro-2-(2-(methylsulfonyl)phenyl)-3-quinolinyl)ethyl)-9H-purin-6-amine | 0.006821 |
| N-((1S)-1-(7-fluoro-2-(2-pyridinyl)-3-quinolinyl)ethyl)-9H-purin-6-amine | 0.009416 |
| N-((1S)-1-(7-fluoro-2-(3-(methylsulfonyl)phenyl)-3-quinolinyl)ethyl)-9H-purin-6-amine | 0.148274 |
| N-((1S)-1-(7-fluoro-2-(3-fluorophenyl)-3-quinolinyl)ethyl)-9H-purin-6-amine | 0.011491 |
| N-((1S)-1-(7-fluoro-2-(3-pyridinyl)-3-quinolinyl)ethyl)-9H-purin-6-amine | 0.01221 |
| N-((1S)-1-(7-fluoro-2-(6-fluoro-2-pyridinyl)-3-quinolinyl)ethyl)-9H-purin-6-amine | 0.00372 |
| N-((1S)-1-(7-fluoro-2-phenyl-3-quinolinyl)ethyl)-9H-purin-6-amine | 0.005114 |
| N-((1S)-1-(8-chloro-2-(1,3-thiazol-2-yl)-3-quinolinyl)ethyl)-9H-purin-6-amine | 0.001636 |
| N-((1S)-1-(8-chloro-2-(1,3-thiazol-4-yl)-3-quinolinyl)ethyl)-9H-purin-6-amine | 0.000537 |
| N-((1S)-1-(8-chloro-2-(1,3-thiazol-5-yl)-3-quinolinyl)ethyl)-9H-purin-6-amine | 0.0219 |
| N-((1S)-1-(8-chloro-2-(2,3-difluorophenyl)-3-quinolinyl)ethyl)-9H-purin-6-amine | 0.007589 |
| N-((1S)-1-(8-chloro-2-(2,4-difluorophenyl)-3-quinolinyl)ethyl)-9H-purin-6-amine | 0.014034 |
| N-((1S)-1-(8-chloro-2-(2-chloro-5-fluorophenyl)-3-quinolinyl)ethyl)-9H-purin-6-amine | 0.046566 |
| N-((1S)-1-(8-chloro-2-(2-chlorophenyl)-3-quinolinyl)ethyl)-9H-purin-6-amine | 0.003602 |
| N-((1S)-1-(8-chloro-2-(2-ethyl-3-pyridinyl)-3-quinolinyl)ethyl)-9H-purin-6-amine | 0.003312 |
| N-((1S)-1-(8-chloro-2-(2-ethyl-5-fluoro-3-pyridinyl)-3-quinolinyl)ethyl)-9H-purin-6-amine | 0.00384 |
| N-((1S)-1-(8-chloro-2-(2-fluorophenyl)-3-quinolinyl)ethyl)-9H-purin-6-amine | 0.003557 |
| N-((1S)-1-(8-chloro-2-(2-fluorophenyl)-3-quinolinyl)ethyl)-9H-purin-6-amine | 0.003557 |
| N-((1S)-1-(8-chloro-2-(2-methoxy-1,3-thiazol-4-yl)-3-quinolinyl)ethyl)-9H-purin-6-amine | 0.017526 |
| N-((1S)-1-(8-chloro-2-(2-methyl-3-pyridinyl)-3-quinolinyl)ethyl)-9H-purin-6-amine | 0.004344 |
| N-((1S)-1-(8-chloro-2-(2-pyridinyl)-3-quinolinyl)ethyl)-2-fluoro-9H-purin-6-amine | 0.013972 |
| N-((1S)-1-(8-chloro-2-(2-pyridinyl)-3-quinolinyl)ethyl)-9H-purin-6-amine | 0.003236 |
| N-((1S)-1-(8-chloro-2-(2-pyrimidinyl)-3-quinolinyl)ethyl)-9H-purin-6-amine | 0.090413 |
| N-((1S)-1-(8-chloro-2-(3-(methylsulfonyl)phenyl)-3-quinolinyl)ethyl)-9H-purin-6-amine | 0.05577 |
| N-((1S)-1-(8-chloro-2-(3-(trifluoromethyl)-1H-pyrazol-1-yl)-3-quinolinyl)ethyl)-9H-purin-6-amine | 0.449196 |
| N-((1S)-1-(8-chloro-2-(3,5-difluorophenyl)-3-quinolinyl)ethyl)-9H-purin-6-amine | 0.005039 |
| N-((1S)-1-(8-chloro-2-(3,5-difluorophenyl)-3-quinolinyl)ethyl)-9H-purin-6-amine | 0.005039 |
| N-((1S)-1-(8-chloro-2-(3,5-dimethyl-1H-pyrazol-1-yl)-3-quinolinyl)ethyl)-9H-purin-6-amine | 0.00263 |
| N-((1S)-1-(8-chloro-2-(3-chlorophenyl)-3-quinolinyl)ethyl)-9H-purin-6-amine | 0.005516 |
| N-((1S)-1-(8-chloro-2-(3-fluorophenyl)-3-quinolinyl)butyl)-9H-purin-6-amine | 0.006521 |
| N-((1S)-1-(8-chloro-2-(3-fluorophenyl)-3-quinolinyl)ethyl)-9H-purin-6-amine | 0.002416 |
| N-((1S)-1-(8-chloro-2-(3-fluorophenyl)-3-quinolinyl)propyl)-9H-purin-6-amine | 0.0053 |
| N-((1S)-1-(8-chloro-2-(3-methyl-2-pyridinyl)-3-quinolinyl)ethyl)-9H-purin-6-amine | 0.033221 |
| N-((1S)-1-(8-chloro-2-(3-pyridazinyl)-3-quinolinyl)ethyl)-9H-purin-6-amine | 0.018032 |
| N-((1S)-1-(8-chloro-2-(3-pyridinyl)-3-quinolinyl)ethyl)-9H-purin-6-amine | 0.003444 |
| N-((1S)-1-(8-chloro-2-(4-fluorophenyl)-3-quinolinyl)ethyl)-9H-purin-6-amine | 0.010478 |
| N-((1S)-1-(8-chloro-2-(5-fluoro-2-(2-methylpropyl)-3-pyridinyl)-3-quinolinyl)ethyl)-9H-purin-6-amine | 0.015529 |

| Compound | IC50 |
|---|---|
| N-((1S)-1-(8-chloro-2-(5-fluoro-2-methyl-3-pyridinyl)-3-quinolinyl)ethyl)-9H-purin-6-amine | 0.016946 |
| N-((1S)-1-(8-chloro-2-(5-fluoro-3-pyridinyl)-3-quinolinyl)ethyl)-9H-purin-6-amine | 0.003571 |
| N-((1S)-1-(8-chloro-2-(6-fluoro-2-pyridinyl)-3-quinolinyl)ethyl)-9H-purin-6-amine | 0.003099 |
| N-((1S)-1-(8-chloro-2-(6-methyl-2-pyridinyl)-3-quinolinyl)ethyl)-9H-purin-6-amine | 0.10543 |
| N-((1S)-1-(8-chloro-2-phenoxy-3-quinolinyl)ethyl)-9H-purin-6-amine | 0.029313 |
| N-((1S)-1-(8-chloro-2-phenyl-3-quinolinyl)ethyl)-9H-purin-6-amine | 0.002654 |
| N-((1S)-1-(8-fluoro-2-(3-fluorophenyl)-3-quinolinyl)ethyl)-7H-purin-6-amine | 0.005152 |
| N-((1S)-1-(8-fluoro-2-(3-pyridinyl)-3-quinolinyl)ethyl)-7H-purin-6-amine | 0.015402 |
| N-((1S)-1-(8-fluoro-2-phenyl-3-quinolinyl)ethyl)-7H-purin-6-amine | 0.00142 |
| N-((2-(2-biphenylyl)-8-chloro-3-quinolinyl)methyl)-9H-purin-6-amine | 0.164542 |
| N-((2-(2-chlorophenyl)-7-fluoro-3-quinolinyl)methyl)-9H-purin-6-amine | 0.088655 |
| N-((3-(2-chlorophenyl)-5-fluoro-2-quinoxalinyl)methyl)-9H-purin-6-amine | 0.299212 |
| N-((3-(2-chlorophenyl)-5-iodo-2-quinoxalinyl)methyl)-9H-purin-6-amine | 0.088387 |
| N-((3-(2-chlorophenyl)-5-methyl-2-quinoxalinyl)methyl)thieno[3,2-d]pyrimidin-4-amine | 0.194243 |
| N-((3-(2-chlorophenyl)-8-(methylsulfonyl)-2-quinoxalinyl)methyl)-9H-purin-6-amine | 2.407455 |
| N-((3-(2-chlorophenyl)-8-fluoro-2-quinoxalinyl)methyl)-9H-purin-6-amine | 0.176806 |
| N-((5-chloro-3-(2-(trifluoromethyl)phenyl)-2-quinoxalinyl)methyl)-9H-purin-6-amine | 0.041805 |
| N-((5-chloro-3-(2-chloro-5-fluorophenyl)-2-quinoxalinyl)methyl)-9H-purin-6-amine | 0.165211 |
| N-((5-chloro-3-(2-chlorophenyl)-2-quinoxalinyl)methyl)-9H-purin-6-amine | 0.082543 |
| N-((5-chloro-3-(3-fluorophenyl)-2-quinolinyl)methyl)-9H-purin-6-amine | 0.130021 |
| N-((5-chloro-3-(3-fluorophenyl)-2-quinoxalinyl)methyl)-9H-purin-6-amine | 0.07192 |
| N-((8-bromo-2-(3-fluorophenyl)-3-quinolinyl)methyl)-9H-purin-6-amine | 0.068766 |
| N-((8-chloro-2-(1,3-thiazol-2-yl)-3-quinolinyl)methyl)-9H-purin-6-amine | 0.208949 |
| N-((8-chloro-2-(1H-pyrazol-4-yl)-3-quinolinyl)methyl)-9H-purin-6-amine | 0.157905 |
| N-((8-chloro-2-(2-(1-methylethyl)-3-pyridinyl)-3-quinolinyl)methyl)-9H-purin-6-amine | 0.030614 |
| N-((8-chloro-2-(2-(1-methylethyl)phenyl)-3-quinolinyl)methyl)-9H-purin-6-amine | 0.017602 |
| N-((8-chloro-2-(2-(2H-tetrazol-5-yl)phenyl)-3-quinolinyl)methyl)-9H-purin-6-amine | 9.706546 |
| N-((8-chloro-2-(2-(methylsulfonyl)phenyl)-3-quinolinyl)methyl)-9H-purin-6-amine | 0.150914 |
| N-((8-chloro-2-(2,5-difluorophenyl)-3-quinolinyl)methyl)-9H-purin-6-amine | 0.038235 |
| N-((8-chloro-2-(2-chloro-5-fluorophenyl)-3-quinolinyl)methyl)-9H-purin-6-amine | 0.03835 |
| N-((8-chloro-2-(2-chlorophenyl)-3-quinolinyl)methyl)-3H-imidazo[4,5-b]pyridin-7-amine | 0.36145 |
| N-((8-chloro-2-(2-methyl-3-pyridinyl)-3-quinolinyl)methyl)-9H-purin-6-amine | 0.013398 |
| N-((8-chloro-2-(2-pyridinyl)-3-quinolinyl)methyl)-9H-purin-6-amine | 0.034112 |
| N-((8-chloro-2-(2-thiophenyl)-3-quinolinyl)methyl)-9H-purin-6-amine | 0.103629 |
| N-((8-chloro-2-(3-(1-methylethyl)phenyl)-3-quinolinyl)methyl)-9H-purin-6-amine | 0.305301 |
| N-((8-chloro-2-(3,5-difluorophenyl)-3-quinolinyl)methyl)-9H-purin-6-amine | 0.055993 |
| N-((8-chloro-2-(3-chlorophenyl)-3-quinolinyl)methyl)-9H-purin-6-amine | 0.411098 |
| N-((8-chloro-2-(3-fluoro-1-piperidinyl)-3-quinolinyl)methyl)-9H-purin-6-amine | 0.09547 |
| N-((8-chloro-2-(3-fluorophenyl)-3-quinolinyl)methyl)-9H-purin-6-amine | 0.027542 |
| N-((8-chloro-2-(3-methyl-2-pyridinyl)-3-quinolinyl)methyl)-9H-purin-6-amine | 0.07904 |
| N-((8-chloro-2-(4-(1-methylethyl)-3-pyridinyl)-3-quinolinyl)methyl)-9H-purin-6-amine | 0.025841 |
| N-((8-chloro-2-(4-(1-methylethyl)-5-pyrimidinyl)-3-quinolinyl)methyl)-9H-purin-6-amine | 0.078872 |
| N-((8-chloro-2-(4-(trifluoromethyl)-3-pyridinyl)-3-quinolinyl)methyl)-9H-purin-6-amine | 0.069518 |
| N-((8-chloro-2-(4-fluorophenyl)-3-quinolinyl)methyl)-7H-purin-6-amine | 0.265255 |
| N-((8-chloro-2-(5-fluoro-2-(1-phenylethoxy)phenyl)-3-quinolinyl)methyl)-9H-purin-6-amine | 0.564971 |
| N-((8-chloro-2-(5-fluoro-2-(3-pyridinylmethoxy)phenyl)-3-quinolinyl)methyl)-9H-purin-6-amine | 0.17832 |
| N-((8-chloro-2-(5-fluoro-2-methoxyphenyl)-3-quinolinyl)methyl)-9H-purin-6-amine | 0.027381 |
| N-((8-chloro-2-(5-isothiazolyl)-3-quinolinyl)methyl)-9H-purin-6-amine | 0.06556 |
| N-((8-chloro-2-phenoxy-3-quinolinyl)methyl)-9H-purin-6-amine | 0.026211 |
| N-((8-chloro-2-phenyl-3-quinolinyl)methyl)-9H-purin-6-amine | 0.219179 |
| N-((8-fluoro-2-phenyl-3-quinolinyl)methyl)-7H-purin-6-amine | 0.239808 |
| N6-((8-chloro-2-(2-chlorophenyl)-3-quinolinyl)methyl)-9H-purine-2,6-diamine | 0.008899 |

Human B Cells Proliferation Stimulate by IL-4
Isolate Human B Cells:

Isolate human PBMCs from Leukopac or from human fresh blood. Isolate human B cells using Miltenyi protocol-B cell isolation kit. Human B cells were Purified by autoMACS® column.

Activation of Human B Cells

Use 96-well flat bottom plate, plate 50000/well purified B cells in B cell proliferation medium (DMEM+5% FCS, 50 µM 2-mercaptoethanol, 10 mM Hepes). The medium (150 µL) contain 250 ng/mL CD40L-LZ recombinant protein (Amgen) and 10 ng/mL IL-4 (R&D system #204-IL-025), mixed with 50 150 µL B cell medium containing compounds and incubate 72 h at 37° C. incubator. After 72 h, pulse labeling B cells with 0.5-1 uCi/well 3H thymidine for overnight ~18 h, and harvest cell using TOM harvester.

Specific T Antigen (Tetanus Toxoid) Induced Human PBMC Proliferation Assays

Human PBMC are prepared from frozen stocks or they are purified from fresh human blood using a Ficoll® gradient. Use 96 well round-bottom plate and plate $2 \times 10^5$ PBMC/well with culture medium (RPMI1640+10% FCS, 50 uM 2-Mercaptoethanol, 10 mM Hepes). For $IC_{50}$ determinations, PI3K inhibitors was tested from 10 µM to 0.001 µM, in half log increments and in triplicate. Tetanus toxoid, T cell specific antigen (University of Massachusetts Lab) was added at 1 µg/mL and incubated 6 days at 37° C. incubator. Supernatants are collected after 6 days for IL2 ELISA assay, then cells are pulsed with $^3$H-thymidine for ~18 h to measure proliferation.

GFP Assays for Detecting Inhibition of Class Ia and Class III PI3K

AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane Forkhead (FKHRL1) is a substrate for AKT1. It is cytoplasmic when phosphorylated by AKT (survival/growth). Inhibition of AKT (stasis/apoptosis)-forkhead translocation to the nucleus FYVE domains bind to PI(3)P. the majority is generated by constitutive action of PI3K Class III AKT Membrane Ruffling Assay (CHO-IR-AKT1-EGFP Cells/GE Healthcare)

Wash cells with assay buffer. Treat with compounds in assay buffer 1 h. Add 10 ng/mL insulin. Fix after 10 min at room temp and image Forkhead Translocation Assay (MDA MB468 Forkhead-DiversaGFP Cells)

Treat cells with compound in growth medium 1 h. Fix and image.

Class III PI(3)P Assay (U2OS EGFP-2XFYVE Cells/GE Healthcare)

Wash cells with assay buffer. Treat with compounds in assay buffer 1 h. Fix and image.

Control for all 3 Assays is 100I Wortmannin:
AKT is cytoplasmic
Forkhead is nuclear
PI(3)P depleted from endosomes Biomarker Assay: B-Cell Receptor Stimulation of CD69 or B7.2 (CD86) Expression Heparinized human whole blood was stimulated with 10 µg/mL anti-IgD (Southern Biotech, #9030-01). 90 µL of the stimulated blood was then aliquoted per well of a 96-well plate and treated with 10 µL of various concentrations of blocking compound (from 10-0.0003 µM) diluted in IMDM+10% FBS (Gibco®). Samples were incubated together for 4 h (for CD69 expression) to 6 h (for B7.2 expression) at 37° C. Treated blood (50 µL) was transferred to a 96-well, deep well plate (Nunc) for antibody staining with 10 µL each of CD45-PerCP (BD™ Biosciences, #347464), CD19-FITC (BD™ Biosciences, #340719), and CD69-PE (BD™ Biosciences, #341652). The second 50 µL of the treated blood was transferred to a second 96-well, deep well plate for antibody staining with 10 µL each of CD19-FITC (BD™ Biosciences, #340719) and CD86-PeCy5 (BD™ Biosciences, #555666). All stains were performed for 15-30 minutes in the dark at room temperature. The blood was then lysed and fixed using 450 µL of FACS lysing solution (BD™ Biosciences, #349202) for 15 minutes at room temperature. Samples were then washed 2× in PBS+2% FBS before FACS analysis. Samples were gated on either CD45/CD19 double positive cells for CD69 staining, or CD19 positive cells for CD86 staining.

Gamma Counterscreen: Stimulation of Human Monocytes for Phospho-AKT Expression

A human monocyte cell line, THP-1, was maintained in RPMI+10% FBS (Gibco®). One day before stimulation, cells were counted using trypan blue exclusion on a hemocytometer and suspended at a concentration of $1 \times 10^6$ cells per mL of media. 100 µL of cells plus media ($1 \times 10^5$ cells) was then aliquoted per well of 4-96-well, deep well dishes (Nunc) to test eight different compounds. Cells were rested overnight before treatment with various concentrations (from 10-0.0003 µM) of blocking compound. The compound diluted in media (12 µL) was added to the cells for 10 minutes at 37° C. Human MCP-1 (12 µL, R&D Diagnostics, #279-MC) was diluted in media and added to each well at a final concentration of 50 µg/mL. Stimulation lasted for 2 minutes at room temperature. Pre-warmed FACS Phosflow™ Lyse/Fix buffer (1 mL of 37° C.) (BD™ Biosciences, #558049) was added to each well. Plates were then incubated at 37° C. for an additional 10-15 minutes. Plates were spun at 1500 rpm for 10 minutes, supernatant was aspirated off, and 1 mL of ice cold 90% MEOH was added to each well with vigorous shaking. Plates were then incubated either overnight at −70° C. or on ice for 30 minutes before antibody staining. Plates were spun and washed 2× in PBS+2% FBS Gibco®). Wash was aspirated and cells were suspended in remaining buffer. Rabbit pAKT (50 µL, Cell Signaling, #4058L) at 1:100, was added to each sample for 1 h at rt with shaking. Cells were washed and spun at 1500 rpm for 10 minutes. Supernatant was aspirated and cells were suspended in remaining buffer. Secondary antibody, goat anti-rabbit Alexa Fluor® 647 (50 µL, Invitrogen™, #A21245) at 1:500, was added for 30 minutes at rt with shaking. Cells were then washed 1× in buffer and suspended in 150 µL, of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.

Gamma Counterscreen: Stimulation of Monocytes for Phospho-AKT Expression in Mouse Bone Marrow Mouse femurs were dissected from five female BALB/c mice (Charles River Labs.) and collected into RPMI+10% FBS media (Gibco®). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5 \times 10^6$ cells per 1 mL of media and 100 µL ($7.5 \times 10^5$ cells) was aliquoted per well into 4-96-well, deep well dishes (Nunc) to test eight different compounds. Cells were rested at 37° C. for 2 h before treatment with various concentrations (from 10-0.0003 μM) of blocking compound. Compound diluted in media (12 μL) was added to bone marrow cells for 10 minutes at 37° C. Mouse MCP-1 (12 μL, R&D Diagnostics, #479-JE) was diluted in media and added to each well at a final concentration of 50 μg/mL. Stimulation lasted for 2 minutes at room temperature. 1 mL of 37° C. pre-warmed FACS Phosflow™ Lyse/Fix buffer (BD™ Biosciences, #558049) was added to each well. Plates were then incubated at 37° C. for an additional 10-15 minutes. Plates were spun at 1500 rpm for 10 minutes. Supernatant was aspirated off and 1 mL of ice cold 90% MEOH was added to each well with vigorous shaking. Plates were then incubated either overnight at −70° C. or on ice for 30 minutes before antibody staining Plates were spun and washed 2× in PBS+2% FBS (Gibco®). Wash was aspirated and cells were suspended in remaining buffer. Fc Block™ (2 μL, BD™ Pharmingen, #553140) was then added per well for 10 minutes at room temperature. After block, 50 μL of primary antibodies diluted in buffer; CD11b-Alexa Fluor® 488 (BD™ Biosciences, #557672) at 1:50, CD64-PE (BD™ Biosciences, #558455) at 1:50, and rabbit pAKT (Cell Signaling, #4058L) at 1:100, were added to each sample for 1 h at RT with shaking. Wash buffer was added to cells and spun at 1500 rpm for 10 minutes. Supernatant was aspirated and cells were suspended in remaining buffer. Secondary antibody; goat anti-rabbit Alexa Fluor® 647 (50 μL, Invitrogen™, #A21245) at 1:500, was added for 30 minutes at rt with shaking. Cells were then washed 1× in buffer and suspended in 100 μL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 min prior to the injection i.v (0.2 mLs) of anti-IgM FITC (50 ug/mouse) (Jackson Immuno Research, West Grove, Pa.). After 45 min the mice are sacrificed within a $CO_2$ chamber. Blood is drawn via cardiac puncture (0.3 mL) (1 cc 25 g Syringes, Sherwood, St. Louis, Mo.) and transferred into a 15 mL conical vial (Nalge/Nunc International, Denmark). Blood is immediately fixed with 6.0 mL of BD™ Phosflow™ Lyse/Fix Buffer (BD™ Bioscience, San Jose, Calif.), inverted 3×'s and placed in 37° C. water bath. Half of the spleen is removed and transferred to an eppendorf tube containing 0.5 mL of PBS (Invitrogen™ Corp, Grand Island, N.Y.). The spleen is crushed using a tissue grinder (Pellet Pestle®, Kimble/Kontes, Vineland, N.J.) and immediately fixed with 6.0 mL of BD™ Phosflow™ Lyse/Fix buffer, inverted 3×'s and placed in 37° C. water bath. Once tissues have been collected the mouse is cervically-dislocated and carcass to disposed. After 15 min, the 15 mL conical vials are removed from the 37° C. water bath and placed on ice until tissues are further processed. Crushed spleens are filtered through a 70 μm cell strainer (BD™ Bioscience, Bedford, Mass.) into another 15 mL conical vial and washed with 9 mL of PBS. Splenocytes and blood are spun @ 2,000 rpms for 10 min (cold) and buffer is aspirated. Cells are resuspended in 2.0 mL of cold (−20° C.) 90% methyl alcohol (Mallinckrodt Chemicals, Phillipsburg, N.J.). Methanol is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 minutes and spun at 10,000 rpm in serum microtainer tubes (Becton Dickinson) for 10 minutes. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 μg of TNP-LPS (Biosearch Tech., #T-5065), 50 μg of TNP-Ficoll® (Biosearch Tech., #F-1300), or 100 μg of TNP-KLH (Biosearch Tech., #T-5060) plus 1% alum (Brenntag, #3501) in PBS. TNP-KLH plus alum solution was prepared by gently inverting the mixture 3-5 times every 10 minutes for 1 hour before immunization. On day 5, post-last treatment, mice were $CO_2$ sacrificed and cardiac punctured. Blood was allowed to clot for 30 minutes and spun at 10,000 rpm in serum microtainer tubes for 10 minutes. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 μg/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2α, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 minutes depending on the Ig analyzed. The reaction was stopped with 2M sulfuric acid and plates were read at an OD of 450 nm.

For the treatment of PI3Kδ-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI3Kδ-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A method of treating cancers which are mediated, dependent on or associated with p110δ activity, comprising the step of administering a compound having the structure:

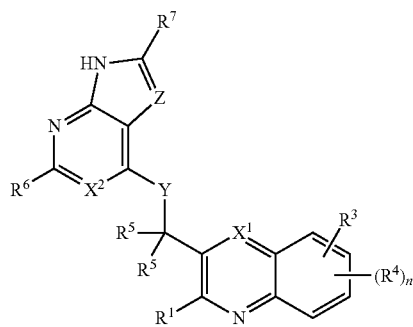

or any pharmaceutically-acceptable salt thereof, wherein:
$X^1$ is $C(R^9)$;
$X^2$ is N;
Y is $N(R^{11})$;
Z is N;
n is 0, 1, 2 or 3;
$R^1$ is a direct bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}$alkyl$)C_{1-4}$alkyl and $C_{1-4}$haloalkyl;
$R^2$ is selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$ and —N$R^a C_{2-6}$alkylO$R^a$; or $R^2$ is selected from $C_{1-6}$alkyl, phenyl, benzyl, heteroaryl, heterocycle, —(C$_{1-3}$alkyl)heteroaryl, —(C$_{1-3}$alkyl)heterocycle, —O(C$_{1-3}$alkyl)heteroaryl, —O(C$_{1-3}$alkyl)heterocycle, —N$R^a$(C$_{1-3}$alkyl)heteroaryl, —N$R^a$(C$_{1-3}$alkyl)heterocycle, —(C$_{1-3}$alkyl)phenyl, —O(C$_{1-3}$alkyl)phenyl and —N$R^a$(C$_{1-3}$alkyl)phenyl all of which are substituted by 0, 1, 2 or 3 substituents selected from $C_{1-4}$haloalkyl, $OC_{1-4}$alkyl, Br, Cl, F, I and $C_{1-4}$alkyl;
$R^3$ is selected from H, halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$, —N$R^a C_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;
$R^4$ is, independently, in each instance, halo, nitro, cyano, $C_{1-4}$alkyl, $OC_{1-4}$alkyl, $OC_{1-4}$haloalkyl, $NHC_{1-4}$alkyl, $N(C_{1-4}$alkyl$)C_{1-4}$alkyl or $C_{1-4}$haloalkyl;
$R^5$ is, independently, in each instance, H, $C_{1-6}$alkyl, $C_{1-4}$haloalkyl, or $C_{1-6}$alkyl substituted by 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}$alkyl$)C_{1-4}$alkyl; or both $R^5$ groups together form a $C_{3-6}$spiroalkyl substituted by 0, 1 or 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}$alkyl$)C_{1-4}$alkyl; $R^6$ is selected from H, halo, $C_{1-6}$alkyl, $C_{1-4}$haloalkyl, cyano, nitro, —C(=O)$R^a$, —C(=O)O$R^a$, —C(=O)N$R^a R^a$, —C(=N$R^a$)N$R^a R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$;
$R^7$ is selected from H, halo, $C_{1-6}$alkyl, $C_{1-4}$haloalkyl, cyano, nitro, —C(=O)$R^a$, —C(=O)O$R^a$, —C(=O)N$R^a R^a$, —C(=N$R^a$)N$R^a R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$;
$R^9$ is selected from H, halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$, —N$R^a C_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$, —N$R^a C_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$ and —N$R^a C_{2-6}$alkylO$R^a$;
$R^{11}$ is H or $C_{1-4}$alkyl;
$R^a$ is independently, at each instance, H or $R^b$;
$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$alkyl, —N(C$_{1-4}$alkyl)C$_{1-4}$alkyl; and
wherein the cancer is acute myeloid leukaemia, B-cell lymphoma, glioblastoma, prostate cancer, neuroblastoma, or breast cancer.

2. A method according to claim 1, having the structure:

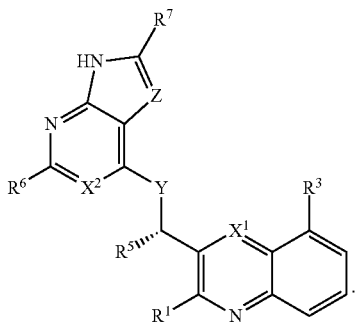

3. A method according to claim 1, having the structure:

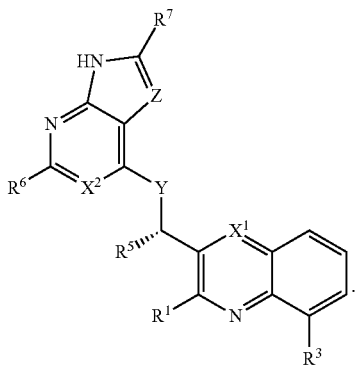

4. A method according to claim 1, having the structure:

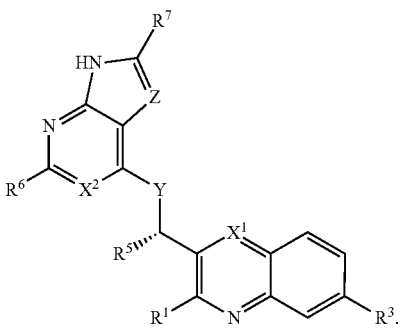

5. A method according to claim 1, wherein $R^3$ is F, Cl or Br; and n is 0.

6. A method according to claim 1, wherein $R^1$ is phenyl substituted by 0 or 1 $R^2$ substituents, and the phenyl is additionally substituted by 0, 1, 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}alkyl)C_{1-4}$alkyl and $C_{1-4}$haloalkyl.

7. A method of claim 1 wherein $R^1$ is a direct bonded saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, $NHC_{1-4}$alkyl, $N(C_{1-4}alkyl)C_{1-4}$alkyl and $C_{1-4}$haloalkyl.

8. A method of claim 1 wherein $R^1$ is selected from pyridyl and pyrimidinyl.

9. A method of claim 1 wherein $R^7$ is H.

10. A method of claim 1 wherein $R^6$ is H.

11. A method of claim 1 wherein $R^9$ is H.

12. A method of claim 1 wherein $R^{11}$ is H.

13. A method of claim 1 wherein $R^3$ is selected from F, Cl, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl.

14. A method of claim 1 wherein at least one $R^5$ is halo, $C_{1-6}$alkyl, $C_{1-4}$haloalkyl, or $C_{1-6}$alkyl substituted by 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}alkyl)C_{1-4}$alkyl.

15. A method of claim 1 wherein the cancer is PI3K-mediated.

16. A method of claim 1 comprising administering N-((1S)-1-(7-fluoro-2-(2-pyridinyl)-3-quinolinyl (ethyl)-9H-purin-6-amine.

* * * * *